US011395877B2

(12) United States Patent
Kamen et al.

(10) Patent No.: US 11,395,877 B2
(45) Date of Patent: *Jul. 26, 2022

(54) SYSTEMS AND METHODS FOR FLUID DELIVERY

(71) Applicant: DEKA Products Limited Partnership, Manchester, NH (US)

(72) Inventors: Dean Kamen, Bedford, NH (US); John M. Kerwin, Manchester, NH (US); Larry B. Gray, Merrimack, NH (US); David Blumberg, Jr., Deerfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 430 days.

This patent is subject to a terminal disclaimer.

(21) Appl. No.: 16/025,591

(22) Filed: Jul. 2, 2018

(65) Prior Publication Data
US 2019/0175822 A1 Jun. 13, 2019

Related U.S. Application Data

(63) Continuation of application No. 12/560,102, filed on Sep. 15, 2009, now Pat. No. 10,010,669, which is a
(Continued)

(51) Int. Cl.
*A61M 5/142* (2006.01)
*A61M 5/168* (2006.01)
(Continued)

(52) U.S. Cl.
CPC ........ *A61M 5/14244* (2013.01); *A61M 5/142* (2013.01); *A61M 5/14224* (2013.01);
(Continued)

(58) Field of Classification Search
CPC .......... A61M 5/14224; A61M 5/16886; A61M 2005/14268; A61M 2005/16863;
(Continued)

(56) References Cited

U.S. PATENT DOCUMENTS

| 2,122,722 A | 7/1938 | O'Neill |
| 2,308,974 A | 1/1943 | Harper |

(Continued)

FOREIGN PATENT DOCUMENTS

| CN | 1556716 | 12/2004 |
| DE | 4329229 | 3/1995 |

(Continued)

OTHER PUBLICATIONS

International Search Report with Written Opinion, dated Oct. 2, 2007, received in international patent application No. PCT/US07/003634, 17 pgs.

(Continued)

*Primary Examiner* — Brandy S Lee
(74) *Attorney, Agent, or Firm* — Reid Knott Cunningham

(57) ABSTRACT

A system for at least partial closed-loop control of a medical condition is disclosed. The system includes at least one medical fluid pump. The medical fluid pump including a sensor for determining the volume of fluid pumped by the pump. Also, at least one continuous analyte monitor, and a controller. The controller is in communication with the medical fluid pump and the at least one continuous analyte monitor. The controller includes a processor. The processor includes instructions for delivery of medical fluid based at least on data received from the at least one continuous analyte monitor.

19 Claims, 52 Drawing Sheets

Related U.S. Application Data continuation-in-part of application No. 11/704,886, filed on Feb. 9, 2007, now Pat. No. 8,545,445, which is a continuation-in-part of application No. 11/704,899, filed on Feb. 9, 2007, now Pat. No. 8,414,522, which is a continuation-in-part of application No. 11/704,896, filed on Feb. 9, 2007, now Pat. No. 8,585,377, which is a continuation-in-part of application No. 11/704,897, filed on Feb. 9, 2007, now Pat. No. 8,113,244.

(60) Provisional application No. 61/141,996, filed on Dec. 31, 2008, provisional application No. 61/141,781, filed on Dec. 31, 2008, provisional application No. 61/101,077, filed on Sep. 29, 2008, provisional application No. 61/101,053, filed on Sep. 29, 2008, provisional application No. 61/101,105, filed on Sep. 29, 2008, provisional application No. 61/101,115, filed on Sep. 29, 2008, provisional application No. 61/097,021, filed on Sep. 15, 2008, provisional application No. 60/793,188, filed on Apr. 19, 2006, provisional application No. 60/789,243, filed on Apr. 5, 2006, provisional application No. 60/772,313, filed on Feb. 9, 2006.

(51) Int. Cl.

| | | |
|---|---|---|
| *G01F 11/08* | (2006.01) | |
| *G05D 7/06* | (2006.01) | |
| *A61M 5/145* | (2006.01) | |
| *A61M 5/172* | (2006.01) | |
| *G08C 17/02* | (2006.01) | |
| *H04B 7/26* | (2006.01) | |

(52) U.S. Cl.
CPC .... *A61M 5/14248* (2013.01); *A61M 5/14586* (2013.01); *A61M 5/16809* (2013.01); *A61M 5/16886* (2013.01); *A61M 5/172* (2013.01); *A61M 5/1723* (2013.01); *G01F 11/086* (2013.01); *G05D 7/0647* (2013.01); *G05D 7/0676* (2013.01); *G08C 17/02* (2013.01); *H04B 7/2609* (2013.01); *A61M 2005/14268* (2013.01); *A61M 2005/16863* (2013.01); *A61M 2205/0266* (2013.01); *A61M 2205/0294* (2013.01); *A61M 2205/18* (2013.01); *A61M 2205/332* (2013.01); *A61M 2205/3331* (2013.01); *A61M 2205/3368* (2013.01); *A61M 2205/3375* (2013.01); *A61M 2205/3546* (2013.01); *A61M 2205/3576* (2013.01); *A61M 2205/50* (2013.01); *A61M 2205/52* (2013.01); *A61M 2205/8237* (2013.01); *A61M 2206/22* (2013.01); *A61M 2209/045* (2013.01); *A61M 2230/201* (2013.01); *Y10T 29/494* (2015.01); *Y10T 29/49236* (2015.01); *Y10T 29/49412* (2015.01); *Y10T 29/49826* (2015.01); *Y10T 29/49828* (2015.01)

(58) Field of Classification Search
CPC .. A61M 2205/0266; A61M 2205/0294; A61M 2205/18; A61M 2205/332; A61M 2205/3331; A61M 2205/3368; A61M 2205/3375; A61M 2205/3546; A61M 2205/3576; A61M 2205/50; A61M 2205/52; A61M 2205/8237; A61M 2206/22; A61M 2209/045; A61M 2230/201; A61M 5/142; A61M 5/14244; A61M 5/14248; A61M 5/14586; A61M 5/16809; A61M 5/172; A61M 5/1723

See application file for complete search history.

(56) References Cited

U.S. PATENT DOCUMENTS

| | | |
|---|---|---|
| 2,677,372 A | 5/1954 | Barnish, Jr. |
| 3,261,330 A | 7/1966 | Arant |
| 3,631,847 A | 1/1972 | Hobbs, II |
| 3,722,557 A | 3/1973 | Huggins |
| 3,752,510 A | 8/1973 | Windischman et al. |
| 3,762,673 A | 10/1973 | Koslovsky |
| 3,811,121 A | 5/1974 | Heim |
| 3,811,122 A | 5/1974 | Raber |
| 3,833,030 A | 9/1974 | Waldbauer, Jr. et al. |
| 3,837,339 A | 9/1974 | Aisenberg et al. |
| 3,887,393 A | 6/1975 | La Rue |
| 3,951,147 A | 4/1976 | Tucker et al. |
| 3,965,946 A | 6/1976 | D'Alo |
| D248,873 S | 8/1978 | Raitto |
| 4,123,631 A | 10/1978 | Lewis |
| D254,446 S | 3/1980 | Raitto |
| 4,206,274 A | 6/1980 | Peels |
| 4,215,701 A | 8/1980 | Raitto |
| 4,269,908 A | 3/1981 | Stemme |
| 4,265,241 A | 5/1981 | Portner et al. |
| 4,270,532 A | 6/1981 | Franetzki |
| 4,273,121 A | 6/1981 | Jassawalla |
| 4,278,225 A | 7/1981 | Phelps |
| 4,282,872 A | 8/1981 | Franetzki |
| 4,296,949 A | 10/1981 | Muetterties et al. |
| 4,303,376 A | 12/1981 | Siekmann |
| 4,331,262 A | 5/1982 | Snyder |
| 4,371,594 A | 2/1983 | Ohara et al. |
| 4,373,527 A | 2/1983 | Fischell |
| 4,391,883 A | 7/1983 | Williamson |
| 4,392,849 A | 7/1983 | Petre |
| 4,395,259 A | 7/1983 | Prestele |
| 4,437,859 A | 3/1984 | Whitehouse |
| 4,443,218 A | 4/1984 | Decant |
| 4,452,532 A | 6/1984 | Grollimund et al. |
| 4,464,170 A | 8/1984 | Clemens |
| 4,469,481 A | 9/1984 | Kobayashi |
| 4,474,061 A | 10/1984 | Parker |
| 4,475,901 A | 10/1984 | Kraegen |
| 4,486,190 A | 12/1984 | Reinicke |
| 4,494,950 A | 1/1985 | Fischell |
| 4,498,843 A | 2/1985 | Schneider |
| 4,525,165 A | 6/1985 | Fischell |
| 4,533,346 A | 8/1985 | Cosgrove |
| 4,542,532 A | 9/1985 | McQuilkin |
| 4,543,093 A | 9/1985 | Christinger |
| 4,550,731 A | 11/1985 | Bartina |
| 4,559,037 A | 12/1985 | Franetzki |
| 4,559,038 A | 12/1985 | Berg |
| 4,562,751 A | 1/1986 | Nason |
| 4,596,575 A | 6/1986 | Rosenberg |
| 4,604,090 A | 8/1986 | Reinicke |
| 4,633,878 A | 1/1987 | Bombardieri |
| 4,645,489 A | 2/1987 | Krumme et al. |
| 4,673,396 A | 6/1987 | Urbaniak |
| 4,678,408 A | 7/1987 | Nason |
| 4,685,903 A | 8/1987 | Cable |
| 4,690,878 A | 9/1987 | Nakamura |
| 4,696,671 A | 9/1987 | Epstein |
| 4,699,615 A | 10/1987 | Fischell et al. |
| 4,731,051 A | 3/1988 | Fischell |
| 4,731,726 A | 3/1988 | Allen |
| 4,735,441 A | 4/1988 | Stephens |
| 4,741,731 A | 5/1988 | Starck |
| 4,743,895 A | 5/1988 | Alexander |
| 4,747,828 A | 5/1988 | Tseo |
| 4,790,028 A | 12/1988 | Ramage |
| 4,803,625 A | 2/1989 | Fu |
| 4,804,368 A | 2/1989 | Skakoon |
| 4,809,697 A | 3/1989 | Causey |

(56) References Cited

U.S. PATENT DOCUMENTS

| | | |
|---|---|---|
| 4,811,595 A | 3/1989 | Marciniak et al. |
| 4,826,810 A | 5/1989 | Oaki |
| 4,849,852 A | 7/1989 | Mullins |
| 4,856,340 A | 8/1989 | Garrison |
| 4,871,351 A | 10/1989 | Feingold |
| 4,880,712 A | 11/1989 | Gardecki |
| 4,881,063 A | 11/1989 | Fawcett |
| 4,898,578 A | 2/1990 | Rubalcaba |
| 4,919,650 A | 4/1990 | Feingold |
| 4,930,494 A | 6/1990 | Takehana et al. |
| 4,959,640 A | 9/1990 | Hall |
| 4,972,508 A | 11/1990 | King |
| 4,976,162 A | 12/1990 | Kamen |
| 4,988,337 A | 1/1991 | Ito |
| 4,997,423 A | 3/1991 | Okuda |
| 5,009,646 A | 4/1991 | Sudo |
| 5,019,974 A | 5/1991 | Beckers |
| 5,034,004 A | 7/1991 | Crankshaw |
| 5,049,141 A | 9/1991 | Olive |
| 5,050,612 A | 9/1991 | Matsumura |
| 5,055,830 A | 10/1991 | Cousins |
| 5,056,744 A | 10/1991 | Ludwig |
| 5,063,291 A | 11/1991 | Buehring |
| 5,067,532 A | 11/1991 | Lang et al. |
| 5,075,653 A | 12/1991 | Ito et al. |
| 5,078,683 A | 1/1992 | Sancoff |
| 5,080,653 A | 1/1992 | Voss |
| 5,087,245 A | 2/1992 | Doan |
| 5,101,814 A | 4/1992 | Palti |
| 5,102,388 A | 4/1992 | Richmond |
| 5,103,216 A | 4/1992 | Sisselman |
| 5,104,374 A | 4/1992 | Bishko |
| 5,150,314 A | 9/1992 | Garratt |
| 5,153,827 A | 10/1992 | Couture |
| 5,165,406 A | 11/1992 | Wong |
| 5,165,407 A | 11/1992 | Wilson et al. |
| 5,174,716 A | 12/1992 | Hora |
| 5,176,502 A | 1/1993 | Sanderson |
| 5,176,644 A | 1/1993 | Srisathapat |
| 5,176,662 A | 1/1993 | Bartholomew |
| 5,187,746 A | 2/1993 | Narisawa |
| 5,191,855 A | 3/1993 | Conforti |
| 5,197,322 A | 3/1993 | Indravudh |
| 5,197,895 A | 3/1993 | Stupecky |
| 5,211,201 A | 5/1993 | Kamen et al. |
| 5,216,597 A | 6/1993 | Beckers |
| 5,217,442 A | 6/1993 | Davis |
| 5,222,946 A | 6/1993 | Kamen |
| 5,248,569 A | 9/1993 | Pine |
| 5,254,093 A | 10/1993 | Bartlett |
| 5,254,096 A | 10/1993 | Rondelet |
| 5,257,971 A | 11/1993 | Lord |
| 5,257,980 A | 11/1993 | Van Antwerp |
| 5,266,013 A | 11/1993 | Aubert et al. |
| 5,270,702 A | 12/1993 | Krolak |
| 5,290,639 A | 3/1994 | Mallory |
| 5,307,263 A | 4/1994 | Brown |
| 5,314,416 A | 5/1994 | Lewis |
| 5,317,506 A | 5/1994 | Couture |
| 5,337,215 A | 8/1994 | Sunderland |
| 5,338,157 A | 8/1994 | Blomquist |
| 5,339,821 A | 8/1994 | Fujimoto |
| 5,341,291 A | 8/1994 | Roizen |
| 5,349,852 A | 9/1994 | Kamen et al. |
| 5,350,411 A | 9/1994 | Ryan |
| 5,357,427 A | 10/1994 | Langen |
| 5,364,346 A | 11/1994 | Schrezenmeir |
| 5,368,562 A | 11/1994 | Blomquist |
| 5,370,622 A | 12/1994 | Livingston |
| 5,372,133 A | 12/1994 | Hogan Esch |
| 5,376,070 A | 12/1994 | Purvis |
| 5,380,173 A | 1/1995 | Hellstrom |
| 5,383,865 A | 1/1995 | Michel |
| 5,390,671 A | 2/1995 | Lord |
| 5,391,157 A | 2/1995 | Harris et al. |
| 5,399,166 A | 3/1995 | Laing |
| 5,399,823 A | 3/1995 | Mccusker |
| 5,403,648 A | 4/1995 | Chan |
| 5,426,602 A | 7/1995 | Hauser |
| 5,433,710 A | 7/1995 | Van Antwerp |
| 5,456,940 A | 10/1995 | Funderburk |
| 5,460,618 A | 10/1995 | Harreld |
| 5,462,525 A | 10/1995 | Srisathapat |
| 5,464,392 A | 11/1995 | Epstein |
| 5,466,218 A | 11/1995 | Srisathapat |
| 5,472,317 A | 12/1995 | Field |
| 5,476,460 A | 12/1995 | Montalvo |
| 5,478,211 A | 12/1995 | Dominiak |
| 5,482,446 A | 1/1996 | Williamson |
| 5,487,738 A | 1/1996 | Sciulli |
| 5,497,772 A | 3/1996 | Schulman |
| 5,505,709 A | 4/1996 | Funderburk |
| 5,514,103 A | 5/1996 | Srisathapat |
| 5,526,844 A | 6/1996 | Kamen et al. |
| 5,527,307 A | 6/1996 | Srisathapat |
| 5,528,359 A | 6/1996 | Taguchi |
| 5,533,381 A | 7/1996 | Seale |
| 5,533,389 A | 7/1996 | Kamen et al. |
| 5,543,588 A | 8/1996 | Bisset |
| 5,545,140 A | 8/1996 | Conero |
| 5,545,152 A | 8/1996 | Funderburk |
| 5,558,640 A | 9/1996 | Pfeiler |
| 5,569,186 A | 10/1996 | Lord |
| 5,569,187 A | 10/1996 | Kaiser |
| 5,573,310 A | 11/1996 | Rollinson |
| 5,573,506 A | 11/1996 | Vasko |
| 5,575,310 A * | 11/1996 | Kamen ................ A61M 5/365 |
| | | 137/614.11 |
| 5,575,631 A | 11/1996 | Jester |
| 5,582,893 A | 12/1996 | Hultman |
| 5,584,813 A | 12/1996 | Livingston |
| 5,586,868 A | 12/1996 | Lawless et al. |
| 5,593,390 A | 1/1997 | Castellano |
| 5,594,638 A | 1/1997 | Iliff |
| 5,607,418 A | 3/1997 | Arzbaecher |
| 5,609,060 A | 3/1997 | Dent |
| 5,609,575 A | 3/1997 | Larson |
| 5,620,312 A | 4/1997 | Hymann |
| 5,626,144 A | 5/1997 | Tacklind |
| 5,630,710 A | 5/1997 | Tune |
| 5,637,095 A | 6/1997 | Nason |
| 5,637,420 A | 6/1997 | Jones |
| 5,641,892 A | 6/1997 | Larkins et al. |
| 5,643,212 A | 7/1997 | Coutre |
| 5,647,853 A | 7/1997 | Feldmann |
| 5,651,775 A | 7/1997 | Walker |
| 5,658,133 A | 8/1997 | Anderson et al. |
| 5,660,176 A | 8/1997 | Iliff |
| 5,660,529 A | 8/1997 | Hill |
| 5,665,065 A | 9/1997 | Colman et al. |
| 5,669,887 A | 9/1997 | Cooper |
| 5,678,568 A | 10/1997 | Uchikubo |
| 5,681,285 A | 10/1997 | Ford |
| 5,685,844 A | 11/1997 | Martilla |
| 5,687,734 A | 11/1997 | Dempsey |
| 5,704,366 A | 1/1998 | Tacklind |
| 5,713,857 A | 2/1998 | Pierre |
| 5,713,865 A | 2/1998 | Manning et al. |
| 5,716,725 A | 2/1998 | Riveron |
| 5,727,241 A | 3/1998 | Yamana |
| 5,733,673 A | 3/1998 | Kunert |
| 5,752,940 A | 5/1998 | Nicolai |
| 5,755,683 A | 5/1998 | Houle et al. |
| 5,755,744 A | 5/1998 | Shaw |
| 5,764,159 A | 6/1998 | Neftel |
| 5,772,635 A | 6/1998 | Dastur |
| 5,772,637 A | 6/1998 | Heinzmann et al. |
| 5,779,665 A | 7/1998 | Mastrototaro |
| 5,785,681 A | 7/1998 | Indravudh |
| 5,788,673 A | 8/1998 | Young |
| 5,788,678 A | 8/1998 | Van Antwerp |
| 5,795,337 A | 8/1998 | Grimard |
| 5,800,387 A | 9/1998 | Duffy et al. |
| 5,800,420 A | 9/1998 | Gross et al. |

(56) References Cited

U.S. PATENT DOCUMENTS

| | | |
|---|---|---|
| 5,807,336 A | 9/1998 | Russo |
| 5,814,015 A | 9/1998 | Gargano |
| 5,822,715 A | 10/1998 | Worthington |
| 5,827,262 A | 10/1998 | Neftel et al. |
| 5,832,448 A | 11/1998 | Brown |
| 5,840,020 A | 11/1998 | Heinonen |
| 5,840,026 A | 11/1998 | Uber, III |
| 5,851,197 A | 12/1998 | Marano |
| 5,851,692 A | 12/1998 | Potts |
| 5,861,018 A | 1/1999 | Feierbach |
| 5,868,669 A | 2/1999 | Iliff |
| 5,871,465 A | 2/1999 | Vasko |
| 5,871,478 A | 2/1999 | Berrigan |
| 5,879,163 A | 3/1999 | Brown |
| 5,882,256 A | 3/1999 | Shropshire |
| 5,885,245 A | 3/1999 | Lynch |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano |
| 5,927,351 A | 7/1999 | Zhu et al. |
| 5,928,202 A | 7/1999 | Linnebjerg |
| 5,931,791 A | 8/1999 | Saltzstein |
| 5,933,136 A | 8/1999 | Brown |
| 5,935,105 A | 8/1999 | Manning et al. |
| 5,940,801 A | 8/1999 | Brown |
| 5,951,521 A | 9/1999 | Mastrototaro |
| 5,954,697 A | 9/1999 | Srisathapat |
| 5,954,700 A | 9/1999 | Kovelman |
| 5,956,501 A | 9/1999 | Brown |
| 5,957,890 A | 9/1999 | Mann |
| 5,960,403 A | 9/1999 | Brown |
| 5,973,623 A | 10/1999 | Gupta |
| 5,997,476 A | 12/1999 | Brown |
| 6,007,941 A | 12/1999 | Hermann |
| 6,009,339 A | 12/1999 | Bensten |
| 6,014,587 A | 1/2000 | Shaw |
| 6,032,119 A | 2/2000 | Brown |
| 6,056,718 A | 5/2000 | Funderburk |
| 6,073,036 A | 6/2000 | Heikkinen |
| 6,090,081 A | 7/2000 | Sudo |
| 6,093,172 A | 7/2000 | Funderburk |
| 6,101,478 A | 8/2000 | Brown |
| 6,110,152 A | 8/2000 | Kovelman |
| 6,119,684 A | 9/2000 | Nahl et al. |
| 6,135,949 A | 10/2000 | Russo |
| 6,165,154 A | 12/2000 | Gray et al. |
| 6,171,287 B1 | 1/2001 | Lynn |
| 6,206,856 B1 | 3/2001 | Mahurkar |
| 6,211,856 B1 | 4/2001 | Choi |
| 6,225,711 B1 | 5/2001 | Gupta et al. |
| 6,241,704 B1 | 6/2001 | Peterson |
| 6,246,992 B1 | 6/2001 | Brown |
| 6,248,093 B1 | 6/2001 | Moberg |
| 6,253,804 B1 | 7/2001 | Safabash |
| 6,254,586 B1 | 7/2001 | Mann |
| 6,259,587 B1 | 7/2001 | Sheldon |
| 6,269,340 B1 | 7/2001 | Ford |
| 6,270,455 B1 | 8/2001 | Brown |
| 6,280,416 B1 | 8/2001 | Van Antwerp |
| 6,283,943 B1 | 9/2001 | Dy |
| 6,293,925 B1 | 9/2001 | Safabash |
| 6,309,375 B1 | 10/2001 | Glines |
| 6,311,868 B1 | 11/2001 | Krietemeier |
| 6,321,158 B1 | 11/2001 | Delorme |
| 6,362,591 B1 | 3/2002 | Moberg |
| 6,364,859 B1 | 4/2002 | St. Romain |
| 6,375,638 B2 | 4/2002 | Nason |
| 6,416,293 B1 | 7/2002 | Bouchard |
| 6,423,035 B1 | 7/2002 | Kusal |
| 6,427,088 B1 | 7/2002 | Bowman |
| 6,428,509 B1 | 8/2002 | Fiedler |
| 6,447,481 B1 | 9/2002 | Duchon |
| 6,453,956 B2 | 9/2002 | Safabash |
| 6,458,102 B1 | 10/2002 | Mann et al. |
| 6,459,424 B1 | 10/2002 | Resman |
| 6,461,329 B1 | 10/2002 | Van Antwerp |
| 6,461,331 B1 | 10/2002 | Van Antwerp |
| 6,466,203 B2 | 10/2002 | Van Ee |
| 6,475,183 B1 | 11/2002 | Epstein et al. |
| 6,475,196 B1 | 11/2002 | Vachon |
| 6,485,461 B1 | 11/2002 | Mason |
| 6,485,465 B2 | 11/2002 | Moberg |
| 6,520,938 B1 | 2/2003 | Funderburk |
| 6,537,268 B1 | 3/2003 | Gibson |
| 6,549,423 B1 | 4/2003 | Brodnick |
| 6,551,276 B1 | 4/2003 | Mann et al. |
| 6,551,277 B1 | 4/2003 | Ford |
| 6,554,798 B1 | 4/2003 | Mann et al. |
| 6,554,800 B1 | 4/2003 | Nezhadian |
| 6,555,986 B2 | 4/2003 | Moberg |
| 6,558,320 B1 | 5/2003 | Causey |
| 6,558,351 B1 | 5/2003 | Steil et al. |
| 6,562,001 B2 | 5/2003 | Lebel |
| 6,564,105 B2 | 5/2003 | Starkweather |
| 6,565,509 B1 | 5/2003 | Say et al. |
| 6,571,128 B2 | 5/2003 | Lebel |
| 6,572,542 B1 | 6/2003 | Houben |
| 6,577,899 B2 | 6/2003 | Lebel |
| 6,581,648 B1 | 6/2003 | Zolentroff et al. |
| RE38,189 E | 7/2003 | Walker |
| 6,585,644 B2 | 7/2003 | Lebel et al. |
| 6,585,695 B1 | 7/2003 | Adair et al. |
| 6,591,876 B2 | 7/2003 | Safabash |
| 6,592,551 B1 | 7/2003 | Cobb |
| 6,595,756 B2 | 7/2003 | Gray |
| 6,607,509 B2 | 8/2003 | Bobroffe |
| D480,477 S | 10/2003 | Bush |
| 6,641,533 B2 | 11/2003 | Causey |
| 6,642,936 B1 | 11/2003 | Engholm |
| 6,648,821 B2 | 11/2003 | Lebel |
| 6,652,510 B2 | 11/2003 | Lord |
| 6,656,148 B2 | 12/2003 | Das |
| 6,656,158 B2 | 12/2003 | Mahoney et al. |
| 6,656,159 B2 | 12/2003 | Flaherty |
| 6,659,948 B2 | 12/2003 | Lebel |
| 6,665,909 B2 | 12/2003 | Collins |
| 6,669,669 B2 | 12/2003 | Flaherty et al. |
| 6,684,058 B1 | 1/2004 | Karacaglu |
| 6,685,678 B2 | 2/2004 | Evans |
| 6,687,546 B2 | 2/2004 | Lebel |
| 6,689,091 B2 | 2/2004 | Bui |
| 6,691,043 B2 | 2/2004 | Ribeiro |
| 6,692,457 B2 | 2/2004 | Flaherty |
| 6,694,191 B2 | 2/2004 | Starkweather |
| 6,699,218 B2 | 3/2004 | Flaherty et al. |
| 6,704,034 B1 | 3/2004 | Rodriguez |
| 6,716,195 B2 | 4/2004 | Nolan |
| 6,723,072 B2 | 4/2004 | Flaherty et al. |
| 6,733,446 B2 | 5/2004 | Lebel |
| 6,740,059 B2 | 5/2004 | Flaherty |
| 6,740,072 B2 | 5/2004 | Starkweather |
| 6,740,075 B2 | 5/2004 | Sebel |
| 6,743,205 B2 | 6/2004 | Nolan |
| 6,744,350 B2 | 6/2004 | Blomquist |
| 6,749,586 B2 | 6/2004 | Vasko |
| 6,749,587 B2 | 6/2004 | Flaherty |
| 6,752,299 B2 | 6/2004 | Shetler |
| 6,752,785 B2 | 6/2004 | Van Antwerp |
| 6,752,787 B1 | 6/2004 | Causey |
| 6,758,810 B2 | 7/2004 | Lebel |
| 6,768,425 B2 | 7/2004 | Flaherty et al. |
| 6,770,067 B2 | 8/2004 | Lorenzen |
| 6,772,650 B2 | 8/2004 | Ohyama |
| 6,800,071 B1 | 10/2004 | McConnell |
| 6,801,420 B2 | 10/2004 | Talbot |
| 6,805,693 B2 | 10/2004 | Gray |
| 6,810,290 B2 | 10/2004 | Lebel |
| 6,811,533 B2 | 11/2004 | Lebel |
| 6,811,534 B2 | 11/2004 | Bowman |
| 6,813,519 B2 | 11/2004 | Lebel |
| 6,817,990 B2 | 11/2004 | Yap |
| 6,827,702 B2 | 12/2004 | Lebel |

(56) References Cited

U.S. PATENT DOCUMENTS

| | | |
|---|---|---|
| 6,830,558 B2 | 12/2004 | Flaherty et al. |
| 6,845,465 B2 | 1/2005 | Hashemi |
| 6,852,104 B2 | 2/2005 | Blomquist |
| 6,854,620 B2 | 2/2005 | Ramey |
| 6,872,200 B2 | 3/2005 | Mann |
| 6,873,268 B2 | 3/2005 | Lebel |
| 6,879,930 B2 | 4/2005 | Sinclair |
| 6,902,207 B2 | 6/2005 | Lickliter |
| 6,930,602 B2 | 8/2005 | Villaseca |
| 6,932,584 B2 | 8/2005 | Gray |
| 6,936,029 B2 | 8/2005 | Mann |
| 6,945,760 B2 | 9/2005 | Gray |
| 6,950,708 B2 | 9/2005 | Bowman |
| 6,958,705 B2 | 10/2005 | Lebel |
| 6,960,192 B1 | 11/2005 | Flaherty et al. |
| 6,960,195 B2 | 11/2005 | Heinz |
| 6,964,643 B2 | 11/2005 | Hovland |
| 6,974,437 B2 | 12/2005 | Lebel |
| 6,978,517 B2 | 12/2005 | Collins |
| 6,979,326 B2 | 12/2005 | Mann |
| 6,994,619 B2 | 2/2006 | Scholten |
| 6,997,905 B2 | 2/2006 | Gillespie |
| 6,997,907 B2 | 2/2006 | Safabash |
| 6,997,910 B2 | 2/2006 | Howlett |
| 6,997,920 B2 | 2/2006 | Mann |
| 6,997,921 B2 | 2/2006 | Gray |
| 6,999,854 B2 | 2/2006 | Roth |
| 7,011,608 B2 | 3/2006 | Spencer |
| 7,018,360 B2 | 3/2006 | Flaherty et al. |
| 7,021,560 B2 | 4/2006 | Gray et al. |
| 7,024,245 B2 | 4/2006 | Lebel |
| 7,025,226 B2 | 4/2006 | Ramey |
| 7,025,743 B2 | 4/2006 | Mann |
| 7,029,455 B2 | 4/2006 | Flaherty |
| 7,029,456 B2 | 4/2006 | Ware |
| 7,033,339 B1 | 4/2006 | Lynn |
| 7,041,082 B2 | 5/2006 | Blomquist |
| 7,045,361 B2 | 5/2006 | Heiss |
| 7,046,230 B2 | 5/2006 | Zadesky |
| 7,050,927 B2 | 5/2006 | Sinclair |
| 7,052,251 B2 | 5/2006 | Wasco |
| 7,061,140 B2 | 6/2006 | Zhang |
| 7,063,684 B2 | 6/2006 | Moberg |
| 7,066,029 B2 | 6/2006 | Beavis et al. |
| 7,074,209 B2 | 7/2006 | Evans et al. |
| 7,075,512 B1 | 7/2006 | Fabre |
| 7,098,803 B2 | 8/2006 | Mann |
| 7,109,878 B2 | 9/2006 | Mann |
| 7,115,113 B2 | 10/2006 | Evans |
| 7,131,967 B2 | 11/2006 | Gray |
| 7,137,964 B2 | 11/2006 | Flaherty |
| 7,144,384 B2 | 12/2006 | Gorman et al. |
| 7,146,977 B2 | 12/2006 | Beavis et al. |
| 7,238,164 B2 | 7/2007 | Childers et al. |
| 7,297,132 B2 | 11/2007 | Perla et al. |
| 7,303,549 B2 | 12/2007 | Flaherty et al. |
| 7,305,984 B2 | 12/2007 | Altobelli et al. |
| 7,342,660 B2 | 3/2008 | Altobelli et al. |
| 7,548,314 B2 | 6/2009 | Altobelli et al. |
| 7,559,524 B2 | 7/2009 | Gray et al. |
| 7,766,885 B2 | 8/2010 | Olsen |
| 7,806,166 B1 | 10/2010 | Tilton et al. |
| 7,867,189 B2 | 1/2011 | Childers et al. |
| 8,113,244 B2 | 2/2012 | Kamen et al. |
| 8,137,314 B2 | 3/2012 | Mounce et al. |
| 8,211,088 B2 | 7/2012 | Dicarlo et al. |
| 2001/0034502 A1 | 10/2001 | Moberg |
| 2001/0041869 A1 | 11/2001 | Causey |
| 2001/0056258 A1 | 12/2001 | Evans |
| 2002/0002326 A1 | 1/2002 | Causey |
| 2002/0013613 A1 | 1/2002 | Haller |
| 2002/0022807 A1 | 2/2002 | Duchon |
| 2002/0038392 A1 | 3/2002 | De La Huerga |
| 2002/0040208 A1 | 4/2002 | Flaherty et al. |
| 2002/0043951 A1 | 4/2002 | Moberg |
| 2002/0045856 A1 | 4/2002 | Jaafar et al. |
| 2002/0052539 A1 | 5/2002 | Haller |
| 2002/0052574 A1 | 5/2002 | Hochman |
| 2002/0056114 A1 | 5/2002 | Fillebrown |
| 2002/0077852 A1 | 6/2002 | Ford |
| 2002/0082665 A1 | 6/2002 | Haller |
| 2002/0091454 A1 | 7/2002 | Vasko |
| 2002/0107481 A1 | 8/2002 | Reilly |
| 2002/0116080 A1 | 8/2002 | Birnbach et al. |
| 2002/0123672 A1 | 9/2002 | Christophersom |
| 2002/0126036 A1 | 9/2002 | Flaherty |
| 2002/0143290 A1 | 10/2002 | Bui |
| 2002/0158838 A1 | 10/2002 | Smith |
| 2002/0169439 A1 | 11/2002 | Flaherty |
| 2002/0173748 A1 | 11/2002 | McConnell |
| 2002/0193679 A1 | 12/2002 | Malave |
| 2002/0193846 A1 | 12/2002 | Pool |
| 2003/0004492 A1 | 1/2003 | Munis et al. |
| 2003/0028346 A1 | 2/2003 | Sinclair |
| 2003/0076306 A1 | 4/2003 | Zadesky |
| 2003/0088238 A1 | 5/2003 | Poulsen |
| 2003/0114836 A1 | 6/2003 | Estes |
| 2003/0125672 A1 | 7/2003 | Adair |
| 2003/0132922 A1 | 7/2003 | Philipp |
| 2003/0141981 A1 | 7/2003 | Bui |
| 2003/0161744 A1 | 8/2003 | Vilks |
| 2003/0163089 A1 | 8/2003 | Bynum |
| 2003/0163090 A1 | 8/2003 | Blomquist |
| 2003/0171711 A1 | 9/2003 | Rohr et al. |
| 2003/0187525 A1 | 10/2003 | Mann |
| 2003/0191431 A1 | 10/2003 | Mann |
| 2003/0195462 A1 | 10/2003 | Mann |
| 2003/0198558 A1 | 10/2003 | Nason et al. |
| 2003/0212364 A1 | 11/2003 | Mann |
| 2003/0212379 A1 | 11/2003 | Bylund |
| 2003/0229311 A1 | 12/2003 | Morris |
| 2003/0233069 A1 | 12/2003 | Gillespie |
| 2004/0003493 A1 | 1/2004 | Adair |
| 2004/0019312 A1 | 1/2004 | Childers et al. |
| 2004/0059315 A1 | 3/2004 | Erickson et al. |
| 2004/0059316 A1 | 3/2004 | Smedegaard |
| 2004/0064088 A1 | 4/2004 | Gorman et al. |
| 2004/0064096 A1 | 4/2004 | Flaherty et al. |
| 2004/0068230 A1 | 4/2004 | Estes |
| 2004/0073095 A1 | 4/2004 | Causey |
| 2004/0073161 A1 | 4/2004 | Tachibana |
| 2004/0082918 A1 | 4/2004 | Evans |
| 2004/0092873 A1 | 5/2004 | Moberg |
| 2004/0115067 A1 | 6/2004 | Rush et al. |
| 2004/0116893 A1 | 6/2004 | Spohn |
| 2004/0116905 A1 | 6/2004 | Pedersen et al. |
| 2004/0121767 A1 | 6/2004 | Simpson |
| 2004/0127958 A1 | 7/2004 | Mazar |
| 2004/0133166 A1 | 7/2004 | Moberg |
| 2004/0140304 A1 | 7/2004 | Leyendecker |
| 2004/0152961 A1 | 8/2004 | Carlson et al. |
| 2004/0158193 A1 | 8/2004 | Bui |
| 2004/0162528 A1 | 8/2004 | Horvath |
| 2004/0172301 A1 | 9/2004 | Mihai |
| 2004/0176667 A1 | 9/2004 | Mihai |
| 2004/0176725 A1 | 9/2004 | Stutz |
| 2004/0193090 A1 | 9/2004 | Lebel |
| 2004/0204673 A1 | 10/2004 | Flaherty |
| 2004/0207404 A1 | 10/2004 | Zhang |
| 2004/0235446 A1 | 11/2004 | Flaherty |
| 2004/0243065 A1 | 12/2004 | McConnell |
| 2004/0260233 A1 | 12/2004 | Garibotto et al. |
| 2005/0015056 A1 | 1/2005 | Duchon |
| 2005/0021000 A1 | 1/2005 | Adair |
| 2005/0022274 A1 | 1/2005 | Campbell |
| 2005/0027254 A1 | 2/2005 | Vasko |
| 2005/0035956 A1 | 2/2005 | Sinclair |
| 2005/0048900 A1 | 3/2005 | Scholten |
| 2005/0052429 A1 | 3/2005 | Philipp |
| 2005/0055242 A1 | 3/2005 | Bello |
| 2005/0055244 A1 | 3/2005 | Mullan |
| 2005/0062732 A1 | 3/2005 | Sinclair |
| 2005/0063857 A1 | 3/2005 | Alheidt |
| 2005/0065464 A1 | 3/2005 | Talbot |

(56) References Cited

U.S. PATENT DOCUMENTS

| | | |
|---|---|---|
| 2005/0065817 A1 | 3/2005 | Mihai |
| 2005/0069425 A1 | 3/2005 | Gray et al. |
| 2005/0085760 A1 | 4/2005 | Ware |
| 2005/0137530 A1 | 6/2005 | Campbell |
| 2005/0137573 A1 | 6/2005 | McLaughlin |
| 2005/0148938 A1 | 7/2005 | Blomquist |
| 2005/0171512 A1 | 8/2005 | Flaherty |
| 2005/0171513 A1 | 8/2005 | Mann |
| 2005/0177111 A1 | 8/2005 | Ozeri |
| 2005/0182366 A1 | 8/2005 | Vogt |
| 2005/0182389 A1 | 8/2005 | Laporte et al. |
| 2005/0187515 A1 | 8/2005 | Varrichio et al. |
| 2005/0187593 A1 | 8/2005 | Housworth |
| 2005/0192494 A1 | 9/2005 | Ginsberg |
| 2005/0192557 A1 | 9/2005 | Brauker et al. |
| 2005/0197654 A1 | 9/2005 | Edman et al. |
| 2005/0203360 A1* | 9/2005 | Brauker ............... A61B 5/7264 600/345 |
| 2005/0203461 A1 | 9/2005 | Flaherty |
| 2005/0215982 A1 | 9/2005 | Malave |
| 2005/0224705 A1 | 10/2005 | Tobiason |
| 2005/0234404 A1 | 10/2005 | Vilks |
| 2005/0238503 A1 | 10/2005 | Rush |
| 2005/0238507 A1 | 10/2005 | Dilanni |
| 2005/0250368 A1 | 11/2005 | Singer |
| 2005/0261660 A1 | 11/2005 | Choi |
| 2005/0267363 A1 | 12/2005 | Duchon |
| 2005/0267550 A1 | 12/2005 | Hess |
| 2005/0273059 A1 | 12/2005 | Mernoe et al. |
| 2005/0273081 A1 | 12/2005 | Olsen |
| 2005/0273082 A1 | 12/2005 | Olsen |
| 2005/0285880 A1 | 12/2005 | Lai |
| 2006/0009727 A1 | 1/2006 | O'Mahony |
| 2006/0016800 A1 | 1/2006 | Paradiso |
| 2006/0025663 A1 | 2/2006 | Talbot |
| 2006/0026535 A1 | 2/2006 | Talbot |
| 2006/0026536 A1 | 2/2006 | Hotelling |
| 2006/0038791 A1 | 2/2006 | Mackey |
| 2006/0041229 A1 | 2/2006 | Garibotto |
| 2006/0066581 A1 | 3/2006 | Lyon |
| 2006/0079862 A1 | 4/2006 | Genosar |
| 2006/0097991 A1 | 5/2006 | Hotelling |
| 2006/0100591 A1 | 5/2006 | Alheidt |
| 2006/0106346 A1 | 5/2006 | Sullivan |
| 2006/0122577 A1 | 6/2006 | Poulsen et al. |
| 2006/0129112 A1 | 6/2006 | Lynn |
| 2006/0144942 A1 | 7/2006 | Evans |
| 2006/0160670 A1 | 7/2006 | Spencer |
| 2006/0161871 A1 | 7/2006 | Hotelling |
| 2006/0173406 A1 | 8/2006 | Hayes |
| 2006/0173444 A1 | 8/2006 | Choy |
| 2006/0178633 A1 | 8/2006 | Garibotto |
| 2006/0178836 A1 | 8/2006 | Bai |
| 2006/0184084 A1 | 8/2006 | Ware |
| 2006/0184123 A1 | 8/2006 | Gillespie |
| 2006/0184154 A1 | 8/2006 | Moberg |
| 2006/0189926 A1 | 8/2006 | Hall et al. |
| 2006/0200070 A1 | 9/2006 | Callicoat et al. |
| 2006/0200257 A1 | 9/2006 | Kirste |
| 2006/0227117 A1 | 10/2006 | Proctor |
| 2006/0229557 A1 | 10/2006 | Fathallah |
| 2006/0232554 A1 | 10/2006 | Wong |
| 2006/0236262 A1 | 10/2006 | Bathiche |
| 2006/0236263 A1 | 10/2006 | Bathiche |
| 2006/0253085 A1 | 11/2006 | Geismar |
| 2006/0264894 A1 | 11/2006 | Moberg |
| 2006/0270971 A1 | 11/2006 | Gelfand et al. |
| 2006/0282290 A1 | 12/2006 | Flaherty |
| 2007/0016381 A1 | 1/2007 | Kamath et al. |
| 2007/0049870 A1 | 3/2007 | Gray et al. |
| 2007/0060872 A1 | 3/2007 | Hall et al. |
| 2007/0062251 A1* | 3/2007 | Anex ............... A61M 5/14244 73/1.36 |
| 2007/0088333 A1 | 4/2007 | Levin et al. |
| 2007/0104616 A1 | 5/2007 | Keenan et al. |
| 2007/0118405 A1 | 5/2007 | Mizuno |
| 2007/0167912 A1 | 7/2007 | Causey et al. |
| 2007/0179549 A1 | 8/2007 | Russie |
| 2007/0191702 A1 | 8/2007 | Yodfat et al. |
| 2007/0219480 A1 | 9/2007 | Kamen |
| 2007/0219496 A1 | 9/2007 | Kamen |
| 2007/0219597 A1 | 9/2007 | Kamen |
| 2007/0228071 A1 | 10/2007 | Kamen et al. |
| 2007/0265533 A1 | 11/2007 | Tran |
| 2008/0009824 A1 | 1/2008 | Moberg et al. |
| 2008/0058625 A1 | 3/2008 | McGarraugh et al. |
| 2008/0097375 A1 | 4/2008 | Bikovsky |
| 2008/0097381 A1 | 4/2008 | Moberg et al. |
| 2008/0125064 A1 | 5/2008 | Das et al. |
| 2008/0154513 A1 | 6/2008 | Kovatchev et al. |
| 2008/0160492 A1 | 7/2008 | Campbell |
| 2008/0161757 A1 | 7/2008 | Nayak et al. |
| 2008/0242961 A1 | 10/2008 | Brister et al. |
| 2008/0278331 A1 | 11/2008 | Hayter et al. |
| 2008/0281290 A1 | 11/2008 | Yodfat et al. |
| 2008/0294094 A1 | 11/2008 | Mhatre et al. |
| 2008/0294142 A1 | 11/2008 | Patel et al. |
| 2008/0312584 A1 | 12/2008 | Montgomery et al. |
| 2008/0312585 A1 | 12/2008 | Brukalo et al. |
| 2009/0012504 A1 | 1/2009 | Thompson |
| 2009/0018504 A1 | 1/2009 | Pile-Spellman et al. |
| 2009/0043171 A1 | 2/2009 | Rule |
| 2009/0105636 A1 | 4/2009 | Hayter et al. |
| 2009/0105658 A1 | 4/2009 | Jennewine |
| 2009/0124963 A1* | 5/2009 | Hogard ............... A61M 1/3468 604/30 |
| 2009/0163855 A1 | 6/2009 | Shin et al. |
| 2009/0192722 A1 | 7/2009 | Shariati et al. |
| 2009/0198215 A1 | 8/2009 | Chong et al. |
| 2009/0203978 A1 | 8/2009 | Say et al. |
| 2009/0213373 A1 | 8/2009 | Altobelli et al. |
| 2009/0240120 A1 | 9/2009 | Mensinger et al. |
| 2009/0275896 A1 | 11/2009 | Kamen et al. |
| 2009/0299277 A1 | 12/2009 | Kamen et al. |
| 2009/0299289 A1 | 12/2009 | Kamen et al. |
| 2010/0056992 A1 | 3/2010 | Hayter |
| 2010/0063445 A1 | 3/2010 | Sternberg et al. |
| 2010/0137778 A1 | 6/2010 | Kunjan et al. |
| 2011/0009720 A1 | 1/2011 | Kunjan et al. |
| 2011/0009824 A1 | 1/2011 | Yodfat et al. |
| 2011/0011167 A1 | 1/2011 | Gable et al. |
| 2011/0029260 A1 | 2/2011 | Altobelli et al. |
| 2011/0079220 A1 | 4/2011 | Altobelli et al. |
| 2011/0144616 A1 | 6/2011 | Michaud et al. |
| 2011/0190694 A1 | 8/2011 | Lanier, Jr. et al. |
| 2012/0209207 A1 | 8/2012 | Gray et al. |

FOREIGN PATENT DOCUMENTS

| | | |
|---|---|---|
| DE | 19627619 | 1/1998 |
| EP | 0338671 | 10/1989 |
| EP | 0420620 | 4/1991 |
| EP | 0554995 | 8/1993 |
| EP | 0763368 | 3/1997 |
| EP | 763368 | 3/1997 |
| EP | 0806738 | 11/1997 |
| EP | 0970655 | 1/2000 |
| EP | 1095668 | 5/2001 |
| EP | 1338295 | 2/2003 |
| EP | 830597 | 8/2004 |
| EP | 0830597 | 8/2004 |
| EP | 1464351 | 10/2004 |
| EP | 1109586 | 11/2004 |
| EP | 1473050 | 11/2004 |
| EP | 1115435 | 8/2005 |
| EP | 1347705 | 12/2005 |
| EP | 1007137 | 1/2006 |
| EP | 1423079 | 7/2006 |
| EP | 1135056 | 8/2006 |
| EP | 1688085 | 8/2006 |
| EP | 1702635 | 9/2006 |
| EP | 1545657 | 11/2006 |
| EP | 1546556 | 12/2006 |
| EP | 1341569 | 1/2007 |

(56) References Cited

FOREIGN PATENT DOCUMENTS

| | | |
|---|---|---|
| EP | 1461070 | 1/2007 |
| EP | 1309366 | 2/2007 |
| EP | 0944648 | 3/2007 |
| EP | 1646412 | 3/2007 |
| GB | 2218831 | 11/1989 |
| JP | 3155758 | 4/2001 |
| JP | 2005-507688 | 3/2005 |
| JP | 2006-504476 | 2/2006 |
| RU | 1131285 | 4/1995 |
| RU | 2111018 | 5/1998 |
| WO | 9208957 | 5/1992 |
| WO | 9408647 | 4/1994 |
| WO | 9524229 | 9/1995 |
| WO | 9531233 | 11/1995 |
| WO | 9608281 | 3/1996 |
| WO | 9614100 | 5/1996 |
| WO | 9620745 | 7/1996 |
| WO | 9636389 | 11/1996 |
| WO | 9640330 | 12/1996 |
| WO | 9641156 | 12/1996 |
| WO | 9709923 | 3/1997 |
| WO | 9721456 | 6/1997 |
| WO | 9740482 | 10/1997 |
| WO | 9814234 | 4/1998 |
| WO | 9820439 | 5/1998 |
| WO | 9824358 | 6/1998 |
| WO | 9842407 | 10/1998 |
| WO | 9849659 | 11/1998 |
| WO | 9859487 | 12/1998 |
| WO | 9908183 | 2/1999 |
| WO | 9910801 | 3/1999 |
| WO | 9918532 | 4/1999 |
| WO | 9922236 | 5/1999 |
| WO | 9948546 | 9/1999 |
| WO | 9959663 | 11/1999 |
| WO | 0010628 | 3/2000 |
| WO | 0028217 | 3/2000 |
| WO | 0030529 | 6/2000 |
| WO | 0100261 | 1/2001 |
| WO | 0152990 | 7/2001 |
| WO | 0161616 | 8/2001 |
| WO | 0170304 | 9/2001 |
| WO | 0176684 | 10/2001 |
| WO | 02004047 | 1/2002 |
| WO | 0220073 | 3/2002 |
| WO | 0228454 | 4/2002 |
| WO | 0234331 | 5/2002 |
| WO | 0240083 | 5/2002 |
| WO | 0249509 | 6/2002 |
| WO | 02056945 | 7/2002 |
| WO | 02058537 | 8/2002 |
| WO | 02067122 | 8/2002 |
| WO | 02068015 | 9/2002 |
| WO | 02070049 | 9/2002 |
| WO | 02074406 | 9/2002 |
| WO | 03024504 | 3/2003 |
| WO | 03033051 | 4/2003 |
| WO | 03053498 | 7/2003 |
| WO | 03059372 | 7/2003 |
| WO | 03059422 | 7/2003 |
| WO | 03063932 | 8/2003 |
| WO | 03071930 | 9/2003 |
| WO | 03074121 | 9/2003 |
| WO | 03090509 | 11/2003 |
| WO | 03090819 | 11/2003 |
| WO | 03090838 | 11/2003 |
| WO | 03094075 | 11/2003 |
| WO | 03099351 | 12/2003 |
| WO | 03103758 | 12/2003 |
| WO | 03103763 | 12/2003 |
| WO | 2004006981 | 1/2004 |
| WO | 2004006982 | 1/2004 |
| WO | 2004007133 | 1/2004 |
| WO | 2004008956 | 1/2004 |
| WO | 2004009160 | 1/2004 |
| WO | 2004022136 | 3/2004 |
| WO | 2004028596 | 4/2004 |
| WO | 2004030716 | 4/2004 |
| WO | 2004030717 | 4/2004 |
| WO | 2004030726 | 4/2004 |
| WO | 2004032994 | 4/2004 |
| WO | 2004035116 | 4/2004 |
| WO | 2004041330 | 5/2004 |
| WO | 2004058327 | 7/2004 |
| WO | 2004060436 | 7/2004 |
| WO | 2004069095 | 8/2004 |
| WO | 2004070548 | 8/2004 |
| WO | 2004070557 | 8/2004 |
| WO | 2004070994 | 8/2004 |
| WO | 2004070995 | 8/2004 |
| WO | 2004093648 | 11/2004 |
| WO | 2004098390 | 11/2004 |
| WO | 2004098454 | 11/2004 |
| WO | 2004098683 | 11/2004 |
| WO | 2004098684 | 11/2004 |
| WO | 2005000378 | 1/2005 |
| WO | 2005000382 | 1/2005 |
| WO | 2005009514 | 2/2005 |
| WO | 2005010796 | 2/2005 |
| WO | 2005016411 | 2/2005 |
| WO | 2005019766 | 3/2005 |
| WO | 2005019987 | 3/2005 |
| WO | 2005039671 | 5/2005 |
| WO | 2005094920 | 10/2005 |
| WO | 2005097235 | 10/2005 |
| WO | 2005101279 | 10/2005 |
| WO | 2005102416 | 11/2005 |
| WO | 2005112899 | 12/2005 |
| WO | 2005121938 | 12/2005 |
| WO | 2006001929 | 1/2006 |
| WO | 2006015922 | 2/2006 |
| WO | 2006018425 | 2/2006 |
| WO | 2006018447 | 2/2006 |
| WO | 2006023147 | 3/2006 |
| WO | 2006024671 | 3/2006 |
| WO | 2006024672 | 3/2006 |
| WO | 2006032652 | 3/2006 |
| WO | 2006042811 | 4/2006 |
| WO | 2006061354 | 6/2006 |
| WO | 2006072416 | 7/2006 |
| WO | 2006075016 | 7/2006 |
| WO | 2006077262 | 7/2006 |
| WO | 2006077263 | 7/2006 |
| WO | 2006081975 | 8/2006 |
| WO | 2006083831 | 8/2006 |
| WO | 2006084464 | 8/2006 |
| WO | 2006086980 | 8/2006 |
| WO | 2006089547 | 8/2006 |
| WO | 2006089548 | 8/2006 |
| WO | 2006089965 | 8/2006 |
| WO | 2006096746 | 9/2006 |
| WO | 2006097453 | 9/2006 |
| WO | 2006108775 | 10/2006 |
| WO | 2006108809 | 10/2006 |
| WO | 2006116997 | 11/2006 |
| WO | 2006120253 | 11/2006 |
| WO | 2006125692 | 11/2006 |
| WO | 2007000425 | 1/2007 |
| WO | 2007000426 | 1/2007 |
| WO | 2007000427 | 1/2007 |
| WO | 2007035567 | 3/2007 |
| WO | 2007052277 | 5/2007 |
| WO | 2007092618 | 8/2007 |
| WO | 2007092637 | 8/2007 |
| WO | 2007093981 | 8/2007 |
| WO | 2007104756 | 9/2007 |
| WO | 2008067284 | 6/2008 |
| WO | 2008088490 | 7/2008 |
| WO | 2008094249 | 8/2008 |
| WO | 2008134146 | 11/2008 |
| WO | 2008135329 | 11/2008 |
| WO | 2008154312 | 12/2008 |
| WO | 2008157781 | 12/2008 |
| WO | 2009002620 | 12/2008 |

(56) References Cited

FOREIGN PATENT DOCUMENTS

| WO | 2009009528 | 1/2009 |
|----|------------|--------|
| WO | 2009023407 | 2/2009 |
| WO | 2009059187 | 5/2009 |
| WO | 2009088983 | 7/2009 |
| WO | 2009089029 | 7/2009 |
| WO | 2009137777 | 11/2009 |

OTHER PUBLICATIONS

International Search Report with Written Opinion, dated Oct. 17, 2007, received in international patent application No. PCT/US07/003567, 18 pgs.
International Search Report with Written Opinion, dated Nov. 12, 2007, received in international patent application No. PCT/US07/003587, 18 pgs.
International Search Report with Written Opinion, dated Nov. 28, 2007, received in international patent application No. PCT/US07/003490, 20 pgs.
International Preliminary Report on Patentability from corresponding International Application No. PCT/US2007/003587 dated Aug. 12, 2008 (10 pages).
International Preliminary Report on Patentability from corresponding International Application No. PCT/US2007/003490 dated Aug. 12, 2008 (12 pages).
International Preliminary Report on Patentability from corresponding International Application No. PCT/US2007/003634 dated Aug. 12, 2008 (8 pages).
International Preliminary Report on Patentability with Written Opinion, dated Aug. 12, 2008, received in international patent application No. PCT/US2007/003567, 11 pgs.
International Search Report from corresponding International Application No. PCT/US2008/088688 dated Jul. 10, 2009 (7 pages).
Examination Report from corresponding European Application No. 07 763 303.0 dated Aug. 4, 2009 (4 pages).
Examination report, dated Feb. 22, 2010, received in European Patent Application No. 07763498.8, 5 pgs.
International Search Report, dated Jun. 18, 2010, received in international patent application No. PCT/US2009/056999, 4 pages.
International Preliminary Report on Patentability from corresponding International Application No. PCT/US2008/088688 dated Jul. 6, 2010 (11 pages).
Examination Report from corresponding European Application No. 07 750 336.5 dated Aug. 26, 2010 (7 pages).
Office Action from corresponding Chinese Application No. 200780007416.4 dated Dec. 6, 2010 (15 pages with translation).
Partial International Search Report from corresponding International Application No. PCT/US2010/042150 dated Jan. 12, 2011 (7 pages).
Office Action from corresponding Chinese Application No. 200780007335.4 dated Jan. 18, 2011 (7 pages with translation).
Office Action from corresponding Chinese Application No. 200780007306.8 dated Jan. 31, 2011 (16pages with translation).
International Search Report and Written Opinion from corresponding International Application No. PCT/US2010/042150 dated Jun. 28, 2011 (14 pages).
Extended Search Report from corresponding European Appln. No. 11154417.7 dated Jul. 21, 2011 (7 pages).
Partial Search Report from corresponding European Appln. No. 11154414.4 dated Jul. 21, 2011 (7 pages).
Extended Search Report from corresponding European Appln. No. 11154418.5 dated Jul. 21, 2011 (7 pages).
Decision on Grant issued in corresponding Russian Appln. No. 2008136190/14(046261) dated Oct. 11, 2011 and its English translation (26 pages).
International Partial Search Report, dated Oct. 18, 2011, received in International patent application No. PCT/US2011/030553, 6 pgs.
European Search Report, dated Nov. 8, 2011, received in European patent application No. EP11154414, 11 pgs.
Partial European Search Report issued in corresponding European Appln. No. 11154419.3 dated Nov. 14, 2011 (6 pages).
Official Action issued in corresponding Japanese Appln. No. 2008-554411 dated Nov. 18, 2011 with translation (9 pages).
Official Action issued in corresponding Japanese Appln. No. 2008-554376 dated Dec. 15, 2011 with translation (10 pages). Provided in U.S. Appl. No. 11/704,899.
International Search Report & Written Opinion, dated Dec. 23, 2011, received in International patent application No. PCT/US2011/030553, 12 pgs.
International Preliminary Report on Patentability & Written Opinion, dated Jan. 26, 2012, received in International patent application No. PCT/US2010/042150 10 pages.
International Search Report & Written Opinion, dated Jan. 27, 2012, received in International patent application No. PCT/US2011/030553, 14 pgs.
Notice of Opposition from corresponding European Appln. No. 07763686.8 dated Mar. 26, 2012 (47 pages).
Notice of Opposition from corresponding European Appln. No. 07763686.8 dated Apr. 18, 2012 (47 pages).
International Preliminary Report on Patentability from International Appln. No. PCT/US2010/062443 dated Jul. 4, 2012 (12 pages).
International Preliminary Report on Patentability from International Appln. No. PCT/US2010/062426 dated July 4, 2012 (8 pages).
International Preliminary Report on Patentability & Written Opinion, dated Jul. 12, 2012, received in International patent application No. PCT/US2010/062443 13 pgs.
International Preliminary Report on Patentability & Written Opinion, dated Jul. 12, 2012, received in International patent application No. PCT/US2010/062426 9 pgs.
International Preliminary Report on Patentability issued in corresponding International Appln. No. PCT/US2011/022073 dated Jul. 24, 2012.
International Preliminary Report on Patentability issued in corresponding International Appln. No. PCT/US2011/023757 dated Aug. 7, 2012.
Official Action issue in corresponding Japanese application No. 2010-540955 dated Mar. 5, 2013 with translation (10 pages).
International Search Report and Written Opinion from PCT/US2012/071280 dated Mar. 7, 2013 (13 pages).
Office Action issued in corresponding Russian Application No. 2010132226 dated May 13, 2013 with translation (8 pages).
U.S. Appl. No. 11/704,897, filed Feb. 2, 2007.
U.S. Appl. No. 11/704,886, filed Feb. 2, 2007.
U.S. Appl. No. 11/704,896, filed Feb. 2, 2007.
U.S. Appl. No. 11/704,899, filed Feb. 2, 2007.
U.S. Appl. No. 12/560,102, filed Sep. 15, 2009.

\* cited by examiner

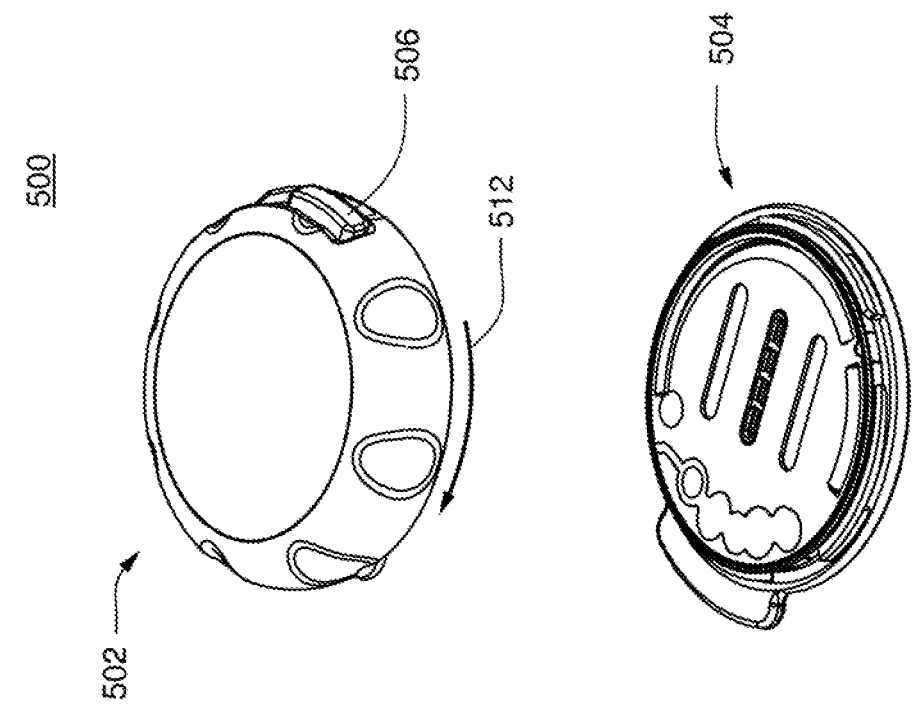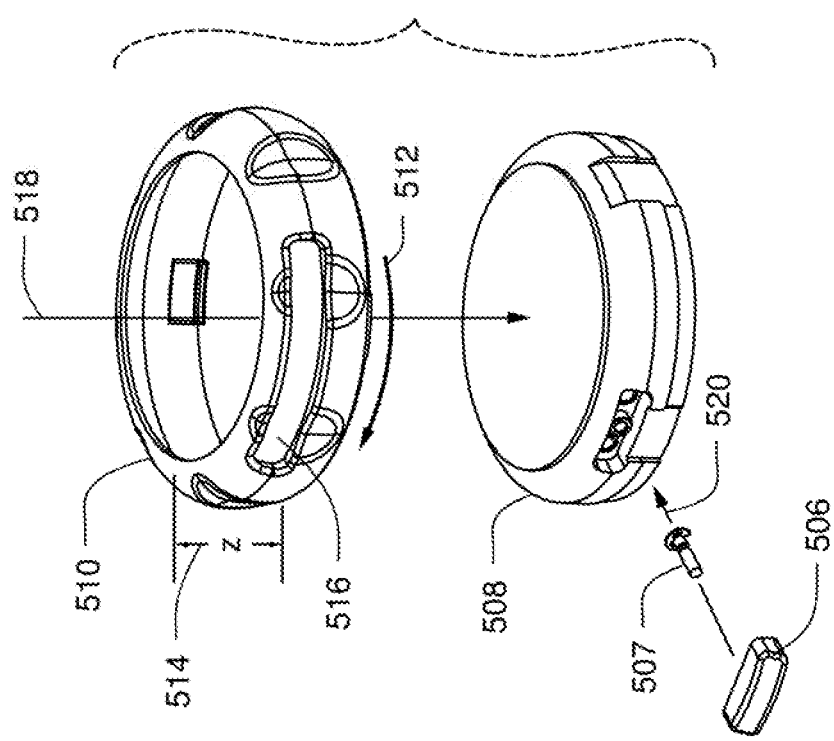
FIG. 11

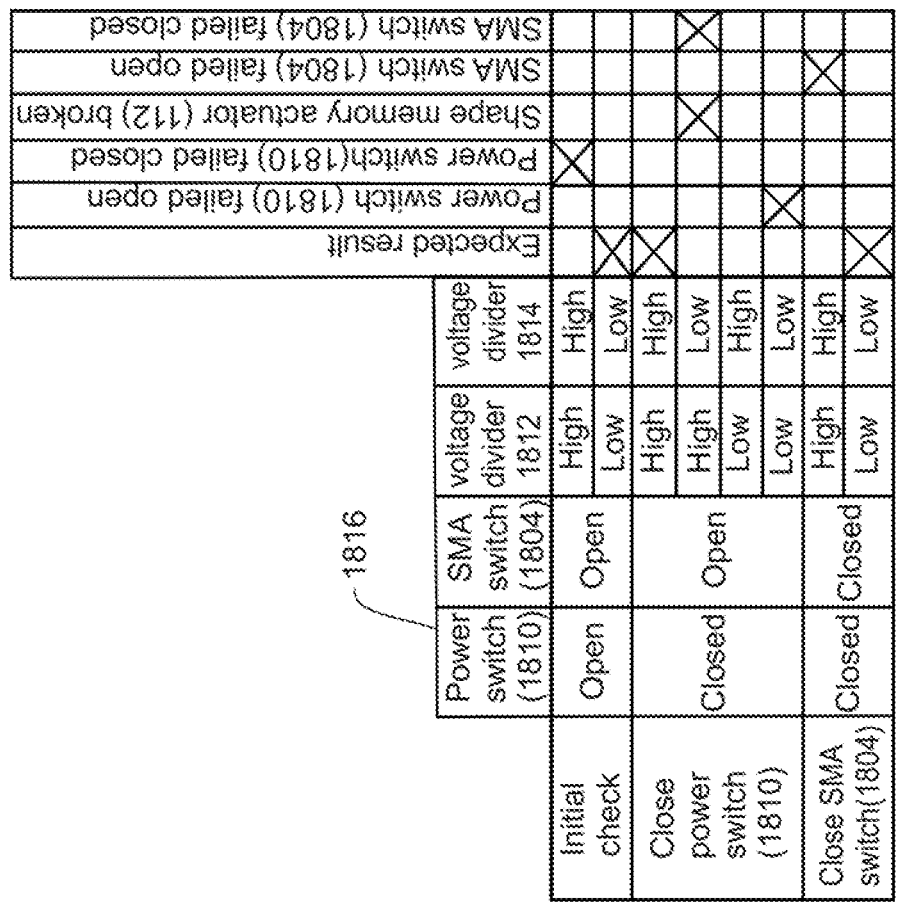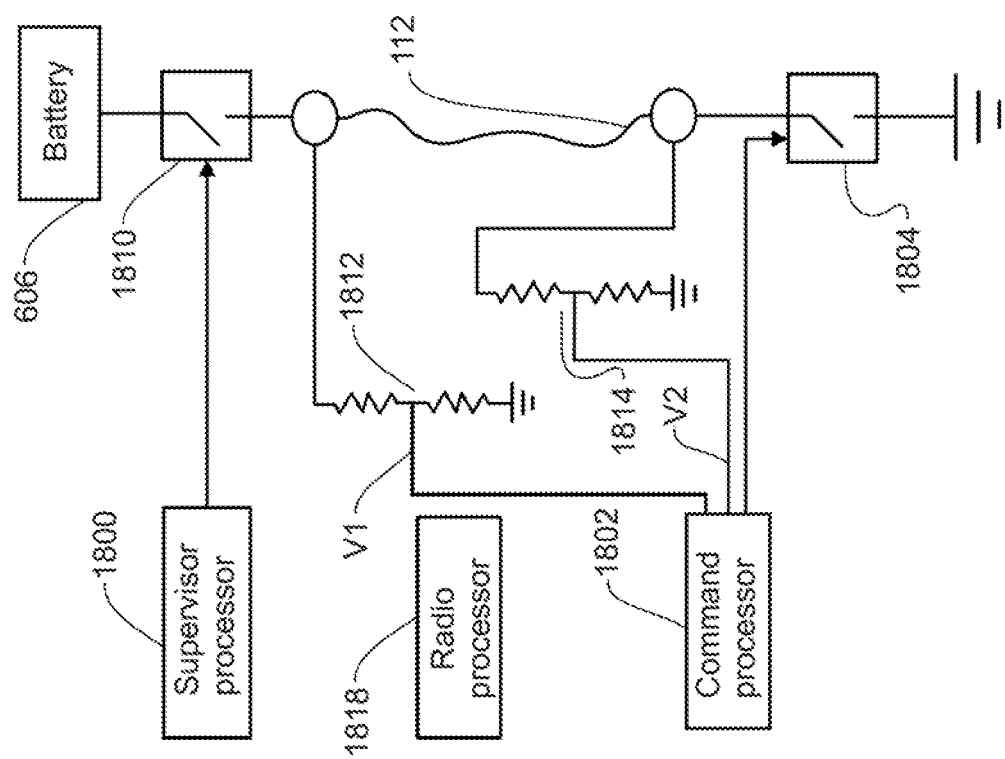
FIG. 40

SYSTEMS AND METHODS FOR FLUID DELIVERY

CROSS REFERENCE TO RELATED APPLICATIONS

The present application is a Continuation of U.S. patent application Ser. No. 12/560,102, filed Sep. 15, 2009 and entitled System and Methods for Fluid Delivery, now U.S. Pat. No. 10,010,669, issued Jul. 3, 2018, which is a Non-Provisional application which claims priority from U.S. Provisional Patent Application Ser. No. 61/097,021, filed Sep. 15, 2008 and entitled Systems and Methods for Fluid Delivery; U.S. Provisional Patent Application Ser. No. 61/101,053, filed Sep. 29, 2008 and entitled Infusion Pump Assembly with a Switch Assembly; U.S. Provisional Patent Application Ser. No. 61/101,077, filed Sep. 29, 2008 and entitled Infusion Pump Assembly with Tubing Storage; U.S. Provisional Patent Application Ser. No. 61/101,105, filed Sep. 29, 2008 and entitled Improved Infusion Pump Assembly; U.S. Provisional Patent Application Ser. No. 61/101,115, filed Sep. 29, 2008 and entitled Filling Apparatus and Methods for an Infusion Pump Assembly; U.S. Provisional Patent Application Ser. No. 61/141,996, filed Dec. 31, 2008 and entitled Acoustic Volume Sensing Methods, Systems and Apparatus; and U.S. Provisional Patent Application Ser. No. 61/141,781, filed Dec. 31, 2008 and entitled Split Ring Resonator Antenna Adapted for Use in Wirelessly Controlled Medical Device, all of which are hereby incorporated herein by reference in their entireties.

U.S. patent application Ser. No. 12/560,102, is also a Continuation in Part of U.S. patent application Ser. No. 11/704,899, filed Feb. 9, 2007 and entitled Fluid Delivery Systems and Methods, now U.S. Pat. No. 8,414,522, issued Apr. 9, 2013, which is a non-provisional of U.S. Provisional Patent Application Ser. No. 60/772,313, filed Feb. 9, 2006, and entitled Portable Injection System, U.S. Provisional Patent Application Ser. No. 60/789,243, filed Apr. 5, 2006 and entitled Method of Volume Measurement for Flow Control, and U.S. Provisional Patent Application Ser. No. 60/793,188, filed Apr. 19, 2006, and entitled Portable Injection and Adhesive System, which are hereby incorporated herein by reference in their entireties.

U.S. patent application Ser. No. 12/560,102, present application is also a Continuation in Part of U.S. patent application Ser. No. 11/704,896, filed Feb. 9, 2007 and entitled Pumping Fluid Delivery Systems and Methods Using Force Application Assembly, now U.S. Pat. No. 8,585,377, issued Nov. 19, 2013, which is a non-provisional of U.S. Provisional Patent Application Ser. No. 60/772,313, filed Feb. 9, 2006 and entitled Portable Injection System, U.S. Provisional Patent Application Ser. No. 60/789,243, filed Apr. 5, 2006 and Method of Volume Measurement for Flow Control, and U.S. Provisional Patent Application Ser. No. 60/793,188, filed Apr. 19, 2006, and entitled Portable Injection and Adhesive System, which are hereby incorporated herein by reference in their entireties.

U.S. patent application Ser. No. 12/560,102, is also a Continuation in Part of U.S. patent application Ser. No. 11/704,886, filed Feb. 9, 2007 and entitled Patch-Sized Fluid Delivery Systems and Methods, now U.S. Pat. No. 8,545,445, issued Oct. 1, 2013, which is a non-provisional of U.S. Provisional Patent Application Ser. No. 60/772,313, filed Feb. 9, 2006 and entitled Portable Injection System; U.S. Provisional Patent Application Ser. No. 60/789,243, filed Apr. 5, 2006 and entitled Method of Volume Measurement for Flow Control"; and U.S. Provisional Patent Application Ser. No. 60/793,188, filed Apr. 19, 2006 and entitled Portable Injection and Adhesive System, which are hereby incorporated herein by reference in their entireties.

U.S. patent application Ser. No. 12/560,102, is also a Continuation in Part of U.S. patent application Ser. No. 11/704,897, filed Feb. 9, 2007 and entitled Adhesive and Peripheral Systems and Methods for Medical Devices, now U.S. Pat. No. 8,113,244, issued Feb. 14, 2012, which is a non-provisional of U.S. Provisional Patent Application Ser. No. 60/772,313, filed Feb. 9, 2006 and entitled Portable Injection System; U.S. Provisional Patent Application Ser. No. 60/789,243, filed Apr. 5, 2006 and entitled Method of Volume Measurement for Flow Control; and U.S. Provisional Patent Application Ser. No. 60/793,188, filed Apr. 19, 2006 and entitled "Portable Injection and Adhesive System", which are hereby incorporated herein by reference in their entireties.

TECHNICAL FIELD

The present invention relates to the delivery of a fluid and more particularly, to systems and methods for fluid delivery.

BACKGROUND INFORMATION

Millions of people live with diabetes mellitus. These patients are further commonly classified into one of two types of diabetes, Type I and Type II. Type I, historically referred to as Juvenile Diabetes, is an autoimmune disease, and is characterized by the inability to secrete insulin. Type II is a disease that compromises the ability to respond to insulin and/or produce enough insulin. Both types of diabetes are characterized by hyperglycemia. Patient's living with Type I diabetes require multiple injections of insulin, a hormone that lowers blood glucose levels, everyday to survive. However, to maintain long-term health people living with diabetes strive to maintain as close to a "non-diabetic" blood glucose level as possible. Maintaining a healthy blood glucose level, however, is a very difficult goal to achieve.

To this end, there have been efforts to design portable devices, e.g. insulin pumps, for the controlled release of insulin. There are many different forms of insulin available. Most patients using an insulin pump currently use U-100 insulin rapid-acting insulin (e.g., HUMALOG insulin lispro injection or the like) in the pump. Insulin pump devices are known to have a reservoir such as a cartridge, syringe, or bag, and to be electronically controlled. However, the delivery rates must be manually entered by the person living with diabetes or a caregiver of that person. Thus, the diabetic patient determines/dictates the amount of insulin delivered for any given time/period of time (i.e., the "basal" and "bolus" rate/amount) using information or factors available to them, for example, their blood glucose readings determined using a blood glucose meter, past data from like situations, the food they intend to eat or have eaten, anticipated or previously completed exercise, and/or stress or illness.

However, although the diabetic patient determines the rate/amount based on one or more of these factors (or additional factors), managing diabetes is not an exact science. There are many reasons for this, including, but not limited to, inaccurate methods of delivery of insulin, inaccurate blood glucose meters, inability to correctly count carbohydrate intake, inability to determine approaching illness, inability to predict the exact effects of exercise, and the inability to anticipate or forecast the effect of many additional hormones or processes in the body.

The nature of managing diabetes is further complicated by the risk of hypoglycemia which may be fatal. Thus, over-calculating the amount of insulin required may be life-threatening. Short-term effects of hyperglycemia are not fatal; however, complications due to long-term hyperglycemia are known and include shorter life span, increased risk of heart attack or stroke, kidney failure, adult blindness, nerve damage and non-traumatic amputations. Thus, under-calculating the amount of insulin required may, in the long-term, substantially affect quality of life as well as lead to fatal complications.

Accordingly, there is a need for systems and methods for delivering the appropriate amount (i.e., the amount of insulin required to maintain a desired blood glucose level) of insulin at the appropriate time in a safe and effective manner.

SUMMARY

In accordance with one aspect of the present invention, a system for at least partial closed-loop control of a medical condition. The system includes at least one medical fluid pump. The medical fluid pump including a sensor for determining the volume of fluid pumped by the pump. Also, at least one continuous analyte monitor, and a controller. The controller is in communication with the medical fluid pump and the at least one continuous analyte monitor. The controller includes a processor. The processor includes instructions for delivery of medical fluid based at least on data received from the at least one continuous analyte monitor.

Some embodiments of this aspect of the invention include one or more of the following. Where the sensor further includes an acoustic volume sensor. Where the system further includes a network operation center, the network operation center in communication with the processor. Where the pump further includes a pumping chamber having an inlet connectable to provide fluid communication with a fluid source, and a pump outlet and a force application assembly adapted to provide a compressive stroke to the pumping chamber, wherein the compressive stroke causes a restriction of retrograde flow of fluid from the pumping chamber through the inlet while urging fluid from the pumping chamber to the pump outlet. Where the force application assembly is coupled to an inlet valve actuator and to a pump actuator, so that the compressive stroke actuates an inlet valve coupled between the inlet and the fluid source to close the valve when the pump actuator causes fluid to be urged from the pumping chamber to the pump outlet. Where the force application assembly comprising a motor for coordinated operation of the valve actuator and the pump actuator, wherein the motor includes at least one shape-memory actuator. Where at least one of the continuous analyte monitors is a continuous glucose monitor. Where the system includes at least one accelerometer. Where the system includes at least one blood oxygen sensor. Where the system further includes at least one inertial measurement unit comprising at least one accelerometer and at least one gyroscope. Where the system includes at least one temperature sensor.

In accordance with one aspect of the present invention, a method for at least partial closed-loop control of a medical condition is disclosed. The method includes receiving glucose data during a time frame or an event, comparing the glucose data to a previous and similar time frame or event, determining an unexpected result during the time frame or the event, and sending an alert signal to indicate an unexpected result.

Some embodiments of this aspect of the invention include one or more of the following. Wherein sending an alert signal includes alerting a user of the unexpected result. Where the method further includes prompting the user to enter information regarding the unexpected result. Where the system, not receiving information regarding the unexpected result from the user, shutting down the system. Wherein shutting down the system includes alerting the user of the shutdown through a series of alarms. Wherein alerting the user of the shutdown through a series of alarms includes alerting the user of the shutdown through a series of increasing alarms.

In accordance with one aspect of the present invention, a method for at least partial closed-loop control of a medical condition. The method includes receiving medical fluid delivery data during a time frame or an event, comparing the medical fluid delivery data to a previous and similar time frame or event, determining an unexpected result during the time frame or the event, and sending an alert signal to indicate an unexpected result.

Some embodiments of this aspect of the invention include one or more of the following. Wherein sending an alert signal includes alerting a user of the unexpected result. Where the method further includes prompting the user to enter information regarding the unexpected result. Where the system, not receiving information regarding the unexpected result from the user, shutting down the system. Wherein shutting down the system includes alerting the user of the shutdown through a series of alarms. Wherein alerting the user of the shutdown through a series of alarms includes alerting the user of the shutdown through a series of increasing alarms.

In accordance with one aspect of the present invention, a method for monitoring the integrity of an analyte sensor. The method includes injecting a volume of an analyte having a predetermined concentration in close proximity to a continuous analyte sensor for the analyte, receiving data from the continuous analyte sensor, and analyzing the data to determine whether the analyte sensor is responsive to the injected volume of analyte.

Some embodiments of this aspect of the invention include wherein the analyte is glucose.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 11 is an isometric view of an alternative embodiment of the infusion pump assembly of FIG. 7;

FIG. 40 is a diagrammatic view of a multi-processor control configuration that may be included within the infusion pump assembly of FIG. 7;

Like reference symbols in the various drawings indicate like elements.

DETAILED DESCRIPTION OF THE PREFERRED EMBODIMENTS

Although insulin and diabetes are discussed herein, this disclosure is not limited to use of the systems and methods for the treatment of diabetes. The disclosed methods and systems may be used for the delivery of any fluid, including any medical or therapeutic fluid, including but not limited to, insulin, for the treatment of a medical condition, including, but not limited to, diabetes mellitus.

Described herein are methods and systems for closed loop, or partially closed loop, control of diabetes. As described above, many factors affect the amount of insulin a patient or user requires to maintain an appropriate blood glucose level. The term "appropriate" is used herein to mean a blood glucose level which has been chosen by the patient and/or their health-care provider as healthy for the patient. The appropriate blood glucose level for each patient may vary, as will the appropriate blood glucose level at any given time for any given patient. In general, many health-care providers recommend maintaining blood glucose levels between 90-140 mm/dl. However, depending on the circumstance, the range may vary. For example, a patient may deem a blood glucose level of 150 mg/dl appropriate before bedtime, but would consider the same reading inappropriate before mealtime.

Figure 1:
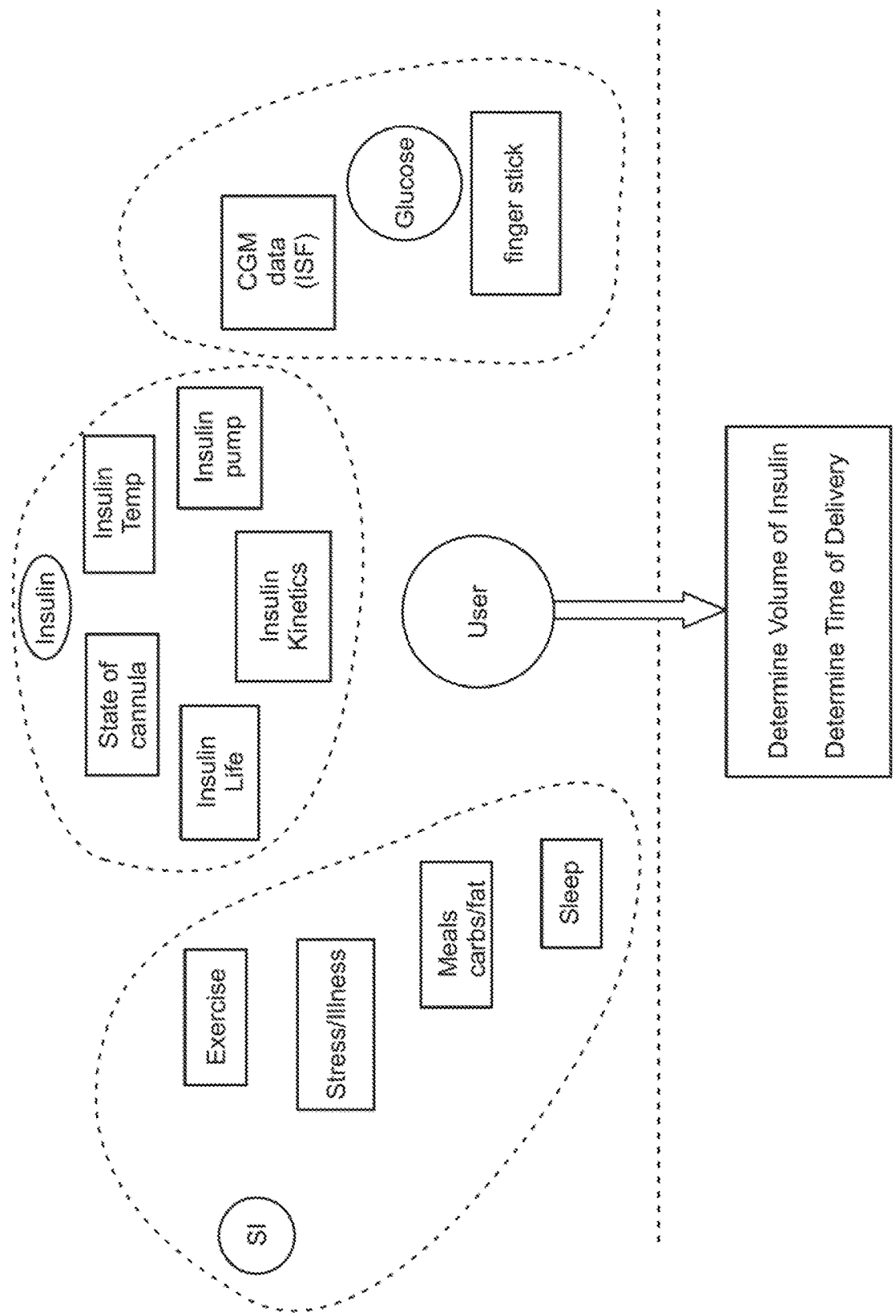
FIG. 1 is a diagram of some variables used in diabetes management.

Referring first to FIG. 1, a non-limiting chart of variables used in diabetes management are depicted. These variables shown are those currently taken into consideration by patients living with diabetes. These variables include blood glucose levels, exercise, illness, food, sleep and stress.

Blood glucose levels may be determined by using at least one blood glucose meter, for example, the FREESTYLE blood glucose meter by Abbott Diabetes Care of Alameda, Calif. Some blood glucose meters may wirelessly transmit the reading to a pump. However, in addition, blood glucose levels may be determined using at least one continuous glucose monitor ("CGM"). In the various embodiments, any CGM may be used, for example, a FREESTYLE NAVIGATOR Continuous Glucose Monitoring System from Abbott Diabetes Care of Alameda, Calif., or a similar device. The various CGMs include an analyte sensor worn by the patient that transmits electric signals that correlate to interstitial fluid glucose level readings to a handheld or other device at predetermined intervals.

Further, the sensor for the CGM may be any as described in U.S. Published Application No. US-2009-0099522, published Apr. 16, 2009 and entitled Microneedle Systems and Apparatus (G34), which is hereby incorporated herein by reference in its entirety.

Exercise affects people with diabetes differently. Also, depending on the rigor of the exercise, the type of exercise (i.e., aerobic or anaerobic) and the duration, any given patient will experience different effects both during and following the exercise. In some circumstances, blood glucose levels may increase during the exercise, but decrease following the exercise. In some circumstances, the duration and blood glucose level lowering effect may vary.

Stress may cause elevated blood glucose levels. The duration and intensity of the stress may produce different results. Similarly, illness may cause elevated blood glucose levels, with illness duration and intensity producing various results.

Food includes any item ingested by the patient, including but not limited to, solids and liquids. The food composition, including fat, protein and carbohydrates, greatly impacts the resulting blood glucose level as well as the rate of absorption of the food. The absorption rate may translate to the rate of increase of blood glucose levels. For example, a meal high in fat and carbohydrates may absorb at a slower rate and thus, the increased levels of blood glucose may be seen at a later time as compared with a meal low in fat. Additionally, with respect to carbohydrates, the glycemic index of the food will greatly affect the rate of change of blood glucose levels.

Various types of insulin may be used either together or individually. Long-acting, intermediate-acting, short-acting and rapid-acting insulins may be used. Examples include NPH, Regular, HUMALOG, by Eli Lilly, and NOVALOG, by Novo Nordisk, however, any insulin may be used. Insulins are also available in various concentrations. For example U-100 and U-400. Various embodiments of the system and methods may use various concentrations of insulin.

Insulin and other biologicals/therapeutic and/or medical fluid compounds are not orally active due to poor absorption, hepatic metabolism or other pharmacokinetic factors. Additionally, some therapeutic compounds, although they may be orally absorbed, are sometimes required to be administered so often it is difficult for a patient to maintain the desired schedule. In these cases, parenteral delivery is often employed or could be employed.

Effective parenteral routes of insulin and other fluid drug delivery include subcutaneous injection, intramuscular injection, and intravenous (IV) administration include puncture of the skin with a needle or stylet. Many diabetics prefer an automatic delivery of insulin which is possible through the use of insulin pumps. These pumps may be used in the subcutaneous delivery of other fluids as well.

Pumps deliver the therapeutic fluid subcutaneously using a cannula, which is a tube or needle that is introduced to the subcutaneous region of the skin, and remains in the skin for a pre-approved period of time, typically, no longer than 3 days. The cannula is fluidly connected to a reservoir of therapeutic fluid. The pump pumps the fluid from the reservoir to the cannula for delivery to the patient.

Examples of pumps include any pump known, including, but not limited to, those described in U.S. Published Application No. US-2007-0219480, published Sep. 20, 2007 and entitled Patch-Sized Fluid Delivery Systems and Methods (E72); U.S. Pat. No. 7,306,578, issued Dec. 11, 2007 and entitled Loading Mechanism for Infusion Pump (C54); U.S. Pat. No. 7,498,563, issued Mar. 3, 2009 and entitled Optical Displacement Sensor for Infusion Devices (D78); or U.S. Published Application No. US-2007-0228071, published Oct. 4, 2007 and entitled Fluid Delivery Systems and Methods (E70), which are hereby incorporated herein by reference in their entirety, or other fluid delivery pumps.

Additionally, in some embodiments, a fluid delivery pump that delivers more than one type of fluid may be used. The pumps described in the aforementioned U.S. Published Application No. US-2007-0219480, published Sep. 20, 2007 and entitled Patch-Sized Fluid Delivery Systems and Methods (E72); U.S. Pat. No. 7,306,578, issued Dec. 11, 2007 and entitled Loading Mechanism for Infusion Pump (C54); U.S. Pat. No. 7,498,563, issued Mar. 3, 2009 and entitled Optical Displacement Sensor for Infusion Devices (D78); or U.S. Published Application No. US-2007-0228071, published Oct. 4, 2007 and entitled Fluid Delivery Systems and Methods (E70) may be altered slightly to incorporate one or more additional reservoirs. These reservoirs may be fluidly connected to the same cannula, or to separate cannulas. Additionally, for all the above described cannulas, cannulas such as those described in U.S. Published Application No. US-2009-0099522, published Apr. 16, 2009 and entitled Microneedle Systems and Apparatus (G34), which is hereby incorporated herein by reference in its entirety.

The exemplary embodiment includes the use of at least one pump similar to the ones described and shown at least in U.S. Published Application No. US-2007-0219480, published Sep. 20, 2007 and entitled Patch-Sized Fluid Delivery Systems and Methods (E72); U.S. Published Application No. US-2007-0228071, published Oct. 4, 2007 and entitled Fluid Delivery Systems and Methods (E70); U.S. Published Application No. US-2007-0219496, published Sep. 20, 2007 and entitled Pumping Fluid Delivery Systems and Methods Using Force Application Assembly (E71); U.S. Published Application No. US-2007-0219597, published Sep. 20, 2007 and entitled Adhesive and Peripheral Systems and Methods for Medical Devices (E73); U.S. patent application Ser. No. 12/347,985, filed Dec. 31, 2008 and entitled Infusion Pump Assembly (G75); U.S. patent application Ser. No. 12/347,982, filed Dec. 31, 2008 and entitled Wearable Pump Assembly (G76); U.S. patent application Ser. No. 12/347,981, filed Dec. 31, 2008 and entitled Infusion Pump Assembly (G77); and U.S. patent application Ser. No. 12/347,984, filed Dec. 31, 2008 and entitled Pump Assembly With Switch (G79), which are hereby incorporated herein by reference in their entirety.

Specifically, the exemplary embodiment includes a pump having an acoustic volume sensor apparatus capable of measuring the volume of fluid pumped by the pump.

In various embodiments, the system includes at least one continuous analyte sensor, and in some embodiments, at least one continuous glucose monitor ("CGM"), an infusion pump, fluid pump or medical fluid pump to pump at least one medical fluid, e.g., insulin, and a controller. In some embodiments, the system additionally includes one or more additional continuous sensors, whether analyte or other. The system components transmit data or are controlled by the controller.

Figure 2:
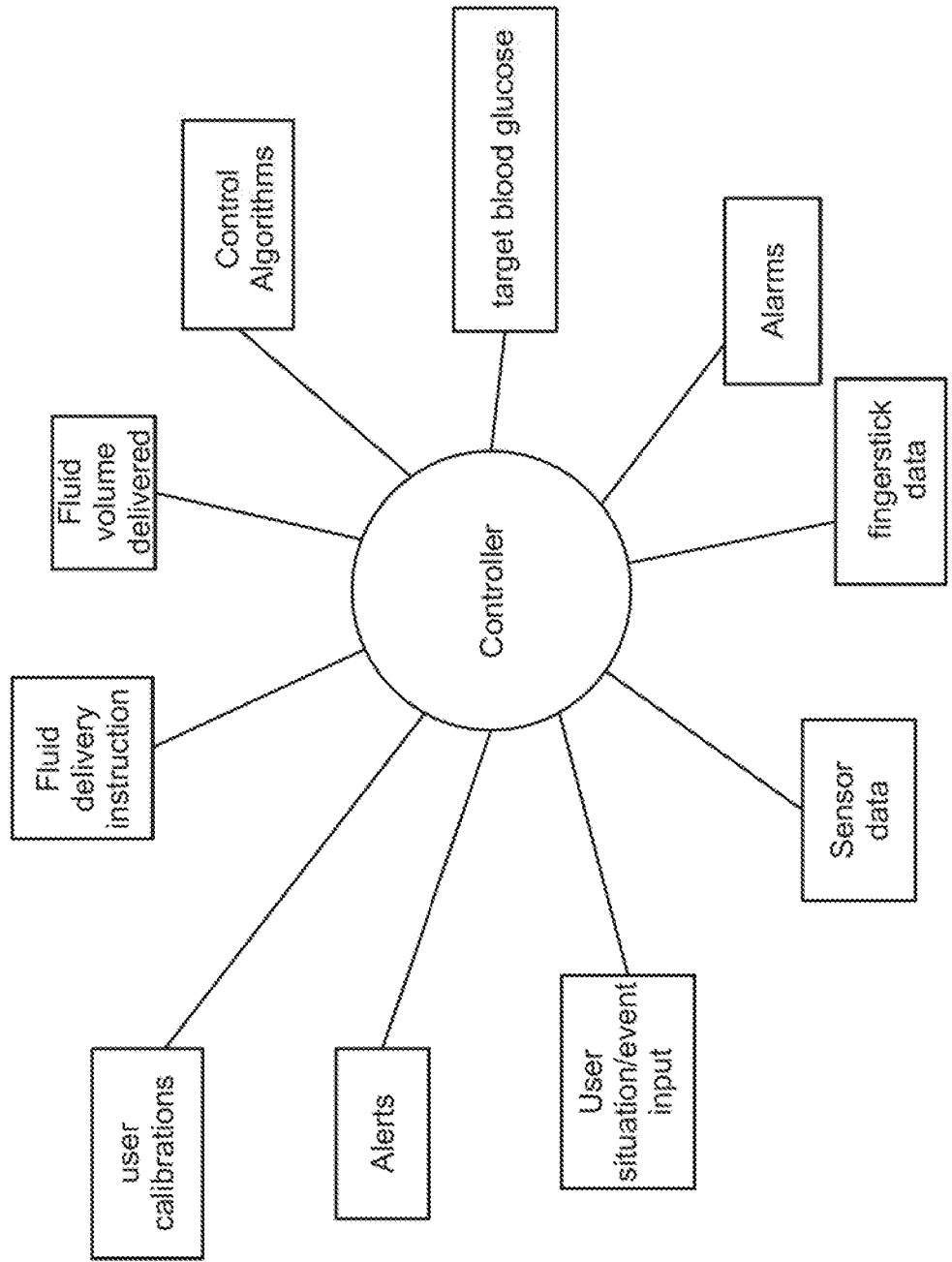
FIG. 2 is a diagram of some variables used in various embodiments of the at least partially closed-loop methods.

Referring now to FIG. 2, the system controller, or the methods of determining fluid delivery volume and timing, takes a number of factors into consideration when determining timing volume for dispensing fluids. These factors presented in FIG. 2 are a non-exhaustive list of factors in which the controller may take into consideration. The system and the methods aim to take data into consideration and deliver insulin or a counter-regulatory to insulin, in response, to maintain a desired blood glucose level.

The system may use at least one CGM. CGMs include a glucose sensor (referred to as a "sensor" or "analyte sensor"). In various embodiments, the CGM sensor is introduced and remains in the user's interstitial fluid located on the body, e.g., on the abdomen. The CGM sends electrical signals at predetermined intervals to a receiver or controller. The receiver or controller correlates these electric signals to a glucose value. In some embodiments, redundant CGMs are used to provide more than one interstitial glucose reading at any given reading time for safety concerns. In some embodiments, the redundant CGMs may be one or more additional CGMs (the same CGM) located in different parts of the patient. In other embodiments, the redundancy may be provided by one or more sensors integrated onto a single CGM apparatus where all of the sensors are introduced into a similar place on the patient and in some embodiments, using the same auto inserter. In some embodiments, one or more redundant sensors may be sensors introduced to different depths in the patient, e.g., if there are 4 redundant sensors, each sensor is introduced to a different depth in the patient.

Redundant sensors provide additional safety. The sensor readings may be sent to a processor which may use various methods to determine if the system should accept the reading, or which reading the system should accept, for use in determining the amount of insulin to deliver. For example, the processor may determine if the values vary more than 6%, for example (in other embodiments, the percentage different may be different and may be determined and/or specified based one or more calibration techniques) then the readings may not be used for delivery and re-calibration (i.e., by a finger-stick) is required. If the processor does not receive a signal from one, the processor may be programmed to ignore that sensor. If all redundant sensors read the same or similar value (again, within a percentage that may be pre-programmed or may be pre-determined), then the system may be more confident the value is closer to correct.

In some embodiments, the redundant sensors may be calibrated differently. For example, one sensor may be calibrated to be more sensitive than the other sensor(s). In some embodiments, the various sensors are tuned to different dynamic ranges. For example, where two sensors are used, each of the two sensors are tuned to a different range, one is tuned to be very sensitive to low blood glucose levels, the other tuned to high blood glucose levels. If for example, the sensor tuned low is reading 60 mg/dl, the system will recognize that the sensor is in the patient and reading. If the sensor tuned high is reading 250 mg/dl, the system may confirm the sensor is in the patient and reading. In other embodiments, the redundant sensors may be tuned based on a time-constant, i.e., one sensor reads faster than the next, etc.

In some embodiments, a patient may stagger the introduction of one of more CGMs such that for any given day, there is always a calibrated sensor providing data to the controller/system. In some embodiments, one or more CGMs is an implantable CGM.

In various embodiments, the system may include one or more additional sensors sensing various conditions/health or other analytes of the patient. The conditions sensed, in the exemplary embodiments, are those analytes or other health indicators that affect the patient's insulin requirements. The additional sensors may include, but are not limited to, one or more of the following:

Heart rate sensor;
Analyte sensor for one or more hormones;
Thermistor: monitor patient temperature;
Temperature sensor: monitor medical fluid temperature;
Accelerometers;
Gyroscsopes;
Inertial Measurement Unit ("IMU");
Respiratory rate monitor;
Carbox-symmetry sensor;
Galvanic skin;
Adrenaline sensor;
Oxygen saturation sensor;
Hydration sensor;
White blood cells count sensor; and/or
Signaling hormone sensor.

Additionally, one or more of the sensors, in some embodiments, may be embodied as micro needle-sensors, similar to those described in U.S. Published Application No. US-2009-0099522, published Apr. 16, 2009 and entitled Microneedle Systems and Apparatus (G34), which is hereby incorporated herein by reference in its entirety.

In some embodiments, system may include at least one inertial measurement unit ("IMU"). In various embodiments, any type of IMU may be used. In some embodiments, the IMU is a device capable of sensing motion using a combination of sensors. Various IMUs may include, e.g., one or more accelerometers and/or one or more gyroscopes, to measure orientation relative to gravity, including, but not limited to, sensing type, rate, and direction, using a combination of accelerometers and/or gyroscopes. The data collected from the at least one IMU may be used to determine whether a user is moving. In some embodiments, the data collected may be used to determine whether a user is sleeping or has fallen. In other embodiments, the IMU may be used to determine the user's speed and direction changes, which may indicate the type of activity the user is performing, e.g., running, skiing, playing tennis, etc. Thus, at least one IMU may be used to determine the movement of the user and the data may be collected by the controlled and used by the processor.

It should be understood that although the use of at least one IMU for determination of movement of a user is described herein, the at least one IMU may be used in conjunction with any one or more various devices and/or sensors to determine the movement or activity of a user, including, but not limited to, an blood oxygen sensor. In some embodiments, the IMU may be a MICROSTRAIN® 3DM-GX1® by Microstrain, Inc., Williston, Vt. In some embodiments, the IMU may be located in the pump or in the controller or may be a separate device worn by or on the user. In some embodiments, the IMU used may be a 3-axis IMU including accelerometers and gyropscopes. In some embodiments, the IMU may include 3 accelerometers and 3 gyroscopes. These IMUs include output relating to pitch, roll and yaw. However, these devices may be large and/or heavy and/or have large power requirements. Thus, it may be desirable, in some embodiments, to use an IMU with including at least one accelerometer and at least one gyroscope.

In some embodiments, one or more, but not limited to, the following may be used may be used to determine whether a user is exercising or otherwise stressed or experiencing a situation which may change the insulin sensitivity or insulin requirements: a heart rate monitor, respiratory rate monitor, adrenaline sensor, thermister, and/or hydration sensor. In some embodiments, a hydration sensor may be used to determine whether a user may be dehydrated, which may contribute to unexpected glucose data. In some embodiments, a temperature sensor may be used to monitor the temperature of the medical fluid, which may include insulin, which may be used to predict unexpected results or alarm/alert the user when the temperature is higher or lower than recommended. In various other embodiments, additional sensors may be used. In various embodiments, one or more sensors may be used and these sensors may be used on the user, in the pump, and/or in the controller and/or as a separate device, or in combination thereof.

The controller serves as at least one user interface, and also a central user interface for the CGM(s)/sensors, the pump, and the patient's/user's interface with the control system. For purposes herein, the controller may be programmed by a patient, a "user", a care-giver, a health-care provider or any combination thereof. For purposes of this description however, the term "patient" or "patient/user" or "user" refers to anyone entering information into to controller, or utilizing the controller to provide care for the patient. In the exemplary embodiment, the system controller communicates with the various system components via wireless, e.g., radio frequency ("RF") communication and/or other types of remote communication. In the exemplary embodiment, the controller includes a graphical user interface ("GUI") and one or more input device, e.g., button(s), capacitive slider(s), jog wheel, touch screen, keypad, electronic keypad, and any other input device. The controller also includes at least one processor, although in the exemplary embodiments, the controller includes at least two processors, a control processor and a safety processor. These processors may be redundant processors, or two different processors providing redundant processing or checking the processing of one another.

Some embodiments of the controller may include at least one "event" or specialty button, e.g., a "food" button, an "exercise" button, and a "bolus" button. In some embodiments, the controller may contain a single "event" button. Pressing or actuating this button may bring the user to an event menu, which may include a list of potential events, one or more of which may be customizable to the user.

With respect to all event buttons, these buttons, when pressed, would bring the patient/user either to a menu or a processing logic that enables the patient/user to input directly into the processing logic for exercise, food or bolus, for example. The logic may then query the patient/user to enter additional information, for example, how long the exercise is expected to last, how rigorous, how much food (i.e., how may carbohydrates), glycemic index, fat content and protein content of the food. With respect to bolus, the patient/user would be able to input the volume of a bolus by using a series of button presses or by using another input device, i.e., jog wheel, button or slider, to input the requested volume of insulin, i.e., the units of insulin. In some embodiments, the user interface includes many of the same features as found on insulin pumps and pump controllers known in the art.

In the exemplary embodiment, the controller also includes a "strip reader", e.g., a space that accepts a glucose test strip for use in "finger stick" or "fingerstick" readings, e.g., the patient pricks their fingers and uses the blood from the finger to apply to the "finger stick". The "strip reader", using electrochemical testing, determines the blood glucose level of the blood. The strip reader may be used to calibrate the CGM, to double check unexpected or unusual readings, or as a back-up to the CGM in case of CGM failure. In some embodiments, the strip reader may be a separate device, such as a glucose meter. In these embodiments, the glucose meter may either wirelessly receive the fingerstick reading or the user may manually input the reading into the controller.

The GUI may be a color GUI, a black on gray screen, and/or a touch screen or other. The GUI may additionally accept and/or give voice commands and/or provide for magnification on request.

The controller additionally includes at least one speaker and in some embodiments, at least one vibration motor. In some embodiments, the controller may include any one or more of the features described in U.S. Published Application No. US-2008-0198012, published Aug. 21, 2008 and entitled Device and Method for Food Management (F21), which is hereby incorporated herein by reference in its entirety.

The controller, in some embodiments, serves as the receiver for the at least one sensor, including but not limited to, the at least one CGM. As such, the user will indicate to the controller when a new sensor is introduced into the body. In some embodiments, the user may additionally input the location of the sensor on the user's body, e.g., which include, but are not limited to, right abdomen, left abdomen, right arm, left arm, right hip, left hip, right left, left leg, etc. This may be desirable as the sensor may perform differently in different areas on the body. As the controller will records and process this data, the controller may calibrate the sensor based on past profile information indicating "lag" and/or "drift" information from the same area of the body.

The medical fluid pump/infusion pump/insulin pump/fluid pump in various embodiments, is used to deliver medical fluid, which includes insulin, and may include one or more reservoirs for delivery of one or more fluids (thus, the various reservoirs may contain the same fluid or different fluids). In some embodiments, the medical pump may deliver more than one type of insulin (for example, one or more of the types described above). However, in some embodiments, the medical pump including more than one reservoir may be used to deliver insulin and at least one counter regulatory hormone, e.g., glucagon. The medical pump may be any of the pumps described in U.S. Published Application No. US-2007-0219480, published Sep. 20, 2007 and entitled Patch-Sized Fluid Delivery Systems and Methods (E72); U.S. Pat. No. 7,306,578, issued Dec. 11, 2007 and entitled Loading Mechanism for Infusion Pump (C54); U.S. Pat. No. 7,498,563, issued Mar. 3, 2009 and entitled Optical Displacement Sensor for Infusion Devices (D78); U.S. Published Application No. US-2007-0228071, published Oct. 4, 2007 and entitled Fluid Delivery Systems and Methods (E70); U.S. Published Application No. US-2007-0219496, published Sep. 20, 2007 and entitled Pumping Fluid Delivery Systems and Methods Using Force Application Assembly (E71); U.S. Published Application No. US-2007-0219597, published Sep. 20, 2007 and entitled Adhesive and Peripheral Systems and Methods for Medical Devices (E73); U.S. patent application Ser. No. 12/347,985, filed Dec. 31, 2008 and entitled Infusion Pump Assembly (G75); U.S. patent application Ser. No. 12/347,982, filed Dec. 31, 2008 and entitled Wearable Pump Assembly (G76); U.S. patent application Ser. No. 12/347,981, filed Dec. 31, 2008 and entitled Infusion Pump Assembly (G77); U.S. patent application Ser. No. 12/347,984, filed Dec. 31, 2008 and entitled Pump Assembly With Switch (G79); U.S. Published Application No. US-2009-0099522, published Apr. 16, 2009 and entitled Microneedle Systems and Apparatus (G34); and U.S. Published Application No. US-2009-0099523, published Apr. 16, 2009 and entitled Infusion Pump Assembly (G46), which are each hereby incorporated herein by reference in their entirety or a modification thereof to accommodate multiple reservoirs.

The system may include one or more alarms, including but not limited to, one or more vibration motors and/or one or more speakers on the controller, and in some embodiments, one or more vibrations and/or speaker motors on the medical pump. Some alarms, in some embodiments, may be progressive alarms, i.e., depending on the alarm type, the alarm progressively become louder or more aggressive. Alarms may be used to indicate any of a myriad of conditions, including but not limited to: high blood sugar, falling blood sugar or low blood sugar, occlusions, empty or near empty reservoir, system failures, dislodged cannula, dislodged sensor, or any other condition that a patient may wish to be aware.

In some embodiments, the alarm system may further include a signal amplifier separate from the pump and controller. The amplifier may receive the alarm signal, and amplify the alarm. The signal amplified, in some embodiments, may be a separate device that may receive wireless transmissions from the pump and/or the controller. In some embodiments, the signal amplifier may signal another device to turn on, e.g., a TV or a stereo, automatically trigger a phone to ring, or in some embodiments, where the alarm is not confirmed by the patient/user, the signal amplifier may place a call to an emergency service or an emergency contact number that is pre-programmed by the patient/user.

In some embodiments, the patient/user may select different types of alarms for different events/times of day. These selections may be pre-programmed (e.g., every night from 6 pm-6 am, a nighttime alarm sequence will be used if an alarm condition sensed), or may be selected when desired (e.g., before swimming, using a menu, the patient/user may select the "swimming alarm", which may be vibratory only, for example). The controller, in the exemplary embodiment, may be fully programmable with respect to the alarms such that a patient/user may elect escalating or progressive alarms for some situations, vibration only for others. Additional alarm conditions that may be programmed by the patient/user include but are not limited to the condition required to silence the alarm (for example, a nighttime alarm silence condition may require a series of inputs to ensure the patient does not turn the alarm off in their sleep without confirming the condition).

The system may use one or more indicators to determine when one or more cannulas have become dislodged from the patient. In some embodiments, a conductivity sensor may be used to determine if the cannula has become dislodged from the patient. In some embodiments, the cannual may include a conductive pad around the cannual e.g., a pad including at least two electrodes electrically coupled to a central processor. Where the cannula is dislodged, the insulin will be delivered into the pad, thus, changing the conductivity of the pad.

Figure 3:
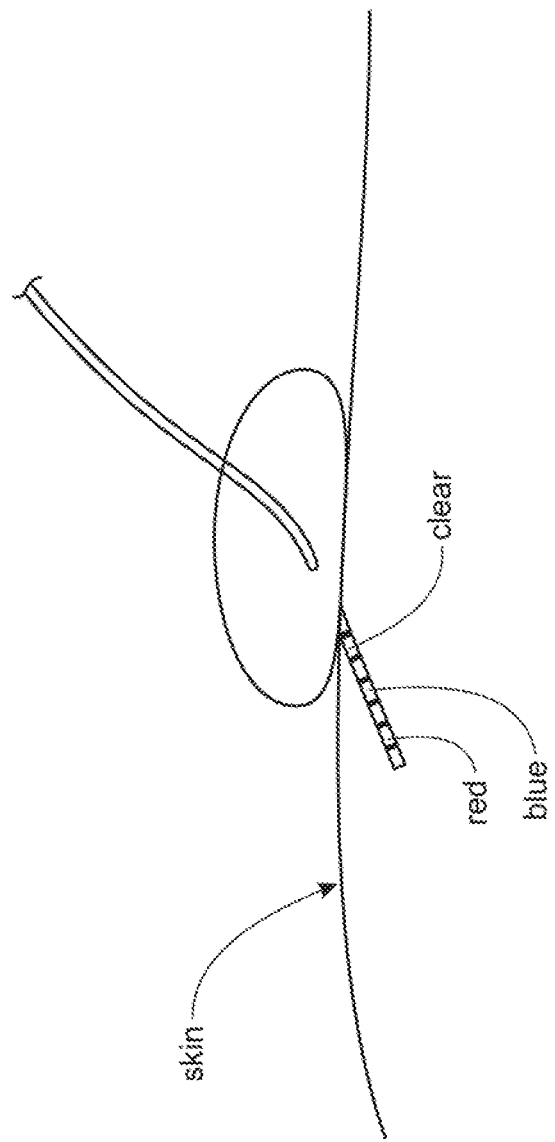
FIG. 3 is an illustration of one embodiment of a cannula having depth indicators indicated by different hatch.

Referring now to FIG. 3, in some embodiments, the cannula used in the system may be a cannula including two of more tubing colors serving as visual indicators of dislodgement. For illustration purposes, the tubing colors are represented with different hatch marks. For example, the tip of the cannual may be red, the center blue and the end, clear tubing. Thus, the patient may determine, through visual inspection, whether the cannula has become dislodged from the patient.

The system may include one or more integrity tests to determine whether the one or more CGM sensors has failed or is providing incorrect or inaccurate information. The terms "incorrect" or "inaccurate" information may be defined as a percentage difference between the CGM reading and a fingerstick reading. The percent difference may refer to when the CGM reading is either a percentage higher or a percentage lower than the fingerstick reading. In some embodiments, any number higher than e.g. a 30% difference between the fingerstick and the CGM, may be termed "incorrect information" or "inaccurate information". In other embodiments, this percentage may be higher of lower than 30%. In some embodiments, this percentage may vary between users and CGM systems.

In some embodiments, a temperature integrity test may be used. Some CGM sensors may experience a drift per degree of temperature shift. For these CGM sensors, in some embodiments, where the temperature is modulated either higher or lower, the system expects a likewise percentage and/or proportional drift in CGM values. In some embodiments, the system may prompt the user to first, take a fingerstick and then, encounter a temperature shift and take a second fingerstick reading as well as note the CGM reading. This may provide an integrity test for the CGM. In some embodiments, the system may prompt the user in this way and may await a temperature shift (which may be determined from a temperature sensor in the pump or controller), then prompt the user to take the second fingerstick. The system may then compare the fingerstick reading to the CGM reading before and after the temperature shift. If the particular CGM, which is expected to experience a shift due to temperature, does not shift, then this may be an indication that the integrity of the CGM system has been compromised. In these cases, the system notifies the user of this error and ceases continuing the semi-closed or closed loop system of control.

In some embodiments, the system may prompt the user to inject a small volume of glucose into an area under the skin, in an area in close proximity to the CGM sensor. The small volume of glucose may be a solution containing a particular concentration of glucose. The system may expect an increase in the glucose readings from the CGM a short time following the injection. In some embodiments, where this same test has been performed on the same user, and where the solution is identical to one used previously, and where the injection was performed in the same manner, and in the same area in relation to the sensor as previously, the results and profile of the user's response may be in the system and thus, the system may compare the new results to old results or an average of old results. If the CGM reading does not indicate the presence of glucose, or does not match the old results or the average of the old results within a margin, then this may be an indication that the integrity of the CGM system has been compromised. In these cases, the system notifies the user of this error and ceases continuing the semi-closed or closed loop system of control.

In some embodiments, the system may prompt the user to take a fingerstick reading on demand. This reading may be used as a system integrity check and/or to calibrate the one or more CGM sensors. With respect to a fingerstick on demand as an integrity check, where the fingerstick reading does not confirm the CGM reading within a percentage, then this may be an indication that the integrity of the CGM system has been compromised. In these cases, the system notifies the user of this error and ceases continuing the semi-closed or closed loop system of control. With respect to a fingerstick on demand as a calibration, where the fingerstick reading does not confirm the CGM reading within a percentage, then this may be an indication that the integrity of the CGM system may have been compromised. The system may request the user enter a second fingerstick to confirm the first fingerstick reading. After the second fingerstick reading, where the second reading confirms the first reading, the system may resume (where the reading confirms the CGM integrity) or, where the readings confirm the integrity may be compromised, the system may notify the user of the error and cease continuing the semi-closed or closed loop system of control.

In some embodiments, with respect to the fingerstick on demand, where the system requests a fingerstick and the system does not receive a fingerstick reading within a predetermined amount of time, e.g., five (5) minutes or ten (10) minutes, the system may default to end closed-loop or semi-closed loop mode. This provides an additional safety and also may increase the accuracy of the CGM readings as the system may require, in some embodiments, frequent calibration to assure reliable CGM readings.

With respect to the various integrity tests described herein, in some embodiments, rather than sending a system error or alert, in some embodiments, and in some instances, with any of the integrity checks, the system may determine the percentage difference in the CGM readings from that which is expected and adjust readings accordingly.

In some embodiments, the CGM may provide different or "bad" data when a user is applying pressure to the sensor, e.g., has rolled onto the sensor during sleep. In some embodiments, the system may turn the sensor off during these times, and may additionally include an indication alert on the controller screen. In some embodiments, when the controller senses the user is at sleep, the system may shut down, and after a certain amount of elapsed time, e.g., 30 minutes, the system may turn the sensor on. If the problem/pressure has corrected itself, then the system may resume. This may be desirable to allow the user to continue sleeping and perhaps, take the pressure off the sensor on their own, rather than waking them in the night. In some embodiments, during the shut down, delivery of insulin will also stop.

In some embodiments, if after the elapsed time, the system does not correct itself, the system will alarm and alert the user that the system has shut down.

To manage diabetes using at least a partially closed-loop method, the components of the system described may be used to deliver controlled volumes of insulin and, in some embodiments, a counter regulatory hormone, e.g., glucagon, according to a variety of methods, some of which are described herein. In the exemplary embodiments, the control methods rely on the use of a system that includes the ability to actively measure the volume of insulin or other fluid that is actually delivered to the patient (as opposed to measuring the volume of insulin requested by the user or pre-programmed by a user to be delivered); at least one CGM and a user interface and processes containing instructions for the at least partial closed loop algorithm. Other sensors and data input models may also be included, as described in more detail above. However, in some embodiments, pumps that do not actively measure the volume of insulin or other fluid that the pump is actually delivering to the patient may also be used. In these embodiments, an assumption is made that the volume delivered to the patient is the volume requested by the processor (unless or until a mechanical malfunction or occlusion is detected).

Figure 6:
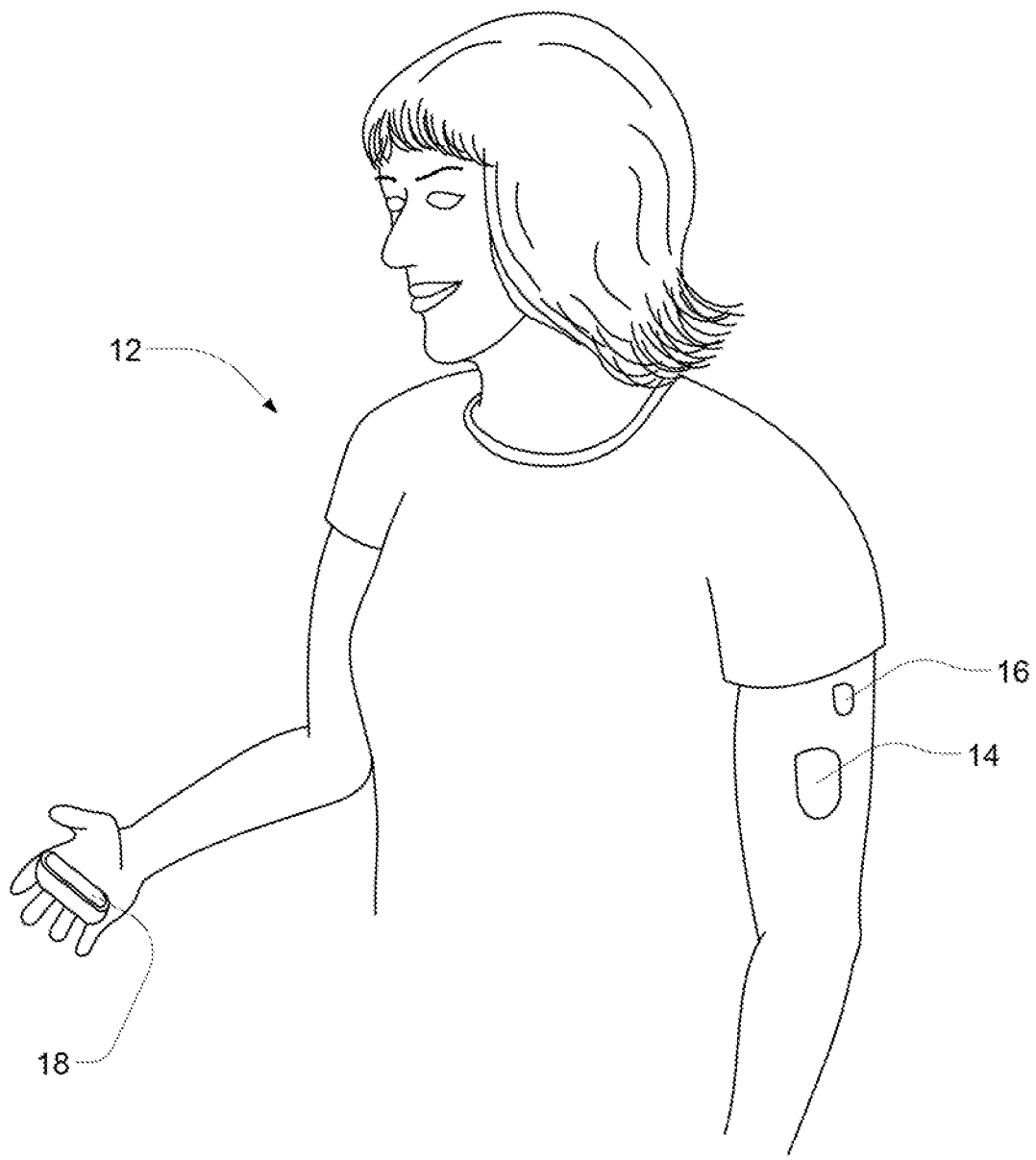
FIG. 6 is an illustration of one embodiment of the system.

Referring to FIG. 6 a patient 12 is shown wearing a medical fluid pump 14, a sensor apparatus 16 and holding a controller 18. The sensor apparatus 16 may contain one or more CGMs, and one or more additional sensors. The sensors transmit data to the controller 18. The medical fluid pump 14 is shown as a patch pump similar to any one of the patch pumps shown and described in U.S. Published Application No. US-2007-0219480, published Sep. 20, 2007 and entitled Patch-Sized Fluid Delivery Systems and Methods (E72); U.S. Published Application No. US-2007-0228071, published Oct. 4, 2007 and entitled Fluid Delivery Systems and Methods (E70); U.S. Published Application No. US-2007-0219496, published Sep. 20, 2007 and entitled Pumping Fluid Delivery Systems and Methods Using Force Application Assembly (E71); U.S. Published Application No. US-2007-0219597, published Sep. 20, 2007 and entitled Adhesive and Peripheral Systems and Methods for Medical Devices (E73); U.S. patent application Ser. No. 12/347,985, filed Dec. 31, 2008 and entitled Infusion Pump Assembly (G75); U.S. patent application Ser. No. 12/347,982, filed Dec. 31, 2008 and entitled Wearable Pump Assembly (G76); U.S. patent application Ser. No. 12/347,981, filed Dec. 31, 2008 and entitled Infusion Pump Assembly (G77); U.S. patent application Ser. No. 12/347,984, filed Dec. 31, 2008 and entitled Pump Assembly With Switch (G79); U.S. Published Application No. US-2009-0099522, published Apr. 16, 2009 and entitled Microneedle Systems and Apparatus (G34); and U.S. Published Application No. US-2009-0099523, published Apr. 16, 2009 and entitled Infusion Pump Assembly (G46), which are hereby incorporated herein by reference in their entirety. The patch pump 14 is controlled by the controller (although in some embodiments, may also include a user interface allowing for control by the patient/user) and transmits information to the controller 18. Thus, the controller receives information relating to the one or more sensors and the pump. The controller additionally receives inputs from the user, e.g., events, and may receive manual inputs for fingerstick readings or fingerstick data. Additionally, the controller, in some embodiments, may receive information relating to food or glucose readings, etc., wirelessly. In some embodiments, the controller includes voice recognition, thus, in these embodiments, the controller may receive commands via voice.

The control methods described herein, in the exemplary embodiments, may include user calibration to the system. User calibration refers to calibrating the system to the user. This may include, but is not limited to, collecting CGM data at prescribed times during or following a prescribed event. These may include, but are not limited to, one or more of the examples given herein.

A prescribed event may include any event the system requests, e.g., a fasting event, an exercise event, a meal event, and/or a sleep event. The system may prescribe that a user undergo a "fasting event". In some embodiments, this includes prompting a user to fast during a certain period of time. For example, fasting times may include, but are not limited to: between midnight and 10 am; between 9 am and 2 pm; between 2 pm and 7 pm; and between 7 pm and midnight. These may correlate to a morning fast, a lunch fast, a dinner fast and an overnight fast. The system may take periodic readings during this time to characterize or profile the user. In some embodiments, the system may require and prompt the user to perform a fingerstick at certain intervals as a verification of the CGM at this time. These resulting profiles may be used in many ways, including but not limited to: recommending basal setting changes, identifying anomalies, and/or recommending changes in basal boundaries. In some embodiments, the system may recommend or prompt a user to complete a fasting profile several times a year, or, as the system identifies anomalies in the insulin requirements or in the CGM data, the system may prompt the user to complete a fasting profile to either identify a potential problem with either the pump, CGM or controller system integrity, or to identify times of day or events where the user may wish to reconsider boundaries and/or the trajectories or rates, etc.

Other prescribed events may include one or more exercise events. During these events, the user may input the type of exercise being performed. The system may take regular CGM readings and prompt fingerstick verification during the event. Again, as with the fasting events, the system may recommend or prompt a user to complete an exercise profile several times a year, or, as the system identifies anomalies in the insulin requirements or in the CGM data, the system may prompt the user to complete an exercise profile to either identify a potential problem with either the pump, CGM or controller system integrity, or to identify times of day or events where the user may wish to reconsider boundaries and/or the trajectories or rates, etc. In some embodiments, the system may prompt or the user may request these events. Also, in some embodiments, many different types of exercise events may take place, for example, but not limited to: anaerobic events, long duration aerobic, short duration anaerobic, long during anaerobic, etc. In this way, the user may input to the system when they are undertaking any of these events and thus, the system may collect additional data that may be used for identification of anomalies and/or recommendations to consider the boundaries and/or trajectories during these events.

An eating event may be performed by request from the system or the user. The eating event may be helpful to the user and/or the system to identify an eating event (where the user fails to input the event into the system, the system itself may recognize the pattern and prompt the user with a question, e.g., "are you eating?"). In some embodiments, more than one type of eating events may be captured, for example, these include, but are not limited to: breakfast, lunch, dinner, morning snack, afternoon snack, and evening snack. In some embodiments, the system may request that the user, e.g., "eat a candy bar". In these embodiments, the user may select a candy bar and through an input, enter the information relating to the candy bar into the controller. Then, the user may elect to begin the requested calibration. The user may eat the candy bar, and the controller may collect various glucose or other types of data, during this time. Thus, the system collects a "profile" for this candy bar, which may be used later either for the same candy bar, and/or for the candy bar at that particular time, under the same or similar circumstances. In some embodiments, the system may specify "no exercise" for non-exercise calibration during a calibration day. In some embodiments, the system may specify that the user "exercise" and then eat a particular meal. In each case, the user may interact with the controller, inputting various information, including, but not limited to, the type and/or duration of meal and/or the type and/or duration of exercise.

In general, patient calibration refers to calibrating the system to any one or more, but not limited to, of the following: the patient's insulin sensitivity, total reaction time (and kinetic profile) for a given insulin in the patient, body fat index, blood glucose profiles for particular foods or types of foods, blood glucose profiles for particular exercises (both type/rigor and duration), current medications, other diseases and blood glucose profiles for any one or more, but not limited to, the following: nighttime/sleep, illness, workdays, school days, exam periods, weekends, travel and the like, i.e., for any life-situation in which the patient may experience frequently enough the patient (or care-giver, health-care provider) renders it helpful for the system to learn the blood glucose profile for that experience/situation.

Once the patient calibration for any of the above (or other) is completed, the system may be able to identify unexpected results (i.e., unexpected blood glucose profiles) for any of the calibration types. In some embodiments, the system may alert the patient that any one or more calibrations must or should be repeated due to unexpected results.

The patient/user may program a preference for when these alerts, e.g., pre-program the percentage off from the expected that will trigger an alert or any given calibration. Thus, the patient/user may limit alerts and re-calibrations based on particular/pre-set aberrations. Also, the patient/user may override the alerts. Further, the patient/user may prefer alerts be triggered where the aberration is 3% during the night, whereas they may prefer 10% during stress.

In some embodiments, the controller may include a menu for calibration for various situations. In some embodiments, the patient may have the ability to add to the calibration menu, and/or customize the menu. Where the patient is experiencing any of the situations, the patient may enter this information into the controller, thus, the processor/controller will know to compare the readings and insulin delivery to the calibrations. Also, the processor may store the data for each situation, and learn from the data, i.e., adjust the delivery based on this data.

In some embodiments, where there is an unexpected result, the user may have the opportunity to explain the aberration/unexpected result. For example, if a patient intended to eat a meal, and input this information into the system, but failed to eat, e.g., changed their mind or forgot, the system, in reviewing the blood glucose readings, may see that the patient's blood glucose levels have not risen, as would be expected, thus, this may qualify as an aberration from the expected. The system may alert the patient of an aberration, and the patient may input (thru a menu or other) that the intended meal did not take place.

In other embodiments, where the user has not entered an event into the system and the system, through CGM or fingerstick data, senses a profile similar to an event, or a profile indicating the unexpected results may be due to a CGM failure, cannula failure, insulin malfunction (e.g., occlusion, decreased activity due to temperature or age, etc.), the system may not changing the volume or schedule of delivery of insulin, rather, the system may prompt the user to enter additional information, e.g., an event, before changing the schedule of insulin delivery. For example, if a user does not enter a meal event into the system, and the system, through CGM or fingerstick data, senses a blood glucose level that is uncharacteristic for the time of day and/or would require the system to exceed a preprogrammed basal boundary, the system may alert the user that there are indications that a greater volume of insulin may be required to be delivered than is either allowed for that time of day, i.e., the volume may exceed a preprogrammed boundary, or that the delivery would exceed the maximum volume for the day. In some embodiments, the user may have the opportunity to enter an event or additional information, within a preprogrammed time from the alert, e.g., within five (5) minutes. The information entered may either confirm the blood glucose data, e.g., based on predetermined profiles, or if the information does not confirm the blood glucose data, the unexpected blood glucose data may be an indication that something unexpected and unpredicted has occurred and may alert the user and shut-down the closed-loop or semi-closed loop system. In these embodiments, if the user fails to provide any information explaining the unexpected blood glucose data, the closed-loop or semi-closed loop system may shut-down.

In various embodiments, the closed-loop and/or semi-closed loop system may not shut down without first notifying the user, i.e., the system will not undergo a silent shut-down, e.g., a shut down without notifying the user before shutting down.

In some embodiments, as discussed above, the system may prompt the user to inject a small volume of glucose into an area under the skin, in an area in close proximity to the CGM sensor. The small volume of glucose may be a solution containing a particular concentration of glucose. The system may expect an increase in the glucose readings from the CGM a short time following the injection. In some embodiments, where this same test has been performed on the same user, and where the solution is identical to one used previously, and where the injection was performed in the same manner, and in the same area in relation to the sensor as previously, the results and profile of the user's response may be in the system and thus, the system may compare the new results to old results or an average of old results. However, this procedure may additionally be used in a user calibration process, where the resulting glucose profile of the user may be used by the system as a reference of the expected response from X grams of quick acting carbohydrate in the user. This profile, in some embodiments, may be used to recommend a type of snack to the user to treat an anticipated or sensed hypoglycemic episode.

Various control algorithms may be applied to the at least partially closed-loop system. In some embodiments, the control algorithm(s) that are applied is patient/user selected. In some embodiments, the various control algorithms include parameters that are patient selected.

The control algorithms may be turned on or off at any time by the patient/user. Various algorithms may be used at different times and are patient driven. Thus, in the exemplary embodiment, the patient/user maintains control over the use of any given algorithm and that algorithm may be overridden at any time.

Any one or more of the algorithms described below may be used at any time. Although some examples of algorithms are discussed below, various embodiments of the systems described above may be used in conjunction with any control algorithm the patient/user desires. Thus, additional algorithms may be developed that would be easily integrated onto the controller to be used to at least partially control the delivery of insulin.

The control algorithms reside, in the exemplary embodiments, on the controller. However, in some embodiments, the control algorithms may reside on the pump, in addition to the controller, or instead of the controller. The myriad of control algorithms may be accessed by a control system. The control system will receive several patient specific inputs which may be utilized by any control algorithm. These inputs include patient calibrations.

In some embodiments, the system includes a network operation center ("NOC"). A NOC may be used to coordinate activities and resources. The NOC may communicate with the controller and/or the pump via a network connection or wirelessly. The NOC being remote from the controller/pump may include greater processing power than the controller or pump, thus, may include adaptive software. In some embodiments, the NOC may include artificial intelligence and/or clinical software. Thus, in these embodiments, the NOC, rather than the pump or controller (or a user's personal computer or "PC") would host the clinical software. This may be desirable to prevent software tampering and also, provide a central point for software updates. These updates may be downloaded via a network onto the pump and/or controller and/or user's PC.

In some embodiments, the patient/user specifies a "target blood glucose value" or a "target blood glucose range" for time ranges or other characterized experiences, i.e., including but not limited to one or more of the following, a target range for exercise, illness, nighttime, pre-meal, post-meal, during meal, etc. These target values may be changed at any time by the patient/user, based on permissions that are granted (i.e., in some embodiments, only particular users, i.e., patient and care-giver, have permission or access to change the target values.

Using the data from the one or more sensors, together with the patient calibration data, the control algorithms serve as methods for controlling the delivery of insulin to the patient.

Figure 4:
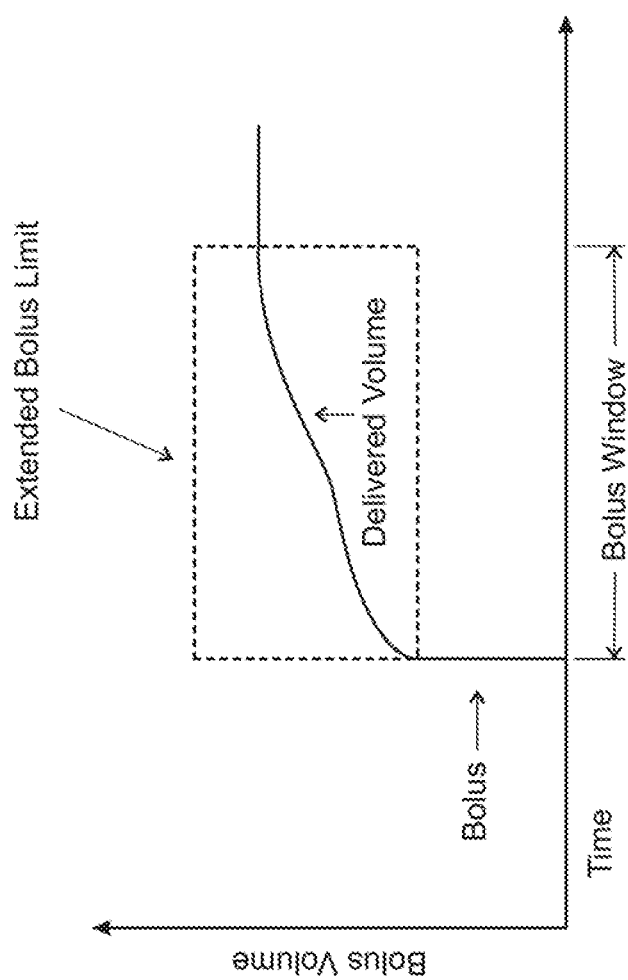
FIG. 4 is a graphical representation of an example of a bounded bolus partial close-loop method.

One algorithm that may be utilized is a partial closed-loop algorithm. This refers to an algorithm that provides for closed-loop control of the delivery of insulin but within a "range" or "set of permissions". For example, referring now to FIG. 4, an embodiment of a "bounded bolus" algorithm is shown. In this embodiment, the user specifies a "bolus window", the time in which "bolus" insulin may be requested for delivery by the controller. Within the specified bolus window, the controller will only be allowed, or only has permission to deliver, a particular "bounded" volume of insulin. Taken differently, the bounded bolus algorithm will prevent delivery of insulin over a particular volume during a particular bolus window.

In some embodiments, where the patient/user determines a bolus is required, the patient/user may request the "bounded bolus" algorithm, and input the duration and volume permissions.

In some embodiments, the user may specify a "bolus maximum", which is the maximum bolus volume, e.g., 15 units, the controller may deliver. In some embodiments, the user may specify a "24 hour bolus maximum" which limits the total volume of bolus insulin delivered during a 24 hours period, e.g., 40 units.

In various embodiments, one or more of these boundaries may be specified and preprogrammed by the user. In various embodiments, where the controller determines, from the blood glucose values, that a particular volume should be delivered, but the particular volume exceeds one or more boundaries, the controller may prompt the user to enter additional information or may shut-down after alerting the user that one or more boundaries have been met. Another algorithm that may be utilized is a closed-loop bolus algorithm. This refers to the controller's ability to deliver insulin, based on patient calibration and input regarding events and targets, at times and at volumes determined by the algorithm. Thus, the closed-loop algorithm will use the data from the myriad of sensors or other inputs and determine the appropriate time and volume for delivery of insulin.

Figure 5:
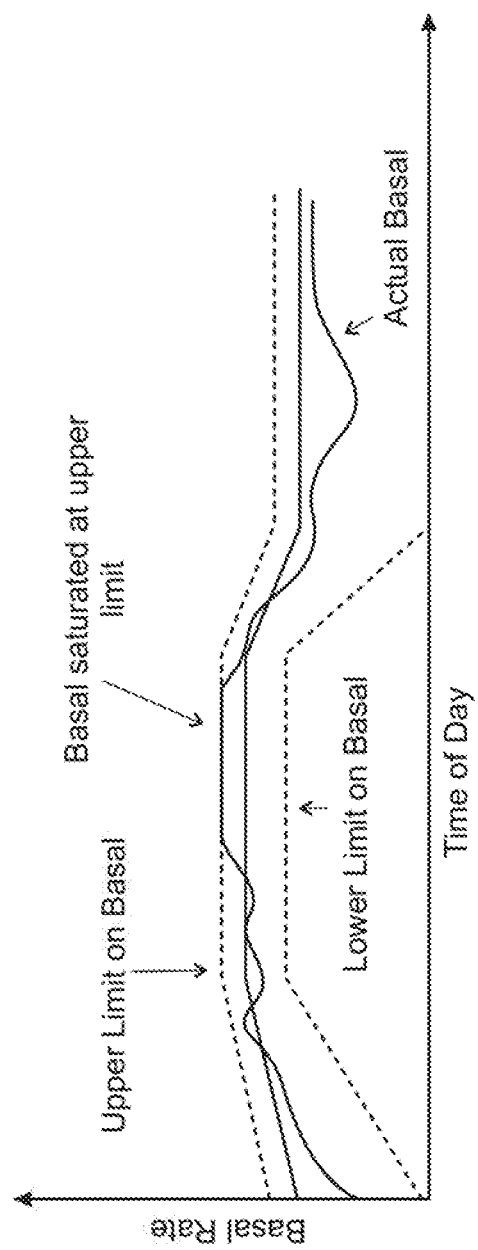
FIG. 5 is a is a graphical representation of an example of a bounded basal partial close-loop method.

Similar to the partial closed-loop bolus algorithm, described above, the partial closed-loop basal refers to algorithms that provide for closed-loop control of the delivery of insulin but within a "range" or "set of permissions". For example, referring now to FIG. 5, an embodiment of a "bounded bolus" algorithm is shown. In this embodiment, the user specifies a "basal window", the time in which "basal" insulin may be requested for delivery by the controller. Within the specified basal window, the controller will only be allowed, or only has permission to deliver, a particular "bounded" volume of insulin. Taken differently, the bounded basal algorithm will prevent delivery of insulin over a particular volume during a particular basal window. In some embodiments, the patient/user may have pre-programmed basal rates. In some embodiments, the number of pre-programmed rates may be from 1-100. Using the bounded basal algorithm, the patient/user allows the controller to change/vary the basal rate for a particular requested time-frame, but within pre-programmed parameters. For example, the system may be allowed to increase or decrease the basal rate during a pre-selected period of time, however, the rate would be "bounded", i.e., the system is free to vary the basal rate during the time period but only within a pre-selected bounded range. The system would not be allowed to deliver at rates higher or lower than the bounded rates for the pre-selected time period.

In some embodiments of the "bounded" algorithms, the system may recommend to the patient/user that the bounded range be extended. In these embodiments, the patient/user would have to agree/grant permission for the system to deliver beyond the bounded range. In some embodiments, the system may recommend permission to deliver outside the bounded range for a single delivery. In other embodiments, the system may recommend permission to deliver outside the bounded range for a recommended period of time.

In some embodiments, the user may specify a "basal rate maximum", which is the maximum basal rate, e.g., 2 units per hour, the controller may deliver. In some embodiments, the user may specify a "24 hour basal maximum" which limits the total volume of basal insulin delivered during a 24 hours period, e.g., 40 units.

In various embodiments, one or more of these boundaries may be specified and preprogrammed by the user. In various embodiments, where the controller determines, from the blood glucose values, that a particular volume should be delivered, but the particular volume exceeds one or more boundaries, the controller may prompt the user to enter additional information or may shut-down after alerting the user that one or more boundaries have been met.

Another algorithm that may be utilized is a closed-loop basal algorithm. This refers to the controller's ability to deliver insulin, based on patient calibration and input regarding events and targets, at times and at volumes determined by the algorithm. Thus, the closed-loop algorithm will use the data from the myriad of sensors or other inputs and determine the appropriate time and volume for delivery of insulin.

Another algorithm is a total closed-loop algorithm. Thus, the system is given full control for determining the time and volume of insulin delivery, both for "basal" and "bolus" deliveries. Thus, in some embodiments of this algorithm, the system may not differentiate between "bolus" and "basal" deliveries, rather, the system would deliver insulin based on patient calibration and data received from the myriad of patient sensors. In some embodiments of the closed-loop algorithm, the system may also accept user inputs with respect to events/experiences and take these inputs into consideration when calculating delivery times and volumes.

In the exemplary embodiments of the systems and methods described herein, for any algorithm used by the system, where unexpected results may occur, the system may automatically shut-down. In some embodiments, the system may recommend an auto-shut down, but will require patient/user confirmation. In other embodiments, the system may employ a method of auto shut-down that includes notifying the patient/user using a series of increasing alarms, and where the system does not receive a confirmation, will automatically shut-down.

In the exemplary embodiment of the system, the user may pre-program an auto shut-down procedure where the system has not received any inputs from the user for a pre-determined interval. For example, where the patient has not taken a finger stick reading between 6 am-10 am, the system may go through the auto-shut down procedure. In the exemplary embodiments, these pre-programmed auto shut-down procedures and the time-frames may be specified by the patient/user.

In some embodiments, an auto-shut down procedures may be triggered where the finger stick readings and CGM readings vary by a percentage higher than that which is either acceptable by the system, or pre-programmed by the patient/user. In some embodiments, similarly, an auto-shut down procedure may be triggered based on data received from any one or more of the sensors used in the system.

In various embodiments, the closed-loop and/or semi-closed loop system detects anomalies which may include, but are not limited to, unexpected glucose data and/or unexpected insulin requirements. Either may be an indication that either one or more of the system components is failing or has failed and/or that the user is experiencing or undergoing an unexpected event and/or an unexpected result from an event, e.g., including, but not limited to, one or more of the following: illness, high carbohydrate meal, long duration meal, long duration exercise, new exercise, and/or stress. In the exemplary embodiments of the semi-closed and/or closed-loop system disclosed herein, the system may shut-down when the system detects an anomaly.

In some embodiments, the anomaly may be "good" control. For example, in some embodiments, where the blood glucose data indicates a consistent and/or steady blood glucose reading over multiple readings, this may indicate that one or more CGM sensors have failed or are failing and/or that the blood glucose meter has failed. Thus, unexpected glucose data does not only refer to unexpectedly "high" or unexpectedly "low", but rather, may refer to unexpectedly consistent.

Further, in some embodiments, where the glucose data indicates an unexpected hypoglycemic event, this may be an indication that the insulin pump is experiencing failure or that the user is undergoing an unexpected event (in which case, as discussed above, the system may prompt the user for further information prior to shutting down).

In some embodiments, where one or more sensors do not confirm either an "event" as indicated by the user or as indicated by the glucose data, this may be an indication that one or more sensors has failed. Thus, as this is a detected anomaly, the system may shut down.

In some embodiments, where an anomaly is detected, the controller may prompt the user with a question, e.g., "are you feeling OK?". Where the user responds "yes", the system may confirm that there is a failure and shut-down. Alternately, if the user responds "no", this may indicate there is an unexpected event occurring in the user, e.g., stress or illness, and the system may shut-down. In some embodiments, the system may prompt the user to enter a fingerstick to confirm the CGM data and in some embodiments, may use the fingerstick data to calibrate the CGM sensor.

In some embodiments, either as an integrity test, or as a calibration, the system may purposely not deliver one or more basal deliveries and record the resulting sensor and/or glucose data. This may provide data indicating the effect on glucose data of each basal delivery which may be used for optimizing therapy. For example, the system may better adjust basal based on calibration data from the purposely not delivered deliveries. This information may also be used to determine insulin sensitivity.

In the exemplary embodiments, where the controller institutes a purposely not delivered delivery, the user may be informed prior to the non delivered delivery and in some embodiments, the user may be prompted to accept or deny this calibration. In some embodiments, where the user fails to respond within a predetermine amount of time, the system may not proceed with the calibration.

In some embodiments, the system may perform an insulin sensitivity test by adding or subtracting a percentage of requested basal (either based on an algorithm or on a trajectory). For example, in some embodiments, the system may subtract or add 10% basal over a duration and record the at least one sensor data. This may be performed regularly, e.g., each month, or during various events, e.g., sleep, exercise, etc. These calibrations are saved and the system may refer back to them to determine insulin sensitivity or identify a change in insulin sensitivity which may, in some embodiments, prompt the system to request a calibration to be performed again. Thus, the system creates profiles routinely, which may be used to identify possible unexpected data which may prompt another calibration. In these embodiments, the system is routinely optimizing the insulin sensitivity factor and basal rates.

In some embodiments, whether a closed-loop control or semi-closed loop control, the system may initialize as an open loop system and in some embodiments, may gradually transition to a closed-loop or semi-closed loop system. In some embodiments, the open loop start-up may be required to perform for a predetermined amount of time, e.g., three (3) hours, prior to transitioning to a closed-loop or semi-closed loop system. In some embodiments, the system may be required to perform a minimum number of calibrations at start-up prior to the transition.

Once the system is ready for transition, in some embodiments, the transition may be gradual. In some embodiments, the system may being delivery with a preset basal delivery. In some embodiments, the preset basal delivery may be a percentage, e.g., 10%, 20%, etc., less than average or requested for that user at that time. In some embodiments, the preset basal delivery may start at 50% less than requested, and then move to 40%, then 30%, etc., until the rate reaches 0% less. Thus, at each step, the system may determine whether it is safe to proceed to the next set based on data from at least one glucose sensor, and in some embodiments, additional sensors and/or fingerstick data.

In some embodiments, the system analyzes the glucose data and determines when an excursion has occurred. An excursion may be defined as a glucose reading that is outside the preprogrammed target range. In some embodiments of the system, many different targets may be pre-programmed, either by time or event. An excursion may be defined relative to either the "time" or "event". For example, during a meal event, it may be expected that the user's glucose will rise above the pre-meal target glucose value and then return to a value within the target. Thus, the system may include one target definition during the first 120 minutes following a meal bolus and another during from 120-180 minutes following a meal bolus.

In any case, the system may determine the total amount of time per day the user spent on "excursion". This may provide additional data for the user to re-evaluate one or more of their pre-programmed values, including but not limited to: insulin sensitivity, carbohydrate ratios, targets, and/or boundaries. In some embodiments, the system may include a "grade" or "rating" of the user's glucose levels. The grade or rating may be determined by taking into account one or more of the following, including but not limited to: the average glucose level, the total amount of time spent within target, the total amount of time spent on excursion, total amount of time the glucose value was changing at greater than a predetermined rate, and/or the total amount of time spent below target. In some embodiments, one or more of these factors may be weighted more heavily in the rating method, e.g., total amount of time spent on excursion may be weighted more heavily than the total amount of time spent below target. In some embodiments, the grade or rating may be determined by weighing more heavily the total amount of time spent above or below the target. In some embodiments, the total amount of time the glucose value was changing at greater than a predetermined rate may be weighed more heavily than other factors.

In some embodiments, the average glucose levels may be correlated to a "predicted" A1C level. For example, if a user has an average glucose value of 135 mg/dl over the past 90 days, the system may indicate to the user that this likely translates to an A1C level of 6.0%.

As discussed above, various embodiments of the system may include one or more of the various infusion pumps incorporated herein by reference. Below is a description of some embodiments of the infusion pump which may be used in some embodiments of the system.

Figure 7:
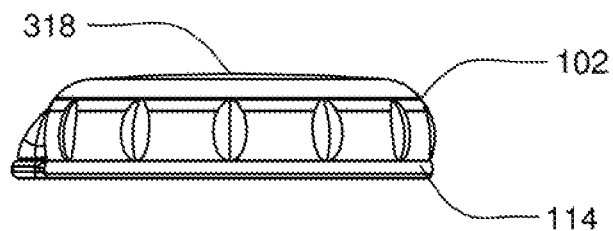
FIG. 7 is a side view of an infusion pump assembly.
Figure 8:
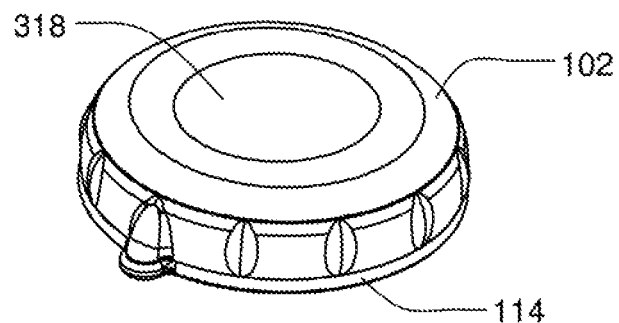
FIG. 8 is a perspective view of the infusion pump assembly of FIG. 7.
Figure 9:
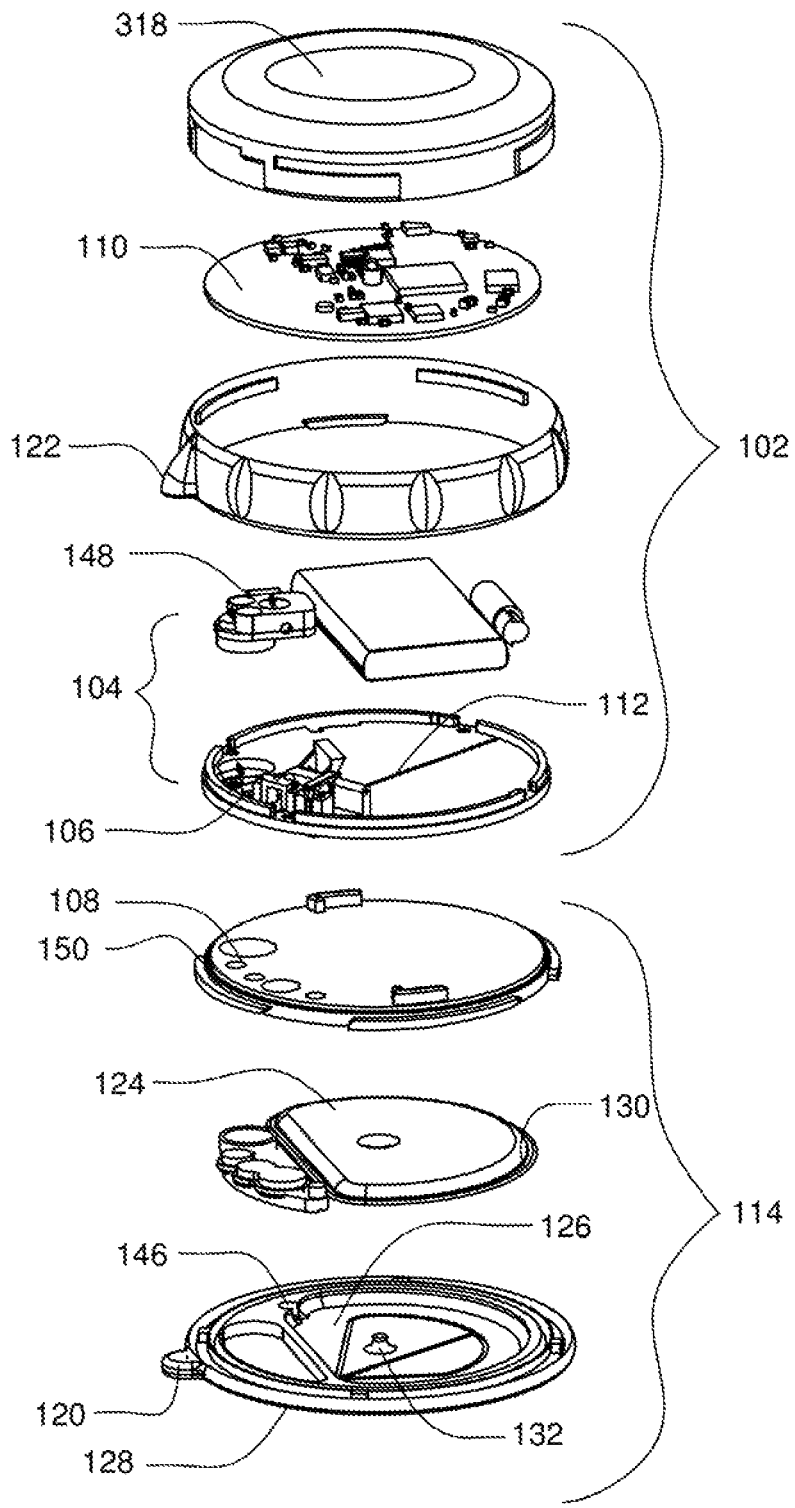
FIG. 9 is an exploded view of various components of the infusion pump assembly of FIG. 7.

Referring to FIGS. 7-9, an infusion pump assembly 100 may include a reusable housing assembly 102. Reusable housing assembly 102 may be constructed from any suitable material, such as a hard or rigid plastic, that will resist compression. For example, use of durable materials and parts may improve quality and reduce costs by providing a reusable portion that lasts longer and is more durable, providing greater protection to components disposed therein.

Reusable housing assembly 102 may include mechanical control assembly 104 having a pump assembly 106 and at least one valve assembly 108. Reusable housing assembly 102 may also include electrical control assembly 110 configured to provide one or more control signals to mechanical control assembly 104 and effectuate the basal and/or bolus delivery of an infusible fluid to a user. Disposable housing assembly 114 may include valve assembly 108 which may be configured to control the flow of the infusible fluid through a fluid path. Reusable housing assembly 102 may also include pump assembly 106 which may be configured to pump the infusible fluid from the fluid path to the user.

Electrical control assembly 110 may monitor and control the amount of infusible fluid that has been and/or is being pumped. For example, electrical control assembly 110 may receive signals from volume sensor assembly 148 and calculate the amount of infusible fluid that has just been dispensed and determine, based upon the dosage required by the user, whether enough infusible fluid has been dispensed. If enough infusible fluid has not been dispensed, electrical control assembly 110 may determine that more infusible fluid should be pumped. Electrical control assembly 110 may provide the appropriate signal to mechanical control assembly 104 so that any additional necessary dosage may be pumped or electrical control assembly 110 may provide the appropriate signal to mechanical control assembly 104 so that the additional dosage may be dispensed with the next dosage. Alternatively, if too much infusible fluid has been dispensed, electrical control assembly 110 may provide the appropriate signal to mechanical control assembly 104 so that less infusible fluid may be dispensed in the next dosage.

Mechanical control assembly 104 may include at least one shape-memory actuator 112. Pump assembly 106 and/or valve assembly 108 of mechanical control assembly 104 may be actuated by at least one shape-memory actuator, e.g., shape-memory actuator 112, which may be a shape-memory wire in wire or spring configuration. Shape memory actuator 112 may be operably connected to and activated by electrical control assembly 110, which may control the timing and the amount of heat and/or electrical energy used to actuate mechanical control assembly 104. Shape memory actuator 112 may be, for example, a conductive shape-memory alloy wire that changes shape with temperature. The temperature of shape-memory actuator 112 may be changed with a heater, or more conveniently, by application of electrical energy. Shape memory actuator 112 may be a shape memory wire constructed of nickel/titanium alloy, such as NITINOL™ or FLEXINOL®.

Infusion pump assembly 100 may include a volume sensor assembly 148 configured to monitor the amount of fluid infused by infusion pump assembly 100. For example, volume sensor assembly 148 may employ, for example, acoustic volume sensing. Acoustic volume measurement technology is the subject of U.S. Pat. Nos. 5,575,310 and 5,755,683 assigned to DEKA Products Limited Partnership, as well as U.S. patent application Publication Nos. US 2007/0228071 A1, US 2007/0219496 A1, US 2007/0219480 A1, US 2007/0219597 A1, the entire disclosures of all of which are incorporated herein by reference. Other alternative techniques for measuring fluid flow may also be used; for example, Doppler-based methods; the use of Hall-effect sensors in combination with a vane or flapper valve; the use of a strain beam (for example, related to a flexible member over a fluid reservoir to sense deflection of the flexible member); the use of capacitive sensing with plates; or thermal time of flight methods. One such alternative technique is disclosed in U.S. patent application Ser. No. 11/704,899, entitled Fluid Delivery Systems and Methods, filed 9 Feb. 2007, the entire disclosure of which is incorporated herein by reference. Infusion pump assembly 100 may be configured so that the volume measurements produced by volume sensor assembly 148 may be used to control, through a feedback loop, the amount of infusible fluid that is infused into the user.

Infusion pump assembly 100 may further include a disposable housing assembly 114. For example, disposable housing assembly 114 may be configured for a single use or for use for a specified period of time, e.g., three days or any other amount of time. Disposable housing assembly 114 may be configured such that any components in infusion pump assembly 100 that come in contact with the infusible fluid are disposed on and/or within disposable housing assembly 114. For example, a fluid path or channel including a reservoir, may be positioned within disposable housing assembly 114 and may be configured for a single use or for a specified number of uses before disposal. The disposable nature of disposable housing assembly 114 may improve sanitation of infusion pump assembly 100.

Figure 10:
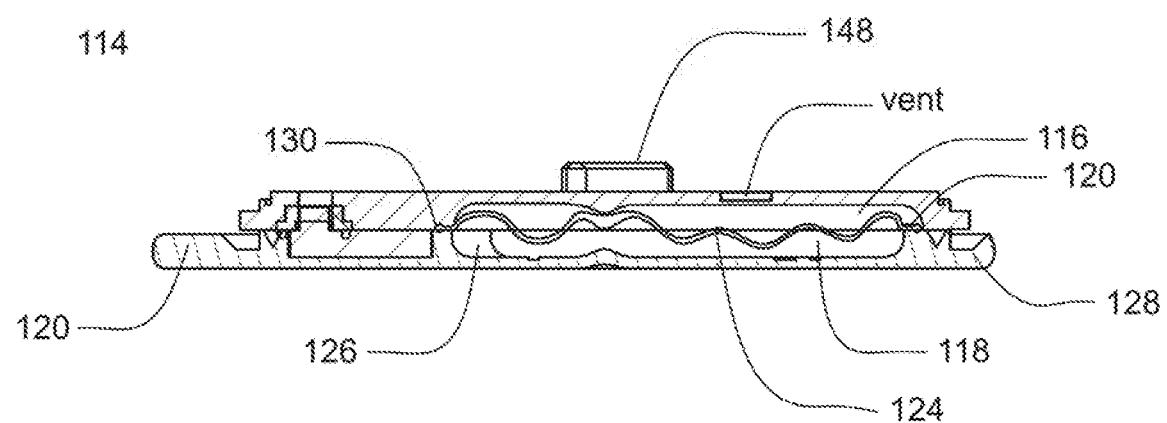
FIG. 10 is a cross-sectional view of the disposable housing assembly of the infusion pump assembly of FIG. 7.

Referring also to FIG. 10, disposable housing assembly 114 may be configured to releasably engage reusable housing assembly 102, and includes a cavity 116 that has a reservoir 118 for receiving an infusible fluid (not shown), e.g., insulin. Such releasable engagement may be accomplished by a screw-on, a twist-lock or a compression fit configuration, for example. Disposable housing assembly 114 and/or reusable housing assembly 102 may include an alignment assembly configured to assist in aligning disposable housing assembly 114 and reusable housing assembly 102 for engagement in a specific orientation. Similarly, base nub 120 and top nub 122 may be used as indicators of alignment and complete engagement.

Cavity 116 may be at least partially formed by and integral to disposable housing assembly 114. Cavity 116 may include a membrane assembly 124 for at least partially defining reservoir 118. Reservoir 118 may be further defined by disposable housing assembly 114, e.g., by a recess 126 formed in base portion 128 of disposable housing assembly 114. For example, membrane assembly 124 may be disposed over recess 126 and attached to base portion 128, thereby forming reservoir 118. Membrane assembly 124 may be attached to base portion 128 by conventional means, such as gluing, heat sealing, and/or compression fitting, such that a seal 130 is formed between membrane assembly 124 and base portion 128. Membrane assembly 124 may be flexible and the space formed between membrane assembly 124 and recess 126 in base portion 128 may define reservoir 118. Reservoir 118 may be non-pressurized and in fluid communication with a fluid path (not shown). Membrane assembly 124 may be at least partially collapsible and cavity 116 may include a vent assembly, thereby advantageously preventing the buildup of a vacuum in reservoir 118 as the infusible fluid is delivered from reservoir 118 to the fluid path. In a preferred embodiment, membrane assembly 124 is fully collapsible, thus allowing for the complete delivery of the infusible fluid. Cavity 116 may be configured to provide sufficient space to ensure there is always some air space even when reservoir 118 is filled with infusible fluid.

The membranes and reservoirs described herein may be made from materials including but not limited to silicone, NITRILE, and any other material having desired resilience and properties for functioning as described herein. Additionally, other structures could serve the same purpose.

The use of a partially collapsible non pressurized reservoir may advantageously prevent the buildup of air in the reservoir as the fluid in the reservoir is depleted. Air buildup in a vented reservoir could prevent fluid egress from the reservoir, especially if the system is tilted so that an air pocket intervenes between the fluid contained in the reservoir and the septum of the reservoir. Tilting of the system is expected during normal operation as a wearable device.

Reservoir 118 may be conveniently sized to hold an insulin supply sufficient for delivery over one or more days. For example, reservoir 118 may hold about 1.00 to 3.00 ml of insulin. A 3.00 ml insulin reservoir may correspond to approximately a three day supply for about 90% of potential users. In other embodiments, reservoir 118 may be any size or shape and may be adapted to hold any amount of insulin or other infusible fluid. In some embodiments, the size and shape of cavity 116 and reservoir 118 is related to the type of infusible fluid that cavity 116 and reservoir 118 are adapted to hold.

Disposable housing assembly 114 may include a support member 132 (FIG. 9) configured to prevent accidental compression of reservoir 118. Compression of reservoir 118 may result in an unintentional dosage of infusible fluid being forced through the fluid path to the user. In a preferred embodiment, reusable housing assembly 102 and disposable housing assembly 114 may be constructed of a rigid material that is not easily compressible. However, as an added precaution, support member 132 may be included within disposable housing assembly 114 to prevent compression of infusion pump assembly 100 and cavity 116 therein. Support member 132 may be a rigid projection from base portion 128. For example, support member 132 may be disposed within cavity 116 and may prevent compression of reservoir 118.

As discussed above, cavity 116 may be configured to provide sufficient space to ensure there is always some air space even when reservoir 118 is filled with infusible fluid. Accordingly, in the event that infusion pump assembly 100 is accidentally compressed, the infusible fluid may not be forced through cannula assembly 136.

Cavity 116 may include a septum assembly 146 (FIG. 9) configured to allow reservoir 118 to be filled with the infusible fluid. Septum assembly 146 may be a conventional septum made from rubber or plastic and have a one-way fluid valve configured to allow a user to fill reservoir 118 from a syringe or other filling device. In some embodiments, septum 146 may be located on the top of membrane assembly 124. In these embodiments, cavity 116 may include a support structure (e.g., support member 132 in FIG. 9) for supporting the area about the back side of the septum so as to maintain the integrity of the septum seal when a needle is introducing infusible fluid into cavity 116. The support structure may be configured to support the septum while still allowing the introduction of the needle for introducing infusible fluid into cavity 116.

Infusion pump assembly 100 may include an overfill prevention assembly (not shown) that may e.g., protrude into cavity 116 and may e.g., prevent the overfilling of reservoir 118.

Figure 12:
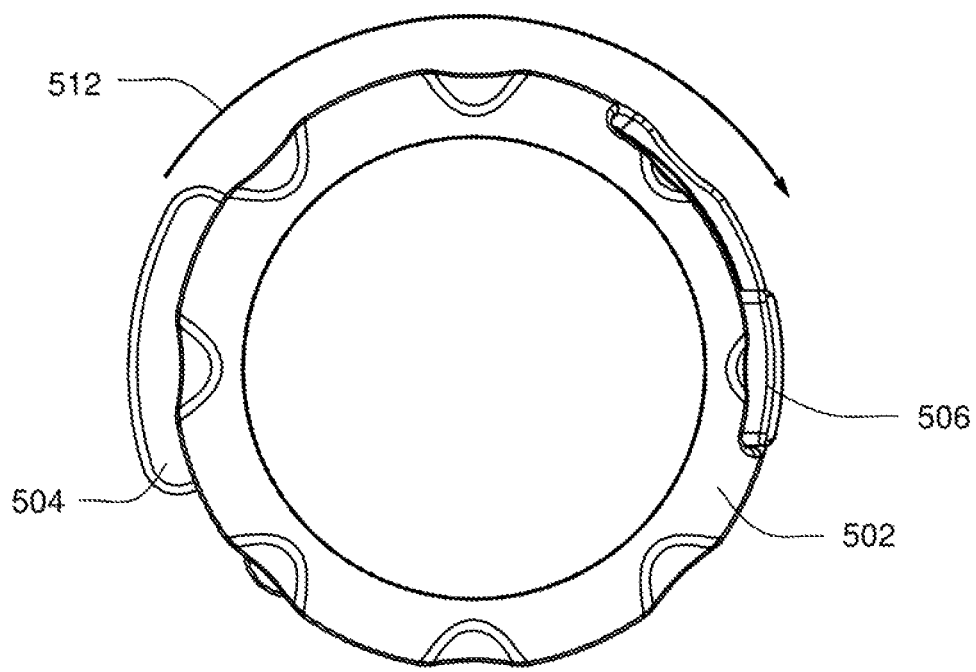
FIG. 12 is an plan view of the infusion pump assembly of FIG. 11.
Figure 13:
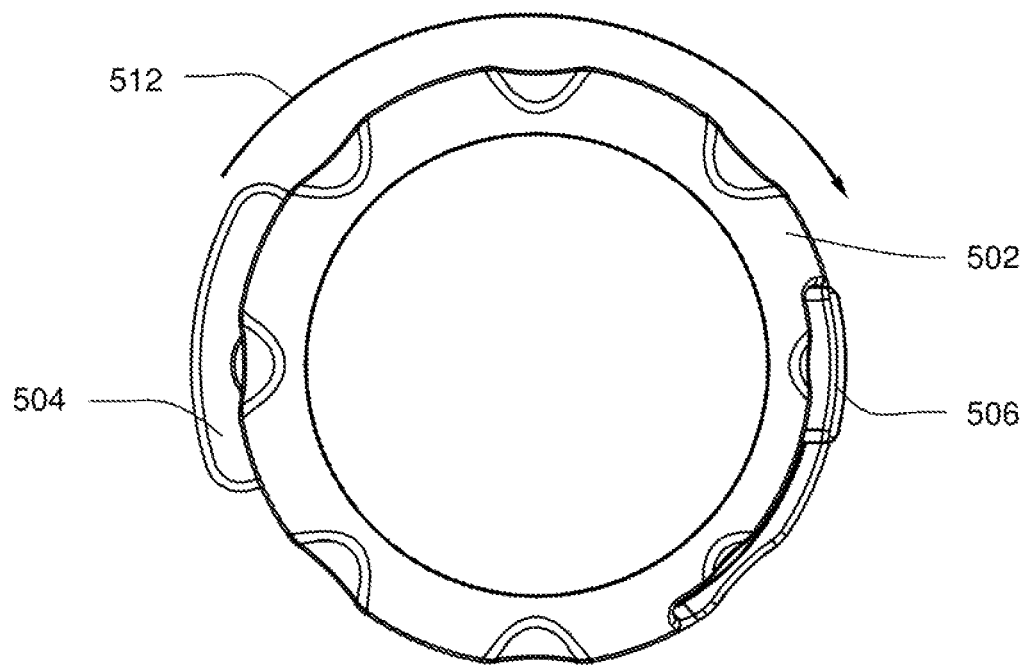
FIG. 13 is a plan view of the infusion pump assembly of FIG. 11.
Figure 14:
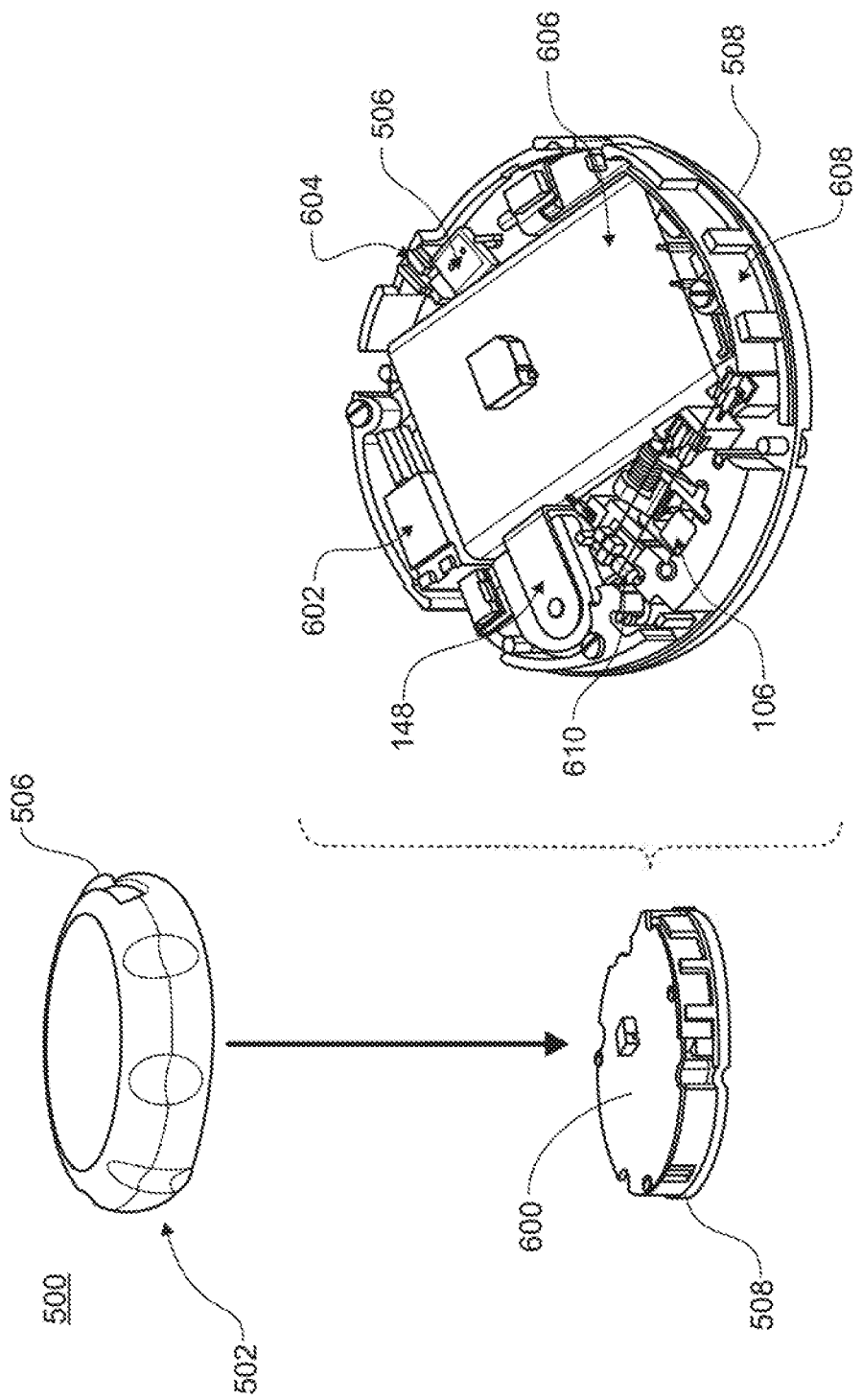
FIG. 14A is an exploded view of various components of the infusion pump assembly of FIG. 16.
FIG. 14B is an isometric view of a portion of the infusion pump assembly of FIG. 11.
Figure 15:
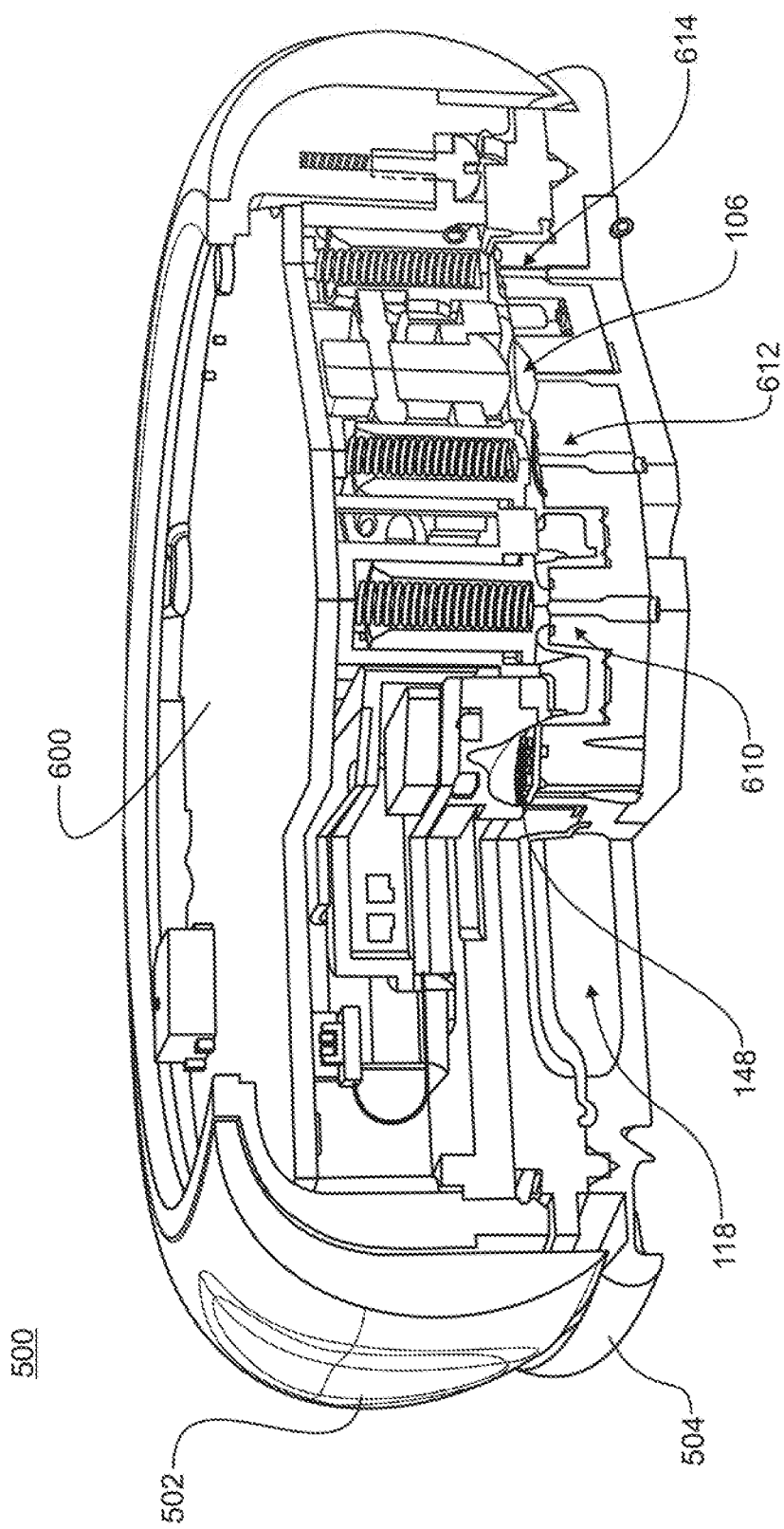
FIG. 15 is a cross-sectional view of the disposable housing assembly of the infusion pump assembly of FIG. 11.
Figure 16:
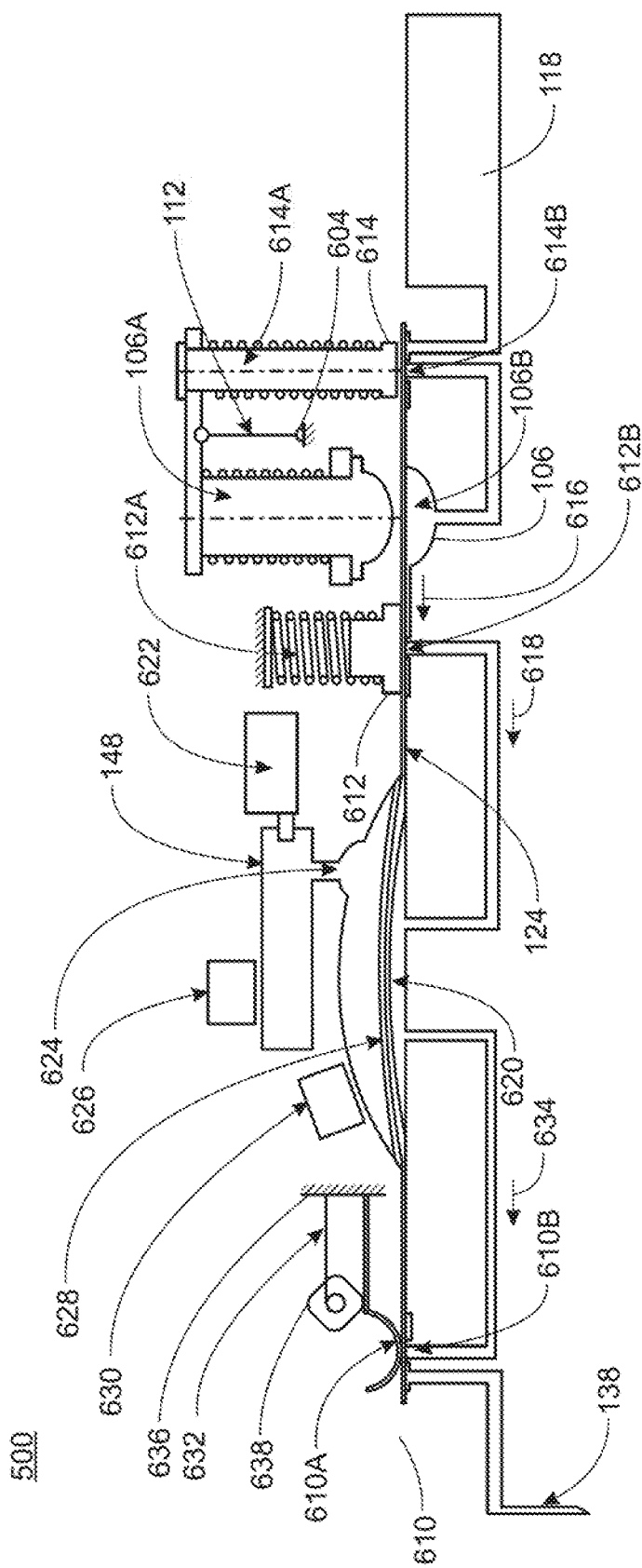
FIG. 16 is a diagrammatic view of a fluid path within the infusion pump assembly of FIG. 11.

Referring also to FIGS. 11-13, there is shown an alternative-embodiment infusion pump assembly 500. As with pump assembly 100, 100', infusion pump assembly 500 may include reusable housing assembly 502 and disposable housing assembly 504.

In a fashion similar to reusable housing assembly 402, reusable housing assembly 502 may include a mechanical control assembly (that includes at least one pump assembly and at least one valve assembly). Reusable housing assembly 502 may also include an electrical control assembly that is configured to provide control signals to the mechanical control assembly and effectuate the delivery of an infusible fluid to a user. The valve assembly may be configured to control the flow of the infusible fluid through a fluid path and the pump assembly may be configured to pump the infusible fluid from the fluid path to the user In a fashion similar to disposable housing assembly 404, disposable housing assembly 504 may be configured for a single use or for use for a specified period of time, e.g., e.g., three days or any other amount of time. Disposable housing assembly 504 may be configured such that any components in infusion pump assembly 500 that come in contact with the infusible fluid are disposed on and/or within disposable housing assembly 504.

In this particular embodiment of the infusion pump assembly, infusion pump assembly 500 may include switch assembly 506 positioned about the periphery of infusion pump assembly 500. For example, switch assembly 506 may be positioned along a radial edge of infusion pump assembly 500, which may allow for easier use by a user. Switch assembly 506 may be covered with a waterproof membrane and/or an o-ring or other sealing mechanism may be included on the stem 507 of the switch assembly 506 configured to prevent the infiltration of water into infusion pump assembly 500. However, in some embodiments, switch assembly 506 may include an overmolded rubber button, thus providing functionality as a waterproof seal without the use of a waterproof membrane or an o-ring. However, in still other embodiments, the overmolded rubber button may additionally be covered by a waterproof membrane and/or include an o-ring. Reusable housing assembly 502 may include main body portion 508 (housing the above-described mechanical and electrical control assemblies) and locking ring assembly 510 that may be configured to rotate about main body portion 508 (in the direction of arrow 512).

In a fashion similar to reusable housing assembly 402 and disposable housing assembly 404, reusable housing assembly 502 may be configured to releasably engage disposable housing assembly 504. Such releasable engagement may be accomplished by a screw-on, a twist-lock or a compression fit configuration, for example. In an embodiment in which a twist-lock configuration is utilized, the user of infusion pump assembly 500 may first properly position reusable housing assembly 502 with respect to disposable housing assembly 504 and may then rotate locking ring assembly 510 (in the direction of arrow 512) to releasably engage reusable housing assembly 502 with disposable housing assembly 404.

As locking ring assembly 510 included within infusion pump assembly 500 may be taller (i.e., as indicated by arrow 514) than locking ring assembly 410, locking ring assembly 510 may include a passage 516 through which button 506 may pass. Accordingly, when assembling reusable housing assembly 502, locking ring assembly 510 may be installed onto main body portion 508 (in the direction of arrow 518). Once locking ring assembly 510 is installed onto main body portion 508, one or more locking tabs (not shown) may prevent locking ring assembly 510 from being removed from main body portion 508. The portion of switch assembly 506 that protrudes through passage 516 may then be pressed into main body portion 508 (in the direction of arrow 520), thus completing the installation of switch assembly 506.

Although button 506 is shown in various locations on infusion pump assembly 500, button 506, in other embodiments, may be located anywhere desirable on infusion pump assembly 500.

Through the use of locking ring assembly 510, reusable housing assembly 502 may be properly positioned with respect to disposable housing assembly 504 and then releasably engaged by rotating locking ring assembly 510, thus eliminating the need to rotate reusable housing assembly 502 with respect to disposable housing assembly 504. Accordingly, reusable housing assembly 502 may be properly aligned with disposable housing assembly 504 prior to engagement, and such alignment may not be disturbed during the engagement process. Locking ring assembly 510 may include a latching mechanism (not shown) that prevents the rotation of locking ring assembly 510 until reusable housing assembly 502 and disposable housing assembly 504 are properly positioned with respect to each other. Passage 516 may be elongated to allow for the movement of locking ring 510 about switch assembly 506.

Referring also to FIGS. 14A-14B & 15-16, there are shown various views of infusion pump assembly 500, which is shown to include reusable housing assembly 502, switch assembly 506, and main body portion 508. As discussed above, main body portion 508 may include a plurality of components, examples of which may include but are not limited to volume sensor assembly 148, printed circuit board 600, vibration motor assembly 602, shape memory actuator anchor 604, switch assembly 506, battery 606, antenna assembly 608, pump assembly 106, measurement valve assembly 610, volume sensor valve assembly 612 and reservoir valve assembly 614. To enhance clarity, printed circuit board 600 has been removed from FIG. 14B to allow for viewing of the various components positioned beneath printed circuit board 600.

The various electrical components that may be electrically coupled with printed circuit board 600 may utilize spring-biased terminals that allow for electrical coupling without the need for soldering the connections. For example, vibration motor assembly 602 may utilize a pair of spring-biased terminals (one positive terminal and one negative terminal) that are configured to press against corresponding conductive pads on printed circuit board 600 when vibration motor assembly 602 is positioned on printed circuit board 600. However, in the exemplary embodiment, vibration motor assembly 602 is soldered directly to the printed circuit board.

As discussed above, volume sensor assembly 148 may be configured to monitor the amount of fluid infused by infusion pump assembly 500. For example, volume sensor assembly 148 may employ acoustic volume sensing, which is the subject of U.S. Pat. Nos. 5,575,310 and 5,755,683 assigned to DEKA Products Limited Partnership, as well as the U.S. patent application Publication Nos. US 2007/0228071 A1, US 2007/0219496 A1, US 2007/0219480 A1, US 2007/0219597 A1, the entire disclosures of all of which are incorporated herein by reference.

Vibration motor assembly 602 may be configured to provide a vibration-based signal to the user of infusion pump assembly 500. For example, in the event that the voltage of battery 606 (which powers infusion pump assembly 500) is below the minimum acceptable voltage, vibration motor assembly 602 may vibrate infusion pump assembly 500 to provide a vibration-based signal to the user of infusion pump assembly 500. Shape memory actuator anchor 604 may provide a mounting point for the above-described shape memory actuator (e.g. shape memory actuator 112). As discussed above, shape memory actuator 112 may be, for example, a conductive shape-memory alloy wire that changes shape with temperature. The temperature of shape-memory actuator 112 may be changed with a heater, or more conveniently, by application of electrical energy. Accordingly, one end of shape memory actuator 112 may be rigidly affixed (i.e., anchored) to shape memory actuator anchor 604 and the other end of shape memory actuator 112 may be applied to e.g. a valve assembly and/or a pump actuator. Therefore, by applying electrical energy to shape memory actuator 112, the length of shape memory actuator 112 may be controlled and, therefore, the valve assembly and/or the pump actuator to which it is attached may be manipulated.

Antenna assembly 608 may be configured to allow for wireless communication between e.g. infusion pump assembly 500 and a remote control assembly. As discussed above, the remote control assembly may allow the user to program infusion pump assembly 500 and e.g. configure bolus infusion events. As discussed above, infusion pump assembly 500 may include one or more valve assemblies configured to control the flow of the infusible fluid through a fluid path (within infusion pump assembly 500) and pump assembly 106 may be configured to pump the infusible fluid from the fluid path to the user. In this particular embodiment of infusion pump assembly 500, infusion pump assembly 500 is shown to include three valve assemblies, namely measurement valve assembly 610, volume sensor valve assembly 612, and reservoir valve assembly 614.

Figure 17A:
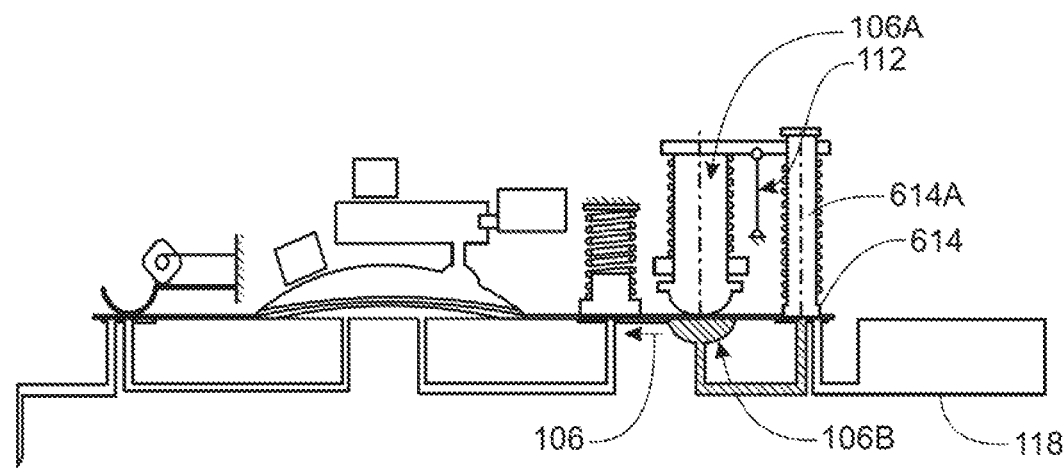
FIGS. 17A-17C are diagrammatic views of a fluid path within the infusion pump assembly of FIG. 16.

As discussed above and referring also to FIG. 16, the infusible fluid may be stored within reservoir 118. In order to effectuate the delivery of the infusible fluid to the user, the processing logic (not shown) included within infusion pump assembly 500 may energize shape memory actuator 112, which may be anchored on one end using shape memory actuator anchor 604. Referring also to FIG. 17A, shape memory actuator 112 may result in the activation of pump assembly 106 and reservoir valve assembly 614. Reservoir valve assembly 614 may include reservoir valve actuator 614A and reservoir valve 614B, and the activation of reservoir valve assembly 614 may result in the downward displacement of reservoir valve actuator 614A and the closing of reservoir valve 614B, resulting in the effective isolation of reservoir 118. Further, pump assembly 106 may include pump plunger 106A and pump chamber 106B and the activation of pump assembly 106 may result in pump plunger 106A being displaced in a downward fashion into pump chamber 106B and the displacement of the infusible fluid (in the direction of arrow 616).

Figure 17B:
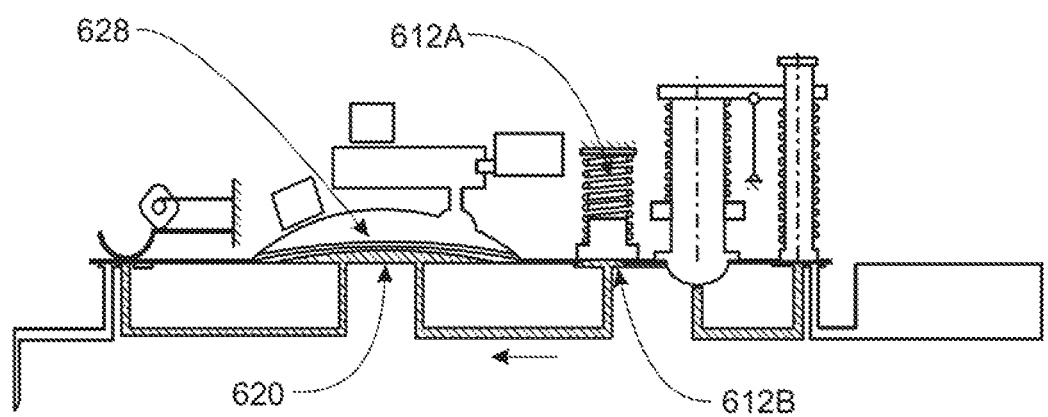

Volume sensor valve assembly 612 may include volume sensor valve actuator 612A and volume sensor valve 612B. Referring also to FIG. 17B, volume sensor valve actuator 612A may be closed via a spring assembly that provides mechanical force to seal volume sensor valve 612B. However, when pump assembly 106 is activated, if the displaced infusible fluid is of sufficient pressure to overcome the mechanical sealing force of volume sensor valve assembly 612, the displacement of the infusible fluid occurs in the direction of arrow 618. This may result in the filling of volume sensor chamber 620 included within volume sensor assembly 148. Through the use of speaker assembly 622, port assembly 624, reference microphone 626, spring diaphragm 628, invariable volume microphone 630, volume sensor assembly 148 may determine the volume of infusible fluid included within volume sensor chamber 620.

Figure 17C:
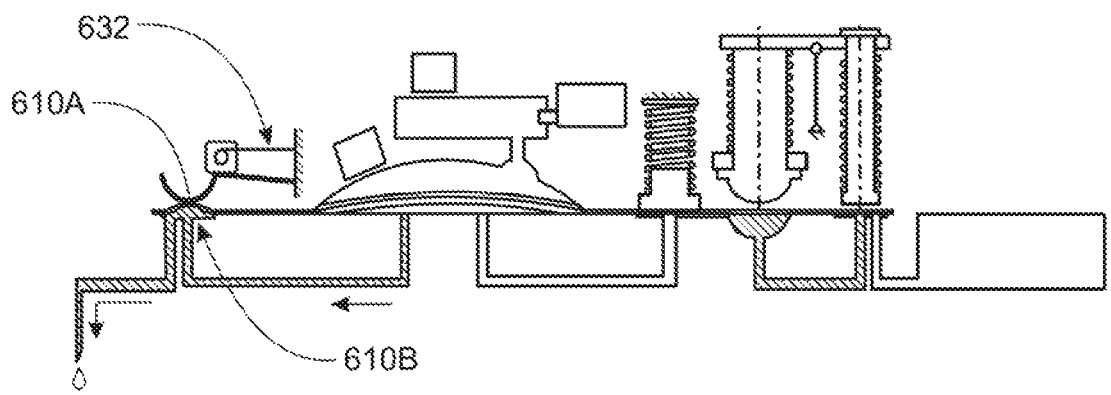

Referring also to FIG. 17C, once the volume of infusible fluid included within volume sensor chamber 620 is calculated, shape memory actuator 632 may be energized, resulting in the activation of measurement valve assembly 610, which may include measurement valve actuator 610A and measurement valve 610B. Once activated and due to the mechanical energy asserted on the infusible fluid within volume sensor chamber 620 by spring diaphragm 628, the infusible fluid within volume sensor chamber 620 may be displaced (in the direction of arrow 634) through disposable cannula 138 and into the body of the user.

Figure 18:
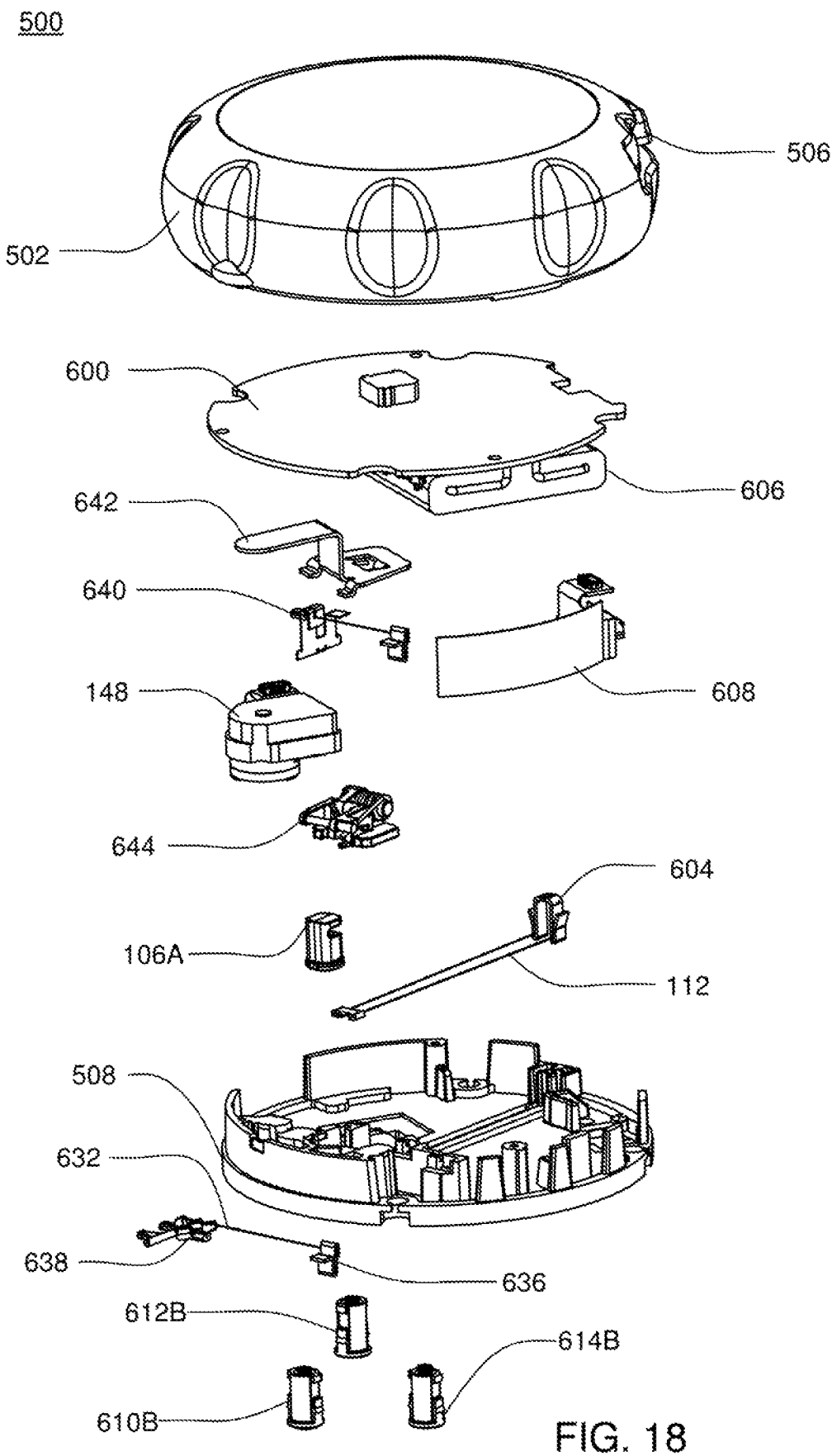
FIG. 18 is an exploded view of various components of the infusion pump assembly of FIG. 11.

Referring also to FIG. 18, there is shown an exploded view of infusion pump assembly 500. Shape memory actuator 632 may be anchored (on a first end) to shape memory actuator anchor 636. Additionally, the other end of shape memory actuator 632 may be used to provide mechanical energy to valve assembly 638, which may activate measurement valve assembly 610. Volume sensor assembly spring retainer 642 may properly position volume sensor assembly 148 with respect to the various other components of infusion pump assembly 500. Valve assembly 638 may be used in conjunction with shape memory actuator 112 to activate pump plunger 106A. Measurement valve 610B, volume sensor valve 612B and/or reservoir valve 614B may be self-contained valves that are configured to allow for installation during assembly of infusion pump assembly 500 by pressing the valves upward into the lower surface of main body portion 508.

As discussed above, infusion pump assembly 100 may include volume sensor assembly 148 configured to monitor the amount of fluid infused by infusion pump assembly 100. Further and as discussed above, infusion pump assembly 100 may be configured so that the volume measurements produced by volume sensor assembly 148 may be used to control, through a feedback loop, the amount of infusible fluid that is infused into the user.

Figure 19:
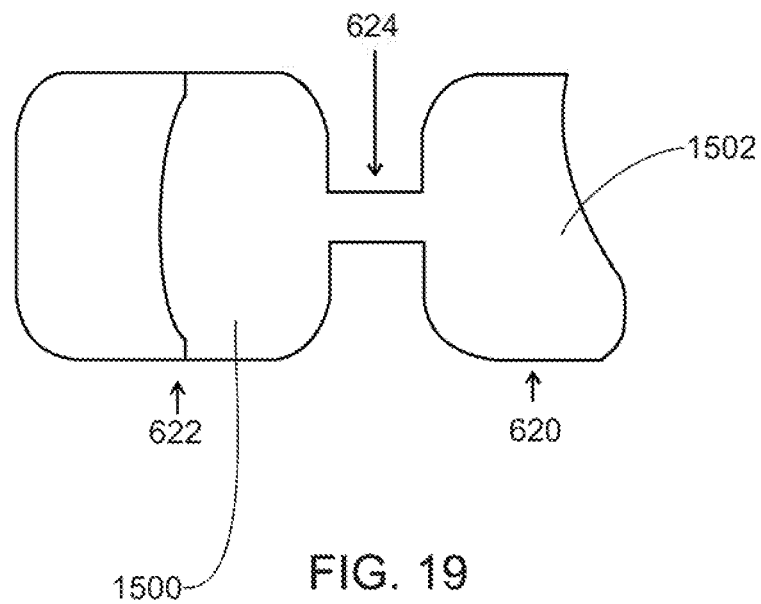
FIG. 19 is a diagrammatic view of a volume sensor assembly included within the infusion pump assembly.

The following discussion concerns the design and operation of volume sensor assembly 148 (which is shown in a simplified form in FIG. 19). For the following discussion, the following nomenclature may be used:

| Symbols | |
| --- | --- |
| P | Pressure |
| p | Pressure Perturbation |
| V | Volume |
| v | Volume Perturbation |
| γ | Specific Heat Ratio |
| R | Gas Constant |
| ρ | Density |
| Z | Impedance |
| f | Flow friction |
| A | Cross sectional Area |
| L | Length |
| ω | Frequency |
| ζ | Damping ratio |
| α | Volume Ratio |
| Subscripts | |
| 0 | Speaker Volume |
| 1 | Reference Volume |
| 2 | Variable Volume |
| k | Speaker |
| r | Resonant Port |
| z | Zero |
| p | Pole |

Derivation of the Equations for Volume Sensor Assembly 148:

Modeling the Acoustic Volumes

The pressure and volume of an ideal adiabatic gas may be related by:

$$PV^\gamma = K \quad [\text{EQ \#1}]$$

where K is a constant defined by the initial conditions of the system.

EQ #1 may be written in terms of a mean pressure, P, and volume, V, and a small time-dependent perturbation on top of those pressures, p(t), v(t) as follows:

$$(P+p(t))(V+v(t))^\gamma = K \quad [\text{EQ \#2}]$$

Differentiating this equation may result in:

$$\dot{p}(t)(V+v(t))^\gamma + \gamma(V+v(t))^{\gamma-1}(P+p(t))\dot{v}(t) = 0 \quad [\text{EQ \#3}]$$

which may simplify to:

$$\dot{p}(t) = \gamma \frac{P+p(t)}{V+v(t)} \dot{v}(t) = 0 \quad [\text{EQ\#4}]$$

If the acoustic pressure levels are much less than the ambient pressure, the equation may be further simplified to:

$$\dot{p}(t) + \frac{\gamma P}{V} \dot{v}(t) = 0 \quad [\text{EQ\#5}]$$

How good is this assumption? Using the adiabatic relation it may be shown that:

$$\frac{P}{V} = \left(\frac{P+p(t)}{V+v(t)}\right)\left(\frac{P+p(t)}{P}\right)^{-\frac{\gamma+1}{\gamma}} \quad [\text{EQ\#6}]$$

Accordingly, the error in the assumption would be:

$$\text{error} = 1 - \left(\frac{P+p(t)}{P}\right)^{-\frac{\gamma+1}{\gamma}} \quad [\text{EQ\#7}]$$

A very loud acoustic signal (120 dB) may correspond to pressure sine wave with amplitude of roughly 20 Pascal. Assuming air at atmospheric conditions (γ=1.4, P=101325 Pa), the resulting error is 0.03%. The conversion from dB to Pa is as follows:

$$\lambda = 20 \log_{10}\left(\frac{p_{rms}}{p_{ref}}\right) \text{ or } p_{rms} = p_{ref} 10^{\frac{\lambda}{20}} \quad [\text{EQ\#8}]$$

where $p_{ref}$=20·μPa.

Applying the ideal gas law, P=ρRT, and substituting in for pressure may result in the following:

$$\dot{p}(t) + \frac{\gamma RT \rho}{V} \dot{v}(t) = 0 \quad [\text{EQ\#9}]$$

EQ #9 may be written in terms of the speed of sound, $$a = \sqrt{\gamma RT}$$

as follows:

$$\dot{p}(t) + \frac{\rho a^2}{V} \dot{v}(t) = 0 \quad [\text{EQ\#10}]$$

Acoustic impedance for a volume may be defined as follows:

$$Z_v = \frac{p(t)}{\dot{v}(t)} = -\frac{1}{\left(\frac{V}{\rho a^2}\right)s} \quad [\text{EQ\#11}]$$

Modeling the Acoustic Port

The acoustic port may be modeled assuming that all of the fluid in the port essentially moves as a rigid cylinder reciprocating in the axial direction. All of the fluid in the channel is assumed to travel at the same velocity, the channel is assumed to be of constant cross section, and the "end effects" resulting from the fluid entering and leaving the channel are neglected.

If we assume laminar flow friction of the form $\Delta p = f \rho \dot{v}$, the friction force acting on the mass of fluid in the channel may be written as follows:

$$F = f\rho A^2 \dot{x} \quad [\text{EQ \#12}]$$

A second order differential equation may then be written for the dynamics of the fluid in the channel:

$$\beta L A \ddot{x} = \Delta p A - f \rho A^2 \dot{x} \quad [\text{EQ \#13}]$$

or, in terms of volume flow rate:

$$\ddot{v} = -\frac{fA}{L}\dot{v} + \Delta p \frac{A}{\rho L} \quad [\text{EQ\#14}]$$

The acoustic impedance of the channel may then be written as follows:

$$Z_p = \frac{\Delta p}{\dot{v}} = \frac{\rho L}{A}\left(s + \frac{fA}{L}\right) \quad [\text{EQ\#15}]$$

System Transfer Functions

Using the volume and port dynamics defined above, volume sensor assembly 148 may be described by the following system of equations: (k=speaker, r=resonator)

$$\dot{p}_0 - \frac{\rho a^2}{V_0}\dot{v}_k = 0 \quad [\text{EQ\#16}]$$

$$\dot{p}_1 + \frac{\rho a^2}{V_1}(\dot{v}_k - \dot{v}_r) = 0 \quad [\text{EQ\#17}]$$

$$\dot{p}_2 + \frac{\rho a^2}{V_2}\dot{v}_r = 0 \quad [\text{EQ\#18}]$$

$$\ddot{v}_r = -\frac{fA}{L}\dot{v}_r + \frac{A}{\rho L}(p_2 - p_1) \quad [\text{EQ\#19}]$$

One equation may be eliminated if $p_0$ is treated as the input substituting in $$\dot{v}_k = \frac{V_0}{\rho a^2}\dot{p}_0.$$

$$\dot{p}_1 + \frac{V_0}{V_1}\dot{p}_0 - \frac{\rho a^2}{V_1}\dot{v}_r = 0 \quad [\text{EQ\#20}]$$

$$\dot{p}_2 + \frac{\rho a^2}{V_2}\dot{v}_r = 0 \quad [\text{EQ\#21}]$$

$$\ddot{v}_r = -\frac{fA}{L}\dot{v}_r + \frac{A}{\rho L}p_2 - \frac{A}{\rho L}p_1 \quad [\text{EQ\#22}]$$

Cross System Transfer Function

The relationship between the speaker volume and the variable volume may be referred to as the Cross System transfer function. This transfer function may be derived from the above equations and is as follows:

$$\frac{p_2}{p_0} = -\frac{V_0}{V_1}\frac{\omega_n^2}{s^2 + 2\zeta\omega_n s + \alpha\omega_n^2} \quad [\text{EQ\#23}]$$

where $$\omega_n^2 = \frac{a^2 A}{L}\frac{1}{V_2}, \zeta = \frac{fA}{2L\omega_n} \text{ and} \quad [\text{EQ\#24}]$$

$$\alpha = \left(1 + \frac{V_2}{V_1}\right)$$

Figure 20:
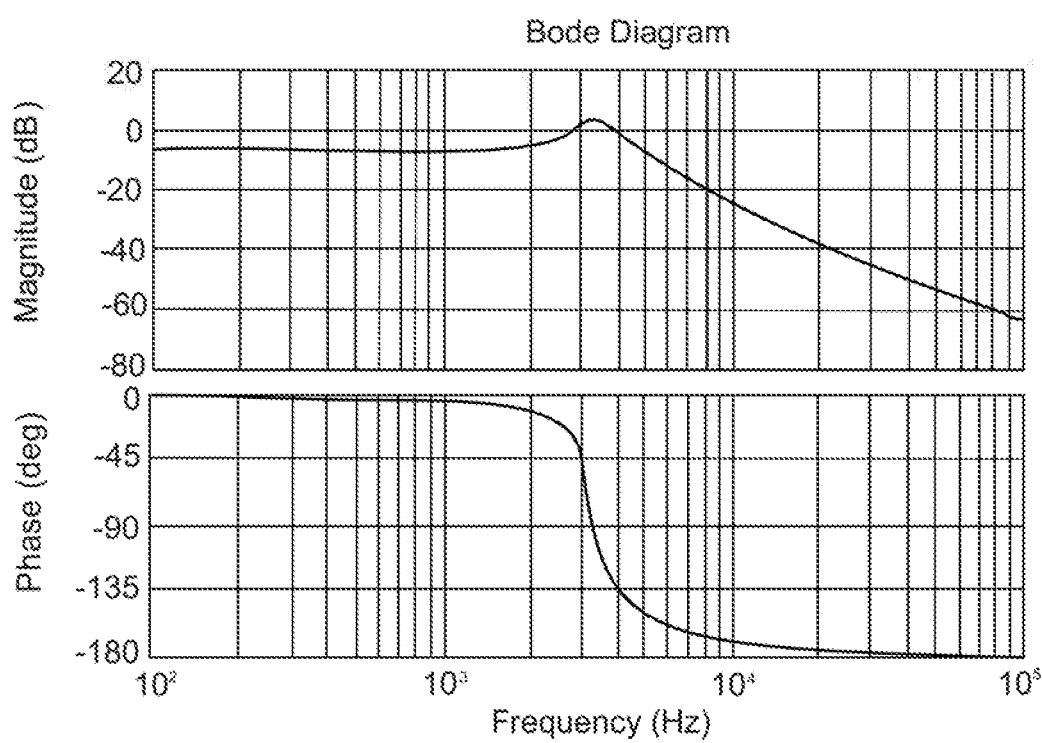
FIG. 20 is a two-dimensional graph of a performance characteristic of the volume sensor assembly of FIG. 19.

Referring also to FIG. 20, a bode plot of EQ #23 is shown.

The difficulty of this relationship is that the complex poles depend on both the variable volume, $V_2$, and the reference volume, $V_1$. Any change in the mean position of the speaker may result in an error in the estimated volume.

Cross Port Transfer Function

Figure 21:
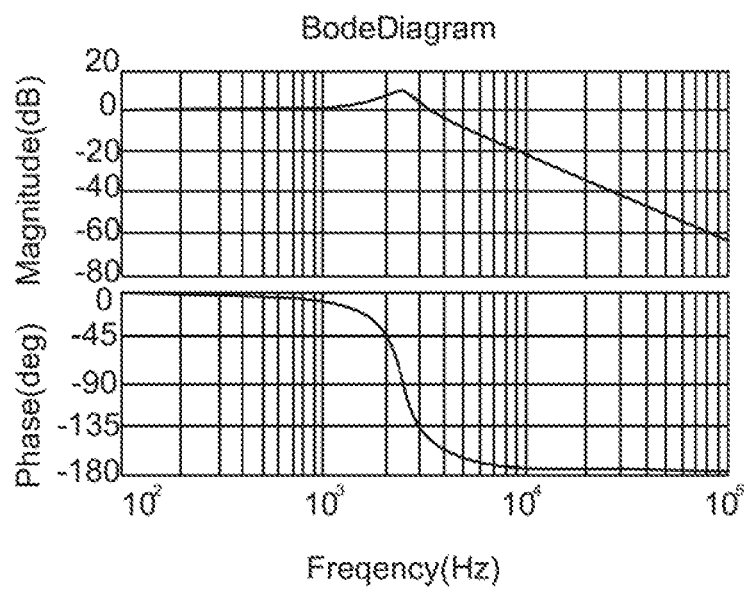
FIG. 21 is a two-dimensional graph of a performance characteristic of the volume sensor assembly of FIG. 19.

The relationship between the two volumes on each side of the acoustic port may be referred to as the Cross Port transfer function. This relationship is as follows:

$$\frac{p_2}{p_1} = \frac{\omega_n^2}{s^2 + 2\zeta\omega_n s + \omega_n^2} \quad [\text{EQ\#25}]$$

which is shown graphically in FIG. 21.

This relationship has the advantage that the poles are only dependent on the variable volume and not on the reference volume. It does, however, have the difficulty that the resonant peak is actually due to the inversion of the zero in the response of the reference volume pressure. Accordingly, the pressure measurement in the reference chamber will have a low amplitude in the vicinity of the resonance, potentially increasing the noise in the measurement.

Cross Speaker Transfer Function

Figure 22:
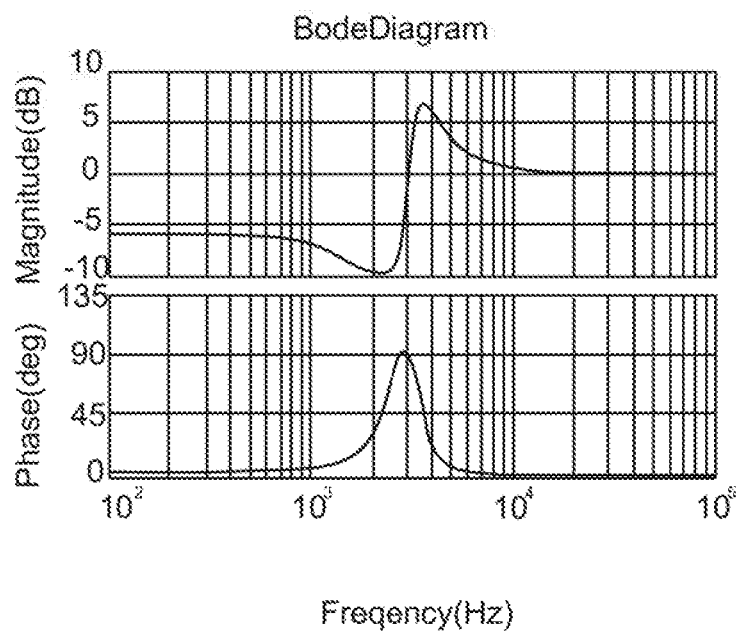
FIG. 22 is a two-dimensional graph of a performance characteristic of the volume sensor assembly of FIG. 19.

The pressures may also be measured on each side of the speaker. This is referred to as the cross speaker transfer function:

$$\frac{p_1}{p_0} = -\frac{V_0}{V_1}\frac{s^2 + 2\zeta\omega_n s + \omega_n^2}{s^2 + 2\zeta\omega_n s + \alpha\omega_n^2} \quad [\text{EQ\#26}]$$

which is shown graphically in FIG. 22.

This transfer function has a set of complex zeros in addition to the set of complex poles.

Looking at the limits of this transfer function: as $$s \to 0, \frac{p_1}{p_0} \to -\frac{V_0}{V_1 + V_2}; \text{ and as } s \to \infty, \frac{p_1}{p_0} \to -\frac{V_0}{V_1}.$$

Resonance Q Factor and Peak Response

The quality of the resonance is the ratio of the energy stored to the power loss multiplied by the resonant frequency. For a pure second-order system, the quality factor may be expressed as a function of the damping ratio:

$$Q = \frac{1}{2\zeta} \quad [\text{EQ\#27}]$$

The ratio of the peak response to the low-frequency response may also be written as a function of the damping ratio:

$$|G|_{\omega_d} = \frac{1}{\zeta\sqrt{5 - 4\zeta}} \quad [\text{EQ\#28}]$$

This may occur at the damped natural frequency:

$$\omega_d = \omega_n\sqrt{1 - \zeta} \quad [\text{EQ\#29}]$$

Volume Estimation

Volume Estimation Using Cross-Port Phase

The variable volume (i.e., within volume sensor chamber 620) may also be estimated using the cross-port phase. The transfer function for the pressure ratio across the resonant port may be as follows:

$$\frac{p_2}{p_1} = \frac{\omega_n^2}{s^2 + bs + \omega_n^2} \quad [\text{EQ\#30}]$$

At the 90° phase point, $\omega = \omega_n$; where $$\omega_n^2 = \frac{1}{V_2}\frac{a^2 A}{L}$$

The resonant frequency may be found on the physical system using a number of methods. A phase-lock loop may be employed to find the 90° phase point—this frequency may correspond to the natural frequency of the system. Alternatively, the resonant frequency may be calculated using the phase at any two frequencies:

The phase, $\phi$, at any given frequency will satisfy the following relation:

$$\tan\phi = \frac{b\omega}{\omega^2 - \omega_n^2} \quad [\text{EQ\#31}]$$

where $$b = \frac{fA}{L}.$$

Solving for $V_2$ results in:

$$V_2 = \frac{\frac{a^2 A}{L}}{\omega^2 - f\omega\cot\phi} \quad [\text{EQ\#32}]$$

Accordingly, the ratio of the phases at two different frequencies $\omega_1$ and $\omega_2$ can be used to compute the natural frequency of the system:

$$\alpha\omega_n^2 = \omega_1\omega_2\frac{\left(\omega_1\frac{\tan\phi_1}{\tan\phi_2} - \omega_2\right)}{\left(\omega_2\frac{\tan\phi_1}{\tan\phi_2} - \omega_1\right)} \quad [\text{EQ\#33}]$$

For computational efficiency, the actual phase does not need to be calculated. All that is needed is the ratio of the real and imaginary parts of the response ($\tan\phi$).

Re-writing EQ #33 in terms of the variable volume results in:

$$\frac{1}{V^2} = \frac{1}{a^2}\frac{L}{A}\omega_1\omega_2\frac{\left(\omega_1\frac{\tan\phi_1}{\tan\phi_2} - \omega_2\right)}{\left(\omega_2\frac{\tan\phi_1}{\tan\phi_2} - \omega_1\right)} \quad [\text{EQ\#34}]$$

Volume Estimation Using Swept Sine

The resonant frequency of the system may be estimated using swept-sine system identification. In this method, the response of the system to a sinusoidal pressure variation may be found at a number of different frequencies. This frequency response data may then used to estimate the system transfer function using linear regression.

The transfer function for the system may be expressed as a rational function of s. The general case is expressed below for a transfer function with an $n^{th}$ order numerator and an $m^{th}$ order denominator. N and D are the coefficients for the numerator and denominator respectively. The equation has been normalized such that the leading coefficient in the denominator is 1.

or $$G(s) = \frac{N_n s^n + N_{n-1}s^{n-1} + \ldots + N_0}{s^m + D_{m-1}s^{m-1} + D_{m-2}s^{m-2} + \ldots + D_0} \quad [\text{EQ\#35}]$$

-continued $$G(s) = \frac{\sum_{k=0}^{n} N_k s^k}{s^m + \sum_{k=0}^{m-1} D_k s^k} \quad [EQ\#36]$$

This equation may be re-written as follows:

$$G s^m = \sum_{k=0}^{n} N_k s^k - G \sum_{k=0}^{m-1} D_k s^k \quad [EQ\#37]$$

Representing this summation in matrix notation resulting in the following:

$$\begin{bmatrix} G_1 s_1^m \\ \vdots \\ G_k s_k^m \end{bmatrix} = \begin{bmatrix} s_1^n & \cdots & s_1^0 & -G_1 s_1^{m-1} & \cdots & -G_1 s_1^0 \\ \vdots & & \vdots & \vdots & & \vdots \\ s_k^n & \cdots & s_k^0 & -G_k s_k^{m-1} & \cdots & -G_k s_k^0 \end{bmatrix} \begin{bmatrix} N_n \\ \vdots \\ N_0 \\ D_{m-1} \\ \vdots \\ D_0 \end{bmatrix} \quad [EQ\#38]$$

where k is the number of data points collected in the swept sine. To simplify the notation, this equation may be summarized using the vectors:

$$y = Xc \quad [EQ\ \#39]$$

where y is k by 1, x is k by (m+n−1) and c is (m+n−1) by 1. The coefficients may then be found using a least square approach. The error function may be written as follows:

$$e = y - Xc \quad [EQ\ \#40]$$

The function to be minimized is the weighted square of the error function; W is a k×k diagonal matrix.

$$e^T W e = (y - Xc)^T W (y - Xc) \quad [EQ\ \#41]$$

$$e^T W e = y^T w y - (y^T W x c)^T - y^T W X c + c^T x^T W X c \quad [EQ\ \#42]$$

As the center two terms are scalars, the transpose may be neglected.

$$e^T W e = y^T W y - 2 y^T W X c + c^T x^T W X c \quad [EQ\#43]$$

$$\frac{\partial e^T W e}{\partial c} = -2 X^T W y + 2 X^T W X c = 0 \quad [E$$

$$c = (X^T W X)^{-1} X^T W y \quad [EQ\#45]$$

It may be necessary to use the complex transpose in all of these cases. This approach may result in complex coefficients, but the process may be modified to ensure that all the coefficients are real. The least-square minimization may be modified to give only real coefficients if the error function is changed to be $$e^T W e = \text{Re}(y - Xc)^T W \, \text{Re}(y - Xc) + \text{Im}(y - Xc)^T W \, \text{Im}(y - Xc) \quad [EQ\ \#46]$$

Accordingly, the coefficients may be found with the relation:

$$c = (\text{Re}(X)^T W \, \text{Re}(X) + \text{Im}(X)^T W \, \text{Im}(X))^{-1} (\text{Re}(X)^T W \, \text{Re}(y) + \text{Im}(X)^T W \, \text{Im}(y)) \quad [EQ\ \#47]$$

Solution for a 2nd Order System

For a system with a $0^{th}$ order numerator and a second order denominator as shown in the transfer function:

$$G(s) = \frac{N_0}{s^2 + D_1 s + D_0} \quad [EQ\#48]$$

The coefficients in this transfer function may be found based on the expression found in the previous section:

$$c = (\text{Re}(X)^T W \, \text{Re}(X) + \text{Im}(X)^T W \, \text{Im}(X))^{-1} (\text{Re}(X)^T W \, \text{Re}(y) + \text{Im}(X)^T W \, \text{Im}(y)) \quad [EQ\ \#49]$$

where:

$$y = \begin{bmatrix} G_1 s_1^2 \\ \vdots \\ G_k s_k^2 \end{bmatrix}, \; X = \begin{bmatrix} 1 & -G_1 s_1 & -G_1 \\ \vdots & \vdots & \vdots \\ 1 & -G_k s_k & -G_k \end{bmatrix}, \text{ and } c = \begin{bmatrix} N_0 \\ D_1 \\ D_0 \end{bmatrix} \quad [EQ\#50]$$

To simplify the algorithm, we may combine some of terms:

$$c = D^{-1} b \quad [EQ\ \#51]$$

where:

$$D = \text{Re}(X)^T W \, \text{Re}(X) + \text{Im}(X)^T W \, \text{Im}(X) \quad [EQ\ \#52]$$

$$b = \text{Re}(X)^T W \, \text{Re}(y) + \text{Im}(X)^T W \, \text{Im}(y) \quad [EQ\ \#53]$$

To find an expression for D in terms of the complex response vector G and the natural frequency $s = j\omega$, X may be split into its real and imaginary parts:

$$\text{Re}(X) = \begin{bmatrix} 1 & \omega_k \, \text{Im}(G_1) & -\text{Re}(G_1) \\ \vdots & \vdots & \vdots \\ 1 & \omega_k \, \text{Im}(G_k) & -\text{Re}(G_k) \end{bmatrix}, \quad [EQ\#54]$$

$$\text{Im}(X) = \begin{bmatrix} 1 & -\omega_k \, \text{Re}(G_1) & -\text{Im}(G_1) \\ \vdots & \vdots & \vdots \\ 1 & -\omega_k \, \text{Re}(G_k) & -\text{Im}(G_k) \end{bmatrix}$$

The real and imaginary portions of the expression for D above may then become:

$$\text{Re}(X)^T W \, \text{Re}(X) = \begin{bmatrix} \sum_{i=1}^{k} w_i & \sum_{i=1}^{k} w_i \, \text{Im}(G_i) \omega_i & -\sum_{i=1}^{k} w_i \, \text{Re}(G_i) \\ \sum_{i=1}^{k} w_i \, \text{Im}(G_i) \omega_i & \sum_{i=1}^{k} w_i \, \text{Im}(G_i)^2 \omega_i^2 & -\sum_{i=1}^{k} w_i \, \text{Im}(G_i) \, \text{Re}(G_i) \omega_i \\ -\sum_{i=1}^{k} w_i \, \text{Re}(G_i) & -\sum_{i=1}^{k} w_i \, \text{Im}(G_i) \, \text{Re}(G_i) \omega_i & \sum_{i=1}^{k} w_i \, \text{Re}(G_i)^2 \end{bmatrix} \quad [EQ\#55]$$

$$\text{Im}(X)^T \, W \, \text{Im}(X) = \begin{bmatrix} 0 & 0 & 0 \\ 0 & \sum_{i=1}^{k} w_i \, \text{Re}(G_i)^2 \omega_i^2 & \sum_{i=1}^{k} w_i \, \text{Im}(G_i) \, \text{Re}(G_i) \omega_i \\ 0 & \sum_{i=1}^{k} w_i \, \text{Im}(G_i) \, \text{Re}(G_i) \omega_i & \sum_{i=1}^{k} w_i \, \text{Im}(G_i)^2 \end{bmatrix} \quad [\text{EQ\#56}]$$

Combining these terms results in the final expression for the D matrix, which may contain only real values.

$$D = \begin{bmatrix} \sum_{i=1}^{k} w_i & \sum_{i=1}^{k} w_i \, \text{Im}(G_i) \omega_i & -\sum_{i=1}^{k} w_i \, \text{Re}(G_i) \\ \sum_{i=1}^{k} w_i \, \text{Im}(G_i) \omega_i & \sum_{i=1}^{k} w_i \, (\text{Re}(G_i)^2 + \text{Im}(G_i)^2) \omega_i^2 & 0 \\ -\sum_{i=1}^{k} w_i \, \text{Re}(G_i) & 0 & \sum_{i=1}^{k} w_i \, (\text{Re}(G_i)^2 + \text{Im}(G_i)^2) \end{bmatrix} \quad [\text{EQ\#57}]$$

The same approach may be taken to find an expression for the b vector in terms of G and ω. The real and imaginary parts of y are as follows:

$$\text{Re}(y) = \begin{bmatrix} -\text{Re}(G_1) \omega_1^2 \\ \vdots \\ -\text{Re}(G_k) \omega_k^2 \end{bmatrix}, \, \text{Im}(y) = \begin{bmatrix} -\text{Im}(G_1) \omega_1^2 \\ \vdots \\ -\text{Im}(G_k) \omega_k^2 \end{bmatrix} \quad [\text{EQ\#58}]$$

Combining the real and imaginary parts results in the expression for the b vector as follows:

$$b = \text{Re}(X)^T \, W \, \text{Re}(y) + \text{Im}(X)^T \, W \, \text{Im}(y) = \quad [\text{EQ\#59}]$$

$$\begin{bmatrix} -\sum_{i=1}^{k} w_i \, \text{Re}(G_i) \omega_i^2 \\ 0 \\ \sum_{i=1}^{k} w_i (\text{Re}(G_i)^2 + \text{Im}(G_i)^2) \omega_i^2 \end{bmatrix}$$

The next step is to invert the D matrix. The matrix is symmetric and positive-definite so the number of computations needed to find the inverse will be reduced from the general 3×3 case. The general expression for a matrix inverse is:

$$D^{-1} = \frac{1}{det(D)} adj(D) \quad [\text{EQ\#60}]$$

If D is expressed as follows:

$$D = \begin{bmatrix} d_{11} & d_{12} & d_{13} \\ d_{12} & d_{22} & 0 \\ d_{13} & 0 & d_{33} \end{bmatrix} \quad [\text{EQ\#61}]$$

then the adjugate matrix may be written as follows:

$$adj(D) = \quad [\text{EQ\#62}]$$

$$\begin{bmatrix} \begin{vmatrix} d_{22} & 0 \\ 0 & d_{33} \end{vmatrix} & -\begin{vmatrix} d_{12} & 0 \\ d_{13} & d_{33} \end{vmatrix} & \begin{vmatrix} d_{12} & d_{22} \\ d_{13} & 0 \end{vmatrix} \\ -\begin{vmatrix} d_{12} & d_{13} \\ 0 & d_{33} \end{vmatrix} & \begin{vmatrix} d_{11} & d_{13} \\ d_{13} & d_{33} \end{vmatrix} & -\begin{vmatrix} d_{11} & d_{12} \\ d_{13} & 0 \end{vmatrix} \\ \begin{vmatrix} d_{12} & d_{13} \\ d_{22} & 0 \end{vmatrix} & -\begin{vmatrix} d_{11} & d_{13} \\ d_{12} & 0 \end{vmatrix} & \begin{vmatrix} d_{11} & d_{12} \\ d_{12} & d_{22} \end{vmatrix} \end{bmatrix} = \begin{bmatrix} a_{11} & a_{12} & a_{13} \\ a_{12} & a_{22} & a_{23} \\ a_{13} & a_{32} & a_{33} \end{bmatrix}$$

Due to symmetry, only the upper diagonal matrix may need to be calculated.

The Determinant may then be computed in terms of the adjugate matrix values, taking advantage of the zero elements in the original array:

$$det(D) = a_{12} d_{12} + a_{22} d_{22} \quad [\text{EQ \#63}]$$

Finally, the inverse of D may be written as follows:

$$D^{-1} = \frac{1}{det(D)} adj(D) \quad [\text{EQ\#64}]$$

Since we are trying to solve:

$$c = D^{-1} b = \frac{1}{det(D)} adj(D) b \quad [\text{EQ\#65}]$$

then:

$$c = \frac{1}{det(D)} \begin{bmatrix} a_{11} & a_{12} & a_{13} \\ a_{12} & a_{22} & a_{23} \\ a_{13} & a_{32} & a_{33} \end{bmatrix} \begin{bmatrix} b_1 \\ 0 \\ b_3 \end{bmatrix} = \frac{1}{det(D)} \begin{bmatrix} a_{11} b_1 + a_{13} b_3 \\ a_{12} b_1 + a_{23} b_3 \\ a_{13} b_1 + a_{33} b_3 \end{bmatrix} \quad [\text{EQ\#66}]$$

The final step is to get a quantitative assessment of how well the data fits the model. Accordingly, the original expression for the error is as follows:

$$e^T W e = \text{Re}(y - Xc)^T W \, \text{Re}(y - Xc) + \text{Im}(y - Xc)^T W \, \text{Im}(y - Xc) \quad [\text{EQ \#67}]$$

This may be expressed in terms of the D matrix and the b and c vectors as follows:

$$e^T W e = h - 2c^T b + c^T D c \quad \text{[EQ #68]}$$

where:

$$h = \text{Re}(y^T) W \text{Re}(y) + \text{Im}(y^T) W \text{Im}(y) \quad \text{[EQ #69]}$$

$$h = \sum_{i=1}^{k} w_i (\text{Re}(G_i)^2 + \text{Im}(G_i)^2) \omega_i^4 \quad \text{[EQ#70]}$$

The model fit error may also be used to detect sensor failures.

Alternate Solution for a 2nd Order System $$G(s) = \frac{N_n s^n + N_{n-1} s^{n-1} + \ldots + N_0}{s^m + D_{m-1} s^{m-1} + D_{m-2} s^{m-2} + \ldots + D_0} \quad \text{[EQ#71]}$$

or $$G(s) = \frac{\sum_{k=0}^{n} N_k s^k}{s^m + \sum_{k=0}^{m-1} D_k s^k} \quad \text{[EQ#72]}$$

This equation may be re-written as follows:

$$G = \sum_{k=0}^{n} N_k s^{k-m} - G \sum_{k=0}^{m-1} D_k s^{k-m} \quad \text{[EQ#73]}$$

Putting this summation into matrix notation results in the following:

$$\begin{bmatrix} G_1 \\ \vdots \\ G_k \end{bmatrix} = \begin{bmatrix} s_1^{n-m} & \cdots & s_1^{-m} & -G_1 s_1^{-1} & \cdots & -G_1 s_1^{-m} \\ \vdots & & \vdots & \vdots & & \vdots \\ s_k^{n-m} & \cdots & s_k^{-m} & -G_k s_k^{-1} & \cdots & -G_k s_k^{-m} \end{bmatrix} \begin{bmatrix} N_n \\ \vdots \\ N_0 \\ D_{m-1} \\ \vdots \\ D_0 \end{bmatrix} \quad \text{[EQ#74]}$$

For a system with a $0^{th}$ order numerator and a second order denominator as shown in the transfer function:

$$G(s) = \frac{N_0}{s^2 + D_1 s + D_0} \quad \text{[EQ#75]}$$

The coefficients in this transfer function may be found based on the expression found in the previous section:

$$c = (\text{Re}(X)^T W \text{Re}(X) + \text{Im}(X)^T W \text{Im}(X))^{-1} (\text{Re}(X)^T W \text{Re}(y) + \text{Im}(X)^T W \text{Im}(y)) \quad \text{[EQ #76]}$$

where $$y = \begin{bmatrix} G_1 \\ \vdots \\ G_k \end{bmatrix}, X = \begin{bmatrix} s_1^{-2} & -G_1 s_1^{-1} & -G_1 s_1^{-2} \\ \vdots & \vdots & \vdots \\ s_k^{-2} & -G_k s_k^{-1} & -G_k s_k^{-2} \end{bmatrix}, \text{ and } c = \begin{bmatrix} N_0 \\ D_1 \\ D_0 \end{bmatrix} \quad \text{[EQ#77]}$$

To simplify the algorithm, some terms may be combined:

$$c = D^{-1} b \quad \text{[EQ #78]}$$

where:

$$D = \text{Re}(X)^T W \text{Re}(X) + \text{Im}(X)^T W \text{Im}(X) \quad \text{[EQ #79]}$$

$$b = \text{Re}(X)^T W \text{Re}(y) + \text{Im}(X)^T W \text{Im}(y) \quad \text{[EQ #80]}$$

To find an expression for D in terms of the complex response vector G and the natural frequency $s = j\omega$, split X may be split into its real and imaginary parts:

$$\text{Re}(X) = \begin{bmatrix} -\omega_1^{-2} & -\omega_1^{-1} \text{Im}(G_1) & \omega_1^{-2} \text{Re}(G_1) \\ \vdots & \vdots & \vdots \\ -\omega_k^{-2} & -\omega_k^{-1} \text{Im}(G_k) & \omega_k^{-2} \text{Re}(G_k) \end{bmatrix} \quad \text{[EQ#81]}$$

$$\text{Im}(X) = \begin{bmatrix} 0 & -\omega_1^{-1} \text{Re}(G_1) & \omega_1^{-2} \text{Im}(G_1) \\ \vdots & \vdots & \vdots \\ 0 & -\omega_k^{-1} \text{Re}(G_k) & \omega_k^{-2} \text{Im}(G_k) \end{bmatrix} \quad \text{[EQ#82]}$$

The real and imaginary portions of the expression for D above may then become:

$$\text{Re}(X)^T W \text{Re}(X) = \begin{bmatrix} \sum_{i=1}^{k} w_i \omega_i^{-4} & \sum_{i=1}^{k} w_i \text{Im}(G_i) \omega_i^{-3} & -\sum_{i=1}^{k} w_i \text{Re}(G_i) \omega_i^{-4} \\ \sum_{i=1}^{k} w_i \text{Im}(G_i) \omega_i^{-3} & \sum_{i=1}^{k} w_i \text{Im}(G_i)^2 \omega_i^{-2} & -\sum_{i=1}^{k} w_i \text{Im}(G_i) \text{Re}(G_i) \omega_i^{-3} \\ -\sum_{i=1}^{k} w_i \text{Re}(G_i) \omega_i^{-4} & -\sum_{i=1}^{k} w_i \text{Im}(G_i) \text{Re}(G_i) \omega_i^{-3} & \sum_{i=1}^{k} w_i \text{Re}(G_i)^2 \omega_i^{-4} \end{bmatrix} \quad \text{[EQ#83]}$$

$$\text{Im}(X)^T W \text{Im}(X) = \begin{bmatrix} 0 & 0 & 0 \\ 0 & \sum_{i=1}^{k} w_i \text{Re}(G_i)^2 \omega_i^{-2} & -\sum_{i=1}^{k} w_i \text{Im}(G_i) \text{Re}(G_i) \omega_i^{-3} \\ 0 & -\sum_{i=1}^{k} w_i \text{Im}(G_i) \text{Re}(G_i) \omega_i^{-3} & \sum_{i=1}^{k} w_i \text{Im}(G_i)^2 \omega_i^{-4} \end{bmatrix} \quad \text{[EQ#84]}$$

Combining these terms results in the final expression for the D matrix, which may contain only real values.

$$D = \begin{bmatrix} \sum_{i=1}^{k} w_i \omega_i^{-4} & \sum_{i=1}^{k} w_i \text{Im}(G_i) \omega_i^{-3} & -\sum_{i=1}^{k} w_i \text{Re}(G_i) \omega_i^{-4} \\ \sum_{i=1}^{k} w_i \text{Im}(G_i) \omega_i^{-3} & \sum_{i=1}^{k} w_i (\text{Re}(G_i)^2 + \text{Im}(G_i)^2) \omega_i^{-2} & -2\sum_{i=1}^{k} w_i \text{Im}(G_i) \text{Re}(G_i) \omega_i^{-3} \\ -\sum_{i=1}^{k} w_i \text{Re}(G_i) \omega_i^{-4} & -2\sum_{i=1}^{k} w_i \text{Im}(G_i) \text{Re}(G_i) \omega_i^{-3} & \sum_{i=1}^{k} w_i (\text{Re}(G_i)^2 + \text{Im}(G_i)^2) \omega_i^{-4} \end{bmatrix} \quad [EQ\#85]$$

The same approach may be taken to find an expression for the b vector in terms of G and ω. The real and imaginary parts of y areas follows:

$$\text{Re}(y) = \begin{bmatrix} -\text{Re}(G_1) \\ \vdots \\ -\text{Re}(G_k) \end{bmatrix}, \text{Im}(y) = \begin{bmatrix} -\text{Im}(G_1) \\ \vdots \\ -\text{Im}(G_k) \end{bmatrix} \quad [EQ\#86]$$

Combining the real and imaginary parts results in the expression for the b vector as follows:

$$b = \text{Re}(X)^T W \text{Re}(y) + \quad [EQ\#87]$$

$$\text{Im}(X)^T W \text{Im}(y) = \begin{bmatrix} -\sum_{i=1}^{k} w_i \text{Re}(G_i) \omega_i^{-2} \\ -\sum_{i=1}^{k} w_i (\text{Im}(G_i) + \text{Re}(G_i)) \omega_i^{-1} \\ \sum_{i=1}^{k} w_i (\text{Re}(G_i)^2 + \text{Im}(G_i)^2) \omega_i^{-2} \end{bmatrix}$$

Implementing Acoustic Volume Sensing

Collecting the Frequency Response Data and Computing the Complex Response

To implement volume sensor assembly 148, volume sensor assembly 148 should determine the relative response of reference microphone 626 and invariable volume microphone 630 to the acoustic wave set up by speaker assembly 622. This may be accomplished by driving speaker assembly 622 with a sinusoidal output at a known frequency; the complex response of microphones 626, 630 may then be found at that driving frequency. Finally, the relative response of microphones 626, 630 may be found and corrected for alternating sampling by e.g., an analog-to-digital converter (i.e., ADC).

Additionally, the total signal variance may be computed and compared to the variance of pure tone extracted using the discrete Fourier transform (i.e., DFT). This may result in a measure of how much of the signal power comes from noise sources or distortion. This value may then be used to reject and repeat bad measurements.

Computing the Discrete Fourier Transform

The signal from the microphone may be sampled synchronously with the output to speaker assembly 622 such that a fixed number of points, N, are taken per wavelength. The measured signal at each point in the wavelength may be summed over an integer number of wavelengths, M, and stored in an array x by the ISR for processing after all the data for that frequency has been collected.

A DFT may be performed on the data at the integer value corresponding to the driven frequency of the speaker. The general expression for the first harmonic of a DFT is as follows:

$$x_k = \frac{2}{MN} \sum_{n=0}^{N-1} x_n e^{-\frac{2\pi i}{N} kn} \quad [EQ\#88]$$

The product MN may be the total number of points and the factor of two may be added such that the resulting real and imaginary portions of the answer match the amplitude of the sine wave:

$$x_n = \text{re}(x_k) \cos\left(\frac{2\pi}{N} kn\right) + \text{im}(x_k) \sin\left(\frac{2\pi}{N} kn\right) \quad [EQ\#89]$$

This real part of this expression may be as follows:

$$\text{re}(x) = \frac{2}{MN} \sum_{n=0}^{N-1} x_n \cos\left(\frac{2\pi}{N} n\right) \quad [EQ\#90]$$

We may take advantage of the symmetry of the cosine function to reduce the number of computations needed to compute the DFT. The expression above may be equivalent to:

$$\text{re}(x) = \frac{2}{MN} \left[ (x_0 - x_{\frac{1}{2}N}) + \sum_{n=1}^{\frac{1}{4}N-1} \sin\left(\frac{\pi}{2} - \frac{2\pi}{N} n\right) \left[ (x_n - x_{\frac{1}{2}N+n}) - (x_{\frac{1}{2}N+n} - x_{N-n}) \right] \right] \quad [EQ\#91]$$

Similarly, for the imaginary portion of the equation:

$$\text{im}(x) = -\frac{2}{MN} \sum_{n=0}^{N-1} x_n \sin\left(\frac{2\pi}{N} n\right) \quad [EQ\#92]$$

which may be expressed as follows:

$$\text{im}(x) = -\frac{2}{MN}\left[\left(x_{\frac{1}{4}N} - x_{\frac{3}{4}N}\right) + \sum_{n=1}^{\frac{1}{4}N-1}\sin\left(\frac{2\pi}{N}n\right)\left[\left(x_n - x_{\frac{1}{2}N+n}\right) + \left(x_{\frac{1}{2}N+n} - x_{N-n}\right)\right]\right] \quad [\text{EQ\#93}]$$

The variance of this signal may be calculated as follows:

$$\sigma^2 = \frac{1}{2}(\text{re}(x)^2 + \text{im}(x)^2) \quad \{\text{EQ\#94}\}$$

The maximum possible value of the real and imaginary portions of x may be $2^{11}$; which corresponds to half the AD range. The maximum value of the tone variance may be $2^{21}$; half the square of the AD range.

Computing the Signal Variance

The pseudo-variance of the signal may be calculated using the following relation:

$$\sigma^2 = \frac{1}{NM^2}\sum_{n=0}^{N-1}x_n^2 - \frac{1}{N^2M^2}\left(\sum_{n=0}^{N-1}x_n\right)^2 \quad [\text{EQ\#95}]$$

The result may be in the units of AD counts squared. It may only be the "pseudo-variance" because the signal has been averaged over M periods before the variance is calculated over the N samples in the "averaged" period. This may be a useful metric, however, for finding if the "averaged" signal looks like a sinusoid at the expected frequency. This may be done by comparing the total signal variance to that of the sinusoid found in the discrete Fourier transform.

The summation may be on the order of $$\sum_{n=0}^{N-1}x_n^2 = O(NM^2 2^{24})$$

for a 12-bit ADC. If $N<2^7=128$ and $M<2^6=64$, then the summation will be less than $2^{43}$ and may be stored in a 64-bit integer. The maximum possible value of the variance may result if the ADC oscillated between a value of 0 and $2^{12}$ on each consecutive sample. This may result in a peak variance of $$\frac{1}{4}(2^{12})^2 = 2^{22}$$

so the result may be stored at a maximum of a $\frac{1}{2}^9$ resolution in a signed 32-bit integer.

Computing the Relative Microphone Response

The relative response (G) of microphones 626, 630 may be computed from the complex response of the individual microphones:

$$G = \frac{x_{var}}{x_{ref}} = \frac{x_{var}}{x_{ref}}\frac{x_{ref}^*}{x_{ref}^*} \quad [\text{EQ\#96}]$$

$$\text{Re}(G) = \frac{\text{Re}(x_{var})\text{Re}(x_{ref}) + \text{Im}(x_{var})\text{Im}(x_{ref})}{\text{Re}(x_{ref})^2 + \text{Im}(x_{ref})^2} \quad [\text{EQ\#97}]$$

$$\text{Im}(G) = \frac{\text{Re}(x_{ref})\text{Im}(x_{var}) - \text{Re}(x_{var})\text{Im}(x_{ref})}{\text{Re}(x_{ref})^2 + \text{Im}(x_{ref})^2} \quad [\text{EQ\#98}]$$

The denominator of either expression may be expressed in terms of the reference tone variance computed in the previous section as follows:

$$\text{Re}(x_{ref})^2 + \text{Im}(x_{ref})^2 = 2\sigma_{ref}^2 \quad [\text{EQ\#99}]$$

Correcting for A/D Skew

The signals from microphones 626, 630 may not be sampled simultaneously; the A/D ISR alternates between microphones 626, 630, taking a total of N samples per wavelength for each of microphones 626, 630. The result may be a phase offset between two microphones 626, 630 of $$\frac{\pi}{N}.$$

To correct for this phase offset, a complex rotation may be applied to the relative frequency response computed in the previous section:

$$G_{rotated} = G \cdot \left(\cos\left(\frac{\pi}{N}\right) + i\sin\left(\frac{\pi}{N}\right)\right) \quad [\text{EQ\#100}]$$

Reference Models

Second and Higher Order Models

Figure 23:
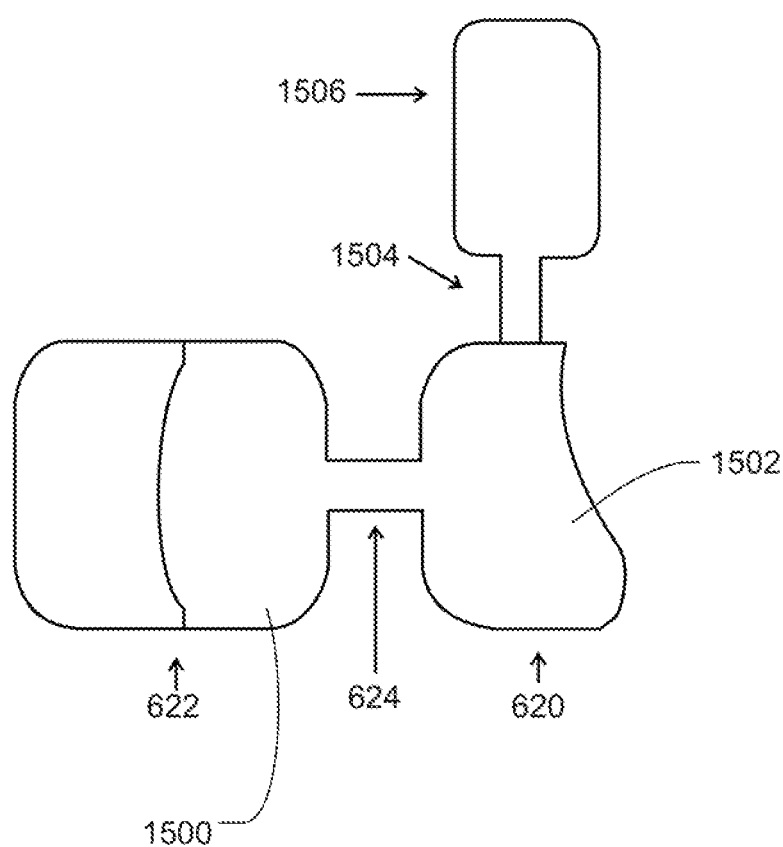
FIG. 23 is a diagrammatic view of a volume sensor assembly included within the infusion pump assembly of FIG. 7.

Leakage through the seals (e.g., seal assembly 1404) of volume sensor chamber 620 may be modeled as a second resonant port (e.g., port 1504, FIG. 23) connected to an external volume (e.g., external volume 1506, FIG. 23).

The system of equations describing the three-chamber configuration may be as follows:

$$\dot{p}_1 + \frac{\rho a^2}{V_1}(\dot{v}_k - \dot{v}_{r12}) = 0 \quad [\text{EQ\#101}]$$

$$\dot{p}_2 + \frac{\rho a^2}{V_2}(\dot{v}_{12} - \dot{v}_{r23}) = 0 \quad [\text{EQ\#102}]$$

$$\dot{v}_{r12} = -\frac{f_{12}A_{12}}{L_{12}}\dot{v}_{r12} + \frac{A_{12}}{\rho L_{12}}(p_2 - p_1) \quad [\text{EQ\#103}]$$

$$\dot{p}_3 + \frac{\rho a^2}{V_3}\dot{v}_{r23} = 0 \quad [\text{EQ\#104}]$$

$$\dot{v}_{r23} = -\frac{f_{23}A_{23}}{L_{23}}\dot{v}_{r23} + \frac{A_{23}}{\rho L_{23}}(p_3 - p_2) \quad [\text{EQ\#105}]$$

Figure 24:
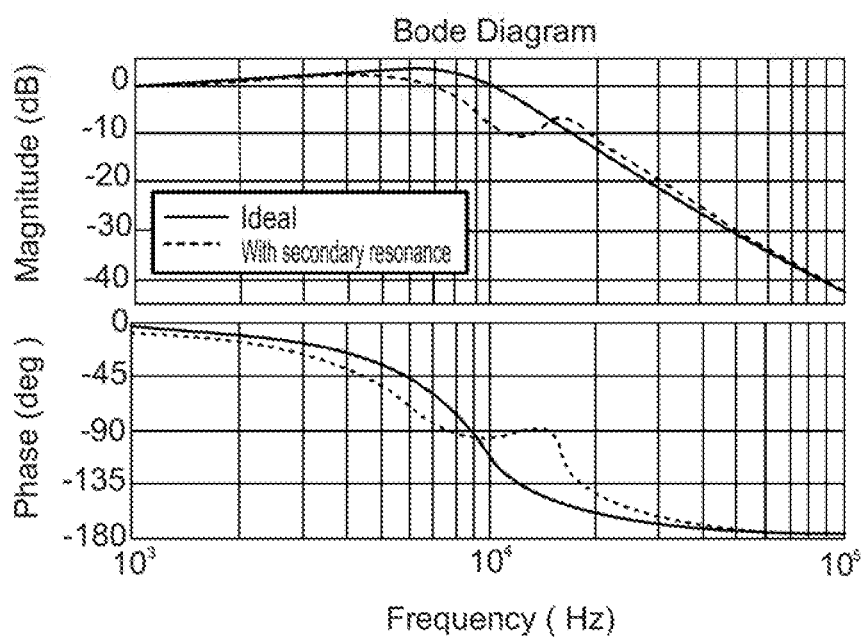
FIG. 24 is a two-dimensional graph of a performance characteristic of the volume sensor assembly of FIG. 23.

Putting these equations into state-space results in the following:

$$\begin{bmatrix} \dot{p}_1 \\ \dot{p}_2 \\ \dot{p}_3 \\ \dot{v}_{12} \\ \dot{v}_{23} \end{bmatrix} = \begin{bmatrix} 0 & 0 & 0 & \frac{\rho a^2}{V_1} & 0 \\ 0 & 0 & 0 & -\frac{\rho a^2}{V_2} & \frac{\rho a^2}{V_2} \\ 0 & 0 & 0 & 0 & -\frac{\rho a^2}{V_3} \\ -\frac{A_{12}}{\rho L_{12}} & \frac{A_{12}}{\rho L_{12}} & 0 & -b_{12} & 0 \\ 0 & -\frac{A_{23}}{\rho L_{23}} & \frac{A_{23}}{\rho L_{23}} & 0 & -b_{23} \end{bmatrix}$$ [EQ#106]

$$\begin{bmatrix} p_1 \\ p_2 \\ p_3 \\ v_{12} \\ v_{23} \end{bmatrix} + \begin{bmatrix} -\frac{\rho a^2}{V_1} \\ 0 \\ 0 \\ 0 \\ 0 \end{bmatrix} [\dot{v}_k]$$

the frequency response of which may be represented graphically in the Bode diagram shown in FIG. 24 and which may also be written in transfer function form:

$$\frac{p_2}{p_1} = \frac{\omega_{12}^2(s^2 + b_{23}s + \omega_{23}^2)}{(s^2 + b_{12}s + \omega_{12}^2)(s^2 + b_{23}s + \omega_{23}^2) + \frac{V_3}{V_2}\omega_{23}^2(s + b_{12})s}$$ [EQ#107]

Expanding the denominator results in the following:

$$\frac{p_2}{p_1} = \frac{\omega_{12}^2(s^2 + b_{23}s + \omega_{23}^2)}{s^4 + (b_{12} + b_{23})s^3 + \left(b_{12}b_{23} + \omega_{12}^2 + \omega_{23}^2\left(1 + \frac{V_3}{V_2}\right)\right)s^2 + \left(b_{23}\omega_{12}^2 + b_{12}\omega_{23}^2\left(1 + \frac{V_3}{V_2}\right)\right)s + \omega_{12}^2\omega_{23}^2}$$ [EQ#108]

A bubble underneath the diaphragm material in the variable volume will follow the same dynamic equations as a leakage path. In this case, the diaphragm material may act as the resonant mass rather than the leakage port. Accordingly, the equation may be as follows:

$$m\ddot{x} = \Delta pA - b_m \dot{x}$$ [EQ #109]

wherein m is the mass of the diaphragm, A is the cross sectional area of the diaphragm that can resonate, and $b_m$ is the mechanical damping. EQ #106 may be written in terms of the volume flow rate:

$$\dot{v} = -\frac{b}{m}v + \Delta p \frac{A^2}{m}$$ [EQ#110]

wherein the volume of the air bubble is $V_3$. If the bubble volume is substantially smaller than the acoustic volume $V_3 \ll V_2$ than the transfer function may be simplified to:

$$\frac{p_2}{p_1} = \frac{\omega_{12}^2(s^2 + b_{23}s + \omega_{23}^2)}{(s^2 + b_{12}s + \omega_{12}^2)\left(s^2 + b_{23}s + \omega_{23}^2\left(1 + \frac{V_3}{V_2}\right)\right)}$$ [EQ#111]

Second Order with Time Delay

The volume sensor assembly 148 equations derived above assume that the pressure is the same everywhere in the acoustic volume. This is only an approximation, as there are time delays associated with the propagation of the sound waves through the volume. This situation may look like a time delay or a time advance based on the relative position of the microphone and speakers.

Figure 25:
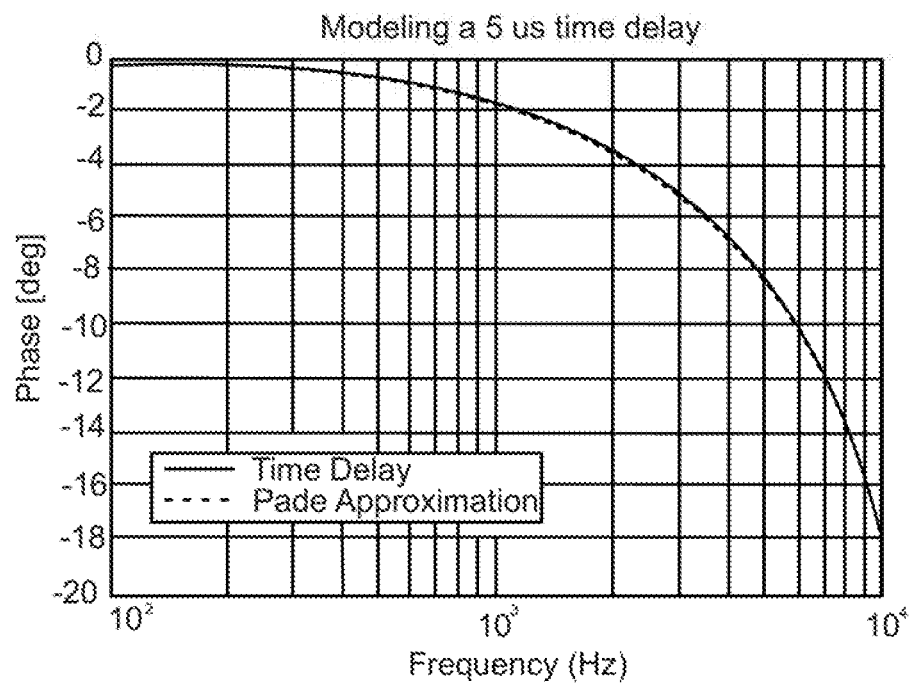
FIG. 25 is a two-dimensional graph of a performance characteristic of the volume sensor assembly of FIG. 23.

A time delay may be expressed in the Laplace domain as:

$$G(s) = e^{-\Delta Ts}$$ [EQ #12]

which makes for a non-linear set of equations. However, a first-order Pade approximation of the time delay may be used as follows:

$$G(s) = -\frac{s + \frac{2}{\Delta T}}{s - \frac{2}{\Delta T}}$$ [EQ#113]

which is shown graphically in FIG. 25.

Three Chamber Volume Estimation

Figure 26:
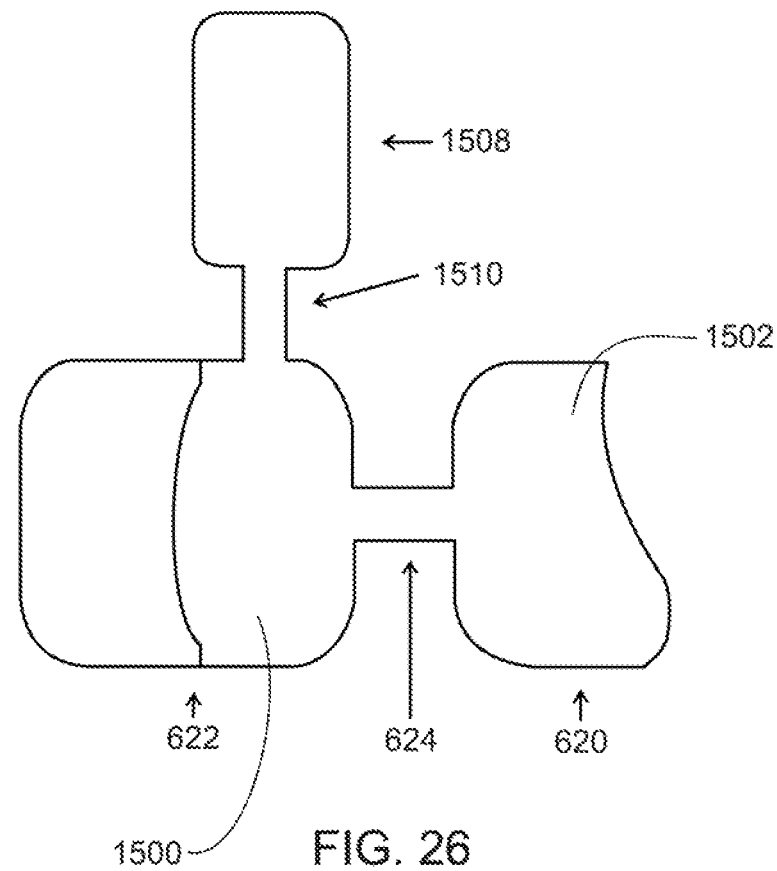
FIG. 26 is a diagrammatic view of a volume sensor assembly included within the infusion pump assembly of FIG. 7.

Volume sensor assembly 148 may also be configured using a third reference volume (e.g., reference volume 1508; FIG. 26) connected with a separate resonant port (e.g., port 1510; FIG. 26). This configuration may allow for temperature-independent volume estimation.

The system of equations describing the three-chamber configuration are as follows:

$$\dot{p}_1 + \frac{\rho a^2}{V_1}(\dot{v}_k - \dot{v}_{r12} - \dot{v}_{r13}) = 0$$ [EQ#114]

$$\dot{p}_2 + \frac{\rho a^2}{V_2}\dot{v}_{r12} = 0$$ [EQ#115]

$$\ddot{v}_{r12} = -\frac{f_{12}A_{12}}{L_{12}}\dot{v}_{r12} + \frac{A_{12}}{\rho L_{12}}(p_2 - p_1)$$ [EQ#116]

$$\dot{p}_3 + \frac{\rho a^2}{V_3}\dot{v}_{r13} = 0$$ [EQ#117]

$$\ddot{v}_{r13} = -\frac{f_{13}A_{13}}{L_{13}}\dot{v}_{r13} + \frac{A_{13}}{\rho L_{13}}(p_2 - p_1)$$ [EQ#118]

Using these equations and solving for the transfer function across each of the resonant ports results in the following:

$$\frac{p_2}{p_1} = \frac{\omega_{n12}^2}{s^2 + 2\zeta_{12}\omega_{n12}s + \omega_{n12}^2}$$ [EQ#119]

where

-continued $$\omega_{n12} = \frac{1}{V_2} \frac{a^2 A_{12}}{L_{12}} \text{ and } \zeta = \frac{f_{12} A_{12}}{2 L_{12} \omega_{n12}}$$ [EQ#120]

$$\frac{p_3}{p_1} = \frac{\omega_{n13}^2}{s^2 + 2\zeta_{13}\omega_{n13}s + \omega_{n13}^2}$$ [EQ#121]

where $$\omega_{n13} = \frac{1}{V_3} \frac{a^2 A_{13}}{L_{13}} \text{ and } \zeta = \frac{f_{13} A_{13}}{2 L_{13} \omega_{n13}}$$ [EQ#122]

The volume of volume sensor chamber 620 may be estimated using the ratio of the natural frequency of the two resonant ports as follows:

$$\frac{\omega_{n13}^2}{\omega_{n12}^2} = \frac{V_2}{V_3} \frac{A_{13}}{A_{12}} \frac{L_{12}}{L_{13}}$$ [EQ#123]

EQ #120 illustrates that the volume of volume sensor chamber 620 may be proportional to reference volume 1508. The ratio of these two volumes (in the ideal model) may only depend on the geometry of the resonant port (e.g., port 1510; FIG. 26) and has no dependence upon temperature.

Exponential Volume Model

Assume the flow out through the flow resistance has the following form:

$$\dot{V}_{out} = \frac{V_{avs}}{\tau}$$ [EQ#124]

Assuming a fixed input flow rate from the pump chamber, the volume of volume sensor chamber 620 is based upon the following differential equation:

$$\dot{V}_{avs} = \dot{V}_{in} - \dot{V}_{out} = \dot{V}_{in} - \frac{V_{avs}}{\tau}$$ [EQ#125]

which gives the following solution assuming a zero initial volume:

$$V_{avs} = \dot{V}_{in}\tau\left(1 - e^{-\frac{t}{\tau}}\right)$$ [EQ#126]

Accordingly, the output flow rate flows:

$$\dot{V}_{out} = \dot{V}_{in}\left(1 - e^{-\frac{t}{\tau}}\right)$$ [EQ#127]

The volume delivered during the pump phase may be written:

$$V_{out} = \dot{V}_{in}\left(t - \tau\left(1 - e^{-\frac{t}{\tau}}\right)\right)$$ [EQ#128]

Device Calibration

The model fit allows the resonant frequency of the port to be extracted from the sine sweep data. The next step is to relate this value to the delivered volume. The ideal relationship between the resonant frequency and the delivered volume to be expressed as follows:

$$\omega_n^2 = \frac{a^2 A}{L} \frac{1}{V_2}$$ [EQ#129]

The speed of sound will vary with temperature, so it may be useful to split out the temperature effects.

$$\omega_n^2 = \frac{\gamma R A}{L} \frac{T}{V_2}$$ [EQ#130]

The volume may then be expressed as a function of the measured resonant frequency and the temperature:

$$V_2 = C \frac{T}{\omega_n^2}$$ [EQ#131]

Where c is the calibration constant $$C = \frac{\gamma R A}{L}$$

Implementation Details

End Effects

The air resonating in the port (e.g., port assembly 624) may extend out into the acoustic volumes at the end of each oscillation. The distance the air extends may be estimated based on the fundamental volume sensor assembly equations. For any given acoustic volume, the distance the air extends into the volume may be expressed as a function of the pressure and port cross-sectional area:

$$x = \frac{V}{\rho a^2 A} p$$ [EQ#132]

If we assume the following values:

$$V = 28.8 \times 10^{-6} L$$ [EQ#133]

$$\rho = 1.292 \frac{\text{kg}}{\text{m}^3}$$ [EQ#134]

$$a = 340 \frac{\text{m}}{\text{s}}$$ [EQ#135]

$$d = 0.5 \cdot \text{mm}$$ [EQ#136]

$$p = 1 \cdot \text{Pa (Approximately 100 dB)}$$ [EQ#137]

Accordingly, the air will extend roughly 1.9 mm in to the acoustic chamber.

Sizing V1 (i.e., the Fixed Volume) Relative to V2 (i.e., the Variable Volume)

Sizing $V_1$ (e.g., fixed volume 1500) may require trading off acoustic volume with the relative position of the poles and zeros in the transfer function. The transfer function for both $V_1$ and $V_2$ (e.g., variable volume 1502) are shown below relative to the volume displacement of speaker assembly 622.

$$\frac{p_2}{v_k} = -\frac{\rho a^2}{V_1} \frac{\omega_n^2}{s^2 + 2\zeta\omega_n s + \alpha\omega_n^2} \quad \text{[EQ\#138]}$$

$$\frac{p_1}{v_k} = -\frac{\rho a^2}{V_1} \frac{s^2 + 2\zeta\omega_n s + \alpha\omega_n^2}{s^2 + 2\zeta\omega_n s + \omega_n^2} \quad \text{[EQ\#139]}$$

where $$\omega_n^2 = \frac{a^2 A}{L} \frac{1}{V_2}, \zeta = \frac{fA}{2L\omega_n} \text{ and } \alpha = \left(1 + \frac{V_2}{V_1}\right) \quad \text{[EQ\#140]}$$

As $V_1$ is increased the gain may decrease and the speaker may be driven at a higher amplitude to get the same sound pressure level. However, increasing $V_1$ may also have the benefit of moving the complex zeros in the $p_1$ transfer function toward the complex poles. In the limiting case where $V_1 \to \infty$, $\alpha \to 1$ and you have pole-zero cancellation and a flat response. Increasing $V_1$, therefore, may have the benefit of reducing both the resonance and the notch in the $p_1$ transfer function, and moving the $p_2$ poles toward $\omega_n$; resulting in a lower sensitivity to measurement error when calculating the $p_2/p_1$ transfer function.

Figure 27:
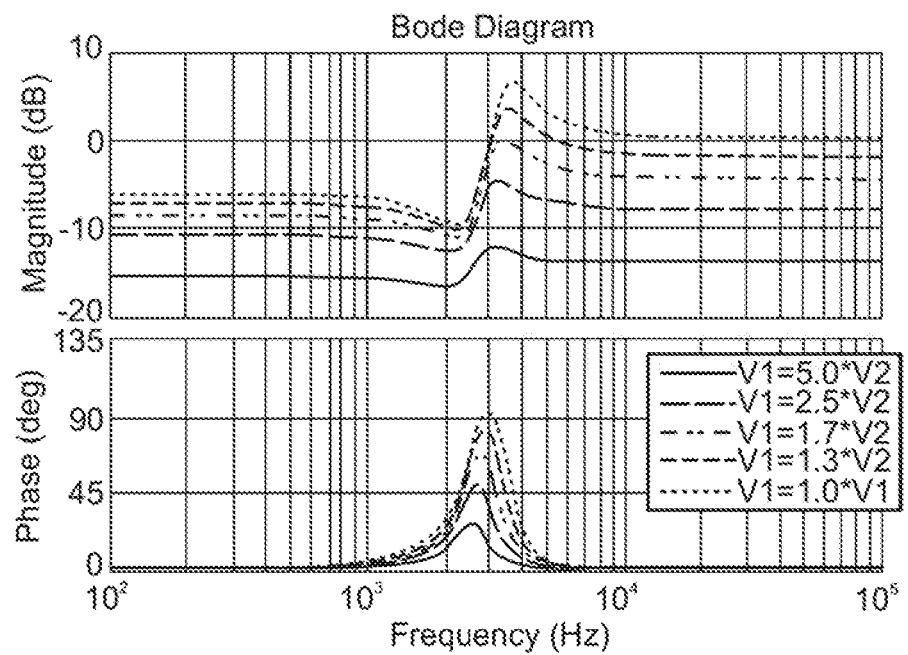
FIG. 27 is a two-dimensional graph of a performance characteristic of a volume sensor assembly included within the infusion pump assembly of FIG. 7.

FIG. 27 is a graphical representation of:

$$\frac{p_1}{v_k} \quad \text{[EQ\#141]}$$

Figure 28:
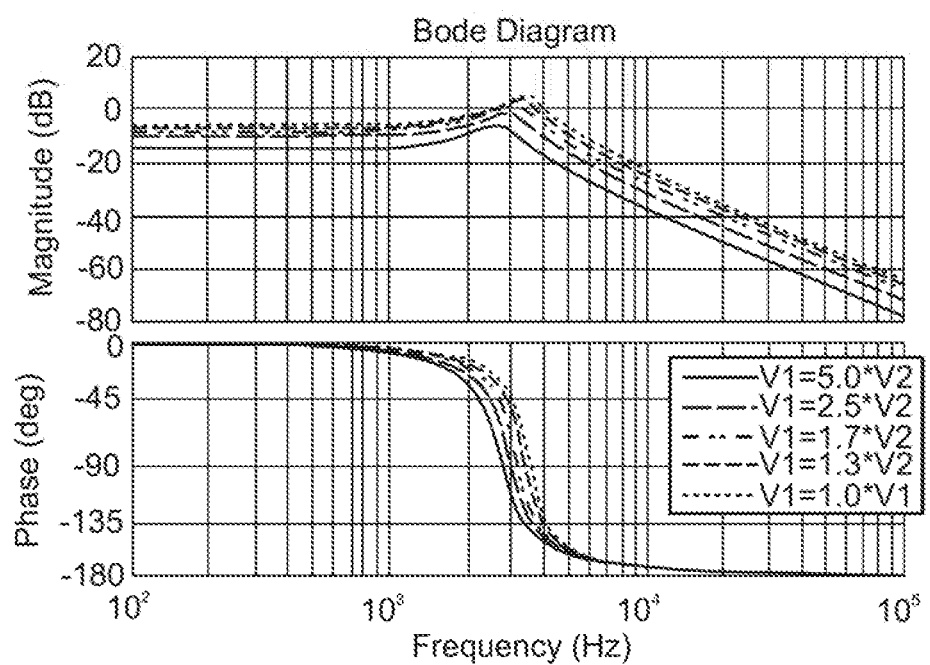
FIG. 28 is a two-dimensional graph of a performance characteristic of a volume sensor assembly included within the infusion pump assembly of FIG. 7.
Figure 29:
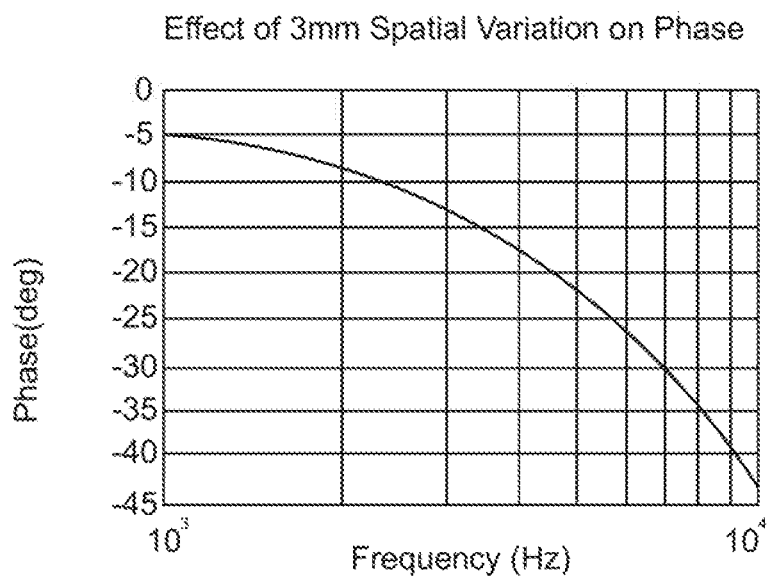
FIG. 29 is a two-dimensional graph of a performance characteristic of a volume sensor assembly included within the infusion pump assembly of FIG. 7.

FIG. 28 is a graphical representation of $$\frac{p_2}{v_k} \quad \text{[EQ \#142]}$$

Aliasing

Higher frequencies may alias down to the frequency of interest, wherein the aliased frequency may be expressed as follows:

$$f = |f_n - nf_s| \quad \text{[EQ \#143]}$$

where $f_s$ is the sampling frequency, $f_n$ is the frequency of the noise source, n is a positive integer, and f is the aliased frequency of the noise source.

The demodulation routine may effectively filter out noise except at the specific frequency of the demodulation. If the sample frequency is set dynamically to be a fixed multiple of the demodulation frequency, then the frequency of the noise that can alias down to the demodulation frequency may be a fixed set of harmonics of that fundamental frequency.

For example, if the sampling frequency is eight times the demodulation frequency, then the noise frequencies that can alias down to that frequency are as follows:

$$\frac{f_n}{f} = \left\{\frac{1}{n\beta+1}, \frac{1}{n\beta-1}\right\} \quad \text{[EQ \#144]}$$

$$= \left\{\frac{1}{7}, \frac{1}{9}, \frac{1}{15}, \frac{1}{17}, \frac{1}{23}, \frac{1}{25}, \cdots\right\}$$

where $$\beta = \frac{f_s}{f} = 8.$$

For $\beta$=16, the following series would result:

$$\frac{f_n}{f} = \left\{\frac{1}{15}, \frac{1}{17}, \frac{1}{31}, \frac{1}{33}, \cdots\right\} \quad \text{[EQ \#145]}$$

Performance

Sensitivity to Temperature

The sensitivity to temperature may be split into a gain change and a noise change. If the temperature is off by a factor of dT, the resulting gain error may be:

$$V_2 = c\left(\frac{T_2}{\omega_2^2} - \frac{T_1}{\omega_1^2}\right) \quad \text{[EQ \#147]}$$

Accordingly, if the same temperature is used for both sine sweeps, any error in the temperature measurement may look like a gain change to the system.

$$e_{gain} = 1 - \frac{T_{measured}}{T_{actual}} \quad \text{[EQ \#148]}$$

Therefore, for a 1° K temperature error, the resulting volume error may be 0.3% at 298° K. This error may include both the error in the temperature sensor and the difference between the sensor temperature and the temperature of the air within volume sensor assembly 148.

The measurement, however, may be more susceptible to noise in the temperature measurement. A temperature change during the differential sine sweeps may result in an error that looks more like an offset rather than a gain change:

$$V_{error} = \frac{c}{\omega^2} \Delta T \quad \text{[EQ \#149]}$$

Figure 30:
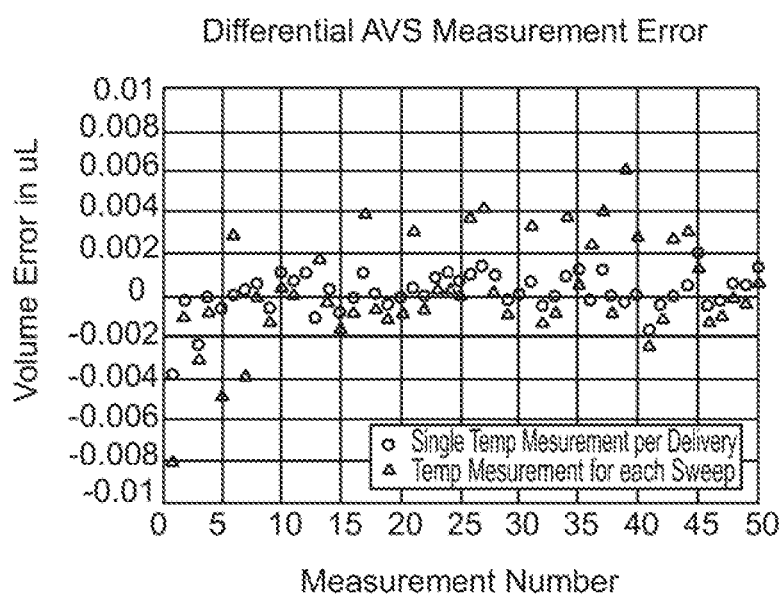
FIG. 30 is a two-dimensional graph of a performance characteristic of a volume sensor assembly included within the infusion pump assembly of FIG. 7.

Accordingly, if the measurement varies by 0.1 K during the two measurement sine sweeps, the difference may be 0.012 uL. Therefore, it may be better to use a consistent temperature estimate for each delivery rather than taking a separate temperature measurement for each sine sweep (as shown in FIG. 30).

Figure 31:
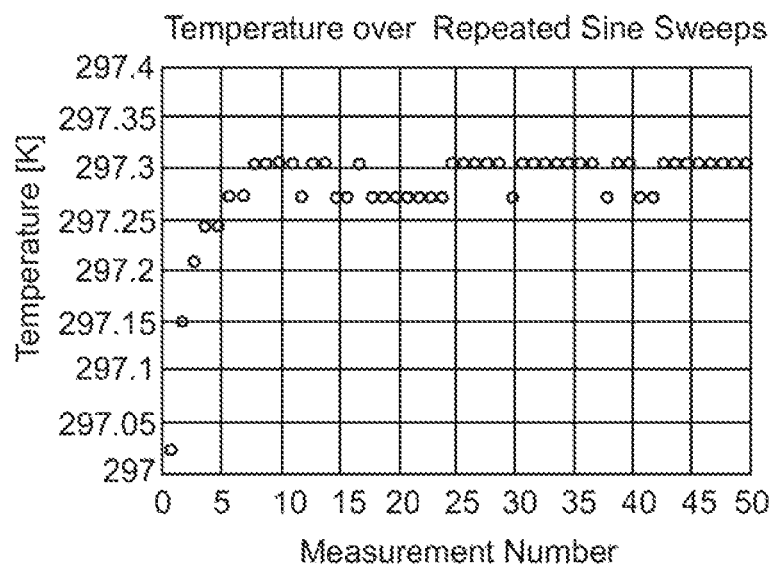
FIG. 31 is a two-dimensional graph of a performance characteristic of a volume sensor assembly included within the infusion pump assembly of FIG. 7.
Figure 32:
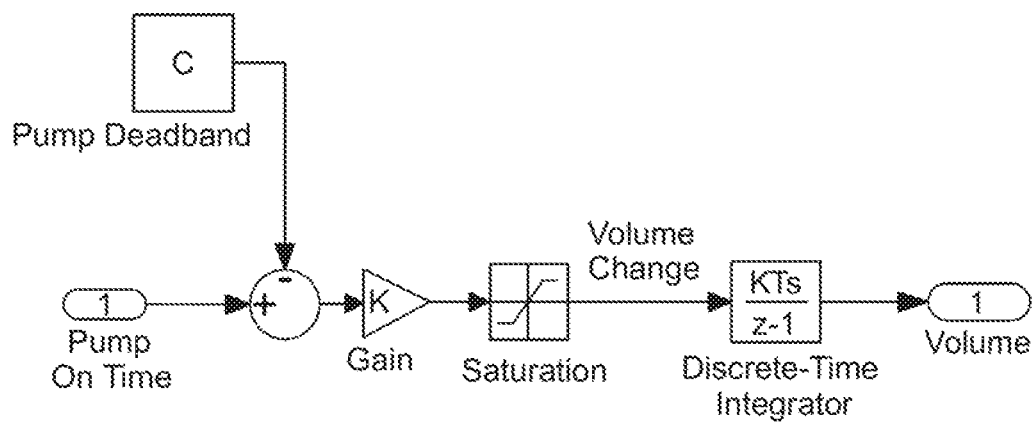
FIG. 32 is a diagrammatic view of a control model for a volume sensor assembly included within the infusion pump assembly of FIG. 7.

The LM73 temperature sensor has a published accuracy of +/−1° C. and a resolution of 0.03 C. Further, the LM73 temperature sensor seems to consistently have a startup transient of about 0.3° C. that takes about five sine sweeps to level out (as shown in FIG. 31). Since the above-described infusion pump assemblies (e.g., infusion pump assembly 100, 100', 400, 500) provides discrete deliveries of infusible fluid, the above-described infusion pump assemblies may be modeled entirely in the discrete domain (in the manner shown in FIG. 32), which may be reduced to the following:

$$G_p(z) = \frac{Kz}{z-1}$$ [EQ #150]

A discrete-time PI regulator may perform according to the following:

$$G_c(z) = K_p\left(1 + \frac{T_s}{T_I}\frac{z}{z-1}\right)$$ [EQ #151]

The AVS system described above works by comparing the acoustic response in fixed volume 1500 and variable volume 1502 to a speaker driven input and extracting the volume of the variable volume 1502. As such, there is a microphone in contact with each of these separate volumes (e.g., microphones 626, 630). The response of variable volume microphone 630 may also be used in a more gross manner to detect the presence or absence of disposable housing assembly 114. Specifically, if disposable housing assembly 114 is not attached to (i.e., positioned proximate) variable volume 1502, essentially no acoustic response to the speaker driven input should be sensed. The response of fixed volume 1500, however, should remain tied to the speaker input. Thus, the microphone data may be used to determine whether disposable housing assembly 114 by simply ensuring that both microphones exhibit an acoustic response.

In the event that microphone 626 (i.e., the microphone positioned proximate fixed volume 1500) exhibits an acoustic response and microphone 630 (i.e., the microphone positioned proximate variable volume 1502) does not exhibit an acoustic response, it may be reasonably concluded that disposable housing assembly 114 is not attached to reusable housing assembly 102. It should be noted that a failure of variable volume microphone 630 may also appear to be indicative of disposable housing assembly 114 not being attached, as the failure of variable volume microphone 630 may result in a mid-range reading that is nearly indistinguishable from the microphone response expected when disposable housing assembly 114 is not attached.

For the following discussion, the following nomenclature may be used:

| Symbols | |
|---|---|
| $\alpha_{max}(f)$ | maximum read at a given frequency |
| $\alpha_{min}(f)$ | minimum read at a given frequency |
| $\delta$ | difference between max and min sums |
| $f$ | individual frequency |
| F | set of sine sweep frequencies |
| N | number of frequencies in each sine sweep, F |
| $\phi$ | boolean disposable attached flag |
| $\sigma_{max}$ | sum of maximum ADC reads |
| $\sigma_{min}$ | sum of minimum ADC reads |
| T | max/min ADC difference threshold |
| Subscripts | |
| i | sweep number |
| ref | reference volume |
| var | variable volume |

As part of the demodulation routine employed in each frequency response calculation, the minimum and maximum readings of both fixed volume microphone 626 and variable volume microphone 630 may be calculated. The sum of these maximum and minimum values may be calculated over the entire sine-sweep (as discussed above) for both microphone 626 and microphone 630 as follows.

$$\sigma\text{max} = \sum^{f \in F} \alpha_{max}(f)$$ [EQ #152]

$$\sigma\text{min} = \sum^{f \in F} \alpha_{min}(f)$$ [EQ #153]

and the difference between these two summations may be simplified as follows:

$$\delta = \sigma\text{max} - \sigma\text{min}$$ [EQ #154]

While $\delta$ may be divided by the number of sine sweeps to get the average minimum/maximum difference for the sine sweep (which is then compared to a threshold), the threshold may equivalently be multiplied by N for computational efficiency. Accordingly, the basic disposable detection algorithm may be defined as follows:

$$\phi_i = \begin{cases} 1 & \text{if } \delta_{var} > N*T \\ 0 & \text{if } \delta_{var} < N*T \ \& \ \delta_{ref} > N*T \end{cases}$$ [EQ #155]

The additional condition that the maximum/minimum difference be greater than the threshold is a check performed to ensure that a failed speaker is not the cause of the acoustic response received. This algorithm may be repeated for any sine-sweep, thus allowing a detachment of disposable housing assembly 114 to be sensed within e.g., at most two consecutive sweeps (i.e., in the worst case scenario in which disposable housing assembly 114 is removed during the second half of an in-progress sine sweep).

Thresholding for the above-described algorithm may be based entirely on numerical evidence. For example, examination of typical minimum/maximum response differences may show that no individual difference is ever less than five hundred ADC counts. Accordingly, all data examined while disposable housing assembly 114 is detached from reusable housing assembly 102 may show that all minimum/maximum response differences as being well under five hundred ADC counts. Thus, the threshold for $\delta$ may be set at T=500.

While volume sensor assembly 148 is described above as being utilized within an infusion pump assembly (e.g., infusion pump assembly 100), this is for illustrative purposes only and is not intended to be a limitation of this disclosure, as other configurations are possible and are considered to be within the scope of this disclosure. For example, volume sensor assembly 148 may be used within a process control environment for e.g., controlling the quantity of chemicals mixed together. Alternatively, volume sensor assembly 148 may be used within a beverage dispensing system to control e.g., the quantity of ingredients mixed together.

While volume sensor assembly 148 is described above as utilizing a port (e.g., port assembly 624) as a resonator, this is for illustrative purposes only, as other configurations are possible and are considered to be within the scope of this disclosure. For example, a solid mass (not shown) may be suspended within port assembly 624 and may function as a resonator for volume sensor assembly 148. Specifically, the mass (not shown) for the resonator may be suspended on a diaphragm (not shown) spanning port assembly 624. Alternatively, the diaphragm itself (not shown) may act as the mass for the resonator. The natural frequency of volume sensor assembly 148 may be a function of the volume of variable volume 1502. Accordingly, if the natural frequency of volume sensor assembly 148 can be measured, the volume of variable volume 1502 may be calculated.

The natural frequency of volume sensor assembly 148 may be measured in a number of different ways. For example, a time-varying force may be applied to the diaphragm (not shown) and the relationship between that force and the motion of the diaphragm (not shown) may be used to estimate the natural frequency of volume sensor assembly 148. Alternately the mass (not shown) may be perturbed and then allowed to oscillate. The unforced motion of the mass (not shown) may then be used to calculate the natural frequency of volume sensor assembly 148.

The force applied to the resonant mass (not shown) may be accomplished in various ways, examples of which may include but are not limited to:

speaker assembly 622 may create a time-varying pressure within fixed volume 1500;

the resonant mass (not shown) may be a piezoelectric material responding to a time-varying voltage/current; and the resonant mass (not shown) may be a voice coil responding to a time-varying voltage/current The force applied to the resonant mass may be measured in various ways, examples of which may include but are not limited to:

measuring the pressure in the fixed volume;

the resonant mass (not shown) may be a piezoelectric material; and a strain gauge may be connected to the diaphragm (not shown) or other structural member supporting the resonant mass (not shown).

Similarly, the displacement of the resonant mass (not shown) may be estimated by measuring the pressure in the variable volume, or measured directly in various ways, examples of which may include but are not limited to:

via piezoelectric sensor;
  via capacitive sensor;
  via optical sensor;
  via Hall-effect sensor;
  via a potentiometer (time varying impedance) sensor;
  via an inductive type sensor; and
  via a linear variable differential transformer (LVDT)

Further, the resonant mass (not shown) may be integral to either the force or displacement type sensor (i.e. the resonant mass (not shown) may be made of piezoelectric material).

The application of force and measurement of displacement may be accomplished by a single device. For example, a piezoelectric material may be used for the resonant mass (not shown) and a time-varying voltage/current may be applied to the piezoelectric material to create a time-varying force. The resulting voltage/current applied to the piezoelectric material may be measured and the transfer function between the two used to estimate the natural frequency of volume sensor assembly 148.

As discussed above, the resonant frequency of volume sensor assembly 148 may be estimated using swept-sine system identification. Specifically, the above-described model fit may allow the resonant frequency of the port assembly to be extracted from the sine sweep data, which may then be used to determine the delivered volume. The ideal relationship between the resonant frequency and the delivered volume may be expressed as follows:

$$\omega_n^2 = \frac{a^2 A}{L} \frac{1}{V_2} \quad \text{[EQ \#126]}$$

The speed of sound will vary with temperature, so it may be useful to split out the temperature effects.

$$\omega_n^2 = \frac{\gamma R A}{L} \frac{T}{V_2} \quad \text{[EQ \#126]}$$

The volume may then be expressed as a function of the measured resonant frequency and the temperature:

$$V_2 = C \frac{T}{\omega_n^2} \quad \text{[EQ \#127]}$$

Where c is the calibration constant $$C = \frac{\gamma R A}{L}.$$

Infusion pump assembly 100 may then compare this calculated volume $V_2$ (i.e., representative of the actual volume of infusible fluid delivered to the user) to the target volume (i.e., representative of the quantity of fluid that was supposed to be delivered to the user). For example, assume that infusion pump assembly 100 was to deliver a 0.100 unit basal dose of infusible fluid to the user every thirty minutes. Further, assume that upon effectuating such a delivery, volume sensor assembly 148 indicates a calculated volume $V_2$ (i.e., representative of the actual volume of infusible fluid delivered to the user) of 0.095 units of infusible fluid.

When calculating volume $V_2$, infusion pump assembly 100 may first determine the volume of fluid within volume sensor chamber 620 prior to the administration of the dose of infusible fluid and may subsequently determine the volume of fluid within volume sensor chamber 620 after the administration of the dose of infusible fluid, wherein the difference of those two measurements is indicative of $V_2$ (i.e., the actual volume of infusible fluid delivered to the user). Accordingly, $V_2$ is a differential measurement.

V2 may be the total air space over the diaphragm in the variable volume chamber. The actual fluid delivery to the patient may be the difference in V2 from when the chamber was full to after the measurement valve was opened and the chamber was emptied. V2 may not directly be the delivered volume. For example, the air volume may be measured and a series of differential measurements may be taken. For occlusion, an empty measurement may be taken, the chamber may be filed, a full measurement may be taken, and then a final measurement may be taken after the exit valve is open. Accordingly, the difference between the first and second measurement may be the amount pumped and the difference between the second and third is the amount delivered to the patient.

Accordingly, electrical control assembly 110 may determine that the infusible fluid delivered is 0.005 units under what was called for. In response to this determination, electrical control assembly 110 may provide the appropriate signal to mechanical control assembly 104 so that any additional necessary dosage may be pumped. Alternatively, electrical control assembly 110 may provide the appropriate signal to mechanical control assembly 104 so that the additional dosage may be dispensed with the next dosage. Accordingly, during administration of the next 0.100 unit dose of the infusible fluid, the output command for the pump may be modified based on the difference between the target and amount delivered.

Figure 33:
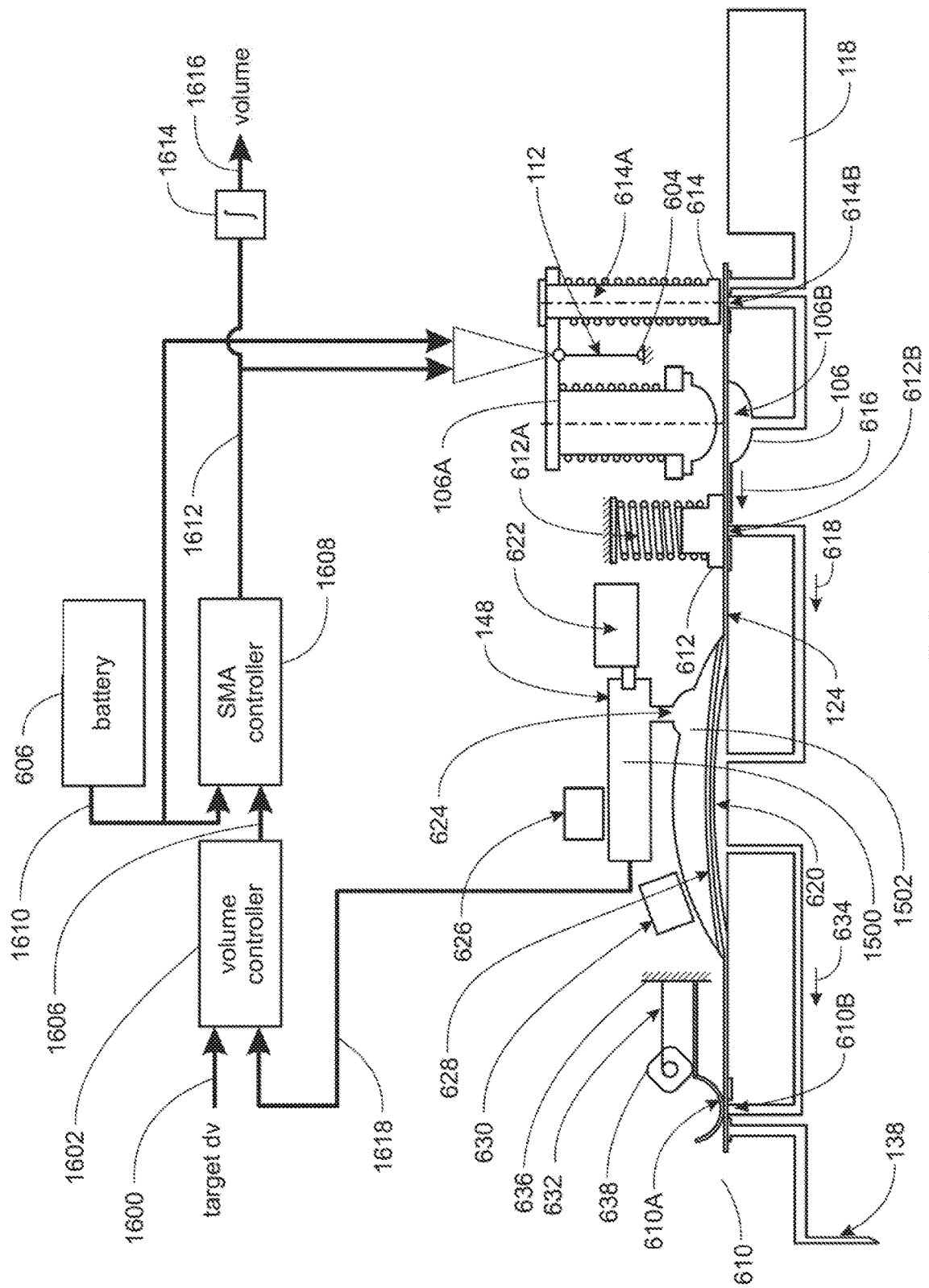
FIG. 33 is a diagrammatic view of an electrical control assembly for the volume sensor assembly included within the infusion pump assembly of FIG. 7.

Referring also to FIG. 33, there is shown one particular implementation of a control system for controlling the quantity of infusible fluid currently being infused based, at least in part, on the quantity of infusible fluid previously administered. Specifically and continuing with the above-stated example, assume for illustrative purposes that electrical control assembly 110 calls for the delivery of a 0.100 unit dose of the infusible fluid to the user. Accordingly, electrical control assembly 110 may provide a target differential volume signal 1600 (which identifies a partial basal dose of 0.010 units of infusible fluid per cycle of shape memory actuator 112) to volume controller 1602. Accordingly and in this particular example, shape memory actuator 112 may need to be cycled ten times in order to achieve the desired basal dose of 0.100 units of infusible fluid (i.e., 10 cycles×0.010 units per cycle=0.100 units). Volume controller 1602 in turn may provide "on-time" signal 1606 to SMA (i.e., shape memory actuator) controller 1608. Also provided to SMA controller 1608 is battery voltage signal 1610.

Specifically, shape-memory actuator 112 may be controlled by varying the amount of thermal energy (e.g., joules) applied to shape-memory actuator 112. Accordingly, if the voltage level of battery 606 is reduced, the quantity of joules applied to shape-memory actuator 112 may also be reduced for a defined period of time. Conversely, if the voltage level of battery 606 is increased, the quantity of joules applied to shape memory actuator 112 may also be increased for a defined period of time. Therefore, by monitoring the voltage level of battery 606 (via battery voltage signal 1610), the type of signal applied to shape-memory actuator 112 may be varied to ensure that the appropriate quantity of thermal energy is applied to shape-memory actuator 112 regardless of the battery voltage level.

SMA controller 1608 may process "on-time" signal 1606 and battery voltage signal 1610 to determine the appropriate SMA drive signal 1612 to apply to shape-memory actuator 112. One example of SMA drive signal 1612 may be a series of binary pulses in which the amplitude of SMA drive signal 1612 essentially controls the stroke length of shape-memory actuator 112 (and therefore pump assembly 106) and the duty cycle of SMA drive signal 1612 essentially controls the stroke rate of shape-memory actuator 112 (and therefore pump assembly 106). Further, since SMA drive signal 1612 is indicative of a differential volume (i.e., the volume infused during each cycle of shape memory actuator 112), SMA drive signal 1612 may be integrated by discrete time integrator 1614 to generate volume signal 1616 which may be indicative of the total quantity of infusible fluid infused during a plurality of cycles of shape memory actuator 112. For example, since (as discussed above) it may take ten cycles of shape memory actuator 112 (at 0.010 units per cycle) to infuse 0.100 units of infusible fluid, discrete time integrator 1614 may integrate SMA drive signal 1612 over these ten cycles to determine the total quantity infused of infusible fluid (as represented by volume signal 1616).

SMA drive signal 1612 may actuate pump assembly 106 for e.g. one cycle, resulting in the filling of volume sensor chamber 620 included within volume sensor assembly 148. Infusion pump assembly 100 may then make a first measurement of the quantity of fluid included within volume sensor chamber 620 (as discussed above). Further and as discussed above, measurement valve assembly 610 may be subsequently energized, resulting in all or a portion of the fluid within volume sensor chamber 620 being delivered to the user. Infusion pump assembly 100 may then make a measurement of the quantity of fluid included within volume sensor chamber 620 (as described above) and use those two measurements to determine $V_2$ (i.e., the actual volume of infusible fluid delivered to the user during the current cycle of shape memory actuator 112). Once determined, $V_2$ (i.e., as represented by signal 1618) may be provided (i.e., fed back) to volume controller 1602 for comparison to the earlier-received target differential volume.

Continuing with the above-stated example in which the differential target volume was 0.010 units of infusible fluid, assume that $V_2$ (i.e., as represented by signal 1618) identifies 0.009 units of infusible fluid as having been delivered to the user. Accordingly, infusion pump assembly 100 may increase the next differential target volume to 0.011 units to offset the earlier 0.001 unit shortage. Accordingly and as discussed above, the amplitude and/or duty cycle of SMA drive signal 1612 may be increased when delivering the next basal dose of the infusible fluid to the user. This process may be repeated for the remaining nine cycles of shape memory actuator 112 (as discussed above) and discrete time integrator 1614 may continue to integrate SMA drive signal 1612 (to generate volume signal 1616) which may define the total quantity of infusible fluid delivered to the user.

Figure 34:
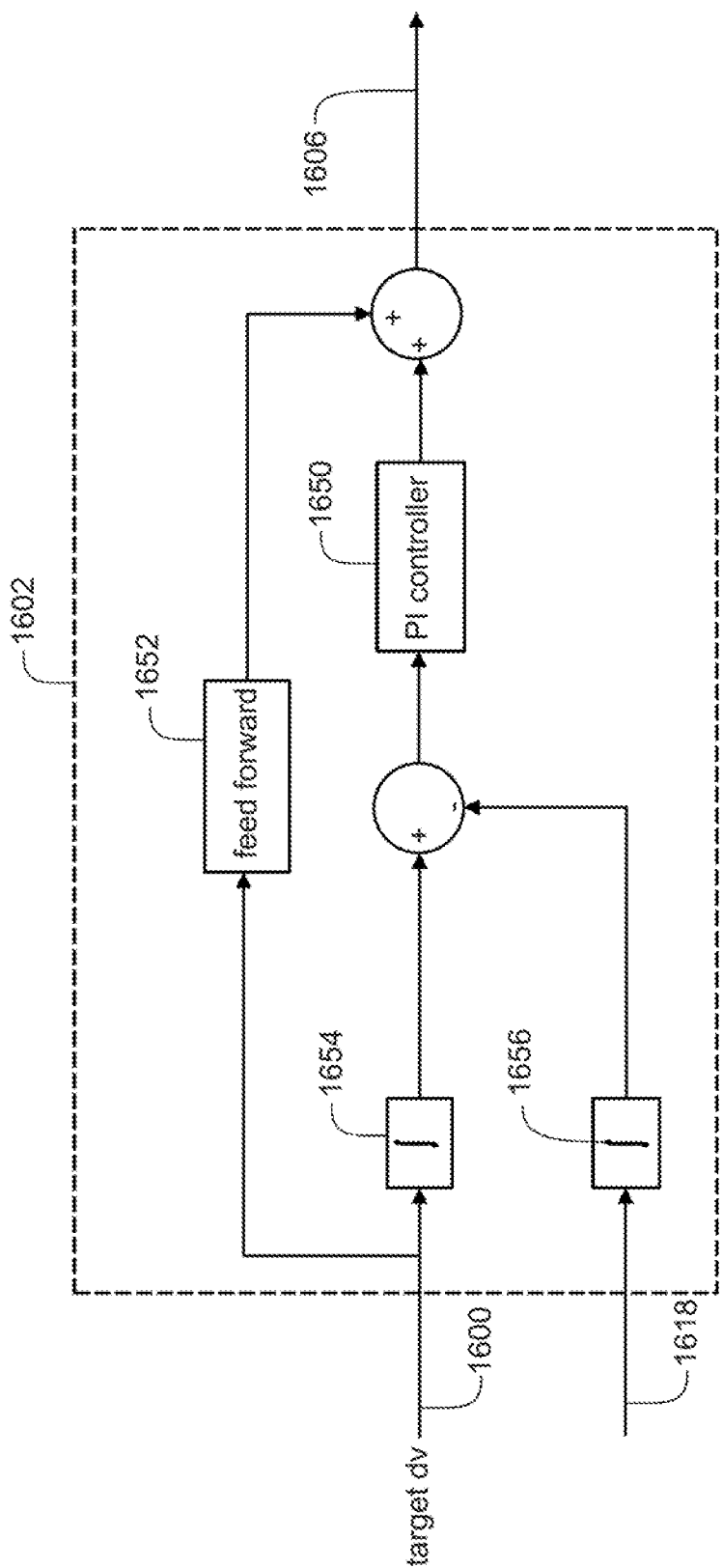
FIG. 34 is a diagrammatic view of a volume controller for the volume sensor assembly included within the infusion pump assembly of FIG. 7.

Referring also to FIG. 34, there is shown one possible embodiment of volume controller 1602. In this particular implementation, volume controller 1602 may include PI (proportional-integrator) controller 1650. Volume controller 1602 may include feed forward controller 1652 for setting an initial "guess" concerning "on-time" signal 1606. For example, for the situation described above in which target differential volume signal 1600 identifies a partial basal dose of 0.010 units of infusible fluid per cycle of shape memory actuator 112, feed forward controller 1652 may define an initial "on-time" of e.g., one millisecond. Feed forward controller 1652 may include e.g., a lookup table that define an initial "on-time" that is based, at least in part, upon target differential volume signal 1600. Volume controller 1602 may further include discrete time integrator 1654 for integrating target differential volume signal 1600 and discrete time integrator 1656 for integrating $V_2$ (i.e., as represented by signal 1618).

Figure 35:
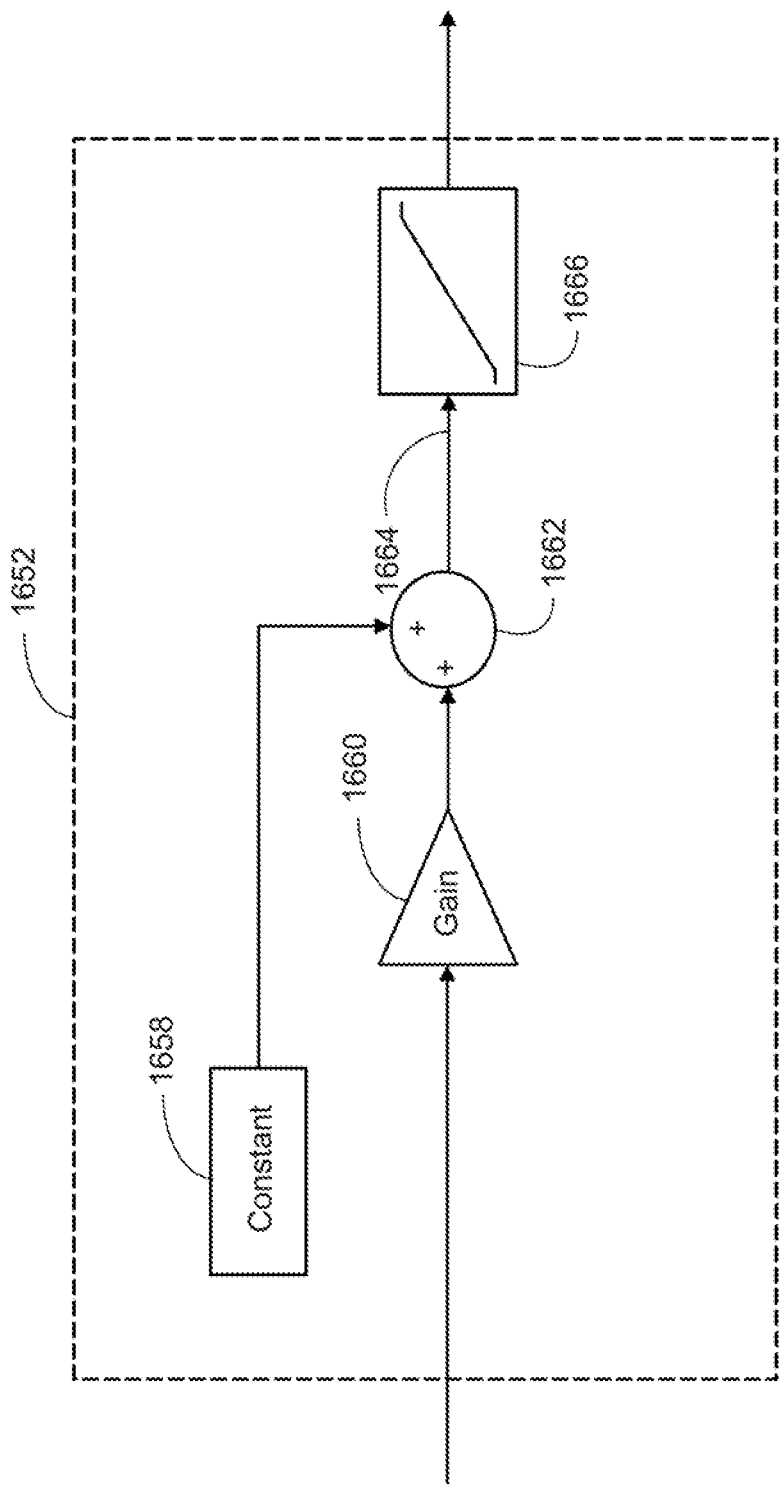
FIG. 35 is a diagrammatic view of a feed forward controller of the volume controller of FIG. 34.

Referring also to FIG. 35, there is shown one possible embodiment of feed forward controller 1652. In this particular implementation, feed forward controller 1652 may define a constant value signal 1658 and may include amplifier 1660 (e.g., a unity gain amplifier), the output of which may be summed with constant value signal 1658 at summing node 1662. The resulting summed signal (i.e., signal 1664) may be provided to as an input signal to e.g., lookup table 1666, which may be processed to generate the output signal of feed forward controller 1652.

As discussed above, pump assembly 106 may be controlled by shape memory actuator 112. Further and as discussed above, SMA controller 1608 may process "on-time" signal 1606 and battery voltage signal 1610 to determine the appropriate SMA drive signal 1612 to apply to shape-memory actuator 112.

Figure 36:
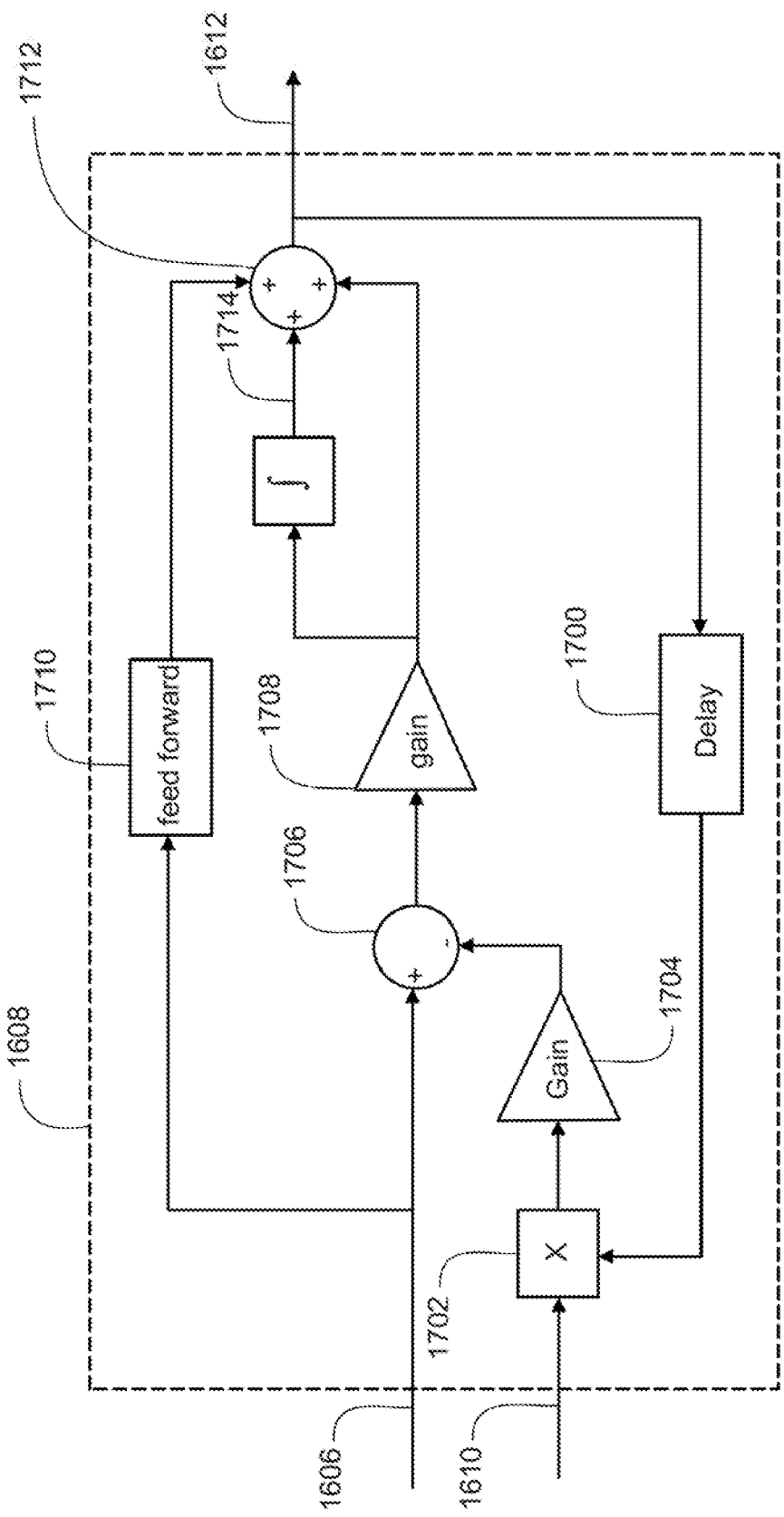
FIGS. 36-37 diagrammatically depicts an implementation of an SMA controller of the volume controller of FIG. 34.
Figure 37:
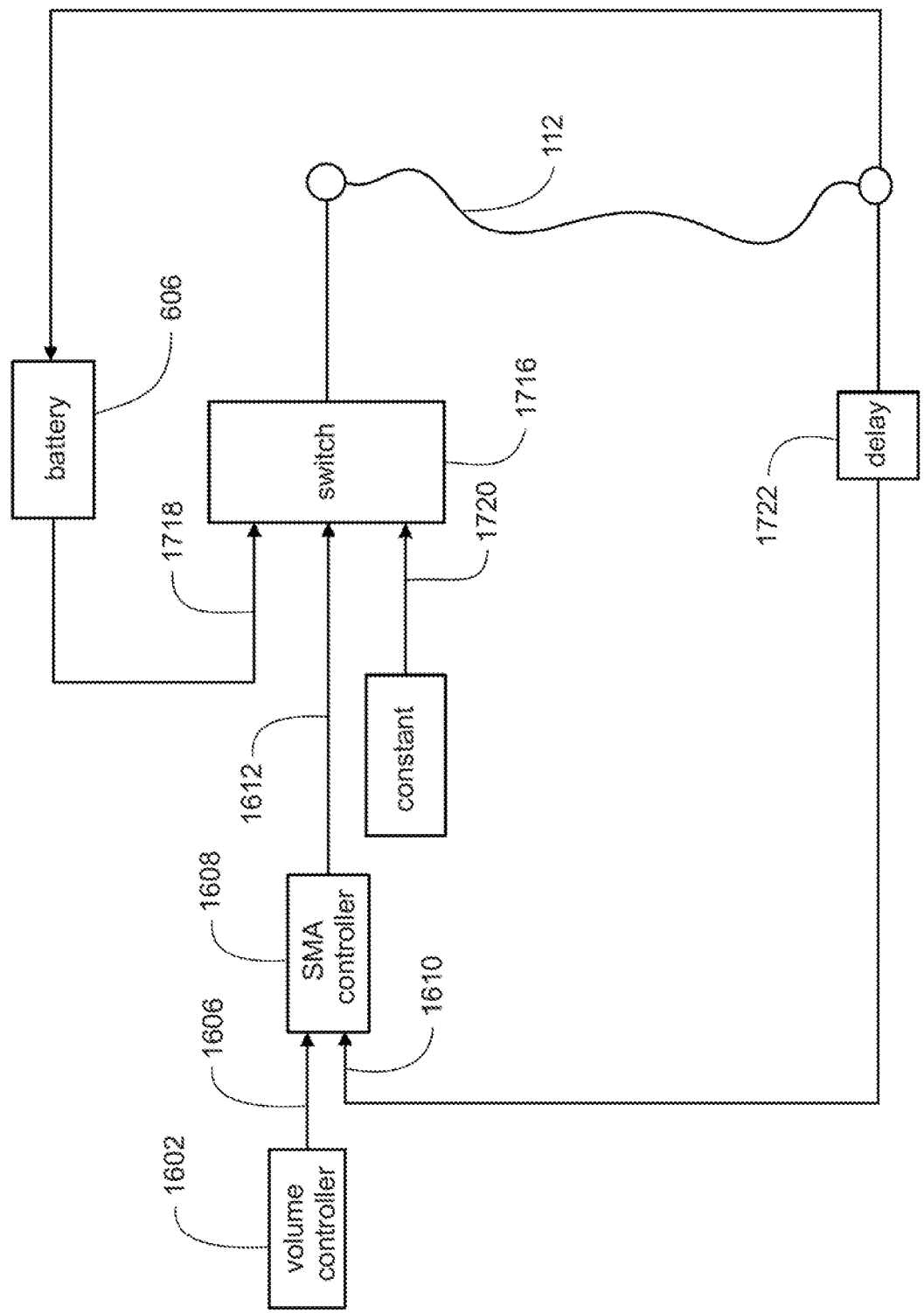

Referring also to FIGS. 36-37, there is shown one particular implementation of SMA controller 1608. As discussed above, SMA controller 1608 may be responsive to "on-time" signal 1606 and battery voltage signal 1610 and may provide SMA drive signal 1612 to shape-memory actuator 112. SMA controller 1608 may include a feedback loop (including unit delay 1700), the output of which may be multiplied with battery voltage signal 1610 at multiplier 1702. The output of multiplier 1702 may be amplified with e.g., unity gain amplifier 1704. The output of amplifier 1704 may be applied to the negative input of summing node 1706 (to which "on-time" signal 1606 is applied). The output of summing node 1706 may be amplified (via e.g., unity gain amplifier 1708). SMA controller may also include feed forward controller 1710 to provide an initial value for SMA drive signal 1612 (in a fashion similar to feed forward controller 1652 of volume controller 1602; See FIG. 35). The output of feed forward controller 1710 may be summed at summing node 1712 with the output of amplifier 1708 and an integrated representation (i.e., signal 1714) of the output of amplifier 1708 to form SMA drive signal 1612.

SMA drive signal 1612 may be provided to control circuitry that effectuates the application of power to shape-memory actuator 112. For example, SMA drive signal 1612 may be applied to switching assembly 1716 that may selectively apply current signal 1718 (supplied from battery 606) and/or fixed signal 1720 to shape-memory actuator. For example, SMA drive signal 1612 may effectuate the application of energy (supplied from battery 606 via current signal 1718) via switching assembly 1716 in a manner that achieves the duty cycle defined by SMA drive signal 1612. Unit delay 1722 may generate a delayed version of the signal applied to shape-memory actuator 112 to form battery voltage signal 1610 (which may be applied to SMA controller 1608).

When applying power to shape-memory actuator 112, voltage may be applied for a fixed amount of time and: a) at a fixed duty cycle with an unregulated voltage; b) at a fixed duty cycle with a regulated voltage; c) at a variable duty cycle based upon a measured current value; d) at a variable duty cycle based upon a measured voltage value; and e) at a variable duty cycle based upon the square of a measured voltage value. Alternatively, voltage may be applied to shape-memory actuator 112 for a variable amount of time based upon a measured impedance.

When applying an unregulated voltage for a fixed amount of time at a fixed duty cycle, inner loop feedback may not be used and shape memory actuator may be driven at a fixed duty cycle and with an on-time determined by the outer volume loop.

When applying a regulated voltage for a fixed amount of time at a fixed duty cycle, inner loop feedback may not be used and shape memory actuator 112 may be driven at a fixed duty cycle and with an on-time determined by the outer volume loop.

When applying an unregulated voltage at a variable duty cycle based upon a measured current value, the actual current applied to shape-memory actuator 112 may be measured and the duty cycle may be adjusted during the actuation of shape-memory actuator 112 to maintain the correct mean current.

When applying an unregulated voltage at a variable duty cycle based upon a measured voltage value, the actual voltage applied to shape-memory actuator 112 may be measured and the duty cycle may be adjusted during the actuation of shape-memory actuator 112 to maintain the correct mean voltage.

When applying an unregulated voltage at a variable duty cycle based upon the square of a measured voltage value, the actual voltage applied to shape-memory actuator 112 may be measured and the duty cycle may be adjusted during the actuation of shape-memory actuator 112 to maintain the square of the voltage at a level required to provide the desired level of power to shape-memory actuator 112 (based upon the impedance of shape-memory actuator 112).

Figure 38A:
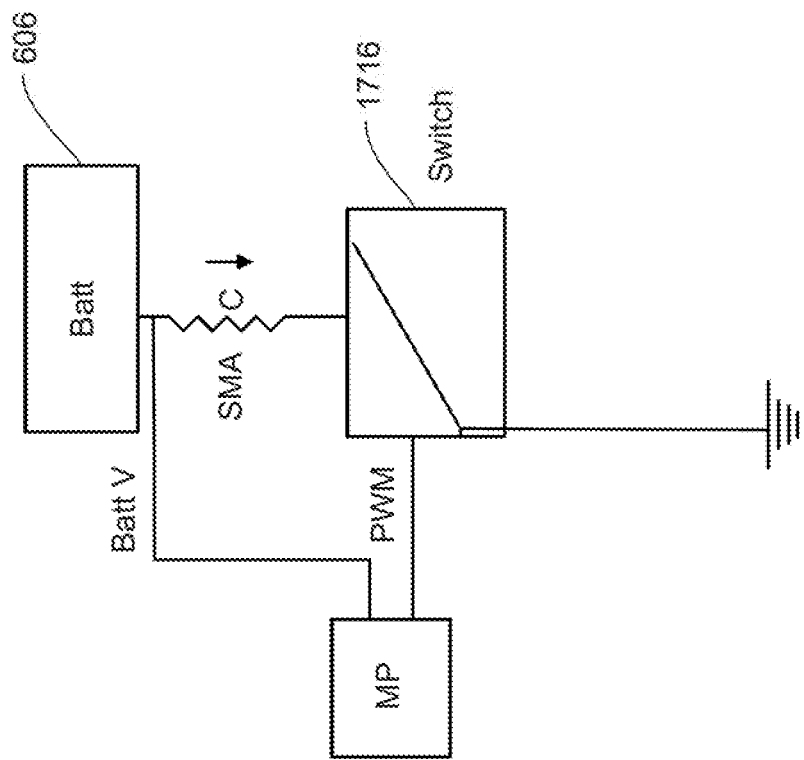
FIG. 38A-38B is an alternate implementation of an SMA controller.
Figure 38B:
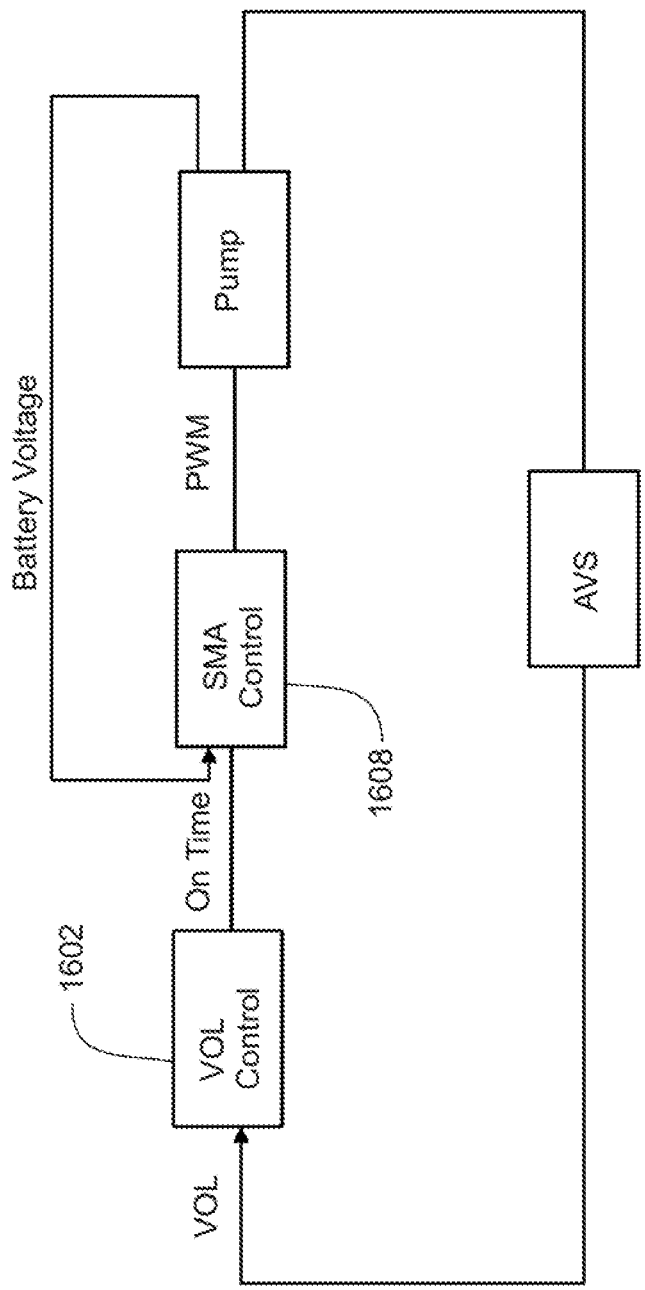

Referring also to FIG. 38A-38B, there is shown other implementations of SMA controller 1608. Specifically, FIG. 38A is an electrical schematic that includes a microprocessor and various control loops that may be configured to provide a PWM signal that may open and close the switch assembly. The switch assembly may control the current that is allowed to flow through the shape memory actuator. The battery may provide the current to the shape memory actuator. Further, 114B discloses a volume controller and an inner shape memory actuator controller. The shape memory actuator controller may provide a PWM signal to the pump, which may be modified based on the battery voltage. This may occur for a fixed ontime, the result being a volume that may be measured by volume sensor assembly 148 and fed back into the volume controller.

In our preferred embodiment, we vary the duty cycle based on the measured battery voltage to give you approximately consistent power. We adjust the duty cycle to compensate for a lower battery voltage. Battery voltage may change for two reasons: 1) as batteries are discharged, the voltage slowly decreases; and 2) when you apply a load to a battery it has an internal impedance so its voltage dips. This is something that happens in any type of system, and we compensate for that by adjusting the duty cycle, thus mitigating the lower or varying battery voltage. Battery voltage may be measured by the microprocessor. In other systems: 1) voltage may be regulated (put a regulator to maintain the voltage at a steady voltage); 2) feedback based on something else (i.e., speed or position of a motor, not necessarily measuring the battery voltage).

Other configurations may be utilized to control the shape memory actuator. For example: A) the shape memory actuator may be controlled at fixed duty cycle with unregulated voltage. As voltage varies, the repeatability of heating the shape memory actuator is reduced. B) a fixed duty cycle, regulated voltage may be utilized which compensates for changes in battery voltage. However, regulate the voltage down is less efficient due to energy of energy. C) the duty cycle may be varied based on changes in current (which may required more complicated measurement circuitry. D) The duty cycle may be varied based on measured voltage. E) The duty cycle may be varied based upon the square of the current. or the square of the voltage divided by resistance. F) the voltage may be applied for a variable amount of time based on the measured impedance (e.g., may measure impedance using Wheatstone gauge (not shown)). The impedance of the shape memory actuator may be correlated to strain (i.e., may correlate how much the SMA moves based on its impedance).

Figure 39:
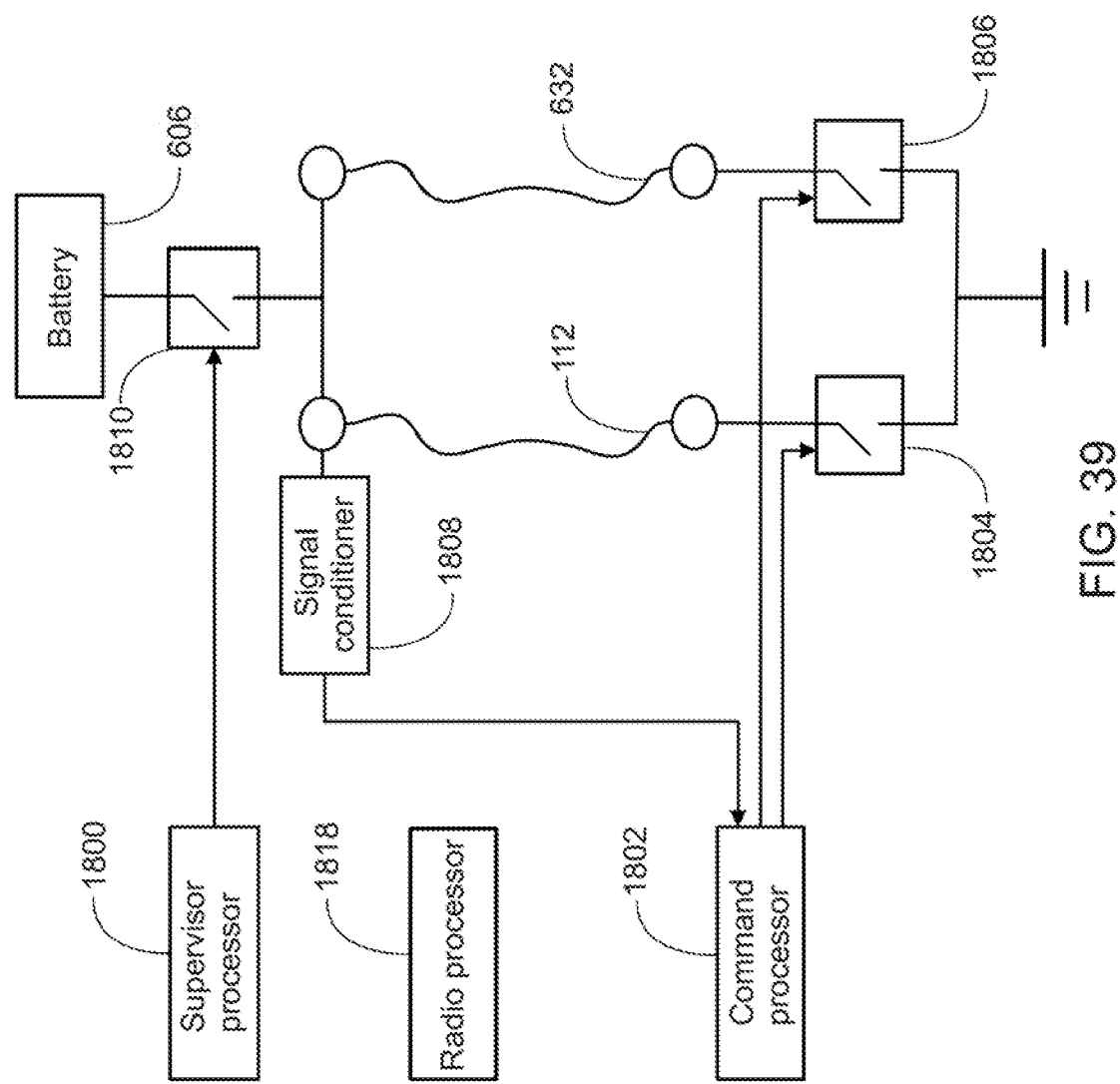
FIG. 39 diagrammatically depicts a multi-processor control configuration that may be included within the infusion pump assembly of FIG. 7.

Referring also to FIG. 39 and as discussed above, to enhance the safety of infusion pump assembly 100, electrical control assembly 110 may include two separate and distinct microprocessors, namely supervisor processor 1800 and command processor 1802. Specifically, command processor 1802 may perform the functions discussed above (e.g., generating SMA drive signal 1612) and may control relay/switch assemblies 1804, 1806 that control the functionality of (in this example) shape memory actuators 112, 632 (respectively). Command processor 1802 may receive feedback from signal conditioner 1808 concerning the condition (e.g., voltage level) of the voltage signal applied to shape memory actuators 112, 632. Command processor 1800 may control relay/switch assembly 1810 independently of relay/switch assemblies 1804, 1806. Accordingly, when an infusion event is desired, both of supervisor processor 1800 and command processor 1802 must agree that the infusion event is proper and must both actuate their respective relays/switches. In the event that either of supervisor processor 1800 and command processor 1802 fails to actuate their respective relays/switches, the infusion event will not occur. Accordingly through the use of supervisor processor 1800 and command processor 1802 and the cooperation and concurrence that must occur, the safety of infusion pump assembly 100 is enhanced. \

The supervisor processor may prevent the command processor from delivering when it is not supposed and also may alarm if the command processor does not deliver when it should be delivering. The supervisor processor may deactivate the relay/switch assembly if the command processor actuates the wrong switch, or if the command processor it tries to apply power for too long.

The supervisor processor may redundantly doing calculations for how much insulin should be delivered (i.e., double checking the calculations of the command processor). Command processor may decide the delivery schedule, and the supervisor processor may redundantly check those calculations.

Supervisor also redundantly holds the profiles (delivery profiles) in RAM, so the command processor may be doing the correct calculations, but if is has bad RAM, would cause the command to come up with the wrong result. The Supervisor uses its local copy of the basal profile, etc., to double check.

Supervisor can double check AVS measurements, looks at the AVS calculations and applies safety checks. Every time AVS measurement is taken, it double checks.

Referring also to FIG. 40, one or more of supervisor processor 1800 and command processor 1802 may perform diagnostics on various portions of infusion pump assembly 100. For example, voltage dividers 1812, 1814 may be configured to monitor the voltages (V1 & V2 respectively) sensed at distal ends of e.g., shape memory actuator 112. The value of voltages V1 & V2 in combination with the knowledge of the signals applied to relay/switch assemblies 1804, 1810 may allow for diagnostics to be performed on various components of the circuit shown in FIG. 40 (in a manner similar to that shown in illustrative diagnostic table 1816).

As discussed above and as illustrated in FIGS. 39-40, to enhance the safety of infusion pump assembly 100, electrical control assembly 110 may include a plurality of microprocessors (e.g., supervisor processor 1800 and command processor 1802), each of which may be required to interact and concur in order to effectuate the delivery of a dose of the infusible fluid. In the event that the microprocessors fail to interact/concur, the delivery of the dose of infusible fluid may fail and one or more alarms may be triggered, thus enhancing the safety and reliability of infusion pump assembly 100.

A master alarm may be utilized that tracks the volume error over time. Accordingly, if the sum of the errors becomes too large, the master alarm may be initiated, indicating that something may be wrong with the system. Accordingly, the master alarm may be indicative of a total volume comparison being performed and a discrepancy being noticed. A typical value of the discrepancy required to initiate the master alarm may be 1.00 milliliters. The master alarm may monitor the sum in a leaky fashion (i.e., Inaccuracies have a time horizon).

Figure 41A:
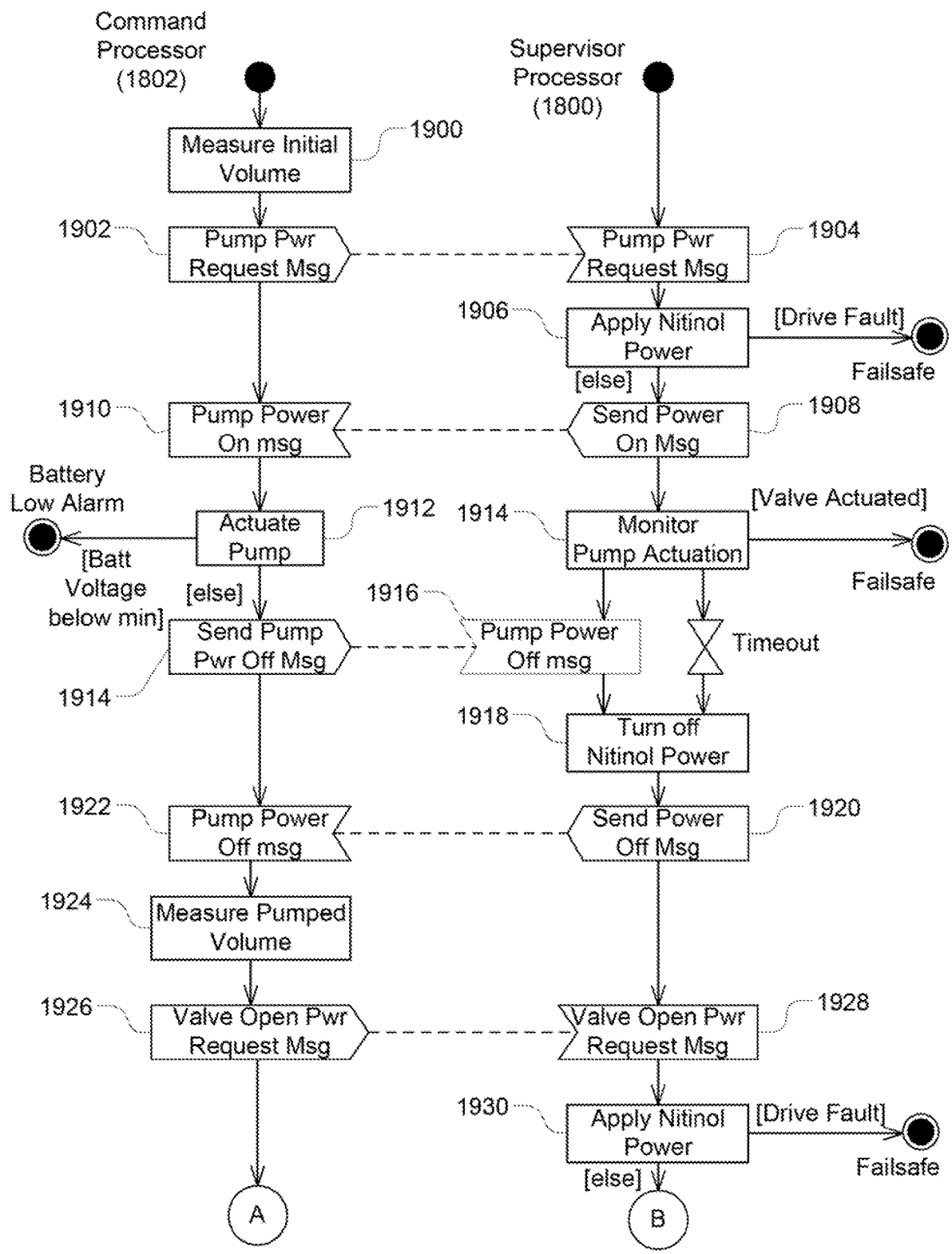
FIG. 41A-41B diagrammatically depicts multi-processor functionality.
Figure 41B:
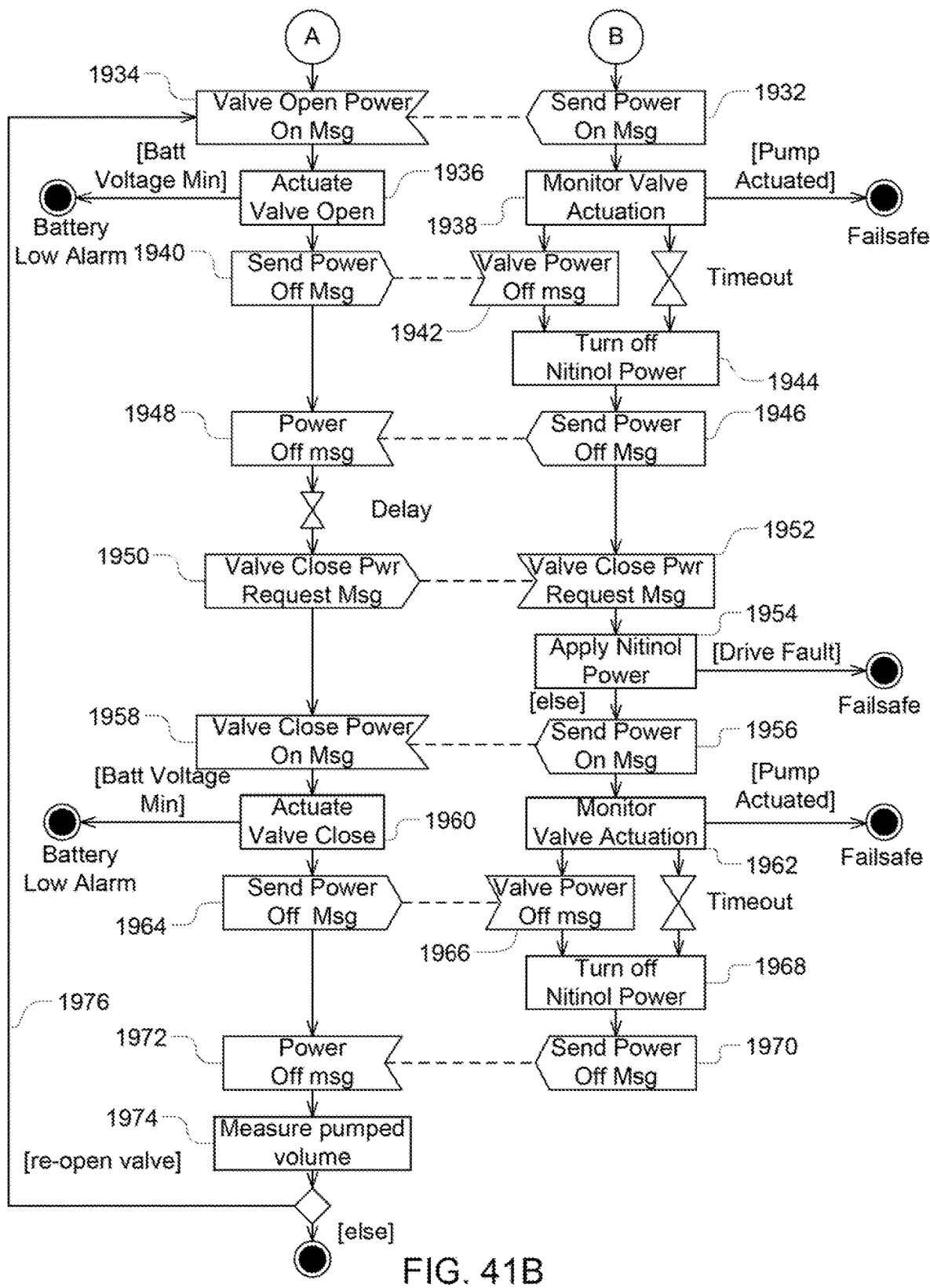

Referring also to FIGS. 41A-41B, there is shown one such illustrative example of such interaction amongst multiple microprocessors during the delivery of a dose of the infusible fluid. Specifically, command processor 1802 may first determine 1900 the initial volume of infusible fluid within volume sensor chamber 620. Command processor 1802 may then provide 1902 a "pump power request" message to supervisor processor 1800. Upon receiving 1904 the "pump power request" message, supervisor processor 1800 may e.g., energize 1906 relay/switch 1810 (thus energizing shape memory actuator 112) and may send 1908 a "pump power on" message to command processor 1802. Upon receiving 1910 the "pump power on" message, command processor 1802 may actuate 1912 e.g., pump assembly 106 (by energizing relay/switch 1804), during which time supervisor processor 1800 may monitor 1914 the actuation of e.g., pump assembly 106.

Once actuation of pump assembly 106 is complete, command processor 1802 may provide 1914 a "pump power off" message to supervisor processor 1800. Upon receiving 1916 the "pump power off" message, supervisor processor 1800 may deenergize 1918 relay/switch 1810 and provide 1920 a "pump power off" message to command processor 1802. Upon receiving 1922 the "pump power off" message, command processor 1802 may measure 1924 the quantity of infusible fluid pumped by pump assembly 106. This may be accomplished by measuring the current quantity of fluid within volume sensor chamber 620 and comparing it with the quantity determined above (in step 1900). Once determined 1924, command processor 1802 may provide 1926 a "valve open power request" message to supervisor processor 1800. Upon receiving 1928 the "valve open power request" message, supervisor processor 1800 may energize 1930 relay/switch 1810 (thus energizing shape memory actuator 632) and may send 1932 a "valve open power on" message to command processor 1802. Upon receiving 1934 the "valve open power on" message, command processor 1802 may actuate 1936 e.g., measurement valve assembly 610 (by energizing relay/switch 1806), during which time supervisor processor 1800 may monitor 1938 the actuation of e.g., measurement valve assembly 610.

Once actuation of measurement valve assembly 610 is complete, command processor 1802 may provide 1940 a "valve power off" message to supervisor processor 1800. Upon receiving 1942 the "valve power off" message, supervisor processor 1800 may deenergize 1944 relay/switch 1810 and provide 1946 a "valve power off" message to command processor 1802.

Upon receiving 1948 the "valve power off" message, command processor 1802 may provide 1950 a "valve close power request" message to supervisor processor 1800. Upon receiving 1952 the "valve close power request" message, supervisor processor 1800 may energize 1954 relay/switch 1810 (thus energizing shape memory actuator 652) and may send 1956 a "power on" message to command processor 1802. Upon receiving 1958 the "power on" message, command processor 1802 may actuate 1960 an energizing relay/switch (not shown) that is configured to energize shape memory actuator 652, during which time supervisor processor 1800 may monitor 1962 the actuation of e.g., shape memory actuator 652.

Shape memory actuator 652 may be anchored on a first end using electrical contact 654. The other end of shape memory actuator 652 may be connected to bracket assembly 656. When shape memory actuator 652 is activated, shape memory actuator 652 may pull bracket assembly 656 forward and release valve assembly 634. As such, measurement valve assembly 610 may be activated via shape memory actuator 632. Once measurement valve assembly 610 has been activated, bracket assembly 656 may automatically latch valve assembly 610 in the activated position. Actuating shape memory actuator 652 may pull bracket assembly 656 forward and release valve assembly 634. Assuming shape memory actuator 632 is no longer activated, measurement valve assembly 610 may move to a de-activated state once bracket assembly 656 has released valve assembly 634. Accordingly, by actuating shape memory actuator 652, measurement valve assembly 610 may be deactivated.

Once actuation of shape memory actuator 652 is complete, command processor 1802 may provide 1964 a "power off" message to supervisor processor 1800. Upon receiving 1966 the "power off" message, supervisor processor 1800 may deenergize 1968 relay/switch 1810 and may provide 1970 a "power off" message to command processor 1802. Upon receiving 1972 the "power off" message, command processor 1802 may determine the quantity of infusible fluid within volume sensor chamber 620, thus allowing command processor 1802 to compare this measured quantity to the quantity determined above (in step 1924) to determine 1974 the quantity of infusible fluid delivered to the user.

In the event that the quantity of infusible fluid delivered 1974 to the user is less than the quantity of infusible fluid specified for the basal/bolus infusion event, the above-described procedure may be repeated (via loop 1976).

Figure 42:
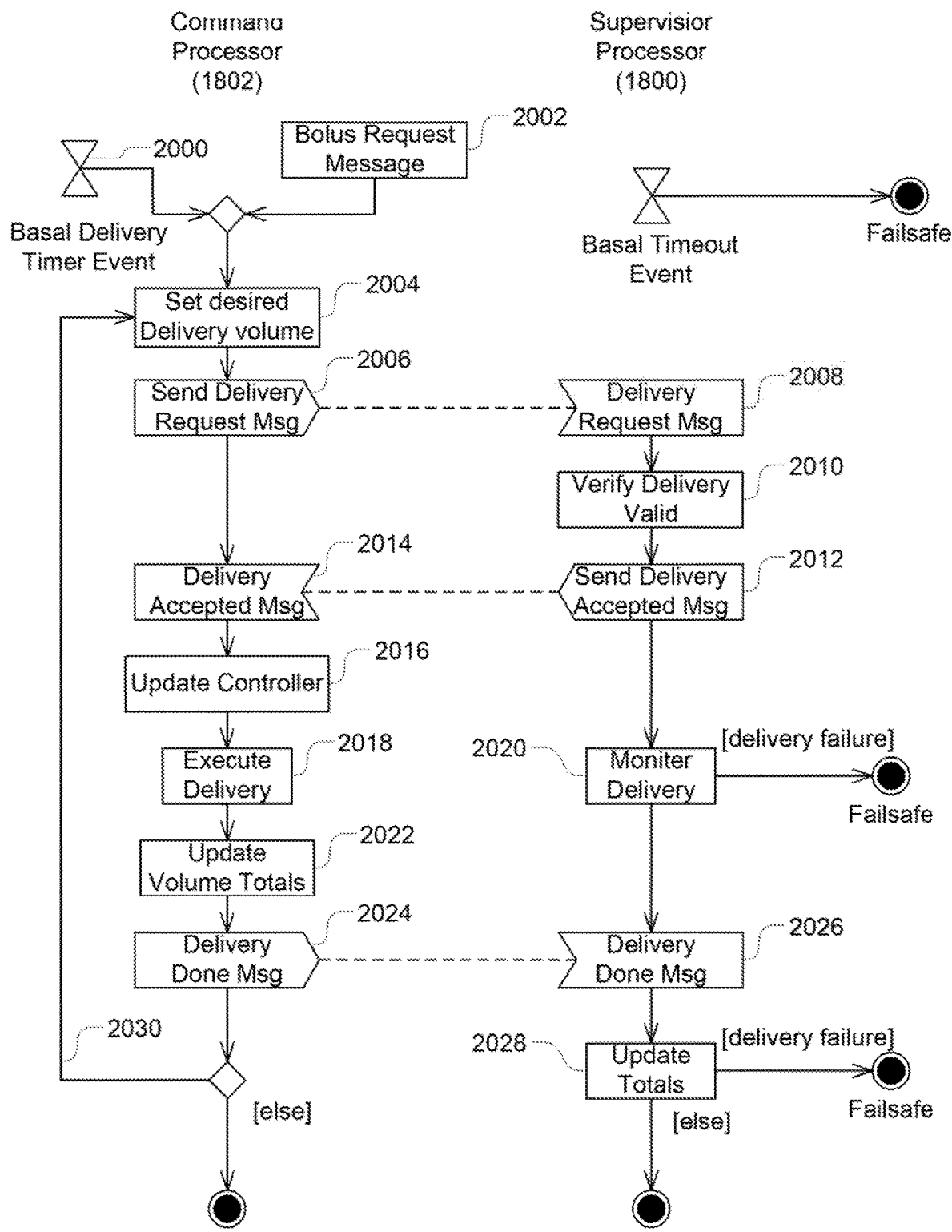
FIG. 42 diagrammatically depicts multi-processor functionality.

Referring also to FIG. 42, there is shown another illustrative example of the interaction amongst processors 1800, 1802, this time during the scheduling of a dose of infusible fluid. Command processor 1802 may monitor 2000, 2002 for the receipt of a basal scheduling message or a bolus request message (respectively). Upon receipt 2000, 2002 of either of these messages, command processor 1802 may set 2004 the desired delivery volume and may provide 2006 a "delivery request" message to supervisor processor 1800. Upon receiving 2008 the "delivery request" message, supervisor processor 1800 may verify 2010 the volume defined 2004 by command processor 1802. Once verified 2010, supervisor processor 1800 may provide 2012 a "delivery accepted" message to command processor 1802. Upon receipt 2014 of the "delivery accepted" message, command processor 1802 may update 2016 the controller (e.g., the controller discussed above and illustrated in FIG. 33) and execute 2018 delivery of the basal/bolus dose of infusible fluid. Command processor 1808 may monitor and update 2022 the total quantity of infusible fluid delivered to the user (as discussed above and illustrated in FIGS. 41A-41B). Once the appropriate quantity of infusible fluid is delivered to the user, command processor 1802 may provide 2024 a "delivery done" message to supervisor processor 1800. Upon receipt 2026 of the "delivery done" message, supervisor processor 1800 may update 2028 the total quantity of infusible fluid delivered to the user. In the event that the total quantity of infusible fluid delivered 2018 to the user is less than the quantity defined above (in step 2004), the infusion process discussed above may be repeated (via loop 2030).

Figure 43:
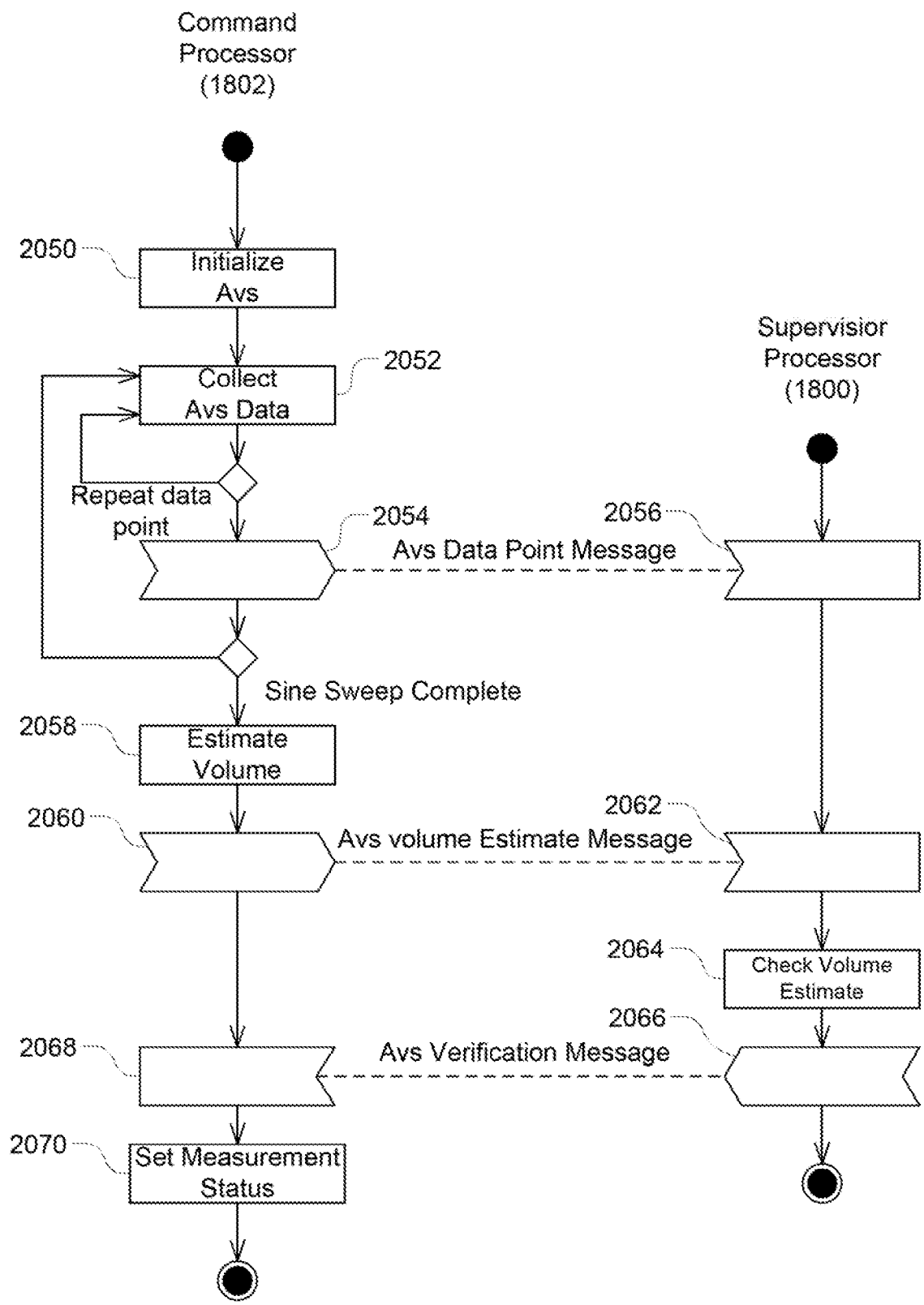
FIG. 43 diagrammatically depicts multi-processor functionality.

Referring also to FIG. 43, there is shown an example of the manner in which supervisor processor 1800 and command processor 1802 may interact while effectuating a volume measurements via volume sensor assembly 148 (as described above).

Specifically, command processor 1802 may initialize 2050 volume sensor assembly 148 and begin collecting 2052 data from volume sensor assembly 148, the process of which may be repeated for each frequency utilized in the above-described sine sweep. Each time that data is collected for a particular sweep frequency, a data point message may be provided 2054 from command processor 1802, which may be received 2056 by supervisor processor 1800.

Once data collection 2052 is completed for the entire sine sweep, command processor 1802 may estimate 2058 the volume of infusible fluid delivered by infusion pump assembly 100. Command processor 1802 may provide 2060 a volume estimate message to supervisor processor 1800. Upon receiving 2062 this volume estimate message, supervisor processor 1800 may check (i.e., confirm) 2064 the volume estimate message. Once checked (i.e., confirmed), supervisor processor 1800 may provide 2066 a verification message to command processor 1802. Once received 2068 from supervisor processor 1800, command processor 1802 may set the measurement status for the dose of infusible fluid delivered by volume sensor assembly 148.

Figure 44:
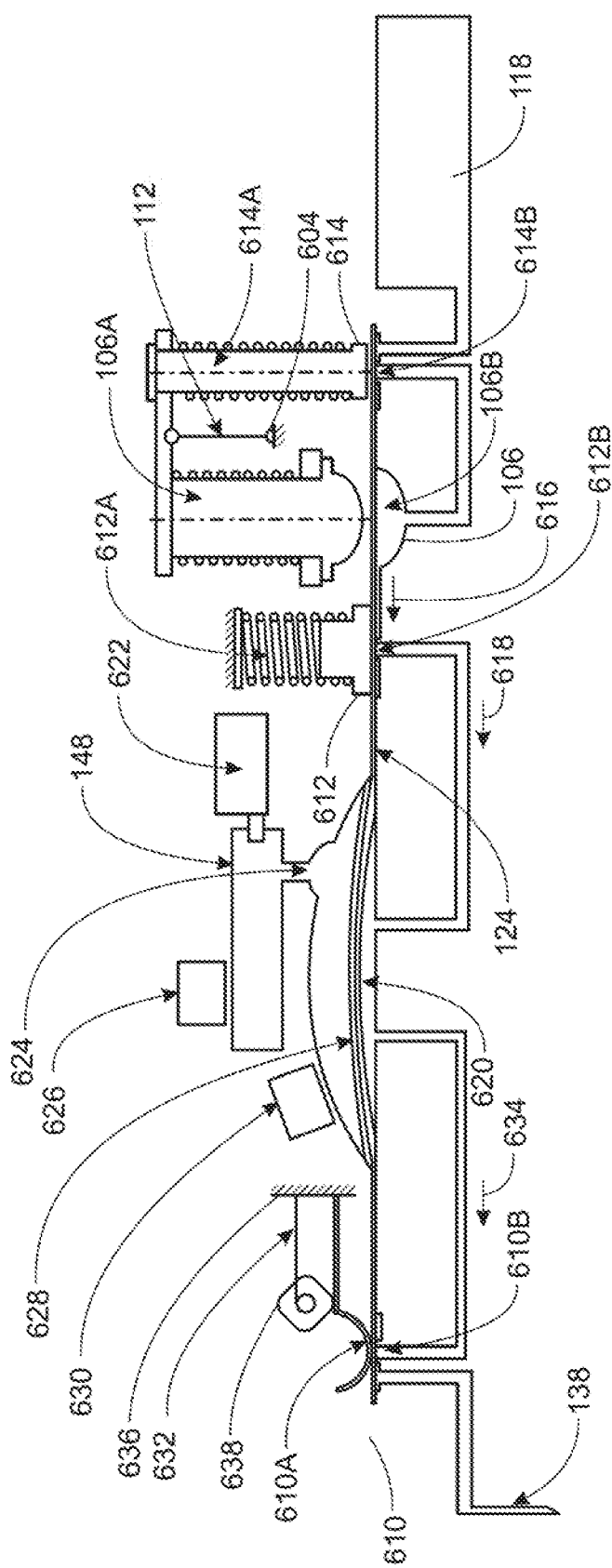
FIG. 44 diagrammatically depicts a volume sensor assembly included within the infusion pump assembly of FIG. 7.

Occlusions and/or leaks may occur anywhere along the fluid delivery path of infusion pump assembly 100. For example and referring to FIG. 44, occlusions/leaks may occur: in the fluid path between reservoir 118 and reservoir valve assembly 614; in the fluid path between reservoir valve assembly 614 and pump assembly 106; in the fluid path between pump assembly 106 and volume sensor valve assembly 612; in the fluid path between volume sensor valve assembly 612 and volume sensor chamber 620; in the fluid path between volume sensor chamber 620 and measurement valve assembly 610; and in the fluid path between measurement valve assembly 610 and the tip of disposable cannula 138. Infusion pump assembly 100 may be configured to execute one or more occlusion/leak detection algorithms that detect and locate such occlusions/leaks and enhance the safety/reliability of infusion pump assembly 100.

As discussed above, when administering the infusible fluid, infusion pump assembly 100 may first determine the volume of infusible fluid within volume sensor chamber 620 prior to the administration of the dose of infusible fluid and may subsequently determine the volume of infusible fluid within volume sensor chamber 620 after the administration of the dose of infusible fluid. By monitoring these values, the occurrence of occlusions/leaks may be detected.

Occlusion Type—Total:

When a total occlusion is occurring, the difference between the initial measurement prior to the administration of the dose of infusible fluid and the final measurement after the administration of the dose of infusible fluid will be zero (or essentially zero), indicating a large residual quantity of infusible fluid within volume sensor chamber 620. Accordingly, no fluid may be leaving volume sensor chamber 620.

Specifically, if the tip of disposable cannula is occluded, the fluid path down stream of volume sensor chamber 620 will fill with fluid and eventually become pressurized to a level equivalent to the mechanical pressure exerted by spring diaphragm 628. Accordingly, upon measurement valve assembly 610 opening, zero (or essentially zero) fluid will be dispensed and, therefore, the value of the initial and final measurements (as made by volume sensor assembly 148) will essentially be equal.

Upon detecting the occurrence of such a condition, a total occlusion flag may be set and infusion pump assembly 100 may e.g., trigger an alarm, thus indicating that the user needs to seek alternative means for receiving their therapy.

Occlusion Type—Partial:

When a partial occlusion is occurring, the difference between the initial measurement prior to the administration of the dose of infusible fluid and the final measurement after the administration of the dose of infusible fluid will indicate that less than a complete dose of infusible fluid was delivered. For example, assume that at the end of a particular pumping cycle, volume sensor assembly 148 indicated that 0.10 microliters of infusible fluid were present in volume sensor chamber 620. Further, assume that measurement value assembly 610 is subsequently closed and pump assembly 106 is subsequently actuated, resulting in volume sensor chamber 620 being filed with the infusible fluid. Further assume that volume sensor assembly 148 determines that volume sensor chamber 620 is now filled with 1.00 microliters of infusible fluid (indicating a pumped volume of 0.90 microliters).

Accordingly, upon the opening of measurement valve assembly 610, the quantity of infusible fluid included within volume sensor chamber would be expected to drop to 0.10 microliters (or reasonably close thereto). However, in the event of a partial occlusion, due to a slower-than-normal flow rate from volume sensor chamber 620, the quantity of infusible fluid within volume sensor chamber 620 may only be reduced to 0.40 microliters (indicating a delivered volume of 0.60 microliters). Accordingly, by monitoring the difference between the pumped volume (0.90 microliters) and the delivered volume (0.60 microliters), the residual volume may be defined and the occurrence of a partial occlusion may be detected.

Upon detecting the occurrence of such a condition, a partial occlusion flag may be set and infusion pump assembly 100 may e.g., trigger an alarm, thus indicating that the user needs to seek alternative means for receiving their therapy. However, as this is indicative of a partial occlusion (as opposed to a complete occlusion), the issuance of an alarm may be delayed, as the partial occlusion may clear itself.

Alternatively, infusion pump assembly 100 may: calculate a pump ontime to volume delivered ratio; track it through time; and track by using a fast moving and a slow moving exponential average of the pump ontime. The exponential average may be tracked, in a fashion similar to the leaky sum integrator. The infusion pump assembly 100 may filter signal and look for a fast change. The rate of fluid outflow and/or residual volume may be monitored. If the residual volume does not change, then there may be a total occlusion. If the residual volume changed, they may be a partial occlusion. Alternatively still, the residual values may be summed. If the number of valve actuations or the latch time is being varied, the fluid flow rate may be examined, even if you build up pressure in volume sensor assembly 148.

Total/Partial Empty Reservoir:

When reservoir 118 is becoming empty, it will become more difficult to fill volume sensor chamber 620 to the desired level. Typically, pump assembly 106 is capable of pumping 1.0 microliters per millisecond. For example, assume that an "empty" condition for volume sensor chamber 620 is 0.10 microliters and a "full" condition for volume sensor chamber 620 is 1.00 microliters. However, as reservoir 118 begins to empty, it may become harder for pump assembly 106 to fill volume sensor chamber 620 to the "full" condition and may consistently miss the goal. Accordingly, during normal operations, it may take one second for pump assembly 106 to fill volume sensor chamber 620 to the "full" condition and, as reservoir 118 empties, it may take three seconds to fill volume sensor chamber 620 to the "full" condition. Eventually, if reservoir 118 completely empties, volume sensor chamber 620 may never be able to achieve a "full condition". Accordingly, the inability of pump assembly 106 to fill volume sensor chamber 620 to a "full" condition may be indicative of reservoir 118 being empty. Alternatively, the occurrence of such a condition may be indicative of other situations (e.g., the failure of pump assembly 106 or an occlusion in the fluid path prior to volume sensor chamber 620). Infusion pump assembly 100 may determine the difference between the "full" condition and the amount actually pumped. These differences may be summed and the made up for once the reservoir condition is addressed.

Upon detecting the occurrence of such a condition, an empty flag may be set and infusion pump assembly 100 may e.g., trigger an alarm, thus indicating that the user needs to e.g., replace disposable housing assembly 114.

Additionally, as reservoir 118 empties, reservoir 118 will eventually result in a "vacuum" condition and the ability of pump assembly 106 to deliver fluid to volume sensor chamber 620 may be compromised. As discussed above, volume controller 1602 may include feed forward controller 1652 for setting an initial "guess" concerning "on-time" signal 1606, wherein this initial guess is based upon a pump calibration curve. For example, in order for pump assembly 106 to deliver 0.010 units of infusible fluid, feed forward controller 1652 may define an initial "on-time" of e.g., one millisecond. However, as reservoir 118 begins to empty, due to compromised pumping conditions, it may take two milliseconds to deliver 0.010 units of infusible fluid. Further, as reservoir 118 approaches a fully empty condition, it make take ten milliseconds to deliver 0.010 units of infusible fluid. Accordingly, the occurrence of reservoir 118 approaching an empty condition may be detected by monitoring the level at which the actual operation of pump assembly 106 (e.g., two milliseconds to deliver 0.010 units of infusible fluid) differs from the anticipated operation of pump assembly 106 (e.g., one millisecond to deliver 0.010 units of infusible fluid).

Upon detecting the occurrence of such a condition, a reserve flag may be set and infusion pump assembly 100 may e.g., trigger an alarm, thus indicating that the user will need to e.g., replace disposable housing assembly 114 shortly.

Leak Detection:

In the event of a leak (e.g., a leaky valve or a rupture/perforation) within the fluid path, the ability of the fluid path to retain fluid pressure may be compromised. Accordingly, in order to check for leaks within the fluid path, a bleed down test may be performed in which pump assembly 106 is used to pressurize volume sensor chamber 620. Volume sensor assembly 148 may then perform a first volume measurement (as described above) to determine the volume of infusible fluid within volume sensor chamber 620. Infusion pump assembly 100 may then wait a defined period of time to allow for bleed down in the event of a leak. For example, after a sixty second bleed down period, volume sensor assembly 148 may perform a second volume measurement (as described above) to determine the volume of infusible fluid within volume sensor chamber 620. If there are no leaks, the two volume measurements should be essentially the same. However, in the event of a leak, the second measurement may be less then the first measurement. Additionally, depending on the severity of the leak, pump assembly 106 may be incapable of filling volume sensor chamber 620. Typically, a leak check may be performed as part of a delivery of infusible fluid.

Figure 45:
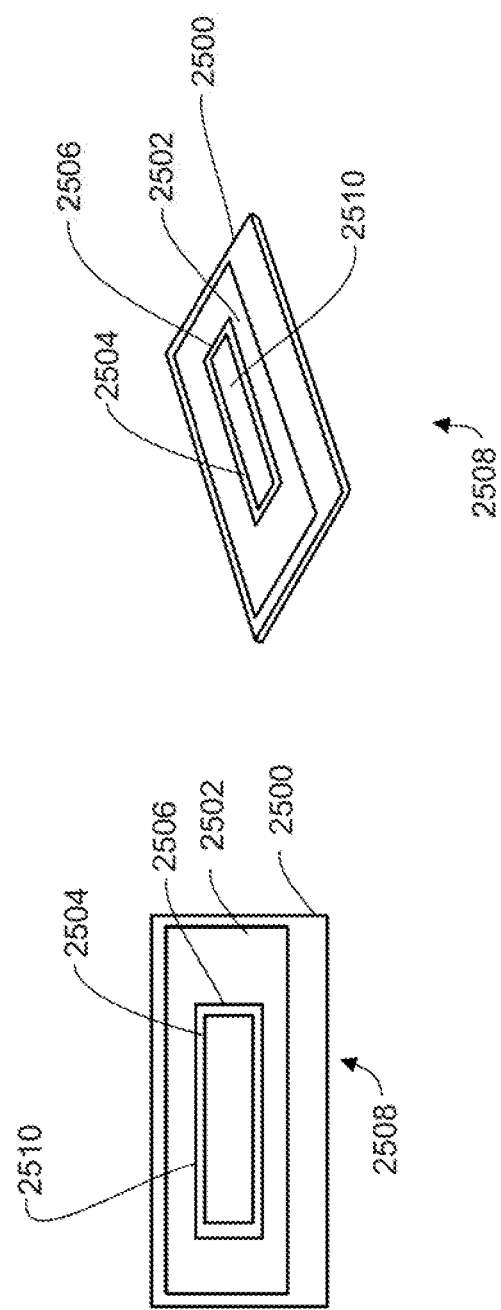
FIG. 45 is an exemplary diagram of a split ring resonator antenna.
Figure 46:
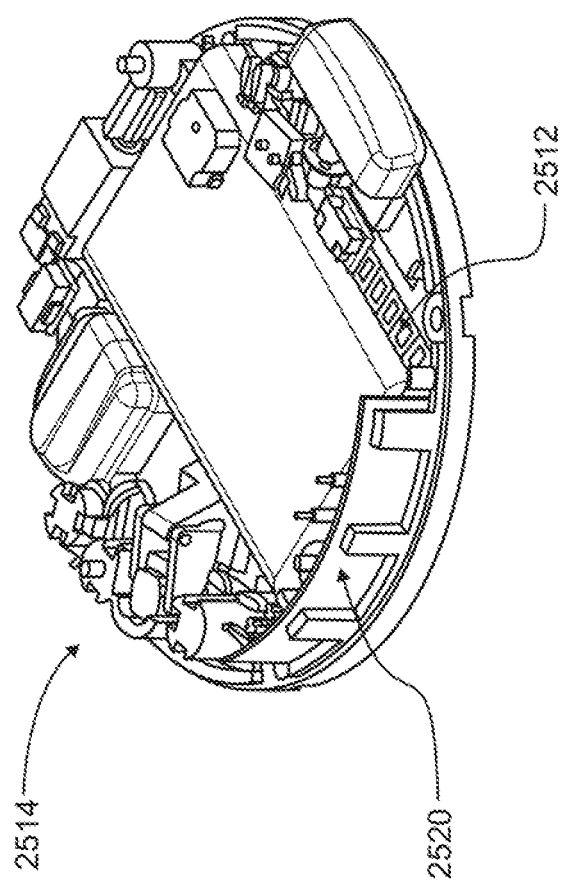
FIG. 46 is an exemplary diagram of a medical device configured to utilize a split ring resonator antenna.

In the event that the difference between the first volume measurement and the second volume measurement exceeds an acceptable threshold, a leak flag may be set and infusion pump assembly 100 may e.g., trigger an alarm, thus indicating that the user needs to seek alternative means for receiving their therapy Referring to FIG. 45 and FIG. 46, an exemplary embodiment of a split ring resonator antenna adapted for use in a wirelessly controlled medical device, and is used in the exemplary embodiment of the infusion pump assembly, includes at least one split ring resonator antenna (hereinafter "SRR antenna") 2508, a wearable electric circuit, such as a wirelessly controlled medical infusion apparatus (hereinafter "infusion apparatus") 2514, capable of powering the antenna, and a control unit 2522.

In various embodiments, a SRR antenna 2508 may reside on the surface of a non-conducting substrate base 2500, allowing a metallic layer (or layers) to resonate at a predetermined frequency. The substrate base 2500 may be composed of standard printed circuit board material such as Flame Retardant 2 (FR-2), FR-3, FR-4, FR-5, FR-6, G-10, CEM-1, CEM-2, CEM-3, CEM-4, CEM-5, Polyimide, Teflon, ceramics, or flexible Mylar. The metallic resonating bodies comprising a SRR antenna 2508 may be made of two rectangular metallic layers 2502, 2504, made of, for example, platinum, iridium, copper, nickel, stainless steel, silver or other conducting materials. In other various embodiments, a SRR antenna 2508 may contain only one metallic resonating body.

In the exemplary embodiment, a gold-plated copper outer layer 2502, surrounds, without physically contacting, a gold-plated copper inner ring 2504. That is, the inner ring 2504 resides in the cavity 2510 (or aperture) formed by the outer layer 2502. The inner ring 2504 may contain a gap, or split 2506, along its surface completely severing the material to form an incomplete ring shape. Both metallic resonating bodies 2502, 2504 may reside on the same planar surface of the substrate base 2500. In such a configuration, the outer layer 2502 may by driven via a transmission line 2512 coupled to the outer layer 2502, for example. Additionally, in various other embodiments, a transmission line 2512 may be coupled to the inner ring 2504.

Figure 50:
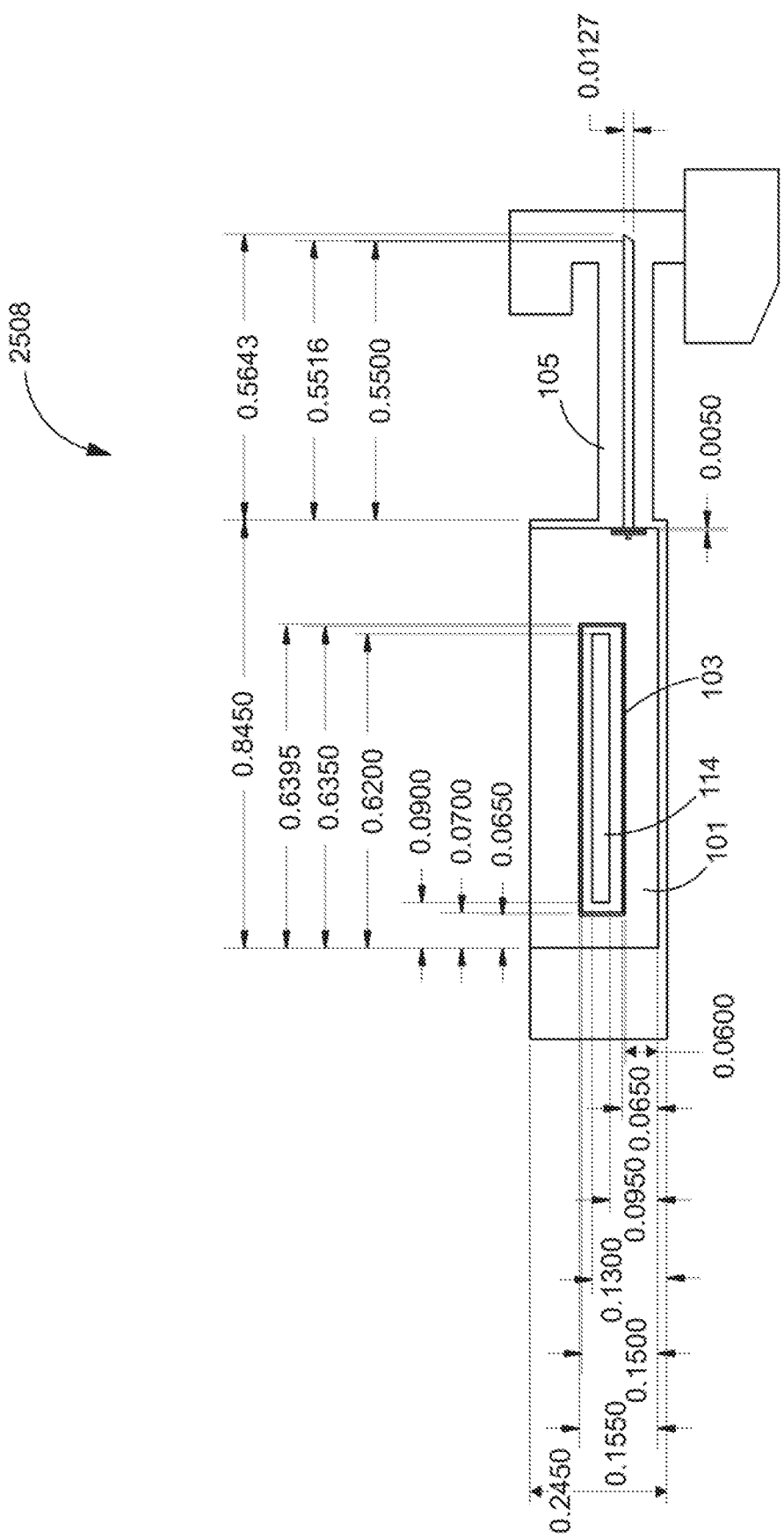
FIG. 50 is a diagram of the dimensions of the inner and outer portion of the exemplary embodiment.

Antenna design software, such as AWR Microwave Office, capable of simulating electromagnetic geometries, such as, antenna performance, may significantly decrease the time required to produce satisfactory dimensions compared to physically fabricating and testing antennas. Accordingly, with aid of such software, the SRR antenna 2508 may be designed such that the geometric dimensions of the resonant bodies 2502, 2504 facilitate an operational frequency of 2.4 GHz. FIG. 50 depicts the exemplary dimensions of the inner ring 2504 and outer layer 2502, and the positioning of the cavity 2510 in which the inner ring 2504 resides. The distance in between the outer layer 2502 and the inner ring 2504 is a constant 0.005 inches along the perimeter of the cavity 2510. However, in other embodiments, the distance between the outer layer and the inner ring may vary and in some embodiments, the operational frequency may vary.

In various embodiments, a SRR antenna 2508 may have dimensions such that it could be categorized as electrically small, that is, the greatest dimension of the antenna being far less than one wavelength at operational frequency.

In various other embodiments, a SRR antenna 2508 may be composed of one or more alternatively-shaped metallic outer layers, such as circular, pentagonal, octagonal, or hexagonal, surrounding one or more metallic inner layers of similar shape. Further, in various other embodiments, one or more metallic layers of a SRR antenna 2508 may contain gaps in the material, forming incomplete shapes.

Figure 48:
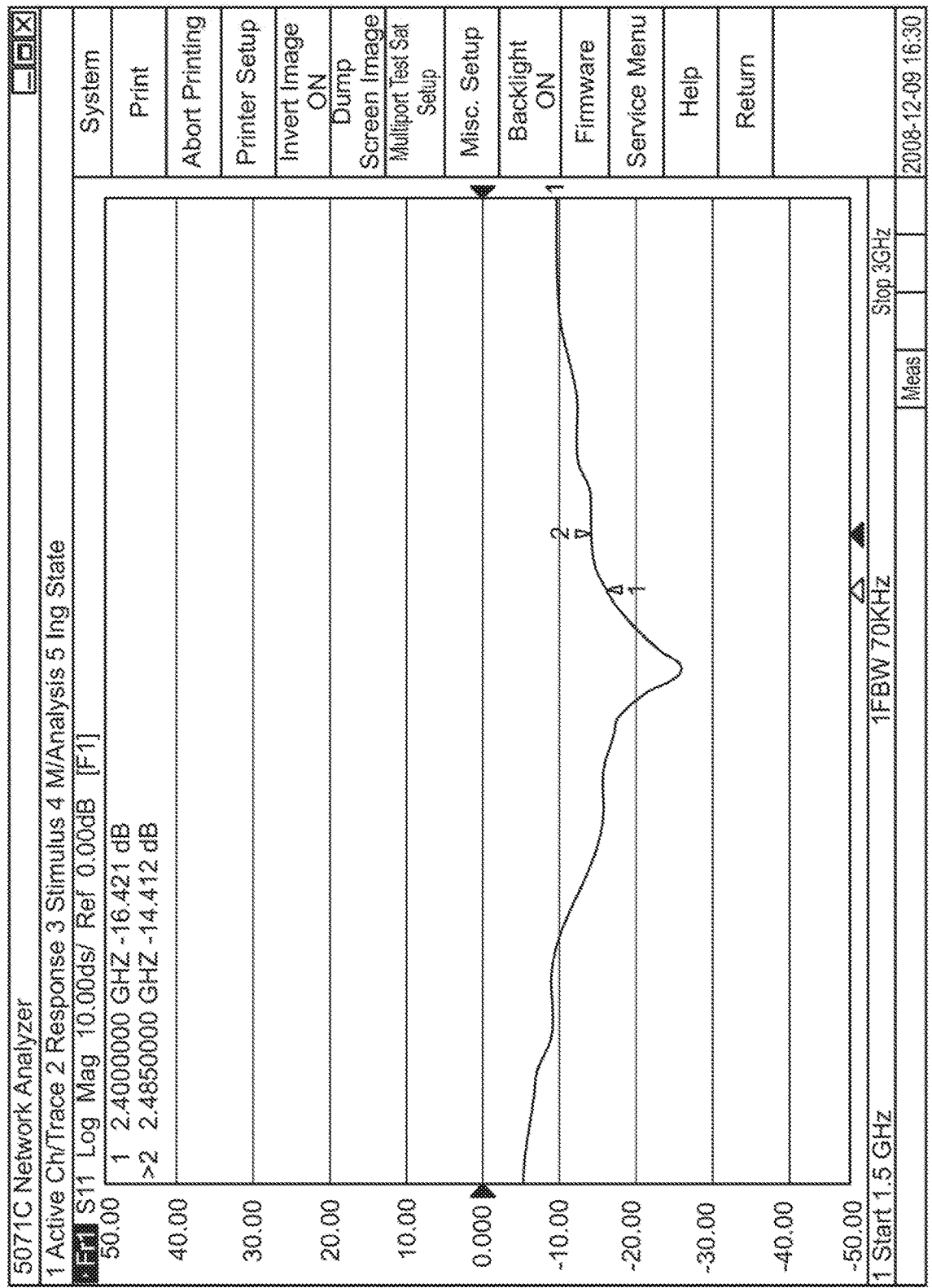
FIG. 48 is a graph of the return loss of a split ring resonator antenna prior to contact with human skin.
Figure 48A:
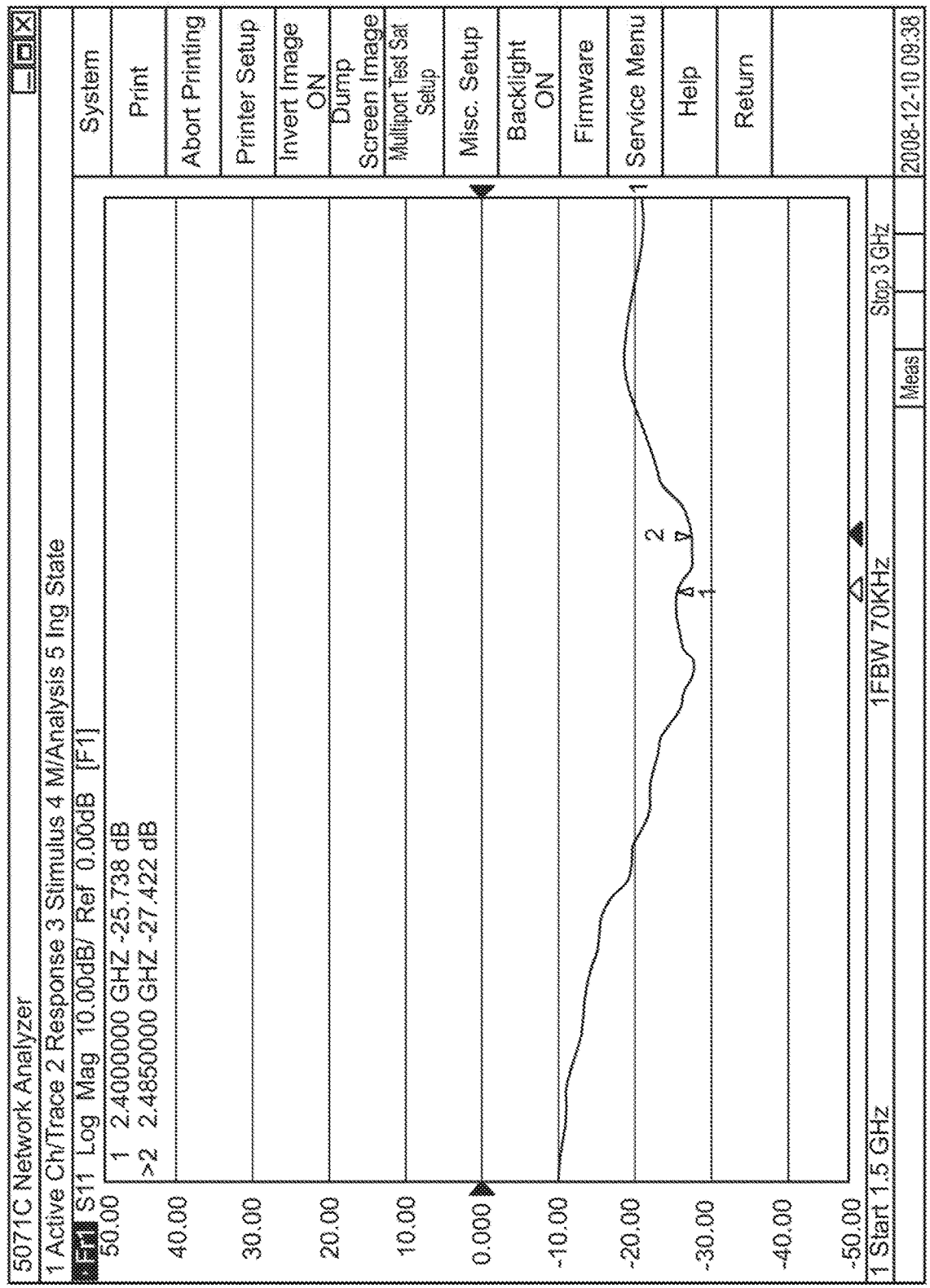
FIG. 48A is a graph of the return loss of a split ring resonator antenna during contact with human skin.

Referring to FIG. 48, a SRR antenna 2508 having the exemplary geometry exhibits acceptable return loss and frequency values when placed in contact with human skin. As shown in FIG. 48, focusing on the band of interest denoted by markers 1 and 2 on the graph, return loss prior to contact with human skin is near −15 dB while monitoring a frequency band centered around 2.44 GHz. Return loss during contact with human skin, as shown in FIG. 48A, remains a suitable value near −25 dB at the same frequency, yielding approximately 97% transmission power.

Figure 51:
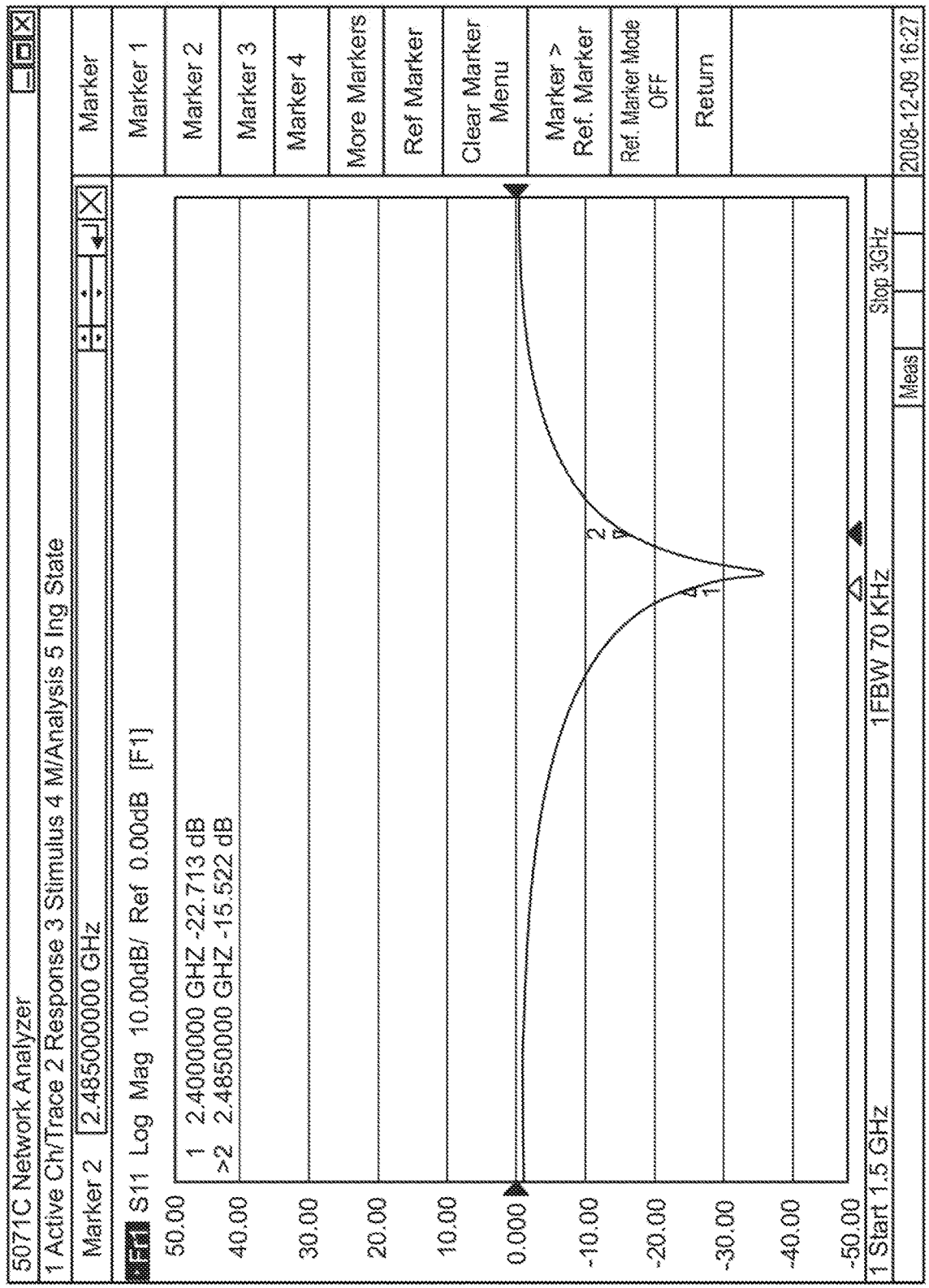
FIG. 51 is a graph of the return loss of a non-split ring resonator antenna prior to contact with human skin.
Figure 52:
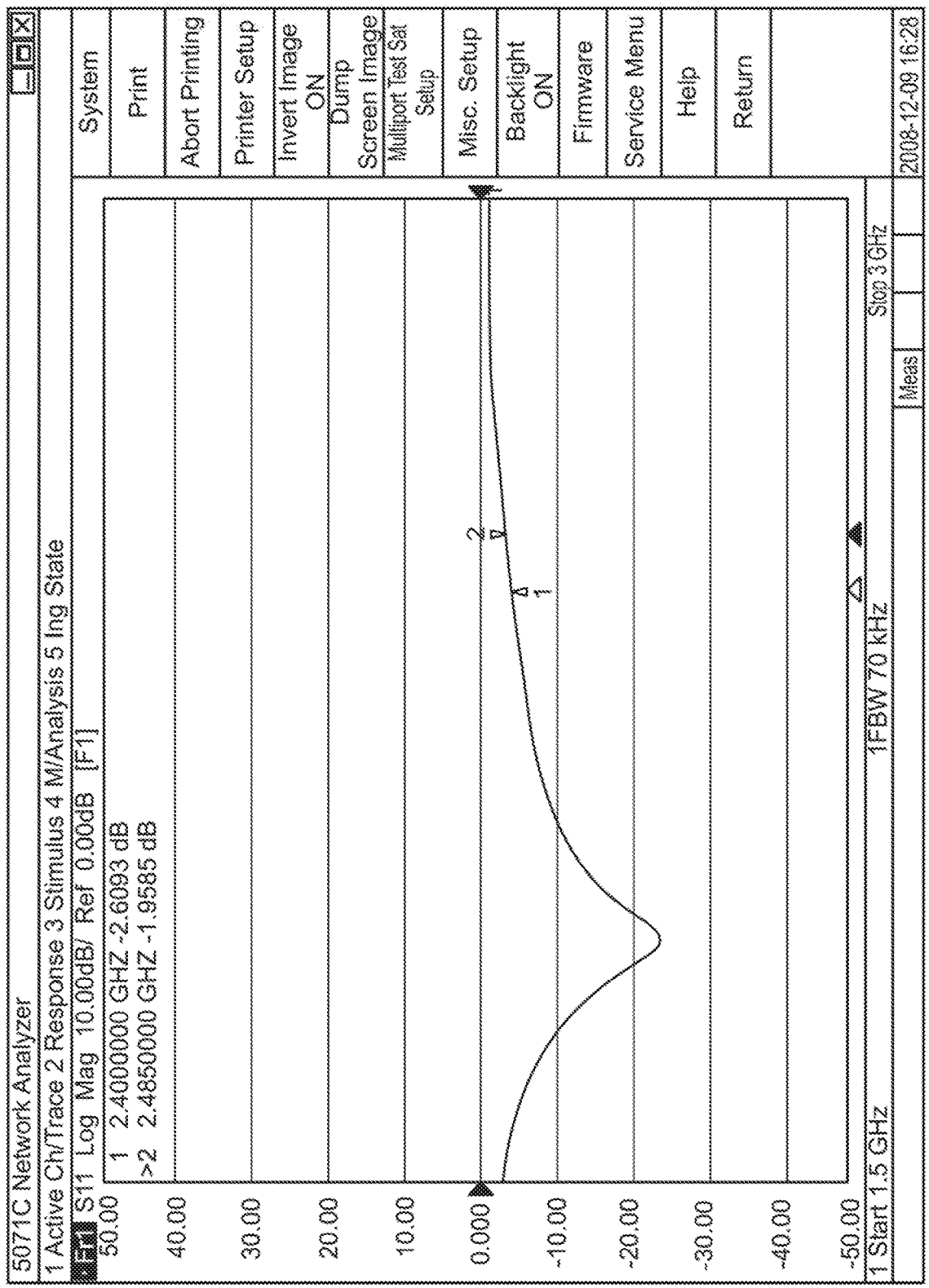
FIG. 52 is a graph of the return loss of a non-split ring resonator antenna during contact with human skin.

These results are favorable especially as compared with a non-split ring resonator antenna type, such as the Inverted-F. Return loss of an Inverted-F antenna may exhibit a difference when the antenna contacts human skin, resulting in a low percentage of power transmitted outward from the antenna. By way of example, as shown in FIG. 51, and again focusing on the band of interest denoted by markers 1 and 2 on the graph, return loss of an Inverted-F antenna prior to contact with human skin is near −25 dB at a frequency centered around 2.44 GHz. Return loss during contact with human skin is nearly −2 dB at the same frequency, yielding approximately 37% power transmission.

Integration with a Wireless Medical Device

In the exemplary embodiment, referring to FIG. 50 and FIG. 46, one application of a SRR antenna 2508 may be integration into a wearable infusion apparatus 2514 capable of delivering fluid medication to a user/patient 2524. In such an application, the safety of the user/patient is dependent on fluid operation between these electrical components, thus reliable wireless transmission to and from a control unit 2522 is of great importance.

Figure 49:
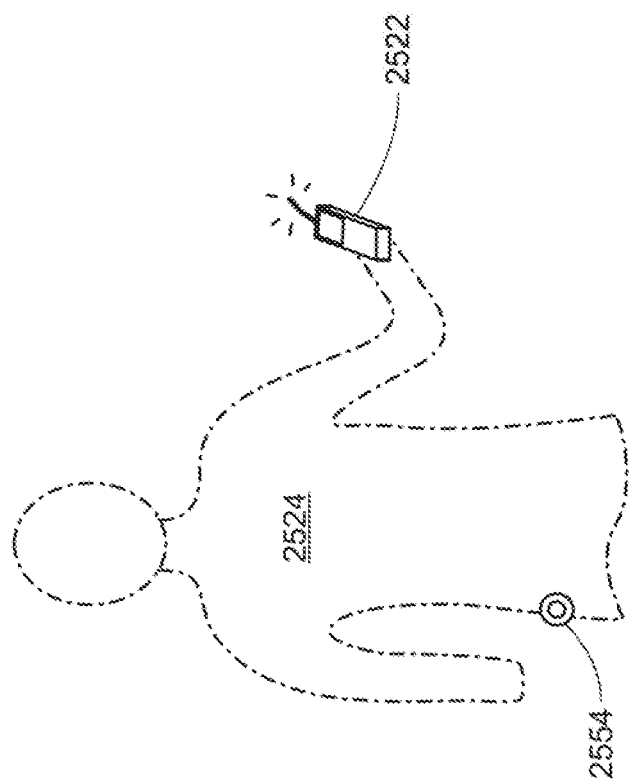
FIG. 49 is an exemplary diagram of a split ring resonator antenna integrated into a device which operates within close proximity to dielectric material.

An infusion apparatus 2514 may be worn directly on the human body. By way of example, such a device may be attached on or above the hip joint in direct contact with human skin, placing the SRR antenna 2508 at risk of unintended dielectric loading causing a frequency shift in electrical operation. However, in such an application, electrical characteristics of the SRR antenna 2508 which allow it to be less sensitive to nearby parasitic objects are beneficial in reducing or eliminating degradation to the performance. A controlling component, such as a control unit 2522 (generally shown in FIG. 49), may be paired with an infusion apparatus 2514, and may be designed to transmit and receive wireless signals to and from the infusion apparatus 2514 at a predetermined frequency, such as 2.4 GHz. In the exemplary embodiment, the control unit 2522 serves as the main user interface through which a patient or third party may manage insulin delivery. In other embodiments, infusion apparatus 2514 may utilize a SRR antenna 2508 to communicate with one or more control units 2522.

In various embodiments, a number of different wireless communication protocols may be used in conjunction with the SRR antenna 2508, as the protocol and data types to be transferred are independent of the electrical characteristics of the antenna. However, in the exemplary embodiment, a bi-directional master/slave means of communication organizes the data transfer through the SRR antenna 2508. The control unit 2522 may act as the master by periodically polling the infusion apparatus 2514, or slave, for information. In the exemplary embodiment, only when the slave is polled, the slave may send signals to the control unit 2522 only when the slave is polled. However, in other embodiments, the slave may send signals before being polled. Signals sent by way of this system may include, but are not limited to, control, alarm, status, patient treatment profile, treatment logs, channel selection and negotiation, handshaking, encryption, and check-sum. In some embodiments, transmission through the SRR antenna 2508 may also be halted during certain infusion operations as an added precaution against electrical disruption of administration of insulin to the patient.

In the exemplary embodiment, the SRR antenna 2508 may be coupled to electrical source circuitry via one or more pins 2516 on a transmission line 2512. In various other embodiments a transmission line may comprise a wire, pairs of wire, or other controlled impedance methods providing a channel by which the SRR antenna 2508 is able to resonate at a certain frequency. The transmission line 2512 may reside on the surface of the substrate base 2500 and may be composed of the same material as the SRR antenna 2508, such as gold-plated copper. Additionally, a ground plane may be attached to the surface of the substrate base opposite the transmission line 2512.

The electrical circuitry coupled to the SRR antenna 2508 may apply an RF signal to the end of the transmission line 2512 nearest the circuitry, creating an electromagnetic field throughout, and propagating from, the SRR antenna 2508. The electrical circuitry coupled to the SRR antenna 2508 facilitates resonance at a predetermined frequency, such as 2.4 GHz. Preferably, transmission line 2512 and SRR antenna 2508 both have impedances of 50 Ohms to simplify circuit simulation and characterization. However, in other various embodiments, the transmission line and split ring resonator antenna may have other impendence values, or a different resonating frequency.

Figure 47:
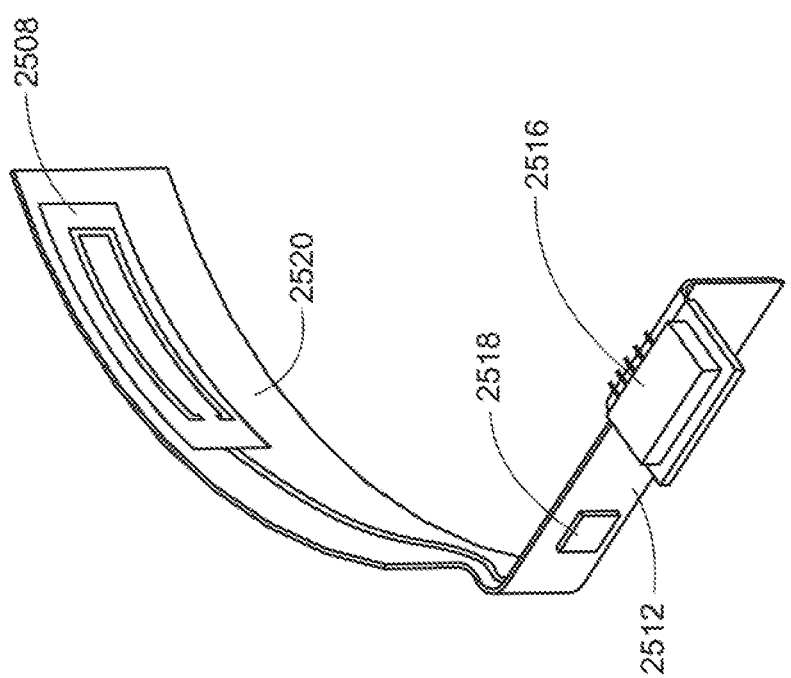
FIG. 47 is an exemplary diagram of a split ring resonator antenna and transmission line from a medical infusion device.

Referring to FIG. 47, a signal processing component(s) 2518, such as, a filter, amplifier, or switch, may be integrated into the transmission line 2512, or at some point between the signal source connection pins 2516 and the SRR antenna 2508. In the exemplary embodiment, the signal processing component 2518 is a band-pass filter to facilitate desired signal processing, such as, allowing only the exemplary frequency to be transmitted to the antenna, and rejecting frequencies outside that range. In the exemplary embodiment, a Combline band-pass filter 2518 may be included in the transmission line 2512 between the antenna and the signal source. However in other embodiments, any other signal processing device, for example, but not limited to, filters, amplifiers, or any other signal processing devices known in the art.

In various embodiments, a SRR antenna 2508 may be composed of metallic bodies capable of resonating on a flexible or rigid substrate. As shown in FIG. 46, the exemplary embodiment incorporates a curved SRR antenna on a flexible Polyimide substrate 2520. Polyimide may be the exemplary material because it tends to be more flexible than alternative substrates. This configuration may allow for simplified integration into circular-shaped devices (such as a wirelessly controlled medical infusion apparatus 2514), devices with irregular-shaped external housing, or devices in which saving space is paramount.

In various embodiments, both control unit 2522 and base unit 2514 may incorporate a split SRR antenna 2508. This configuration may prove beneficial where the control unit is meant to be handheld, in close proximity to human skin, or is likely to be in close proximity to a varying number of materials with varying dielectric constants.

In various embodiments, a SRR antenna 2508 may be integrated into a configuration of medical components in which one or more implantable medical devices, operating within the human body, communicate wirelessly to a handheld, body-mounted, or remote control unit. In certain embodiments, both body-mounted and in-body wireless devices may utilize a SRR antenna 2508 for wireless communication. Additionally, one or more of the components utilizing a SRR antenna 2508 may be completely surrounded by human skin, tissue or other dielectric material. By way of example, such a configuration may be used in conjunction with a heart monitoring/control system where stability and consistency of wireless data transmission are of fundamental concern.

In various other embodiments, a SRR antenna 2508 may be integrated into the embodiments of the infusion pump assembly. Configuration of medical components in which one or more electrical sensors positioned on, or attached to, the human body wirelessly communicate to a remote transceiving unit. By way of example, a plurality of electrodes positioned on the body may be coupled to a wireless unit employing a SRR antenna 2508 for wireless transmission to a remotely located electrocardiogram machine. By way of further example, a wireless temperature sensor in contact with human skin may employ SRR antenna 2508 for wireless communication to a controller unit for temperature regulation of the room in which the sensor resides.

The infusion pump described herein contains a NITINOL, or shape-memory alloy, actuated binary valve (the measurement valve). This valve is actuated by applying an electrical current to the NITINOL wire which causes the wire to change phase, contract, and actuate the valve. It is desirable to minimize the time that current is applied to the NITINOL for many reasons, including, but not limited to, the following: 1) to minimize power consumption; 2) to minimize cycle time; and 3) to maximize NITINOL cycle life. Minimizing power consumption may extend the battery life and thus, provide for longer functionality of the pump between recharging. Maximizing the NITINOL cycle life extends the life of the reusable portion of the infusion pump and provides for longer performance of the pump. Both of these may be desirable in a closed-loop or semi-closed loop system, as well as in an open loop system.

Regular operation of the pump involves the following steps, amongst others. First, an initial volume measurement is taken of the Acoustic Volume Sensor chamber using the Acoustic Volume Sensor (AVS). Next, fluid is pumped from the reservoir to the AVS chamber using the pulse pump. Then, another measurement is taken of the full AVS chamber. Next, the measurement valve is actuated and the fluid released from the AVS chamber and to the user/patient through a tubing set. Finally, a final AVS measurement is taken.

In various embodiments, the difference between the second and first AVS measurements is the pumped volume; this is the volume pumped into the AVS chamber. The difference between the second and the third AVS measurements is the delivered volume; this is the volume delivered to the user/patient. The difference between the pumped volume and the delivered volume is the residual volume; this is the volume remaining in the AVS chamber after the actuation of the measurement valve.

The measurement valve is actuated by allowing current to flow through the Valve NITINOL wire at a given duty cycle and on-time. In the exemplary embodiments the valve may be driven at a nominal 8% duty cycle that is adjusted to compensate for variations in supply voltage. In the exemplary embodiments, the ontime that is varied to minimize the electrical power used to actuate the valve. However, in other embodiments, a similar result may be accomplished by varying the duty cycle instead of the ontime or by using a combination of the two, for example. The ontime is varied using the algorithm described below.

When the controller is initialized the valve ontime, $t_{on}$, is initially set to a low value that is below the minimum ontime needed to actuate the valve (which, in some embodiments, is approximately 200 ms). Deliveries are conducted using the steps #1 to #5 described above. When these steps are complete the following additional steps are taken. The residual volume is calculated; if the residual volume is not close to zero, it is likely that the valve did not open. In this case $t_{on}$ is increased (in the exemplary embodiment, the $t_{on}$ is increased by a fixed 20 ms each iteration, however, in other embodiments, the increase ontime may vary) and steps #4 to #7 are repeated until the valve opens and either the residual volume is close to zero or the maximum allowed valve ontime is reached.

This algorithm effectively increases the valve ontime by just enough (to within the on-time increment) to open the valve. However, it is possible that the necessary on-time may decrease over time or may be abnormally high during a given delivery. If this were the case the valve ontime would increase to compensate, but would then remain high until the controller/algorithm is reset. In the exemplary embodiments, determining whether the AVS valve was actuated for longer than necessary may not be completed. Thus, in some embodiments, to compensate for this non determination, once the valve opens, the residual volume will be close to zero regardless of any extra open time. The valve controller then decrements the valve ontime each delivery (in the exemplary embodiment, the decrease is by 2 ms, however, in other embodiments, this decrease amount may be different). This allows the valve ontime to gradually decrease until it is insufficient to open the valve. At that point the algorithm described above will increase the valve ontime by a larger increment (e.g., 20 ms) and the process will continue. The result is a control profile of valve ontimes close to the minimum value needed to open the valve. In these embodiments, the system uses the minimum amount of power to actuate the measurement valve.

In exemplary embodiments, and referring to the controller described above, volume sensor assembly monitors the amount of fluid infused by the infusion pump assembly. Thus, following the infusion of fluid from the volume sensor chamber, the controller determines whether the volume infused is less than or greater than the desired volume or scheduled volume for that pulse. Following, the controller may either increase or decrease the volume delivered in a pulse, or over a series of pulses, following. This includes, but is not limited to, the controller adding or subtracting a volume from one or more pulse of upcoming scheduled delivery volumes for a given period of time. Thus, embodiments of the fluid delivery system include a controller that both calculates the volume of infusible fluid delivered and also, recalculates, as necessary, upcoming delivery volumes based on the volume delivered in any given pulse. This ensures the desired volume is delivered within a short period of time from any given pulse.

As discussed above, with reference to the delivery of insulin for purposes of illustration, various delivery volumes may be either programmed or requested at a given time. These include, but are not limited to, a normal bolus, an extended bolus, a combination bolus (i.e., a percentage of an extended bolus delivered as a normal bolus, followed by the remaining percentage delivered over a desired/requested or pre-determined period of time), and a basal rate (which, in many embodiments, may include one or more pre-programmed basal rates per a 24 hour period).

The system for controlling the delivery of infusible fluid includes a delivery trajectory, i.e., volumes of fluid, whether basal, normal bolus, extended bolus, and/or combination bolus, which will be delivery, as well as a schedule, i.e., when the various volumes will be delivered. As discussed above, in the exemplary embodiments, the controller includes a feedback mechanism. Thus in some embodiments, the trajectory and the schedule for delivery may vary based on the volume sensor assembly measured volumes.

In the exemplary embodiments, a constant, or approximately constant, trajectory may be beneficial. A constant trajectory may be desired for many reasons, including, but not limited to, maintaining a constant trajectory to eliminate or mitigate transience. Transience may be introduced into the system based on the mapping of the joules applied to the shape-memory actuator and the resulting volume delivered or measured by the volume sensor assembly. Over time, the mapping may vary. Contributing factors that may vary the mapping include, but are not limited to, temperature, reservoir volume, and/or time and use of the shape-memory actuator. Thus, it may be desirable to maintain a close to constant trajectory in order to eliminate the influence of variables which may be introduced and/or may affect the system. Additionally, a constant trajectory gives rise to further opportunities for the controller to adjust delivery volumes in response to volume sensor assembly measurements.

In various embodiments of this delivery method and system, a trajectory is calculated based on delivery commands the system receives, which may include e.g., bolus, extended bolus, combination bolus and basal. The interval for delivery may be determined based on one or more of the following factors: 1) the maximum pulse volume; 2) the minimal pulse volume; 3) power consumption; and/or 4) minimum pulse interval. In the exemplary embodiment, one or more factors may be taken into consideration. In various embodiments the system determines the trajectory, and working within the confines of the interval factors, determines the interval and volume of fluid delivery to meet the desired trajectory, with the preference, in some embodiments, that each delivery be of an equal volume and that the delivery be completed in as many equal volume deliveries as possible (to allow for adjustments in the volume). Thus, the intervals may vary, but in the exemplary embodiment, the volumes delivered per interval will be constant, or approaching constant.

In the exemplary embodiment, with respect to bolus delivery, when determining the interval for delivery of the bolus volume, the system may determine the delivery schedule for the bolus volume to be delivered as quickly as possible within system preferences (i.e., values that may optimize the system performance) and/or system constraints (i.e., minimum and maximum pulses and minimum and maximum intervals). For example, in the exemplary embodiment, the system may include a maximum pulse delivery volume of 2.0 microliters and a minimum pulse delivery volume of 0.5 microliters. Further, in some embodiments, it may be preferred that the minimum pulse interval is six (6) minutes. Thus, given the maximum and minimum pulse volume, together with the minimum interval, the system may determine the optimal schedule for delivery, i.e., the volume of each delivery (with the preference being that each scheduled volume is equal) and the interval between each delivery.

In some embodiments, in determining the number of deliveries for a bolus volume, the system may defer to delivering the bolus volume as quickly as possible, given that each scheduled pulse for the bolus delivery is equal. However, in some embodiments, the system may determine the number of deliveries for a bolus volume by deferring to a set number of pulses, e.g., ten (10). Given this deference, the system may then determine the intervals and volume of each pulse by dividing the bolus volume by 10. Following, if the resulting delivery volume is less than the minimum delivery volume, e.g., 0.5 microliters, then the system may determine the schedule based on less than 10 pulses. If the resulting delivery volume is greater than the maximum delivery volume, e.g., 2.0 microliters, the system may determine the schedule based on more than 10 pulses. Thus, although in the exemplary embodiment, the system may give deference to a given number of pulses to deliver a requested volume, the system may decrease or increase that given number of pulses if the volumes are less than the minimum pulse volume, or greater than the maximum pulse volume. It should be noted that although exemplary embodiments have been described, this is for illustrative purposes only. In other embodiments, the system may have a different deference number for the number of pulses, and/or difference values for minimum and maximum pulse volumes. Further, the exemplary interval may also vary, thus, in some embodiments, the preferred interval may be less than 6 minutes or greater than 6 minutes.

Figure 53A:
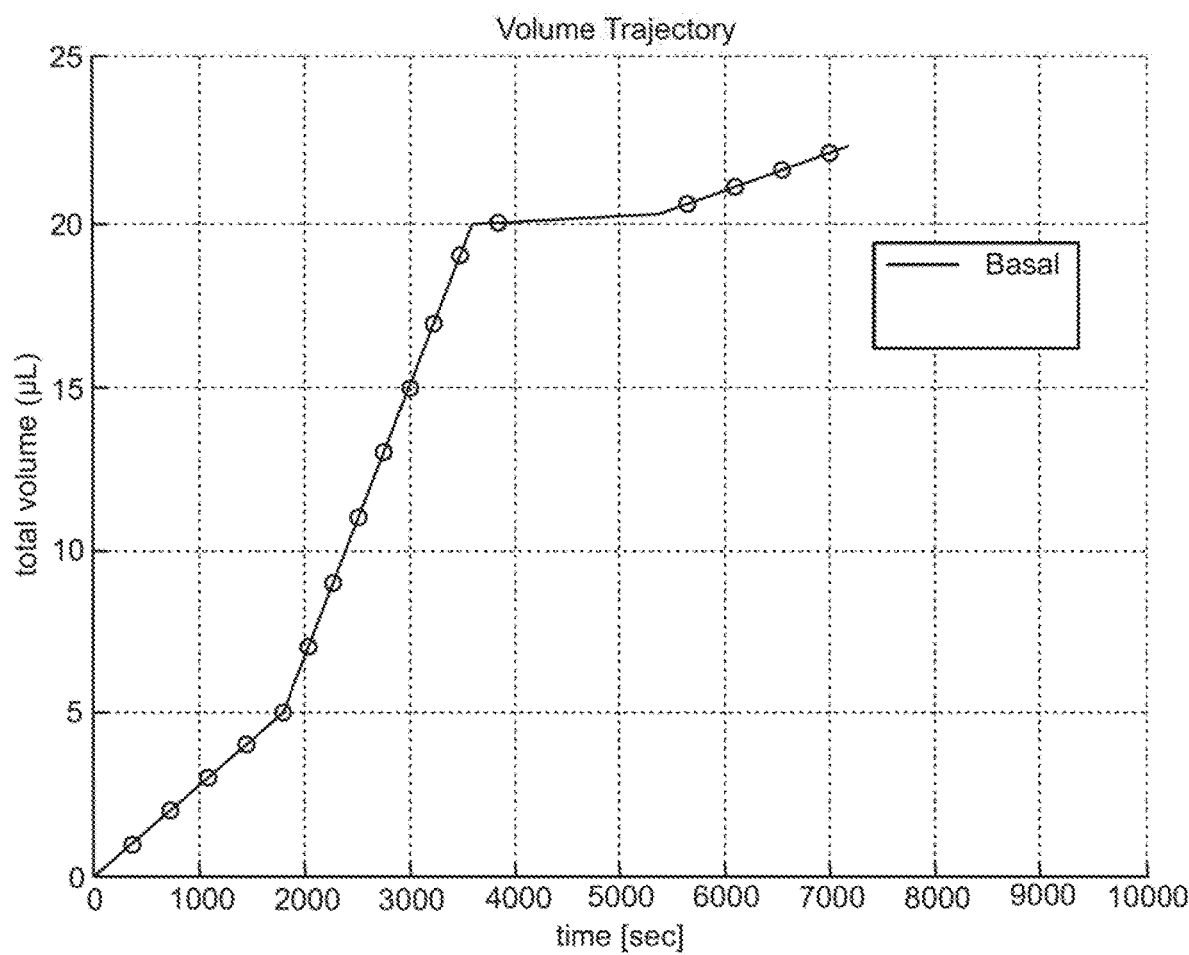
FIGS. 53A-53B are examples of a basal trajectory and a delivery schedule for that trajectory.
Figure 53B:
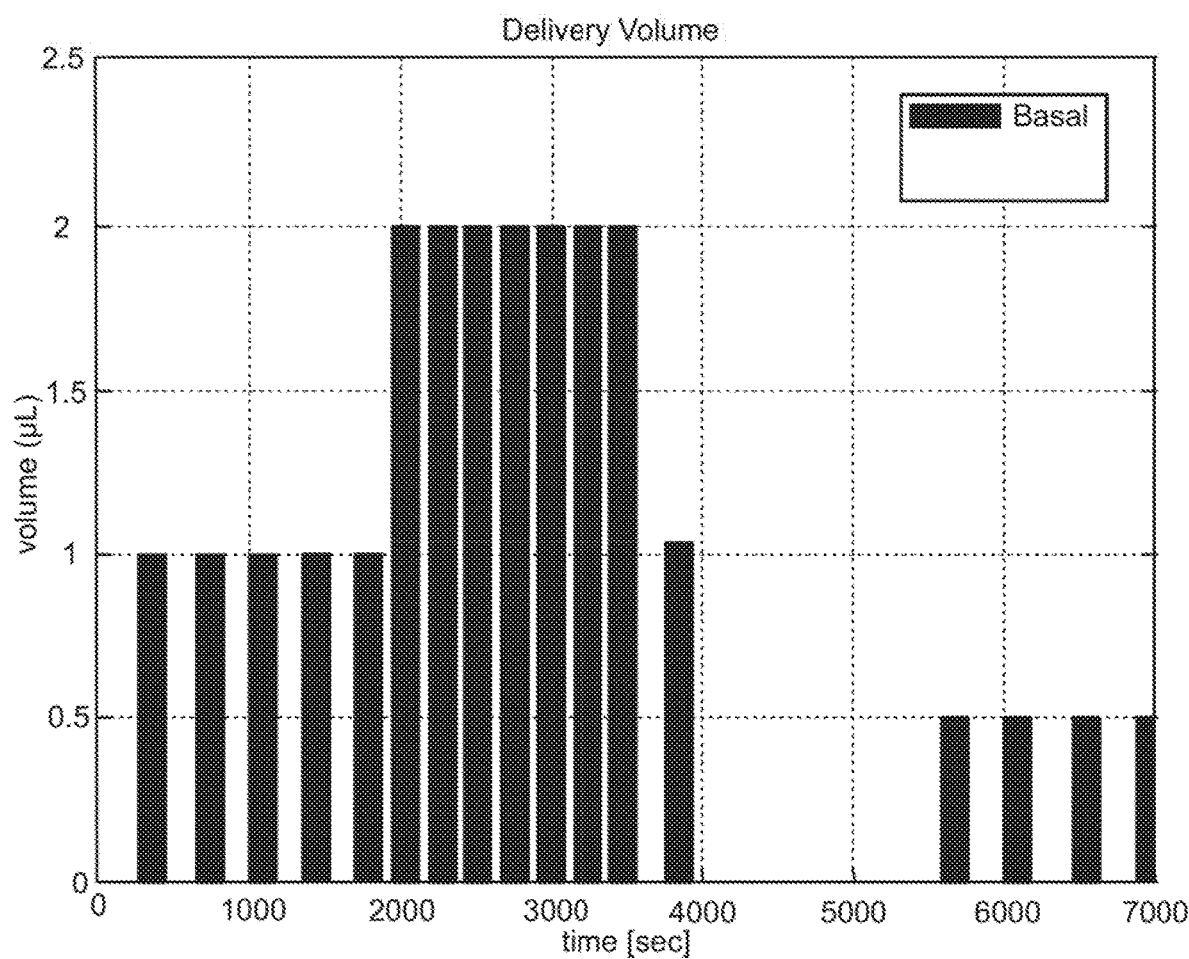

As discussed above, in addition to bolus scheduling, other deliveries intervals, e.g., extended bolus, combination bolus and basal, may also be determined with the desire that each pulse volume is equal. Thus, the intervals may vary; however, as discussed above, the system may include a minimum interval, e.g., 6 minutes. With respect to scheduling basal deliveries, in the exemplary embodiment, the schedule for a given basal rate delivery may be determined by first dividing the rate per hour by a preferred interval (e.g., 6 minutes). For example, with a rate of 1 unit (i.e., in terms of U-100 insulin, 10 microliters) per hour, the schedule may be 1 delivery of 1.0 microliter every 6 minutes, equating to 10 deliveries of 1.0 microliter in one hour. As discussed above, in various embodiments, the system may include a volume per pulse maximum and minimum, thus, similarly to example given above with respect to bolus rate scheduling, where the volume minimum or maximum is reached, the number of pulses may be increased or decreased accordingly, in order to maintain equal volume per pulse. An example of a basal rate trajectory as well as an example of a delivery schedule for that trajectory is shown in FIGS. 53A-53B.

Further to the embodiments of the delivery system and method described herein, where one or more delivery events are desired for a given time interval, i.e., during regular basal delivery, a bolus is requested, this embodiment of the scheduling is beneficial for many reasons, including, but not limited to, determining the volume attributed to basal and the volume attributed to bolus for purposes of other calculations, e.g., "insulin on board" calculations. With respect to some embodiments of this exemplary embodiment, when a basal trajectory and scheduled delivery are in progress and a bolus is requested, the system may calculate the bolus schedule and then recalculate the basal schedule. For example, in some cases, for a single pulse, a portion of the pulse volume may be attributed to the "bolus" and a portion to the "basal", and for a given bolus delivery, together with an ongoing basal, the pulses may deliver equal volumes.

Figure 54A:
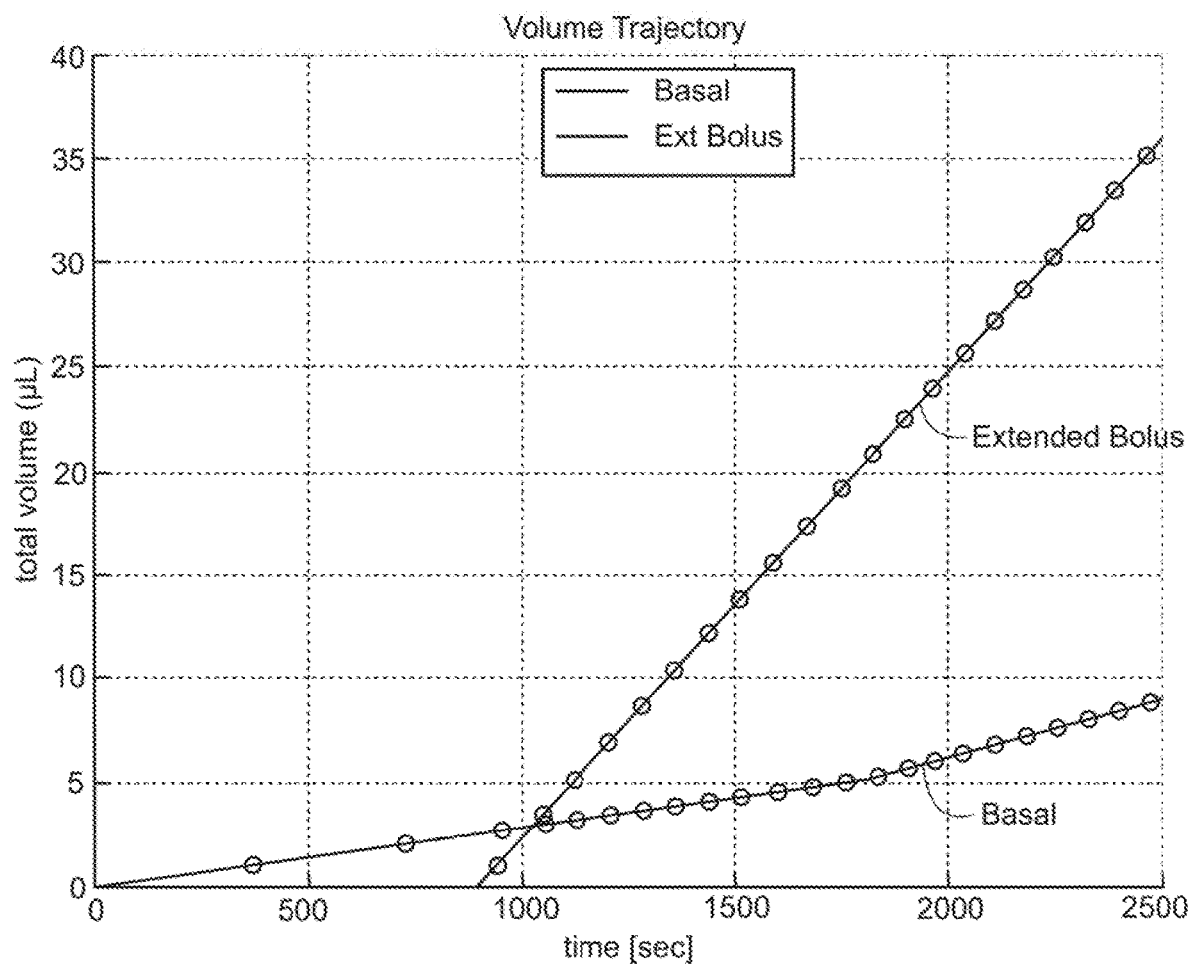
FIGS. 54A-54B are examples of a basal and extended bolus trajectory and a delivery schedule for that trajectory.
Figure 54B:
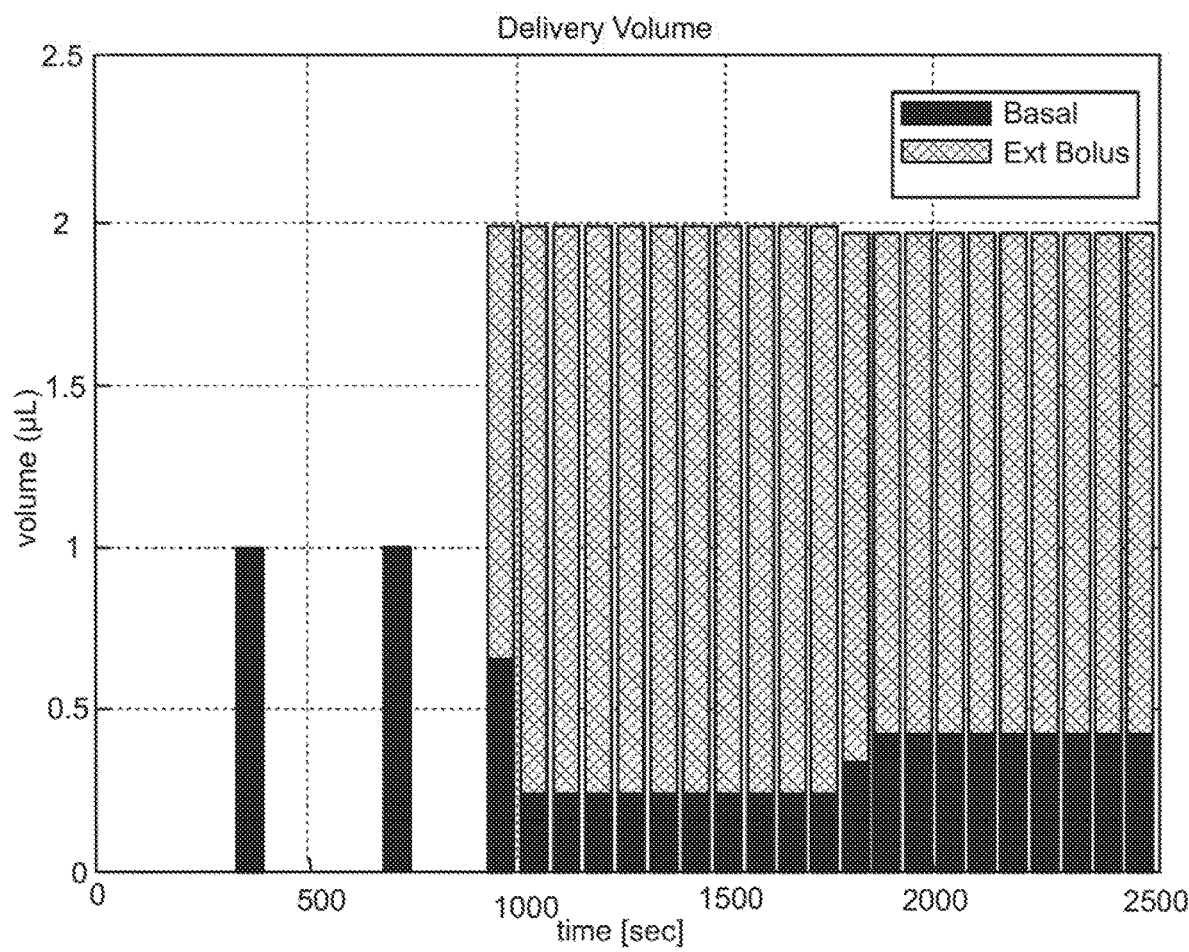

With respect to an extended bolus delivered together with a basal rate, a similar delivery schedule may be calculated. Referring now to FIGS. 54A-54B, an example of a basal and extended bolus trajectory and a delivery schedule for that trajectory, are shown. The basal and extended bolus delivery schedule may be determined by taking into account the timeframe for the extended bolus and the overlapping rate for any basal. Unlike a normal bolus, in the exemplary embodiment, it may not be the goal of the system to deliver the extended bolus "as quickly as possible" given the system constraints, but rather, is delivered over a given period of time. Thus, the delivery schedule may be determined by first calculating the optimal schedule for delivery of the extended bolus, and then recalculating the basal delivery for the timeframe of the extended bolus, such that the basal and extended bolus may be delivered in equal volume pulses over the timeframe for the extended bolus.

Figure 55A:
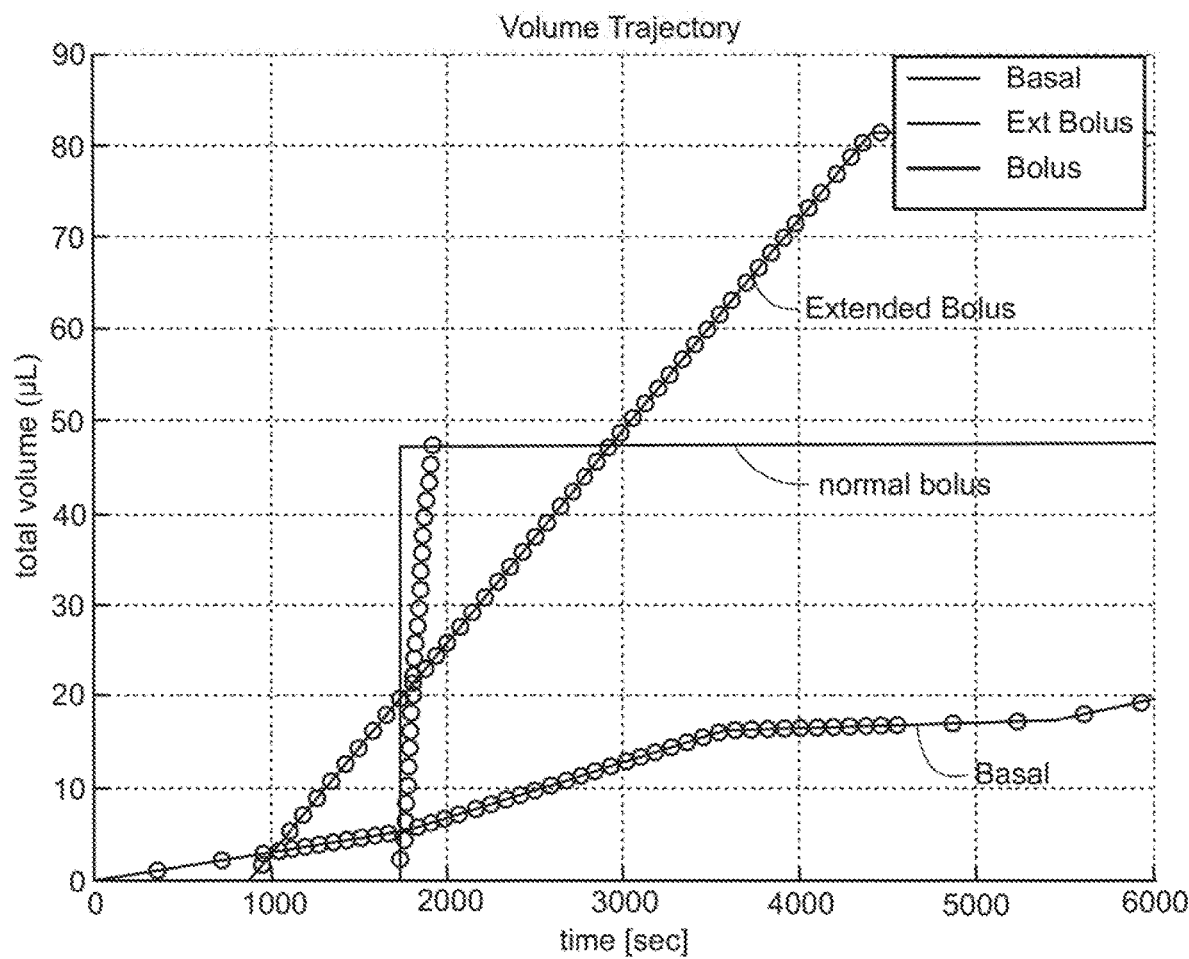
FIGS. 55A-55B are examples of a basal, extended bolus and normal bolus trajectory and a delivery schedule for that trajectory.
Figure 55B:
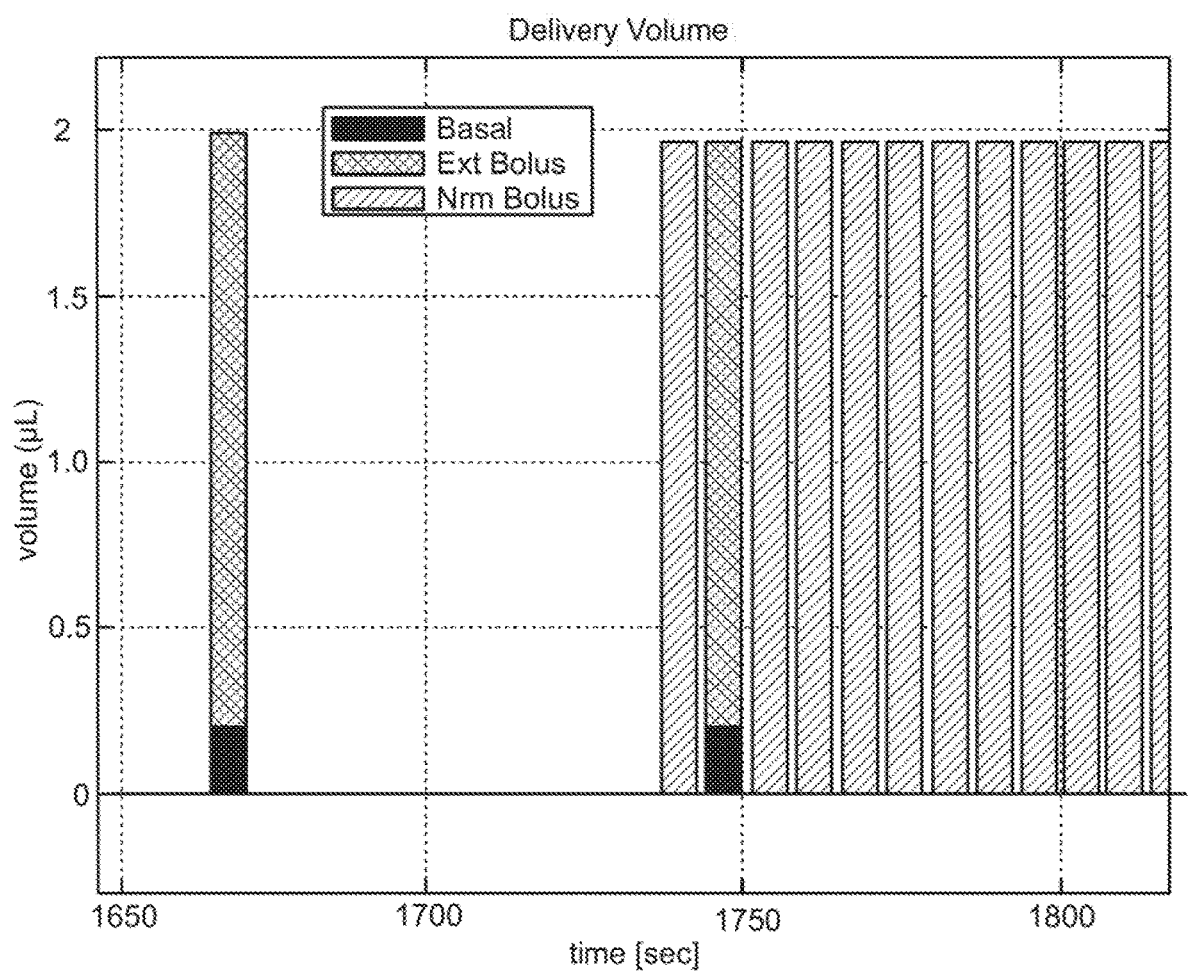

Referring now to FIGS. 55A-55B, an example of a basal, extended bolus and bolus trajectory and a delivery schedule for that trajectory, are shown. Combining the discussion above regarding scheduling the delivery of a basal, a normal bolus, and an extended bolus, when all three are to be delivered during an overlapping time period, FIGS. 55A-55B are an example of a resulting schedule according to an exemplary embodiment. As shown, the basal and extended bolus may be delivered at a first interval while the normal bolus may be delivered at a second interval, however each of the first and the second intervals include equal delivery volumes.

Referring again to FIGS. 54A-54B and FIGS. 55A-55B, it may be understood that the system may differentiate a volume delivered as a "basal" from a volume delivered as a "bolus" (including an extended bolus) even when the combined volumes are delivered in a single pulse of equal volumes over an overlapping timeframe. This differentiation may be beneficial in calculating the amount of bolus or basal "on board", i.e., the time at which a particular volume of "basal" as opposed to a particular volume of "bolus" was a delivered in FIGS. 54B and 55B allow for a more accurate calculation of insulin on board, as insulin on board is a calculation that depends on many factors, including the time and volume of delivery.

Various embodiments of the system may include various control-loop algorithms for either a closed-loop or semi-closed loop control method. In some embodiments, the system includes a baseline trajectory. As discussed above, the system may follow this trajectory until one or more sensor data dictate that the trajectory may change. In some embodiments, the changes to the trajectory may be governed by boundaries which may be preprogrammed by the user/care giver. As discussed above, changes to the trajectory, in some embodiments, may be made upon notification to the user and in some embodiments, upon notification followed by confirmation by the user. In some embodiments, where the trajectory change may be in response to unexpected results, the system may notify the user prior to shutting the system down.

Thus, in the various embodiments, control loop algorithms take into account a physiological model (which may be adaptive from a baseline model); data from at least one sensor, e.g., a CGM system, i.e., representing the interstitial fluid glucose level; and the volume of medical fluid, e.g. insulin, delivered and fingersticks, i.e., representing the blood glucose level.

In various embodiments, an estimator works together with a controller. The controller determines the amount of medical fluid or insulin to deliver based on the estimator's prediction. Thus, errors in the estimator will provide for incorrect delivery requests from the controller.

More importantly, incorrect amounts delivered by the controller (i.e., the controller requests a delivery of 0.250 units and actually delivers 0.20 or 0.30 or another volume, either higher or lower than the volume requested) will then alter the effect of the estimator.

In various embodiments, the estimator works with the physiology to establish a "trajectory". The trajectory may be based on a number of factors and may be continuously updated/changed. The trajectory uses the CGM data (which may be checked or calibrated by fingersticks as discussed herein) and, in some embodiments, an established normalized or "baseline" basal delivery schedule, to predict 1) glucose values and 2) determine delivery volumes and schedule.

As discussed above, the trajectory may be constantly updated or changed based on actual CGM or fingerstick data (fingerstick data may be used to confirm CGM data or calibrate the CGM data) and actual volume of insulin delivered. Thus, in a controlled loop or semi-controlled loop system, both the data from the CGM/fingersticks and the actual volume of insulin delivered are key components to the system. If one or both of these values are inaccurate, the system may not perform as effectively as desired.

In some embodiments, using a pre-established or "baseline" delivery trajectory, the pre-established trajectory may be referred to as an "outer loop", as the trajectory may include a basic "baseline" delivery schedule (volume and time of delivery). The trajectory may be established using one or more limitations of the hardware, including, but not limited to: the minimum and/or maximum stroke of the pump; optimal delivery patterns; and/or energy efficiency, i.e., battery life.

The actual trajectory may be modified in response to detected meals or an input indicating the presence of a factor or an "event" that may affect insulin sensitivity, including, but not limited to, one or more inputs (either via manual user input or sensor data) indicating exercise (including duration and level or type), illness, dehydration, sleep, menstruation and/or stress. Additionally, a meal or carbohydrate being consumed by the user is also an event which may affect or alter the trajectory. As discussed above, through calibration and profile records, and/or through sensor data, the system may predict one or more of these events.

Using the actual volume delivered as the input to the estimator may achieve an accurately met trajectory. Additionally, using the actual volume delivered may result in a more accurate and precise predicative algorithm. For example, if the controller requested an insulin delivery and the actual volume delivered is different from the requested volume or assumed volume delivered, then the predictive algorithm may be inaccurate. Thus, it is desirable that the trajectory or outer loop itself is as close to correct for the duration as possible, however, even where the trajectory is correct, where the pump fails to delivery either the volume desired or at the time desired, the trajectory is not met. This is an example of the actual trajectory varying from the trajectory requested or the outer loop.

Thus, the actual delivery versus the trajectory may be very different where the volume delivered by the pump is inaccurate or varies from requested. Inaccurate delivery may be the result of pump error, occlusion and/or bubbles in the fluid line, or other. In the exemplary embodiments, the system uses the AVS sensor and the methods described herein to accurately and precisely measure the volume of insulin delivered by the pump.

The ability to precisely and accurately determine the volume of insulin delivered effects many aspects of the control loop system. As non-limiting example, the precise and accurate determination of volume of insulin delivered feeds into the precise and accurate determination of insulin-on-board or "IOB". The precise estimation or determination of IOB is a factor with respect to 1) accounting for delivery; and 2) accurate delivery.

Also, in the various embodiments described herein, an accurate measurement of the volume of medical fluid/insulin delivered may also allow for more accurate and precise recognition of sensor failure or the integrity failure of one or more sensors. For example, with respect to one or more CGM sensors, if an e.g. 2 unit delivery of insulin was requested and the control system assumes the pump delivered 2 units and following, receives glucose data indicating an unexpected result, as discussed above, the system, in some embodiments, may instigate default shutdown. Thus, the system would shutdown based on the "unexpected" CGM data. However, assume that the pump actually delivered 1 unit, rather than 2 units, and assume that the glucose data is consistent with a 1 unit delivery, then the CGM sensor has not produced an actual unexpected result, rather, it was a perceived unexpected result based on a lower than expected volume of insulin being delivered. Thus, the precise and accurate determination of the volume of insulin (or other medical fluid) delivered may provide a more accurate and safe controlled loop system for the delivery of medical fluid therapy.

Further, with respect to the various embodiments described herein using the AVS measurement sensor, the presence of occlusions, bubbles and an empty or partially empty reservoir may be determined quickly and accurately. Again, this provides for a more accurate determination of the actual volume of insulin delivered and, also, an accurate detection of an empty reservoir, an occlusion or a bubble. Thus, the AVS measurement sensor provides for a more safe and accurate controlled loop system for the delivery of medical fluid therapy. Further, determining the presence of an occlusion, bubble(s), or an empty or partially empty reservoir may be highly beneficial to the user's therapy and safety.

The precise determination of the volume of insulin delivered also effects the calibration of the system. Thus, having a precise measurement, the system may more accurately calibrate and thus, may determine unexpected results of integrity failure sooner.

Thus, various embodiments of the control loop include an actual volume and the trajectory volume. Where a system includes an actual volume that is closest to the trajectory volume, the estimate of plasma and ISG is closer to true. This may lead to more accurate insulin sensitivity determinations and calculations and more accurate predictive algorithms.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A system for at least partial closed-loop control of a medical condition, the system comprising:
   at least one medical fluid pump for infusing fluid into a user, the at least one medical fluid pump comprising an acoustic volume sensor for determining the volume of fluid infused into the user by the at least one medical fluid pump, wherein the sensor is located a path to the user;
   a pumping chamber having an inlet connectable to provide fluid communication with a fluid source, and a pump outlet; and
   a force application assembly adapted to provide a compressive stroke to the pumping chamber;
   at least one continuous analyte monitor; and
   a controller, the controller in communication with the medical fluid pump and the at least one continuous analyte monitor, the controller comprising a processor, the processor comprising instructions for delivery of medical fluid based at least on data received from the at least one continuous analyte monitor.

2. The system of claim 1 further comprising a network operation center, the network operation center in communication with the processor.

3. The system of claim 1 further comprising wherein the force application assembly is coupled to an inlet valve actuator of an inlet valve and to a pump actuator of the at least one medical fluid pump, so that the compressive stroke actuates the inlet valve coupled between an inlet and a fluid source to close the inlet valve when the pump actuator causes fluid to be urged from the pumping chamber to the pump outlet.

4. The system of claim 3 further comprising wherein the force application assembly comprises a motor for coordinated operation of the valve actuator and the pump actuator, wherein the motor includes at least one shape-memory actuator.

5. The system of claim 1 wherein at least one of the continuous analyte monitors is a continuous glucose monitor.

6. The system of claim 1 further comprising at least one accelerometer.

7. The system of claim 1 further comprising at least one blood oxygen sensor.

8. The system of claim 1 further comprising at least one inertial measurement unit comprising at least one accelerometer and at least one gyroscope.

9. The system of claim 1 further comprising at least one temperature sensor.

10. A system for at least partial closed-loop control of a medical condition, the system comprising:
    at least one medical fluid pump for infusing fluid into a user, the at least one medical fluid pump comprising an acoustic volume sensor for determining the volume of fluid infused into the user by the at least one medical fluid pump, wherein the sensor is located a path to the user;
    a pumping chamber having an inlet connectable to provide fluid communication with a fluid source, and a pump outlet;
    at least one continuous analyte monitor; and
    a controller, the controller in communication with the medical fluid pump and the at least one continuous analyte monitor, the controller comprising a processor, the processor comprising instructions for delivery of medical fluid based at least on data received from the at least one continuous analyte monitor.

11. The system of claim 10 further comprising a network operation center, the network operation center in communication with the processor.

12. The system of claim 10 further comprising a force application assembly adapted to provide a compressive stroke to the pumping chamber.

13. The system of claim 12 further comprising wherein the force application assembly is coupled to an inlet valve actuator of an inlet valve and to a pump actuator of the at least one medical fluid pump, so that the compressive stroke actuates the inlet valve coupled between an inlet and a fluid source to close the inlet valve when the pump actuator causes fluid to be urged from the pumping chamber to the pump outlet.

14. The system of claim 13 further comprising wherein the force application assembly comprises a motor for coordinated operation of the valve actuator and the pump actuator, wherein the motor includes at least one shape-memory actuator.

15. The system of claim 10 wherein at least one of the continuous analyte monitors is a continuous glucose monitor.

16. The system of claim 10 further comprising at least one accelerometer.

17. The system of claim 10 further comprising at least one blood oxygen sensor.

18. The system of claim 10 further comprising at least one inertial measurement unit comprising at least one accelerometer and at least one gyroscope.

19. The system of claim 10 further comprising at least one temperature sensor.

* * * * *